(12) United States Patent
Aicher et al.

(10) Patent No.: US 7,214,673 B2
(45) Date of Patent: May 8, 2007

(54) PIPERAZINE SUBSTITUTED ARYL BENZODIAZEPINES AND THEIR USE AS DOPAMINE RECEPTOR ANTAGONISTS FOR THE TREATMENT OF PSYCHOTIC DISORDERS

(75) Inventors: Thomas Daniel Aicher, Superior, CO (US); Zhaogen Chen, Noblesville, IN (US); Joseph Herman Krushinski, Jr., Brownsburg, IN (US); Yvan Le Huerou, Boulder, CO (US); Marta Maria Pineiro-Nunez, Brownsburg, IN (US); Kevin Michael Ruley, Indianapolis, IN (US); John Mehnert Schaus, Zionsville, IN (US); Dennis Charles Thompson, Indianapolis, IN (US); David Edward Tupper, Reading (GB); Ying Chen, Thousand Oaks, CA (US); Margaret Mary Faul, Zionsville, IN (US); Vincent Patrick Rocco, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 365 days.

(21) Appl. No.: 10/505,805

(22) PCT Filed: Mar. 17, 2003

(86) PCT No.: PCT/US03/06708

§ 371 (c)(1),
(2), (4) Date: Aug. 26, 2004

(87) PCT Pub. No.: WO03/082877

PCT Pub. Date: Oct. 9, 2003

(65) Prior Publication Data

US 2005/0203296 A1    Sep. 15, 2005

Related U.S. Application Data

(60) Provisional application No. 60/368,670, filed on Mar. 28, 2002.

(51) Int. Cl.
*A61P 25/00* (2006.01)
*A61K 31/55* (2006.01)
*C07D 243/10* (2006.01)

(52) U.S. Cl. .................... 514/220; 540/557
(58) Field of Classification Search ............. 514/220; 540/557
See application file for complete search history.

(56) References Cited

U.S. PATENT DOCUMENTS 3,457,264 A    7/1969    Lembo et al. .............. 544/381

4,087,421 A    5/1978    Safir et al. .................. 540/557

FOREIGN PATENT DOCUMENTS

EP    0 054 416 A    6/1982

(Continued)

OTHER PUBLICATIONS

G.M. Singerman, *The Chemistry of Pyrazine and its Derivatives. IX The Pyrazylethylation of Amines*, J. Het. Chem., vol. 1, 1964, pp. 151-152.

(Continued)

*Primary Examiner*—Brenda Coleman
(74) *Attorney, Agent, or Firm*—Robert D. Titus; John A. Cleveland, Jr.

(57) ABSTRACT

Described herein are antipyschotic compounds of formula (I)

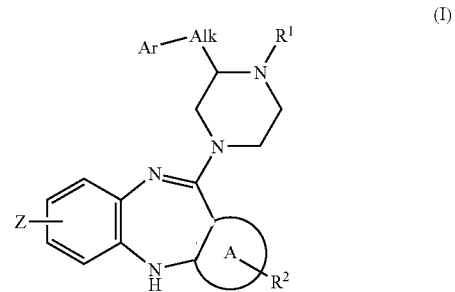

wherein,
A is an optionally benzo-fused five or six member aromatic ring having zero to three hetero atoms independently selected from N, O, and S;
Alk is $(C_{1-4})$ alkylene optionally substituted with OH, methoxy, ethoxy, or F;
Ar is optionally substituted phenyl, naphthyl, monocyclic heteroaromatic, or bicyclic heteroaromatic;
$R^1$ is hydrogen or $(C_{1-4})$ alkyl optionally substituted with OH, $OR^3$, or $OCH_2CH_2OH$,
wherein $R^3$ is $(C_{1-2})$ alkyl;
$R^2$ is H, $(C_{1-6})$ alkyl, halogen, fluorinated $(C_{1-6})$ alkyl, $OR^4$, $SR^4$, $NO_2$, CN, $COR^4$, $CONR^5R^6$, $SO_2NR^5R^6$, $NR^5R^6$, $NR^5COR^4$, $NR^5SO_2R^4$, or optionally substituted phenyl,
wherein
$R^4$ is hydrogen, $(C_{1-6})$ alkyl, fluorinated $(C_{1-6})$ alkyl, or optionally substituted phenyl,
$R^5$ and $R^6$ are independently hydrogen, $(C_{1-6})$ alkyl, or optionally substituted phenyl;
Z is one or two substituents independently selected from hydrogen, halogen, $(C_{1-6})$ alkyl, fluorinated $(C_{1-6})$ alkyl, $OR^7$, $SR^7$, $NO_2$, CN, $COR^7$, $CONR^8R^9$, $SO_2NR^8R^9$, $NR^8SO_2R^7$, $NR^8R^9$, or optionally substituted phenyl,
wherein
$R^7$ is hydrogen, $(C_{1-6})$ alkyl, fluorinated alkyl, or optionally substituted phenyl, $R^8$ and $R^9$ are independently hydrogen, $(C_{1-6})$ alkyl, or optionally substituted phenyl;

and salts, solvates, and crystal forms thereof.

Also described are the use of the compounds of formula (I) as antagonists of the dopamine $D_2$ receptor and as agents for the treatment of psychosis and bipolar disorder, and pharmaceutical formulations of the compounds of formula (I).

9 Claims, No Drawings

FOREIGN PATENT DOCUMENTS

| EP | 0 354 781 A | 2/1990 |
|---|---|---|
| WO | WO 96 18629 A | 6/1996 |

OTHER PUBLICATIONS

J. K. Chakrabarti, *Effects of Conformationally Restricted 4-Piperazinyl-10H- thienobenzodiazepine Neuroleptics on Central Dopaminergic and Cholinergic Systems*, Journal of Medicinal Chemistry, Ameritcan Chemical Society, Washington, US, vol. 25, No. 10, Oct. 1, 1982, pp. 1133-1140.

PIPERAZINE SUBSTITUTED ARYL BENZODIAZEPINES AND THEIR USE AS DOPAMINE RECEPTOR ANTAGONISTS FOR THE TREATMENT OF PSYCHOTIC DISORDERS

This is the national phase application, under 35 USC 371, for PCT/US03/06708, filed 17 Mar. 2003, which, claims the benefit, under 35 USC 119(e), of US provisional application 60/368,670, filed 28 Mar. 2002.

BACKGROUND OF THE INVENTION

Currently there are many drugs available for the treatment of disorders of the central nervous system. Among these drugs is a category known as antipsychotics for treating serious mental conditions such as schizophrenia and schizophreniform illnesses. The drugs available for such conditions are often associated with undesirable adverse events, and there is a need for better products that control or eliminate the symptoms in a safer and more effective way.

Patients suffering from schizophrenia, a condition of unknown etiology, exhibit a group of both positive and negative symptoms. Positive symptoms include delusions, hallucinations, disordered thoughts, and disorganized speech, while negative symptoms include flat affect, anhedonia, social withdrawal, emotional detachment, cognitive deficits, and poverty of speech. Not only does schizophrenia cause personal suffering by the patient, it also severely affects the patient's occupational and social functions, so that often the patient must be institutionalized, which results in a high cost to society.

A leading hypothesis suggests that the positive symptoms of schizophrenia can be effectively treated by compounds that act as antagonists at certain dopamine receptors. Currently, five principal dopamine receptors ($D_1$–$D_5$) that have been identified. Antipsychotic efficacy has been most closely associated with blockade of the D2 class of dopamine receptors. The typical antipsychotic agents (eg. haloperidol) are effective in controlling the positive symptoms of schizophrenia but do not adequately treat the negative symptoms and also induce significant adverse events, principally extrapyramidal side effects, hyperprolactinemia, and tardive dyskinesia.

One approach to developing better antipsychotic agents, involves the identification of compounds that combine D2 receptor blockade with actions at other receptors. One such agent is clozapine.

Clozapine was the first drug identified as an "atypical" antipsychotic, i.e., a drug effective in treating both the positive and negative symptoms of schizophrenia. Additionally, it did not cause EPS and the other adverse events seen with classical, "typical" antipsychotics. Although clozapine is an effective drug, its utility in treating schizophrenia has been limited because of the clinical observation that 1–2% of treated patients developed a potentially fatal blood disorder. More recently, olanzapine has been widely accepted as an atypical antipsychotic with relatively few adverse events. Atypical antipsychotics like clozapine and olanzapine are D2 receptor antagonists and also interact with receptor subtypes for several neurotransmitters, including dopamine, serotonin, norepinephrine, histamine, and acetylcholine. It is believed that some of these additional receptor activities are responsible for the improved efficacy of the atypical antipsychotics and that the adverse events of these agents may be mediated by interactions with others. The success of the atypical antipsychotic drugs has inspired research to produce even more effective drugs for the treatment of schizophrenia that would have negligible instances of adverse events.

The present invention provides antipsychotic compounds and methods of using those compounds to treat psychotic disorders, in particular, schizophrenia and mood disorders, such as bipolar disorders. These compounds offer certain improvements and advantages over the antipsychotics currently in clinical use.

BRIEF SUMMARY OF THE INVENTION

One aspect of the present invention provides compounds of formula (I):

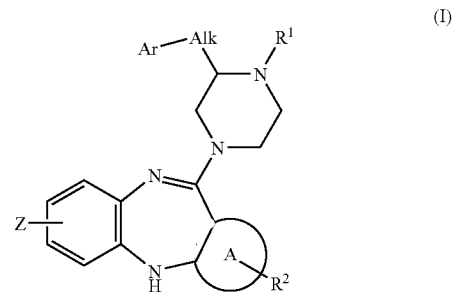

wherein,
A is an optionally benzo-fused five or six member aromatic ring having zero to three hetero atoms independently selected from N, O, and S;

Alk is ($C_{1-4}$) alkylene optionally substituted with OH, methoxy, ethoxy, or F;

Ar is optionally substituted phenyl, naphthyl, monocyclic heteroaromatic, or bicyclic heteroaromatic;

$R^1$ is hydrogen or ($C_{1-4}$) alkyl optionally substituted with OH, $OR^3$, or $OCH_2CH_2OH$,
wherein $R^3$ is ($C_{1-2}$) alkyl;

$R^2$ is H, ($C_{1-6}$) alkyl, halogen, fluorinated ($C_{1-6}$) alkyl, $OR^4$, $SR^4$, $NO_2$, CN, $COR^4$, $CONR^5R^6$, $SO_2NR^5R^6$, $NR^5R^6$, $NR^5COR^4$, $NR^5SO_2R^4$, or optionally substituted phenyl,
wherein
$R^4$ is hydrogen, ($C_{1-6}$) alkyl, fluorinated ($C_{1-6}$) alkyl, benzyl, or optionally substituted phenyl,
$R^5$ and $R^6$ are independently hydrogen, ($C_{1-6}$) alkyl, or optionally substituted phenyl;

Z is one or two substituents independently selected from hydrogen, halogen, ($C_{1-6}$) alkyl, fluorinated ($C_{1-6}$) alkyl, $OR^7$, $SR^7$, $NO_2$, CN, $COR^7$, $CONR^8R^9$, $SO_2NR^8R^9$, $NR^8SO_2R^7$, $NR^8R^9$, or optionally substituted phenyl,
wherein
$R^7$ is hydrogen, ($C_{1-6}$) alkyl, fluorinated ($C_{1-6}$) alkyl, benzyl, or optionally substituted phenyl,
$R^8$ and $R^9$ are independently hydrogen, ($C_{1-6}$) alkyl, or optionally substituted phenyl;

and salts, solvates, and crystal forms thereof.

Another aspect of the present invention provides compounds of formula (Ia):

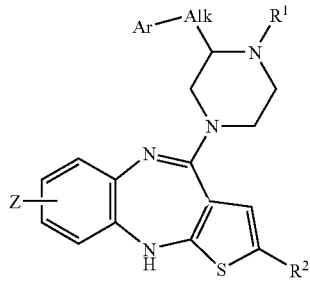

(Ia)

wherein,
  Alk is ($C_{1-4}$) alkylene optionally substituted with OH;
  Ar is optionally substituted phenyl, naphthyl, monocyclic heteroaromatic, or bicyclic heteroaromatic;
  $R^1$ is hydrogen or ($C_{1-4}$) alkyl;
  $R^2$ is H, ($C_{1-6}$) alkyl, fluorinated ($C_{1-6}$) alkyl,
  Z is one or two substituents independently selected from hydrogen, or halogen, and salts, solvates, and crystal forms thereof.

Another aspect of the present invention provides compounds of formula (Ib):

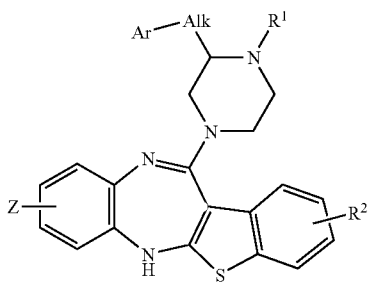

(Ib)

wherein,
  Alk is ($C_{1-4}$) alkylene;
  Ar is optionally substituted phenyl,
  $R^1$ is hydrogen or ($C_{1-4}$) alkyl;
  $R^2$ is H, or ($C_{1-6}$) alkyl;
  Z is one or two substituents independently selected from hydrogen, or halogen; and salts, solvates, and crystal forms thereof.

Another aspect of the present invention provides compounds of formula (Ic):

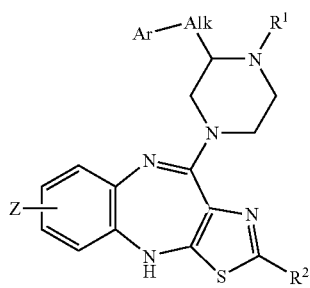

(Ic)

wherein,
  Alk is ($C_{1-4}$) alkylene optionally substituted with OH;
  Ar is optionally substituted phenyl;
  $R^1$ is hydrogen or ($C_{1-4}$) alkyl;
  $R^2$ is H, ($C_{1-6}$) alkyl, halogen, or fluorinated ($C_{1-6}$) alkyl;
  Z is one or two substituents independently selected from hydrogen, or halogen; and salts, solvates, and crystal forms thereof.

Another aspect of the present invention provides compounds of formula (Id):

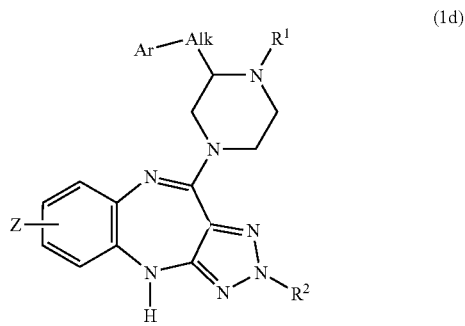

(Id)

wherein,
  Alk is ($C_{1-4}$) alkylene;
  Ar is optionally substituted phenyl;
  $R^1$ is hydrogen or ($C_{1-4}$) alkyl;
  $R^2$ is H, or ($C_{1-6}$) alkyl;
  Z is one or two substituents independently selected from hydrogen, or halogen; and salts, solvates, and crystal forms thereof.

Another aspect of the present invention provides compounds of formula (Ie):

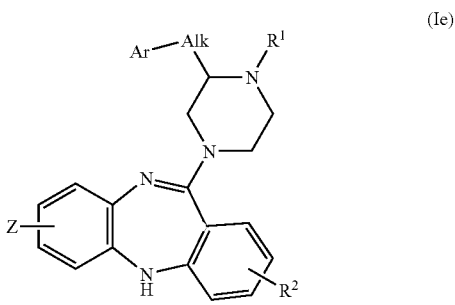

(Ie)

wherein,
  Alk is ($C_{1-4}$) alkylene;
  Ar is optionally substituted phenyl;
  $R^1$ is hydrogen or ($C_{1-4}$) alkyl
  $R^2$ is H, ($C_{1-6}$) alkyl, halogen, fluorinated ($C_{1-6}$) alkyl, or CN;
  Z is one or two substituents independently selected from hydrogen, or halogen; and salts, solvates, and crystal forms thereof.

Another aspect of the present invention is the novel intermediate compounds taught herein in the synthesis of compounds of formula (I).

Another aspect of the present invention is a novel process to intermediate compounds taught herein in the synthesis of compounds of formula (I).

Another aspect of the present invention is the use the compounds of formula (I) as dopamine $D_2$ antagonists, and their use in treating patients suffering from a psychotic condition or mood disorder, including for example schizophrenia and bipolar disorders.

Another aspect is the pharmaceutical formulations which comprises, in association with a pharmaceutically acceptable carrier, diluent or excipient, compound of formula (I).

DETAILED DESCRIPTION OF THE INVENTION

Terms and symbols used herein have meanings consistent with usage in contemporary chemical literature unless otherwise noted. For example, the term "($C_{1-6}$) alkyl" includes saturated and unsaturated alkyl groups that may be branched straight chain or cyclic such as methyl, ethyl, n-propyl, isopropyl, n-butyl, isobutyl, sec-butyl, tert-butyl, pentyl, 2-pentyl, 3-pentyl, neopentyl, n-hexyl, —$CH_2CH_2$=$CH_2$, —$CH_2CH$=$C(CH_3)_2$, —$CH_2C$(=$CH_2$)$CH_3$, cyclopropyl, cyclopropylmethyl, cyclopentyl, cyclohexyl, and the like. The term "($C_{1-4}$) alkylene" refers to —$CH_2$—, —$CH_2CH_2$—, —$CH_2CH_2CH_2$—, and —$CH_2CH_2CH_2CH_2$—. The term "halogen" includes fluoro, chloro, bromo and iodo. The term "fluorinated ($C_{1-6}$) alkyl" refers to a ($C_{1-6}$) alkyl group which is substituted with one or more fluorines, such as, fluoromethyl, difluoromethyl, trifluoromethyl, 2-fluoroethyl, 2,2,2-trifluoroethyl, 1,1,2,2,2-pentafluoroethyl, 3-fluoropropyl, 3,3,3-trifluoropropyl, 1,1,1,3,3,3-hexafluoroprop-2-yl, and 6-fluorohexyl.

The term "optionally substituted phenyl" refers to a phenyl group which may be substituted with one to three substituents selected from hydrogen, halogen, ($C_{1-6}$) alkyl, fluorinated ($C_{1-6}$) alkyl, OH, ($C_{1-6}$) alkoxy, ($C_{1-6}$) fluorinated alkoxy, ($C_{1-6}$) thioalkyl, ($C_{1-6}$) acyl, ($C_1$–$C_4$ alkyl) sulfonyl, $OCF_3$, $NO_2$, CN, carboxamido which may be substituted on the nitrogen by one or two ($C_{1-4}$) alkyl groups, and $NH_2$ in which one of the hydrogens may be replaced by a ($C_{1-4}$) alkyl group and the other hydrogen may be replaced by either a ($C_{1-4}$) alkyl group, a ($C_{1-6}$) acyl group, or a ($C_1$–$C_4$ alkyl)sulfonyl group. The term "($C_{1-6}$) alkoxy" includes such groups as methoxy, ethoxy, isopropoxy, sec-butoxy, tert-butoxy, 2-pentoxy, 3-hexyloxy, and the like. The term "($C_{1-6}$) alkylthio" includes such groups as methylthio, ethylthio, isopropylthio, sec-butylthio, tert-butylthio, 1-hexylthio, and the like. The term "($C_{1-6}$) acyl" includes, for example, formyl, acetyl, propanoyl, butanoyl, 2-methylpropanoyl, hexanoyl, and the like. The term "($C_1$–$C_4$ alkyl)sulfonyl" includes methanesulfonyl, ethanesulfonyl, propanesulfonyl, isopropanesulfonyl, 1-butanesulfonyl and the like.

The term "monocyclic heteroaromatic" refers to a five or six membered aromatic ring containing one to three heteroatoms selected from N, O, and S. Recognize that if one of the heteroatoms is O or S, the heteroaromatic ring must be a five membered ring and that any other heteroatoms contained therein must be N. Examples of such monocyclic heteroaromatic systems include furan, thiophene, pyridine, pyrimidine, thiazole, 1,2,3-triazole, and the like.

The term "bicyclic heteroaromatic" refers to a bicyclic aromatic system containing one to three heteroatoms selected from N, O, and S. Examples include indole, benzofuran, benzothiophene, quinoline, isoquinoline, indazole, benzothiazole, and the like.

The term "optionally substituted phenyl, naphthyl, monocyclic heteroaromatic, or bicyclic heteroaromatic" refers to phenyl, naphthyl, monocyclic heteroaromatic, or bicyclic heteroaromatic which may be substituted with one to three substituents selected from hydrogen, halogen, ($C_{1-6}$) alkyl, fluorinated ($C_{1-6}$) alkyl, OH, ($C_{1-6}$) alkoxy, ($C_{1-6}$) fluorinated alkoxy, ($C_{1-6}$) thioalkyl, ($C_{1-6}$) acyl, ($C_1$–$C_4$ alkyl) sulfonyl, $OCF_3$, $NO_2$, CN, carboxamido which may be substituted on the nitrogen by one or two ($C_{1-4}$) alkyl groups, and $NH_2$ in which one of the hydrogens may be replaced by a ($C_{1-4}$) alkyl group and the other hydrogen may be replaced by either a ($C_{1-4}$) alkyl group, a ($C_{1-6}$) acyl group, or a ($C_1$–$C_4$ alkyl)sulfonyl group.

In the case of optionally benzo-fused five or six member aromatic ring having zero to three hetero atoms independently selected from N, O, and S, the two atoms of the aromatic ring which are fused to the adjoining seven member ring are constrained to both be carbon. If the aromatic ring contains two additional adjacent carbon atoms, a benzene ring may be fused to the aromatic ring at those two adjacent carbon atoms. Examples of optionally benzo-fused five or six member aromatic rings having zero to three hetero atoms independently selected from N, S, and O include benzene, pyridine, furan, pyrrole, thiophene, thiazole, oxazole, pyrazole, imidazole, 1,2,3-triazole, naphthylene, quinoline, isoquinoline, indole, benzofuran, benzothiophene, and the like.

The compounds of the present invention may, depending upon their structure and manner of synthesis and isolation, exist as a pharmaceutically acceptable solvate. These solvates include water, methanol, and ethanol. Solvated forms of the compounds of the present invention represent a further embodiment of the present invention.

The compounds of formula (I) can exist in optically isomeric forms, ie., stereoisomeric forms. That is, these compounds have a least one chiral, ie., asymmetric, center at the carbon atom of the piperazine ring to which "Alk" is attached. Such asymmetry gives rise to at least one pair of enantiomers. An equal mixture of enantiomers is known as a "racemic" mixture or a "racemate." The representation of formula (I) is intended to represent each of those stereoisomers and mixtures thereof.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). Some of the compounds of formula (I) may have two or more chiral centers.

Some of the compounds of the present invention may also be isomeric with respect to one or more double bonds, which introduces geometric, i.e., cis and trans, isomers. A discussion of optical and geometric isomers can be found in standard organic chemistry text books such as *March's Advanced Organic Chemistry*, 5$^{th}$ Ed., Chapter 4, Wiley-Interscience, John Wiley & Sons, Inc., New York (2001). Herein, when a compound of the present invention is named, or its structure presented, without an indication of asymmetric form, all of the possible asymmetric forms are intended This invention is not limited to any particular isomer but includes all possible individual isomers and racemates.

Preferred among the compounds of formula (I) are those wherein:

a) The aromatic ring A is selected from the group consisting of:

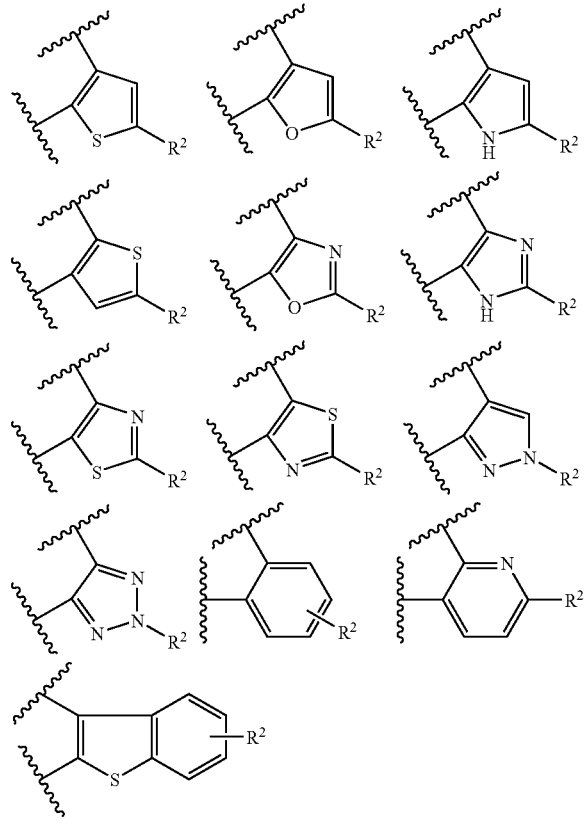

Preferred among the compounds of formula (I) are those wherein:

b) Alk is —CH$_2$—, —CH$_2$CH$_2$—, or —CH$_2$CH$_2$CH$_2$—;

Another preferred embodiment among the compounds of formula (I) are those wherein:

c) Ar is optionally substituted phenyl furan, or thiophene;

Another preferred embodiment among the compounds of formula (I) are those wherein:

d) R$^1$ is hydrogen, methyl, or —CH$_2$CH$_2$—O—CH$_2$CH$_2$—OH;

Another preferred embodiment among the compounds of formula (I) are those wherein:

e) Z is hydrogen or halogen;

Another preferred embodiment among the compounds of formula (I) are those wherein:

f) The stereo configuration is "S" about the carbon of the piperazine group bound to Alk.

Another preferred embodiment among the compounds of formula (I) are those wherein:

g) R$^2$ is hydrogen, (C$_{1-6}$) alkyl, fluorinated (C$_{1-6}$) alkyl, or halogen.

It is an aspect of this invention that any combination of these preferred embodiments are contemplated.

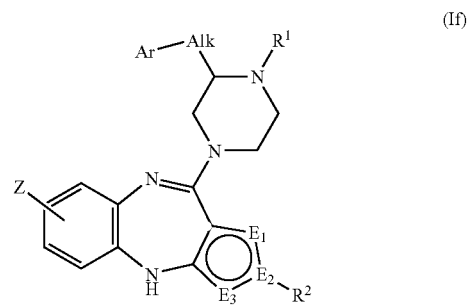

(If)

The compounds of formula (If) listed in Table 1 are of particular interest:

The stereo configuration is "S" about the carbon of the piperazine group bound to Alk unless otherwise indicated.

TABLE 1

| Ex. No. | E$_1$ | E$_2$ | E$_3$ | Alk Ar | R$^1$ | R$^2$ | Z |
|---|---|---|---|---|---|---|---|
| 59 | CH | C | S | CH$_2$CH$_2$Ph | H | CH$_3$ | H |
| 61 | CH | C | S | CH$_2$Ph | H | CH$_3$ | H |
| 62 | CH | C | S | CH$_2$(4-OCH$_2$CH=C(CH$_3$)$_2$)Ph | H | CH$_3$ | H |
| 63 | CH | C | S | CH$_2$(3,4-OCH$_2$O—)Ph | H | CH$_3$ | H |
| 64 | CH | C | S | CH$_2$(3,4-diOCH$_3$)Ph | H | CH$_3$ | H |
| 65 | CH | C | S | CH$_2$(4-iPr)Ph | H | CH$_3$ | H |
| 66 | CH | C | S | CH$_2$(4-PhO)Ph | H | CH$_3$ | H |
| 67 | CH | C | S | CH$_2$(napthalen-2-yl) | H | CH$_3$ | H |
| 68 | CH | C | S | CH$_2$(napthalen-1-yl) | H | CH$_3$ | H |
| 69 | CH | C | S | CH$_2$(4-CH$_3$)Ph | H | CH$_3$ | H |
| 70 | CH | C | S | CH$_2$(3-CH$_3$)Ph | H | CH$_3$ | H |
| 71 | CH | C | S | CH$_2$(2-F)Ph | H | CH$_3$ | H |
| 72 | CH | C | S | CH$_2$(3-F)Ph | H | CH$_3$ | H |
| 73 | CH | C | S | CH$_2$(4-F)Ph | H | CH$_3$ | H |
| 74 | CH | C | S | CH$_2$(2-CF$_3$)Ph | H | CH$_3$ | H |
| 75 | CH | C | S | CH$_2$(2-OCH$_3$)Ph | H | CH$_3$ | H |
| 76 | CH | C | S | CH$_2$(3-OCH$_3$)Ph | H | CH$_3$ | H |
| 77 | CH | C | S | CH$_2$(4-OCH$_3$)Ph | H | CH$_3$ | H |
| 78 | CH | C | S | CH$_2$(3,4-diCl)Ph | H | CH$_3$ | H |
| 79 | CH | C | S | CH$_2$(indol-3-yl) | H | CH$_3$ | H |
| 80 | CH | C | S | CH$_2$(thiophen-2-yl) | H | CH$_3$ | H |
| 81 | CH | C | S | CH$_2$(benzo(b)thiophen-3-yl) | H | CH$_3$ | H |

TABLE 1-continued

| Ex. No. | $E_1$ | $E_2$ | $E_3$ | Alk Ar | $R^1$ | $R^2$ | Z |
|---|---|---|---|---|---|---|---|
| 82 | CH | C | S | CH$_2$(3-O-i-Pr)Ph | H | CH$_3$ | H |
| 83 | CH | C | S | (R)CH$_2$Ph | H | CH$_3$ | H |
| 84 | CH | C | S | CH$_2$(2,4-DiOCH$_3$)Ph | H | CH$_3$ | H |
| 85 | CH | C | S | CH$_2$(4-Cl)Ph | H | CH$_3$ | H |
| 86 | CH | C | S | CH$_2$(2-Cl)Ph | H | CH$_3$ | H |
| 87 | CH | C | S | CH$_2$(3-Cl)Ph | H | CH$_3$ | H |
| 88 | CH | C | S | CH$_2$(3,5-DiF)Ph | H | CH$_3$ | H |
| 89 | CH | C | S | CH$_2$(3-CF$_3$)Ph | H | CH$_3$ | H |
| 90 | CH | C | S | CH$_2$CH$_2$Ph | CH$_3$ | CH$_3$ | H |
| 92 | CH | C | S | CH$_2$Ph | CH$_3$ | CH$_3$ | H |
| 93 | CH | C | S | CH$_2$(4-O—CH$_2$CH=CH$_2$)Ph | CH$_3$ | CH$_3$ | H |
| 94 | CH | C | S | CH$_2$(pyridin-2-yl) | CH$_3$ | CH$_3$ | H |
| 95 | CH | C | S | (R)CH$_2$Ph | CH$_3$ | CH$_3$ | H |
| 100 | CH | C | S | CH$_2$(napthalen-2-yl) | CH$_3$ | CH$_3$ | H |
| 101 | CH | C | S | CH$_2$(napthalen-1-yl) | CH$_3$ | CH$_3$ | H |
| 102 | CH | C | S | CH$_2$(4-CH$_3$)Ph | CH$_3$ | CH$_3$ | H |
| 103 | CH | C | S | CH$_2$(3-CH$_3$)Ph | CH$_3$ | CH$_3$ | H |
| 104 | CH | C | S | CH$_2$(2-F)Ph | CH$_3$ | CH$_3$ | H |
| 105 | CH | C | S | CH$_2$(3-F)Ph | CH$_3$ | CH$_3$ | H |
| 106 | CH | C | S | CH$_2$(4-F)Ph | CH$_3$ | CH$_3$ | H |
| 107 | CH | C | S | CH$_2$(3-CF$_3$)Ph | CH$_3$ | CH$_3$ | H |
| 108 | CH | C | S | CH$_2$(2-CF$_3$)Ph | CH$_3$ | CH$_3$ | H |
| 109 | CH | C | S | CH$_2$(2-OCH$_3$)Ph | CH$_3$ | CH$_3$ | H |
| 110 | CH | C | S | CH$_2$(3-OCH$_3$)Ph | CH$_3$ | CH$_3$ | H |
| 111 | CH | C | S | CH$_2$(4-OCH$_3$)Ph | CH$_3$ | CH$_3$ | H |
| 112 | CH | C | S | CH$_2$(3,4-diCl)Ph | CH$_3$ | CH$_3$ | H |
| 113 | CH | C | S | CH$_2$(indol-3-yl) | CH$_3$ | CH$_3$ | H |
| 114 | CH | C | S | CH$_2$(thiophen-2-yl) | CH$_3$ | CH$_3$ | H |
| 115 | CH | C | S | CH$_2$(benzo(b)thiophen-3-yl) | CH$_3$ | CH$_3$ | H |
| 118 | CH | C | S | CH$_2$(2-Cl)Ph | CH$_3$ | CH$_3$ | H |
| 119 | CH | C | S | CH$_2$(3-Cl)Ph | CH$_3$ | CH$_3$ | H |
| 120 | CH | C | S | CH$_2$(4-Cl—Ph) | CH$_3$ | CH$_3$ | H |
| 121 | CH | C | S | CH$_2$(4-OPh)Ph | CH$_3$ | CH$_3$ | H |
| 122 | CH | C | S | CH$_2$(3-OPh)Ph | CH$_3$ | CH$_3$ | H |
| 123 | CH | C | S | CH$_2$(3-O-iPr)Ph | CH$_3$ | CH$_3$ | H |
| 124 | CH | C | S | CH$_2$(2,4-di OCH$_3$)Ph | CH$_3$ | CH$_3$ | H |
| 132 | CH | C | S | CH$_2$CH$_2$(2-pyridin-2-yl) | H | CH$_3$ | H |
| 133 | CH | C | S | CH$_2$CH$_2$(2-pyridin-4-yl) | H | CH$_3$ | H |
| 176 | CH | C | S | CH$_2$CH$_2$(4-F)Ph | H | CH$_3$ | H |
| 177 | CH | C | S | CH$_2$CH$_2$(3-F)Ph | H | CH$_3$ | H |
| 178 | CH | C | S | CH$_2$CH$_2$(2-F)Ph | H | CH$_3$ | H |
| 179 | CH | C | S | CH$_2$CH$_2$(4-OCH$_3$)Ph | H | CH$_3$ | H |
| 180 | CH | C | S | CH$_2$CH$_2$(3-OCH$_3$)Ph | H | CH$_3$ | H |
| 181 | CH | C | S | CH$_2$CH$_2$(2-OCH$_3$)Ph | H | CH$_3$ | H |
| 182 | CH | C | S | CH$_2$CH$_2$(4-F)Ph | CH$_3$ | CH$_3$ | H |
| 183 | CH | C | S | CH$_2$CH$_2$(3-F)Ph | CH$_3$ | CH$_3$ | H |
| 184 | CH | C | S | CH$_2$CH$_2$(2-F)Ph | CH$_3$ | CH$_3$ | H |
| 185 | CH | C | S | CH$_2$CH$_2$(4-OCH$_3$)Ph | CH$_3$ | CH$_3$ | H |
| 186 | CH | C | S | CH$_2$CH$_2$(3-OCH$_3$)Ph | CH$_3$ | CH$_3$ | H |
| 187 | CH | C | S | CH$_2$CH$_2$(2-OCH$_3$)Ph | CH$_3$ | CH$_3$ | H |
| 188 | CH | C | S | CH$_2$CH$_2$(2-pyridin-4-yl) | CH$_3$ | CH$_3$ | H |
| 189 | CH | C | S | CH$_2$CH$_2$(2-pyridin-3-yl) | H | CH$_3$ | H |
| 190 | CH | C | S | CH$_2$CH$_2$(2-pyridin-3-yl) | CH$_3$ | CH$_3$ | H |
| 191 | CH | C | S | CH$_2$CH$_2$(2-pyridin-2-yl) | CH$_3$ | CH$_3$ | H |
| 194 | CH | C | S | (CH$_2$)$_4$Ph | H | CH$_3$ | H |
| 195 | CH | C | S | (CH$_2$)$_4$Ph | CH$_3$ | CH$_3$ | H |
| 201 | CH | C | S | (CH$_2$)$_3$Ph | H | CH$_3$ | H |
| 202 | CH | C | S | (CH$_2$)$_3$Ph | CH$_3$ | CH$_3$ | H |
| 209 | CH | C | S | CH$_2$(4-Br)Ph | H | CH$_3$ | H |
| 210 | CH | C | S | CH$_2$(4-I)Ph | H | CH$_3$ | H |
| 211 | CH | C | S | CH$_2$(4-O—CH$_2$CH=CH$_2$)Ph | H | CH$_3$ | H |
| 212 | CH | C | S | CH$_2$(thiaphen-3-yl) | H | CH$_3$ | H |
| 213 | CH | C | S | CH$_2$(4-O-isoPropyl)Ph | H | CH$_3$ | H |
| 218 | CH | C | S | CH$_2$(4-Br)Ph | CH$_3$ | CH$_3$ | H |
| 219 | CH | C | S | CH$_2$(thiophen-3-yl) | CH$_3$ | CH$_3$ | H |
| 220 | CH | C | S | CH$_2$(4-I)Ph | CH$_3$ | CH$_3$ | H |
| 221 | CH | C | S | CH$_2$(4-O-isoPropyl)Ph | CH$_3$ | CH$_3$ | H |
| 236 | CH | C | S | CH$_2$(3,5-DiCH$_3$)Ph | H | CH$_3$ | H |
| 237 | CH | C | S | CH$_2$(4-O—CH$_2$C(=CH$_2$)CH$_3$)Ph | H | CH$_3$ | H |
| 238 | CH | C | S | CH$_2$(2-OEt)Ph | H | CH$_3$ | H |
| 239 | CH | C | S | CH$_2$(2-O—iPr)Ph | H | CH$_3$ | H |
| 240 | CH | C | S | CH$_2$(pyridin-2-yl) | H | CH$_3$ | H |
| 240a | CH | C | S | CH$_2$(3-OPh)Ph | H | CH$_3$ | H |

TABLE 1-continued

| Ex. No. | $E_1$ | $E_2$ | $E_3$ | Alk Ar | $R^1$ | $R^2$ | Z |
|---|---|---|---|---|---|---|---|
| 241 | CH | C | S | $CH_2$(4-O—$CH_2CH$=$C(CH_3)_2$)Ph | $CH_3$ | $CH_3$ | H |
| 242 | CH | C | S | $CH_2$(3,4-$OCH_2O$—)Ph | $CH_3$ | $CH_3$ | H |
| 243 | CH | C | S | $CH_2$(3,4-Di($OCH_3$))Ph | $CH_3$ | $CH_3$ | H |
| 244 | CH | C | S | $CH_2$(4-O—$CH_2C$(=$CH_2$)$CH_3$)Ph | $CH_3$ | $CH_3$ | H |
| 245 | CH | C | S | $CH_2$(4-isoPropyl)Ph | $CH_3$ | $CH_3$ | H |
| 246 | CH | C | S | $CH_2$(3,5-Di($CH_3$))Ph | $CH_3$ | $CH_3$ | H |
| 247 | CH | C | S | $CH_2$(2-$OCH_2CH_3$)Ph | $CH_3$ | $CH_3$ | H |
| 248 | CH | C | S | $CH_2$(4-Ph)Ph | $CH_3$ | $CH_3$ | H |
| 249 | CH | C | S | $CH_2$(2-O-isoPropyl)Ph | $CH_3$ | $CH_3$ | H |
| 387 | CH | C | S | $CH_2CH_2$(3-Cl)Ph | H | $CH_3$ | H |
| 388 | CH | C | S | $CH_2CH_2$(4-Cl)Ph | H | $CH_3$ | H |
| 389 | CH | C | S | $CH_2CH_2$(2-Cl)Ph | H | $CH_3$ | H |
| 390 | CH | C | S | $CH_2CH_2$(4-Cl)Ph | $CH_3$ | $CH_3$ | H |
| 391 | CH | C | S | $CH_2CH_2$(3-Cl)Ph | $CH_3$ | $CH_3$ | H |
| 392 | CH | C | S | $CH_2CH_2$(2-Cl)Ph | $CH_3$ | $CH_3$ | H |
| 393 | CH | C | S | $CH_2CH_2$(4-$CF_3$)Ph | H | $CH_3$ | H |
| 394 | CH | C | S | $CH_2CH_2$(2-$CF_3$)Ph | H | $CH_3$ | H |
| 395 | CH | C | S | $CH_2CH_2$(3-$CF_3$)Ph | H | $CH_3$ | H |
| 396 | CH | C | S | $CH_2CH_2$(4-$CF_3$)Ph | $CH_3$ | $CH_3$ | H |
| 397 | CH | C | S | $CH_2CH_2$(2-$CF_3$)Ph | $CH_3$ | $CH_3$ | H |
| 398 | CH | C | S | $CH_2CH_2$(3-$CF_3$)Ph | $CH_3$ | $CH_3$ | H |
| 399 | CH | C | S | $CH_2CH_2$(2,4-diF)Ph | H | $CH_3$ | H |
| 400 | CH | C | S | $CH_2CH_2$(2,4-diF)Ph | $CH_3$ | $CH_3$ | H |
| 401 | CH | C | S | $CH_2CH_2$(3-F)Ph | H | $CH_3$ | 6F |
| 402 | CH | C | S | $CH_2CH_2$(4-$OCH_3$)Ph | H | $CH_3$ | 6F |
| 403 | CH | C | S | $CH_2CH_2$(3-F)Ph | H | $CH_3$ | 7F |
| 404 | CH | C | S | $CH_2CH_2$(4-$OCH_3$)Ph | H | $CH_3$ | 7F |
| 405 | CH | C | S | $CH_2CH_2$(3-F)Ph | $CH_3$ | $CH_3$ | 6F |
| 406 | CH | C | S | $CH_2CH_2$(4-$OCH_3$)Ph | $CH_3$ | $CH_3$ | 6F |
| 407 | CH | C | S | $CH_2CH_2$(3-F)Ph | $CH_3$ | $CH_3$ | 7F |
| 408 | CH | C | S | $CH_2CH_2$(4-$OCH_3$)Ph | $CH_3$ | $CH_3$ | 7F |
| 411 | CH | C | S | $CH_2CH_2$(3-F)Ph | H | $CH_2CH_3$ | 7F |
| 412 | CH | C | S | $CH_2CH_2$(3-F)Ph | $CH_3$ | $CH_2CH_3$ | 7F |
| 413 | CH | C | S | $CH_2CH_2$(4-$OCH_3$)Ph | H | $CH_2CH_3$ | 7F |
| 414 | CH | C | S | $CH_2CH_2$(4-$OCH_3$)Ph | $CH_3$ | $CH_2CH_3$ | 7F |
| 423 | CH | C | S | $CH_2CH_2$(2-napthalen-1-yl) | H | $CH_3$ | H |
| 425 | CH | C | S | $CH_2CH_2$(2-napthalen-1-yl) | $CH_3$ | $CH_3$ | H |
| 428 | CH | C | S | $CH_2CH_2$(2-napthalen-2-yl) | H | $CH_3$ | H |
| 429 | CH | C | S | $CH_2CH_2$(2-napthalen-2-yl) | $CH_3$ | $CH_3$ | H |
| 434 | CH | C | S | $CH_2CH_2$(2-furan-3-yl) | H | $CH_3$ | H |
| 435 | CH | C | S | $CH_2CH_2$(2-furan-3-yl) | $CH_3$ | $CH_3$ | H |
| 439 | CH | C | S | $CH_2CH_2$(2-thiophene-3-yl) | H | $CH_3$ | H |
| 440 | CH | C | S | $CH_2CH_2$(2-thiophene-3-yl) | $CH_3$ | $CH_3$ | H |
| 441 | CH | C | S | $CH_2$Ph | H | $CH(CH_3)_2$ | H |
| 442 | CH | C | S | $CH_2CH_2$Ph | H | $CH(CH_3)_2$ | H |
| 443 | CH | C | S | $CH_2$(2-$OCH_3$)Ph | H | $CH(CH_3)_2$ | H |
| 444 | CH | C | S | $CH_2CH_2$Ph | $CH_3$ | $CH(CH_3)_2$ | H |
| 444a | CH | C | S | $CH_2$Ph | $CH_3$ | $CH(CH_3)_2$ | H |
| 444b | CH | C | S | $CH_2$(2-$OCH_3$)Ph | $CH_3$ | $CH(CH_3)_2$ | H |
| 445 | CH | C | S | $CH_2CH_2$Ph | H | $C(CH_3)_3$ | Z |
| 446 | CH | C | S | $CH_2CH_2$Ph | $CH_3$ | $C(CH_3)_3$ | H |
| 460 | N | C | S | $CH_2CH_2$Ph | H | $CH_3$ | H |
| 461 | N | C | S | $CH_2CH_2$Ph | $CH_3$ | $CH_3$ | H |
| 462 | N | C | S | $CH_2$Ph | H | $CH_3$ | H |
| 463 | N | C | S | $CH_2$(2-$OCH_3$)Ph | H | $CH_3$ | H |
| 464 | N | C | S | $CH_2CH_2$(4-$OCH_3$)Ph | H | $CH_3$ | H |
| 465 | N | C | S | $CH_2CH_2$(4-$OCH_3$)Ph | $CH_3$ | $CH_3$ | H |
| 466 | N | C | S | $CH_2CH_2$(4-F)Ph | H | $CH_3$ | H |
| 467 | N | C | S | $CH_2CH_2$(3-F)Ph | H | $CH_3$ | H |
| 468 | N | C | S | $CH_2CH_2$Ph | H | $CH(CH_3)_2$ | H |
| 469 | N | C | S | $CH_2CH_2$(4-$OCH_3$)Ph | H | $CH(CH_3)_2$ | H |
| 470 | N | C | S | $CH_2$Ph | H | $CH(CH_3)_2$ | H |
| 471 | N | C | S | $CH_2CH_2$(3-F)Ph | H | $CH(CH_3)_2$ | H |
| 472 | N | C | S | $CH_2CH_2$(4-F)Ph | H | $CH(CH_3)_2$ | H |
| 473 | N | C | S | $CH_2$Ph | $CH_3$ | $CH_3$ | H |
| 474 | N | C | S | $CH_2$(2-$OCH_3$)Ph | $CH_3$ | $CH_3$ | H |
| 475 | N | C | S | $CH_2$Ph | $CH_3$ | $CH(CH_3)_2$ | H |
| 476 | N | C | S | $CH_2$(4-$OCH_3$)Ph | $CH_3$ | $CH(CH_3)_2$ | H |
| 477 | N | C | S | $CH_2$Ph | $CH_3$ | $CH(CH_3)_2$ | H |
| 478 | N | C | S | $CH_2CH_2$(4-F)Ph | $CH_3$ | $CH_3$ | H |
| 479 | N | C | S | $CH_2CH_2$(3-F)Ph | $CH_3$ | $CH_3$ | H |
| 480 | N | C | S | $CH_2CH_2$(3-F)Ph | $CH_3$ | $CH(CH_3)_2$ | H |

TABLE 1-continued

| Ex. No. | $E_1$ | $E_2$ | $E_3$ | Alk Ar | $R^1$ | $R^2$ | Z |
|---|---|---|---|---|---|---|---|
| 481 | N | C | S | $CH_2CH_2$(4-F)Ph | $CH_3$ | $CH(CH_3)_2$ | H |
| 484 | N | C | S | $CH_2CH_2$Ph | H | $CH_2CH_2CH_2CH_3$ | H |
| 486 | N | C | S | $CH_2CH_2$Ph | $CH_3$ | $CH_2CH_2CH_2CH_3$ | H |
| 491 | N | C | S | $CH_2CH_2$Ph | H | cyclopentyl | H |
| 492 | N | C | S | $CH_2CH_2$Ph | $CH_3$ | cyclopentyl | H |
| 493 | N | C | S | $CH_2$Ph | H | cyclopentyl | H |
| 494 | N | C | S | $CH_2$Ph | $CH_3$ | cyclopentyl | H |
| 495 | N | C | S | $CH_2CH_2$(3-$OCH_3$)Ph | H | cyclopentyl | H |
| 496 | N | C | S | $CH_2CH_2$(3-$OCH_3$)Ph | $CH_3$ | cyclopentyl | H |
| 497 | N | C | S | $CH_2CH_2$(4-$OCH_3$)Ph | H | cyclopentyl | H |
| 498 | N | C | S | $CH_2CH_2$(4-$OCH_3$)Ph | $CH_3$ | cyclopentyl | H |
| 501 | N | C | S | $CH_2CH_2$(4-$OCH_3$)Ph | H | $CH_2CH_3$ | H |
| 502 | N | C | S | $CH_2CH_2$(4-F)Ph | H | $CH_2CH_3$ | H |
| 503 | N | C | S | $CH_2CH_2$(3-F)Ph | H | $CH_2CH_3$ | H |
| 504 | N | C | S | $CH_2CH_2$(3-$OCH_3$)Ph | H | $CH_2CH_3$ | H |
| 506 | N | C | S | $CH_2CH_2$(4-$OCH_3$)Ph | $CH_3$ | $CH_2CH_3$ | H |
| 507 | N | C | S | $CH_2CH_2$(4-F)Ph | $CH_3$ | $CH_2CH_3$ | H |
| 508 | N | C | S | $CH_2CH_2$(3-F)Ph | $CH_3$ | $CH_2CH_3$ | H |
| 509 | N | C | S | $CH_2CH_2$(3-$OCH_3$)Ph | $CH_3$ | $CH_2CH_3$ | H |
| 512 | N | C | S | $CH_2CH_2$(3-F)Ph | H | $CF_3$ | H |
| 514 | N | C | S | $CH_2CH_2$(4-F)Ph | H | $CF_3$ | H |
| 516 | N | C | S | $CH_2CH_2$(3-$OCH_3$)Ph | H | $CF_3$ | H |
| 518 | N | C | S | $CH_2CH_2$(4-$OCH_3$)Ph | H | $CF_3$ | H |
| 520 | N | C | S | $CH_2CH_2$(3-$OCH_3$)Ph | $CH_3$ | $CF_3$ | H |
| 522 | N | C | S | $CH_2CH_2$(3-F)Ph | $CH_3$ | $CF_3$ | H |
| 524 | N | C | S | $CH_2CH_2$(4-$OCH_3$)Ph | $CH_3$ | $CF_3$ | H |
| 526 | N | C | S | $CH_2CH_2$(4-F)Ph | $CH_3$ | $CF_3$ | H |
| 533 | C | C | S | $CH_2CH_2$Ph | H | benzofused | 9F |
| 534 | C | C | S | $CH_2CH_2$Ph | $CH_3$ | benzofused | 9F |
| 535 | C | C | S | $CH_2CH_2$(4-$OCH_3$)Ph | H | benzofused | 9F |
| 537 | C | C | S | $CH_2CH_2$(3-$OCH_3$)Ph | H | benzofused | 9F |
| 539 | C | C | S | $CH_2CH_2$(3-F)Ph | H | benzofused | 9F |
| 541 | C | C | S | $CH_2CH_2$(4-F)Ph | H | benzofused | 9F |
| 543 | C | C | S | $CH_2CH_2$(4-$OCH_3$)Ph | $CH_3$ | benzofused | 9F |
| 545 | C | C | S | $CH_2CH_2$(3-$OCH_3$)Ph | $CH_3$ | benzofused | 9F |
| 547 | C | C | S | $CH_2CH_2$(3-F)Ph | $CH_3$ | benzofused | 9F |
| 549 | C | C | S | $CH_2CH_2$(4-F)Ph | $CH_3$ | benzofused | 9F |
| 568 | CH | C=CH | CH | $CH_2CH_2$(4-F)Ph | H | 2-$CH_3$ | 8F |
| 569 | CH | C=CH | CH | $CH_2CH_2$(4-F)Ph | $CH_3$ | 2-$CH_3$ | 8F |
| 570 | CH | C=CH | CH | $CH_2CH_2$(4-F)Ph | H | 2-$CH(CH_3)_2$ | 8F |
| 571 | CH | C=CH | CH | $CH_2CH_2$(4-F)Ph | $CH_3$ | 2-$CH(CH_3)_2$ | 8F |
| 572 | CH | C=CH | CH | $CH_2CH_2$(3-F)Ph | H | 2-$CH(CH_3)_2$ | H |
| 573 | CH | C=CH | CH | $CH_2CH_2$(3-F)Ph | $CH_3$ | 2-$CH(CH_3)_2$ | H |
| 575 | CH | CH=C | CH | $CH_2CH_2$Ph | H | 3-$CH_3$ | H |
| 576 | CH | CH=C | CH | $CH_2CH_2$Ph | $CH_3$ | 3-$CH_3$ | H |
| 577 | CH | CH=C | CH | $CH_2CH_2$(3-F)Ph | H | 3-$CH_3$ | H |
| 578 | CH | CH=C | CH | $CH_2CH_2$(3-F)Ph | $CH_3$ | 3-$CH_3$ | H |
| 580 | CH | C=CH | CH | $CH_2CH_2$Ph | H | 2-$CH_3$ | H |
| 581 | CH | C=CH | CH | $CH_2CH_2$Ph | $CH_3$ | 2-$CH_3$ | H |
| 585 | CH | CH=C | CH | $CH_2$Ph | H | 3-H | 8Cl |
| 586 | CH | CH=C | CH | $CH_2CH_2$Ph | H | 3-H | 8Cl |
| 587 | CH | CH=C | CH | $CH_2CH_2$Ph | $CH_3$ | 3-H | 8Cl |
| 588 | CH | CH=C | CH | $CH_2$Ph | $CH_3$ | 3-H | 8Cl |
| 594 | N | N | NH | $CH_2CH_2$Ph | H | $CH(CH_3)_2$ | H |
| 595 | N | N | NH | $CH_2CH_2$Ph | $CH_3$ | $CH(CH_3)_2$ | H |
| 598 | CH | C | S | (S,R)$CH_2CH(OH)$Ph | H | $CH_3$ | H |
| 599 | CH | C | S | (S,S)$CH_2CH(OH)$Ph | H | $CH_3$ | H |
| 600 | CH | C | S | (S,S)$CH_2CH(OH)$Ph | $CH_3$ | $CH_3$ | H |
| 601 | N | C | S | (S,R)$CH_2CH(OH)$Ph | H | $CH(CH_3)_2$ | H |
| 602 | N | C | S | (S,S)$CH_2CH(OH)$Ph | H | $CH(CH_3)_2$ | H |
| 603 | N | C | S | (S,S)$CH_2CH(OH)$Ph | $CH_3$ | $CH(CH_3)_2$ | H |
| 609 | CH | C=CH | CH | $CH_2CH_2$(4-$OCH_3$)Ph | H | 2-$CF_3$ | 8F |
| 610 | CH | C=CH | CH | $CH_2CH_2$(4-$OCH_3$)Ph | $CH_3$ | 2-$CF_3$ | 8F |
| 611 | CH | C=CH | CH | $CH_2CH_2$(4-F)Ph | H | 2-$CF_3$ | 8F |
| 612 | CH | C=CH | CH | $CH_2CH_2$(4-F)Ph | $CH_3$ | 2-$CF_3$ | 8F |

Compound number corresponds to example number in the Examples section.

The compounds of formula (Ib) listed in Table 2 are of particular interest: The stereo configuration is "S" about the carbon of the piperazine group bound to Alk unless otherwise indicated.

TABLE 2

(Ib)

| Ex No.: | Alk-Ar | $R^1$ | $R^2$ | Z |
|---|---|---|---|---|
| 533 | $CH_2CH_2Ph$ | H | H | 9F |
| 534 | $CH_2CH_2Ph$ | $CH_3$ | H | 9F |
| 535 | $CH_2CH_2(4\text{-}OCH_3)Ph$ | H | H | 9F |
| 537 | $CH_2CH_2(3\text{-}OCH_3)Ph$ | H | H | 9F |
| 539 | $CH_2CH_2(3\text{-}F)Ph$ | H | H | 9F |
| 541 | $CH_2CH_2(4\text{-}F)Ph$ | H | H | 9F |
| 543 | $CH_2CH_2(4\text{-}OCH_3)Ph$ | $CH_3$ | H | 9F |
| 545 | $CH_2CH_2(3\text{-}OCH_3)Ph$ | $CH_3$ | H | 9F |
| 547 | $CH_2CH_2(3\text{-}F)Ph$ | $CH_3$ | H | 9F |
| 549 | $CH_2CH_2(4\text{-}F)Ph$ | $CH_3$ | H | 9F |

Compound number corresponds to example number in the Examples section.

Since the compounds of this invention are basic in nature, they react with any of a number of inorganic and organic acids to form acid addition salts. For the therapeutic utility taught herein, the salt of the claimed compounds must be pharmaceutically acceptable. Acids commonly employed to form pharmaceutically acceptable salts are inorganic acids such as hydrochloric acid, hydrobromic acid, hydroiodic acid, sulfuric acid, phosphoric acid, and organic acids, such as p-toluenesulfonic acid, methanesulfonic acid, oxalic acid, p-bromo-phenylsulfonic acid, carbonic acid, succinic acid, citric acid, benzoic acid, acetic acid, lactic acid, maleic acid, tartaric acid, and the like. For further details on pharmaceutically acceptable salts, see *Journal of Pharmaceutical Science*, 66,1 (1977). Salts that are not pharmaceutically acceptable may be used as intermediates to prepare other compounds of formula (I) or a pharmaceutically acceptable salt of compounds of formula (I) and are within the scope of the present invention. Particular pharmaceutically acceptable salts ate those formed with hydrochloric acid, sulfuric acid, or phosphoric acid.

The intermediates and final products described herein may be isolated and purified by the conventional techniques known to artisans of organic chemistry. For example, the well-known techniques of chromatography, recrystallization, distillation, and sublimation may be used singularly and sequentially.

General Synthetic Methods

Compounds of formula (I) of this invention can be prepared by several methods generally known in the art of organic chemistry. Starting materials, the preparation of which are not described, are commercially available or can be readily prepared by known techniques from commercially available starting materials.

As shown in Scheme 1, compounds of formula (I) may be conveniently prepared from compounds of formula (IIa), by removal of the protecting group "ProG" from the amine nitrogen of the seven-member ring of the tricyclic ring system. The methods for introducing and removing these protecting groups are known in the art. See T. W. Green, *Protective Groups in Organic Synthesis*, John Wiley and Sons, Inc., (1981). Examples of such ProG groups include benzyl, acetyl, t-butoxycarbonyl, methanesulfonyl, and the like.

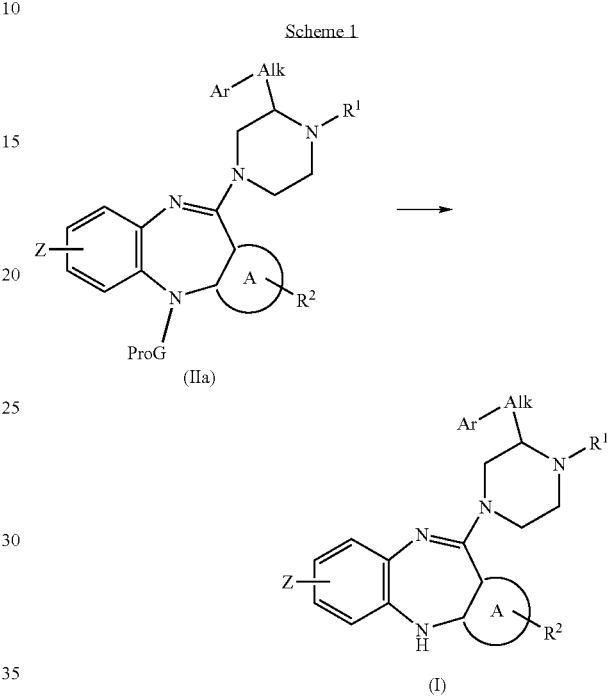

Scheme 1

As used herein, "Pg" represents either hydrogen or an amine protecting group ProG. For those examples in which Pg is an amine protecting group, the penultimate intermediate can be converted to the compound of formula (I) by removal of the protecting group. In the following text, for those intermediates containing a group Pg in which Pg is an amine protecting group, the protecting group may be removed to give the unprotected amine. Similarly, for those intermediates in which Pg is hydrogen, an amine protecting group may be incorporated into the intermediate.

Compounds of formula (IIb) in which $R^1$ is hydrogen can be converted to compounds of formula (IIc) in which $R^1$ is $(C_{1-4})$ alkyl optionally substituted with hydroxy, methoxy, ethoxy, or $OCH_2CH_2OH$. This transformation can be accomplished, as shown in Scheme Ia, by treatment of formula (IIb) with an alkylating agent. Alkylating agents include alkyl halides and alkyl sulfonate esters. Examples include methyl iodide, 1-bromobutane, 2-propyl methanesulfonate, and bromoethylmethyl ether. This reaction is usually performed in the presence of a base and solvent. The base can be either an organic base such as pyridine or diisopropylethylamine or an inorganic base such as potassium carbonate. Solvents include methanol, ethanol, THF, and DMF. This transformation can also be accomplished by reductive alkylation of the piperazine by treatment with an aldehyde or ketone under reducing conditions. Examples of suitable aldehydes include formaldehyde, acetaldehyde, propionaldehyde, butyraldehyde, isobutyraldehyde, and the like. Suitable ketones include acetone, methylethylketone, and the like. Reductive alkylations are often performed under catalytic hydrogenation conditions. Other reducing agents include formic acid, sodium borohydride, sodium cyanoborohydride, and sodium triacetoxyborohydride. This transformation can also be accomplished by acylation of the piperazine nitrogen to form an amide and reduction of the amide to yield the alkylated piperazine. Examples of acylating agents include acyl halides such as acetyl chloride, propionyl chloride, pivaloyl chloride, and cyclopropylcarbonyl chloride, carboxylic acid anhydrides such as formylacetic anhydride and acetic anhydride, and carboxylic acids in the presence of an activating agent such as dicyclohexylcarbodiimide or carbonyldiimidazole. The resulting amides may be reduced to the tertiary amines with reducing agents such as lithium aluminum hydride or borane.

Scheme 1a

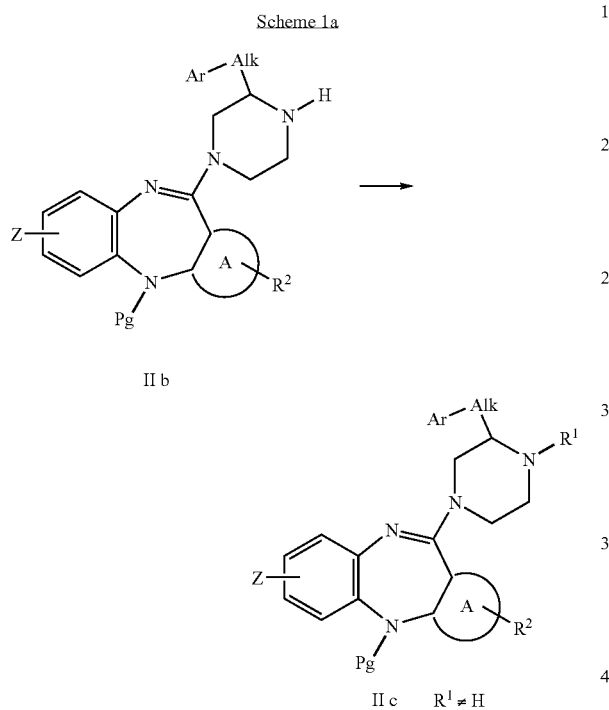

As shown in Scheme 2, compounds of formula (II) may be prepared by reacting an appropriately substituted piperazine of formula (V) with a tricyclic intermediate of formula (IV). "LG" represents a leaving group examples of which include $NH_2$, halo, $OY_1$, or $SY_1$, wherein $Y_1$ is lower alkyl such as methyl, ethyl, or propyl or optionally substituted phenyl or $OP(=O)R^{10}$. $R^{10}$ can be morpholine. This reaction may conveniently be performed with heating in a solvent such as DMSO, toluene, DMF, and N-methylpyrrolidinone.

Scheme 2

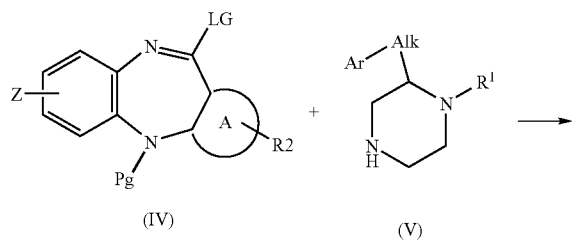

Alternatively, as shown in Scheme 3, tricyclic amide and thioamide intermediates of formula (VI) wherein X is O or S, respectively, can react with substituted piperazines of formula (V) to give corresponding compounds of formula (II). This reaction is conveniently performed in a polar solvent and may be performed in the presence or absence of a Lewis acid such as $TiCl_4$.

Scheme 3

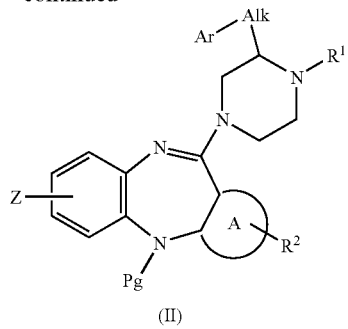

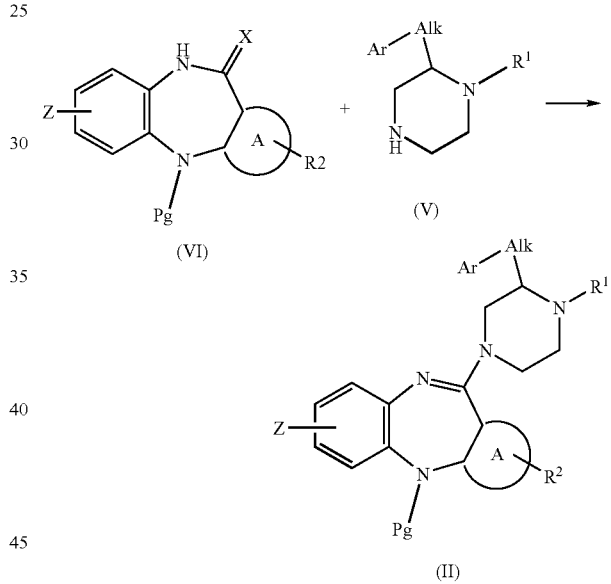

In Scheme 4, compounds of formula (VIb), wherein X is S, may be prepared from compounds of formula (VIa), wherein X is O, by treatment with a dehydrative thiolating agent in the presence of an inert solvent. Examples of such dehydrative thiolating agents include $P_2S_5$ and Lawesson's reagent (2,4-bis(4-methoxyphenyl)-1,3-dithia-2,4-diphosphetane-2,4-disulfide). For a description of Lawesson's reagent and its use, see M. P. Cava and M. I. Levinson, *Tetrahedron*, 41, 5061 (1985).

Scheme 4

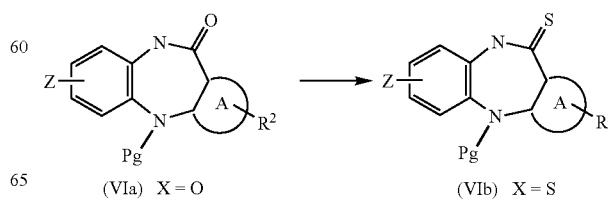

As shown in Scheme 5, tricyclic intermediates of formula (IV) can be prepared from the corresponding tricyclic amide and thioamide intermediates of formula (VI). O-alkylation of an amide of formula (VIa) (X═O) provides an iminoether of formula (IV) (LG═OY$_1$). Suitable alkylating agents include Meerwein's reagent and methyl fluorosulfonate. Iminothioethers of formula (IV), wherein LG is SY$_1$, may be prepared by S-alkylation of thioamides of formula (VIb) (X═S). Suitable alkylating agents include alkyl halides, alkyl sulfonates such as methyl trifluoromethanesulfonate, Meerwein's reagent and methyl fluorosulfonate. Reaction of an amide of formula (VIa) (X═O), with a dehydrative halogenating agent provides an iminohalide of formula (IV), wherein LG is a halo group. Suitable dehydrative halogenating agents include POCl$_3$, SOCl$_2$, PCl$_3$, PCl$_5$, PBr$_3$, PPh$_3$/Br$_2$, P(OPh)$_3$/I$_2$ and PPh$_3$/MeI.

Scheme 5

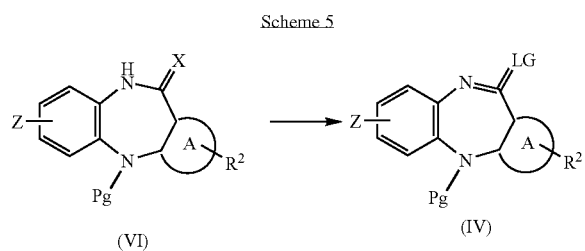

(VI) → (IV)

Compounds of formula (IV) in which LG is NH$_2$, OY$_1$ or SY$_1$ may be prepared from compounds of formula (VI), wherein LG is halo, by reaction with a suitable nucleophile, such as ammonia, an alcohol, or a thiol to give compounds of formula (IV), wherein LG is NH$_2$, OY$_1$ or SY$_1$, respectively. This reaction may be conveniently performed in a solvent and under basic conditions.

As shown in Scheme 6, compounds of formula (II) may also be prepared by ring closure of an intermediate of formula (XIIIa). This reaction may be effected by treatment of an amide of formula (XIIIa) with an activating agent in the presence of an inert solvent. Examples of such activating agents include TiCl$_4$, POCl$_3$, P$_2$S$_5$, and Lawesson's reagent.

Scheme 6

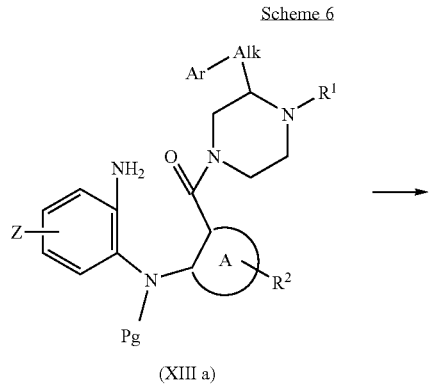

(XIII a)

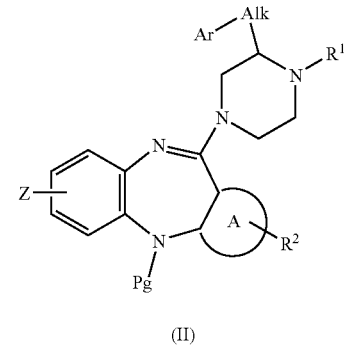

(II)

According to Scheme 7, compounds of formula (VIa), may be prepared by cyclization of an amine compounds of formula (XIIb) in which Y$_2$ is OY$_7$ or NY$_8$Y$_9$ wherein Y$_7$, Y$_8$ and Y$_9$ are independently, hydrogen or lower alkyl such as methyl, ethyl, or propyl.

Scheme 7

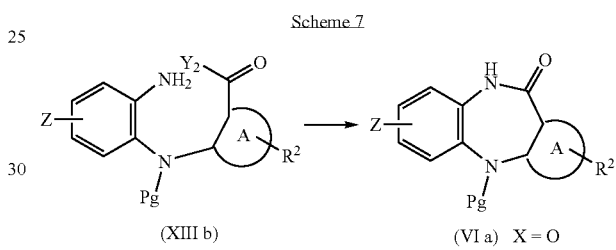

(XIII b) → (VI a)  X = O

As seen in Scheme 8, amines of formula (XIIIb) may be prepared from compounds of formula (XIIIc). The symbol Y$_3$ represents a group that may be converted to an amino group, such as NO$_2$, COOH, and NHCOOY$_4$, wherein Y$_4$ may be an optionally substituted alkyl such as, but not limited to, methyl, ethyl, 2-phenylethyl, t-butyl, 2-(trimethylsilyl)ethyl, 2,2,2-trichloroethyl, vinyl, allyl or optionally substituted benzyl group such as, but not limited to, benzyl, p-methoxybenzyl, p-nitrobenzyl, or diphenylmethyl.

Scheme 8

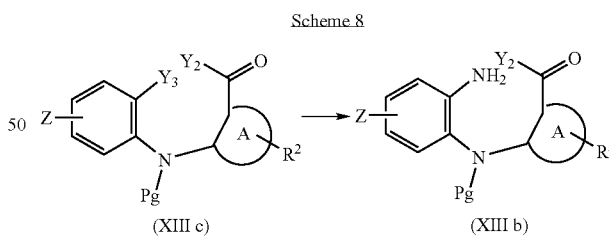

(XIII c) → (XIII b)

If Y$_3$ is NO$_2$, treatment of compounds of formula (XIIIc) under reducing conditions will provide corresponding compounds of formula (XIIIb). Examples of such reducing conditions include catalytic hydrogenation conditions or SnCl$_2$. Compounds of formula (XIIIc), wherein Y$_3$ is NHCOOY$_4$, may be converted to the corresponding compounds of formula (XIIIb) under conditions that allow for removal of the COOY$_4$ group. If Y$_4$ is optionally substituted alkyl, such conditions may include hydrolysis under acidic or basic conditions. If Y$_4$ is optionally substituted benzyl, treatment under reducing conditions, preferably catalytic hydrogenation conditions, provides the corresponding compound of formula (XIIIb). If $Y_4$ is t-butyl, treatment with acid provides a compound of formula (XIIIb). If $Y_4$ is 2,2,2-trichloroethyl, reducing conditions, preferably zinc metal in acidic medium, yield a compound of formula (XIIIb). If $Y_4$ is 2-(trimethylsilyl)ethyl, treatment with fluoride ion yield a compound of formula (XIIIb).

Compounds of formula (XIIIb) may also be prepared by Curtius rearrangement of the correspondent compound of formula (XIIIc) in which $Y_3$ is COOH. The Curtius rearrangement occurs by thermal rearrangement of the acylazide of formula (XIIIc) in which $Y_3$ is $CON_3$ to yield the isocyanate of formula (XIIIc) in which $Y_3$ is NCO. This isocyanate may be hydrolyzed either directly or through the urethane in which $Y_3$ is $NHCO_2Y_4$, to yield the corresponding compound of formula (XIIIb).

According to Scheme 9, compounds of formula (IVa) in which LG is $NH_2$ may be prepared by cyclization of aminonitrile compounds of formula (XIIId).

Scheme 9

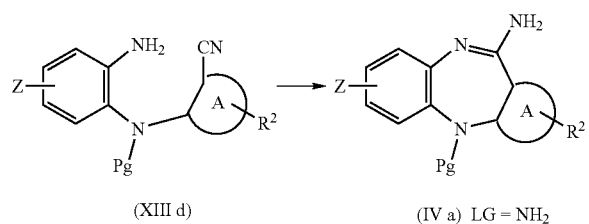

(XIII d)    (IV a) LG = $NH_2$

According to Scheme 10, aminonitrile compounds of formula (XIIId) may be prepared from corresponding compounds of formula (XIIIe), in the manner described for Scheme 8. Alternatively, compounds of formula (XIIId) may be prepared by Curtius rearrangement under conditions also described for Scheme 8.

Scheme 10

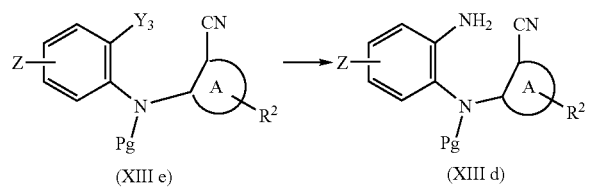

(XIII e)    (XIII d)

As shown in Scheme 11, compounds of formula (XIIIa), wherein all groups are defined as above, may be prepared from corresponding compounds of formula (XIIIf) in which $Y_3$ is a group that may be converted to an amino group.

Scheme 11

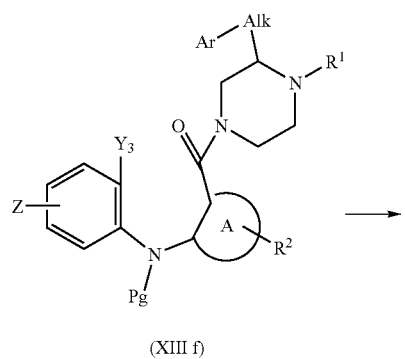

(XIII f)

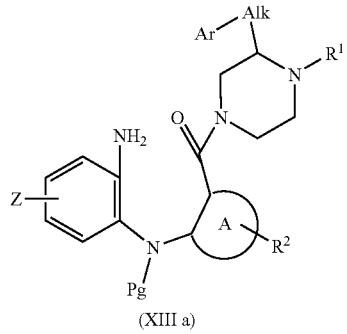

(XIII a)

According to Scheme 12, compounds of formula (XIIIf), wherein $Y_3$ is a group that may be converted to an amino group as defined above, and all other groups are as defined above, may be prepared by coupling a compound of formula (V) with a compound of formula (XIIIg). Such coupling reactions may be performed under conditions commonly employed to form amide bonds. Coupling reagents include dicyclohexylcarbodiimide (DCC), diphenylphosphorylazide (DPPA), and 1-(3-dimethylaminopropyl)-3-ethylcarbodiimide hydrochloride (EDC).

Scheme 12

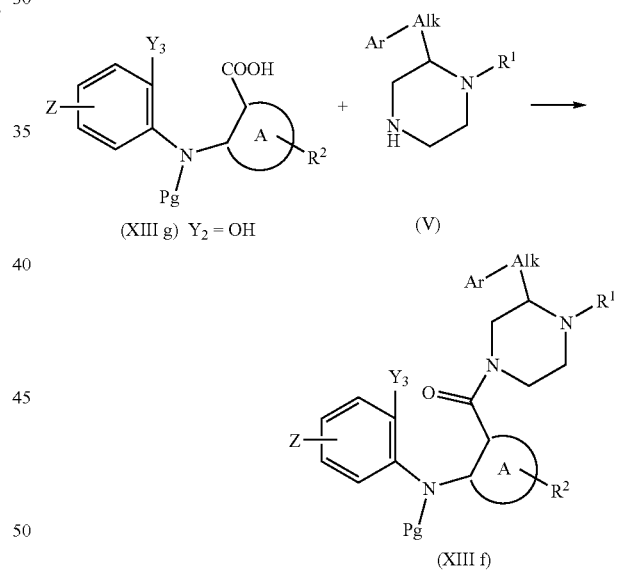

(XIII g) $Y_2$ = OH    (V)

(XIII f)

As shown in Scheme 13, compounds of formula (XIII) in which $Y_3$ may be $NH_2$ or a group that may be converted to an amino group as described above, $Y_{10}$ may be hydrogen, CN, $COOY_7$ or $CONY_8Y_9$, in which $Y_7$, $Y_8$, and $Y_9$ may independently be hydrogen or lower alkyl, or $NY_8Y_9$ is the group (XVI), may be prepared by reaction of compounds of formula (XIV) in which $Y_{11}$ may be a halo group or $OSO_2CF_3$ with compounds of formula (XVa). This reaction may be performed under basic conditions in a polar, aprotic solvent. Suitable bases include NaH, KH, potassium tert-butoxide, lithium hydroxide and cesium carbonate. Suitable solvents include DMF, N-methylpyrrolidinone, DMSO, and THF. The coupling of compounds of formula (XIV) with compounds of formula (XVa) to yield a compound of formula (XIII) may also be performed in the presence of a metal catalyst. Conditions for this transformation may be found in Hartwig, *Angew. Chem. Int. Ed.* (1998) 37, 2046–2067, Wolff, et al., *Acc. Chem. Res.* (1998), 31, 805–818, Yang and Buchwald, *J. Organomet. Chem.* (1999) 576, 125–146, U.S. Pat. No. 6,271,225, U.S. Pat. No. 6,455,542, and references cited therein.

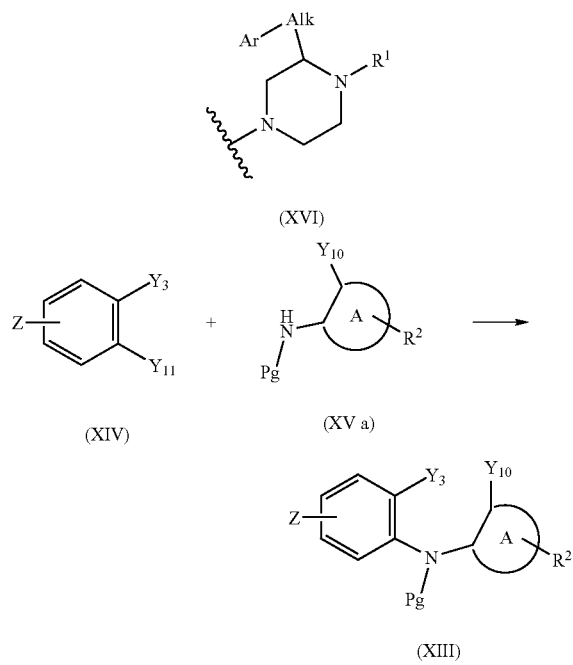

Compounds of formula (XIV) may be prepared by methods known in the art.

Alternatively as shown in Scheme 14, compounds of formula (XIII) in which $Y_3$ may be $NH_2$ or a group that may be converted to an amino group as described above, $Y_{10}$ may be hydrogen, CN, $COOY_7$ or $CONY_8Y_9$, in which $Y_7$, $Y_8$, and $Y_9$ may independently be hydrogen or lower alkyl, or $NY_8Y_9$ is the group (XVI), and the other groups are defined as above, may also be prepared by reaction of compounds of formula (XIVa) with compounds of formula (XV) in which $Y_{12}$ may be a halo group or $OSO_2CF_3$. This reaction may be performed under basic conditions in a polar, aprotic solvent. Suitable bases include NaH, KH, potassium tert-butoxide, lithium hydroxide, and cesium carbonate. Suitable solvents include DMF, N-methylpyrrolidinone, DMSO, and THF. The coupling of compounds of formula (XIVa) with compounds of formula (XV) to yield a compound of formula (XIII) may also be performed in the presence of a metal catalyst. Conditions for this transformation may be found in Hartwig, *Angew. Chem. Int. Ed.* 37, 2046–2067, (1998), Wolff, et al., *Acc. Chem. Res.*, 31, 805–818, (1998), and Yang and Buchwald, *J. Organomet. Chem.* 576, 125–146, (1999), and references cited therein.

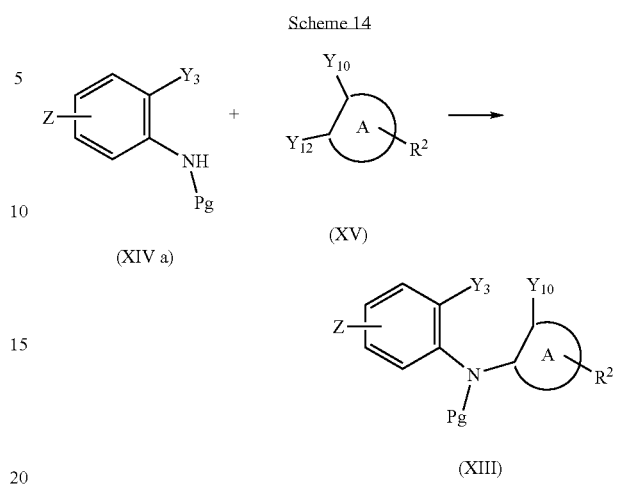

Compounds of formula (XIVa) may be prepared by methods known in the art.

According to Scheme 15, a compound of formula (VIa) can also be prepared by cyclization of isocyanate (XIIIh) under acidic conditions. Isocyanate (XIIIh) may be prepared from compounds of formula (XIII) in which $Y_{10}$ is hydrogen and $Y_3$ is an amino group by reaction with formicacetic anhydride and dehydration of the resulting formamide with a dehydrating agent such as $POCl_3$ or $P_2O_5$. Isocyanate (XIIIh) may also be prepared from compounds of formula (XIII) in which $Y_{10}$ is hydrogen and $Y_3$ is COOH by Curtius rearrangement as described before. Alternatively, a compound of formula (IIb) may also be prepared by reaction urea (XIIIi) in the presence of a Lewis acid. Urea (XIIIi) may be prepared by reaction of isocyanate (XIIIh) with an amine of formula (V).

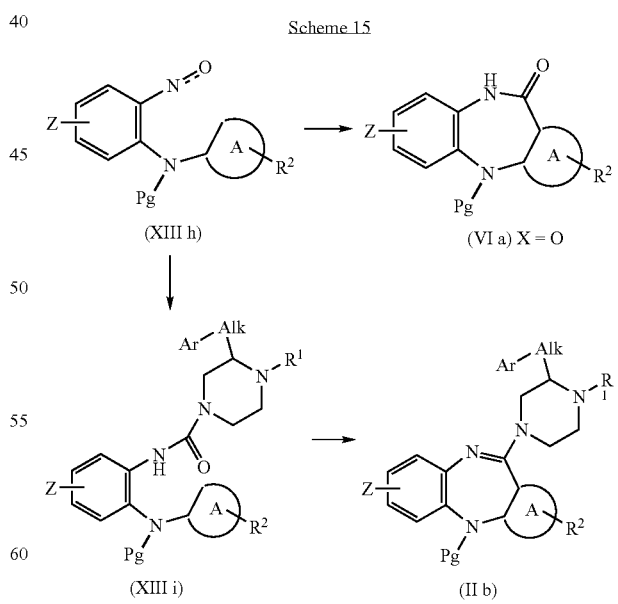

In Scheme 16, compounds of formula (VIc), the aromatic ring is thiazole, may be prepared by cyclization of intermediate of formula (XVIII) with a dehydrative thiolating agent such as $P_2S_5$ or Lawesson's reagent. Compounds of formula (VId), the aromatic ring is an oxazole ring, may be prepared by cyclization of intermediate of formula (XVIII) with a dehydrating agent such as $P_2O_5$ or $PPh_3/Tf_2O$.

Scheme 16

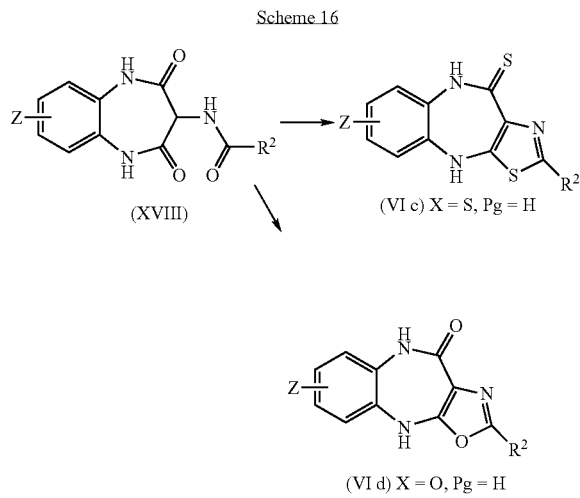

(XVIII)

(VI c) X = S, Pg = H (VI d) X = O, Pg = H

According to Scheme 17, compounds of formula (XVIII) are prepared by acylation of an amine of formula (XIX). This reaction is usually performed by treatment of formula of (XIX) with an acid chloride, or acid anhydride in the presence of a base in an inert solvent. Methods for the synthesis of compounds of formula (XIX) are known in the art; see, for example, Hagishita, et al., *Bioorg. Med. Chem.*, 5(7), 1433–1446, (1997).

Scheme 17

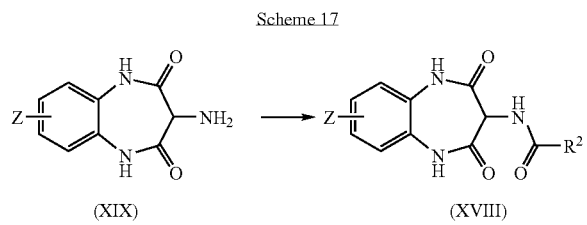

(XIX)  (XVIII)

As shown in Scheme 18, compounds of formula (VIe), the A ring is pyrazole, or (VIf) the A ring is pyrimidine, may also be prepared by reaction of compounds of formula (XX) with a substituted hydrazine or an amidine, respectively. Compounds of formula (XX) are prepared as described in Roma, et al., *Farmaco, Ed. Sci.*, 38, 546–558 (1983).

Scheme 18

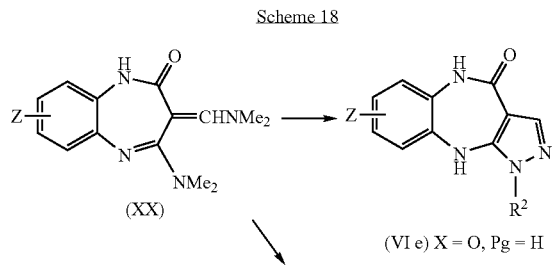

(XX)

(VI e) X = O, Pg = H

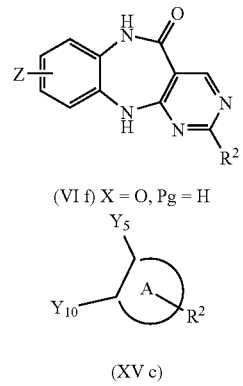

(VI f) X = O, Pg = H

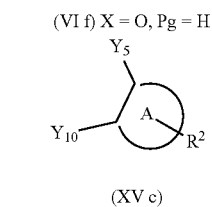

(XV b)  (XV c)

Methods for the preparation of compounds of formula (XVb) and formula (XVc) are known in the art and vary depending on the nature of the aromatic ring A.

The skilled artisan will recognize that substituents $R^2$ and Z in the compounds of formula (I) may be present in the precursor molecules of formulas (XIV), (XIVa), (XVb), and (XVc). Alternatively, these substituents may be introduced at any convenient point during the synthesis either by replacement of a hydrogen (through, for example, an electrophilic aromatic substitution reaction) or by conversion of an existing substituent into the substituents present in the compounds of formula (I). Examples of electrophilic aromatic substitution reactions include halogenation, nitration, Friedel-Crafts acylation, and electrophilic trifluoromethylation under conditions described in the literature. Examples of conversion of an existing substituent into one present in the final compound include conversion of a Br substituent into a substituent such as $SR^{11}$ or $COR^{11}$ by metallation with an organolithium reagent and reaction with an electrophile such as $R^{11}SSR^{11}$ or $R^{11}COOMe$. $R^{11}$ maybe $(C_{1-6})$alkyl, fluorinated $(C_{1-6})$alkyl, benzyl, or optionally substituted phenyl" Additionally, a Br substituent can be converted to an optionally substituted aromatic ring by reaction with an optionally substituted phenylboronic acid in the presence of a palladium catalyst. Many other such functional group transformations are reported in the literature.

General methods and specific examples of the synthesis of these compounds can be found in the following references:
Chakrabarti, et al., *J. Med. Chem.*, 23, 878–884; (1980),
Chakrabarti, et al., *J. Med. Chem.*, 23, 884–889; (1980),
Chakrabarti, et al., *J. Med. Chem.*, 25, 1133–1140; (1982),
Chakrabarti, et al., *J. Med. Chem.*, 32, 2573–2582; (1989),
Liegeois, et al., *J. Med. Chem.*, 36, 2107–2114; (1993),
Liegeois and Delarge, U.S. Pat. No. 5,393,752 (1995);
Chakrabarti and Hotten, Eur. Pat. Appl., EP 354781; (1990),
Bolton, et al., PCT Int. Appl., WO 9700252; (1997),
Chakrabarti, et al., Eur. Pat. Appl., EP 27390; (1981),
Tehim, et al., U.S. Pat. No. 5,602,124 (1998);
Tehim, et al., U.S. Pat. No. 5,824,676 (1998);
Eilingsfeld and Swybold, Ger. Offen. DE 2713573; (1978),
Gallemaers, et al., *Tetrahedron Lett.*, 693–694; (1976),
Durnow and Abele, *Chem. Ber.*, 97, 3349–3353, (1964),
Klempier, et al., *J. Heterocyclic Chem.*, 29, 93–95, (1992).

In Scheme 19, compounds of formula (XVd) may be prepared by regioselectively nitrating 3-bromobenzothiophene compounds to afford the 2-nitro-3-bromobenzothiophene compounds of formula (XVe). Suitable nitrating conditions include nitric acid (optionally in the presence of another acid, such as trifluoroacetic acid, sulfuric acid, or acetic acid, or in the presence of an inert solvent such as dichloromethane or water), fuming nitric acid, or sidium nitrite in the presence of an acid. Displacement of the 3-bromo-group with cyanide can be accomplished using CuCN in the presence of a polar solvent like DMF or N-methylpyrrolidinone to give compounds of formula (XVf). Reduction of the nitro group to the amine can be accomplished by reducing agents such as $SnCl_2/HCl$, Zn/HOAc and Pd—C/$H_2$ to give compounds of formula (XVd) in which Pg is hydrogen. A protecting group may be subsequently introduced.

Scheme 19

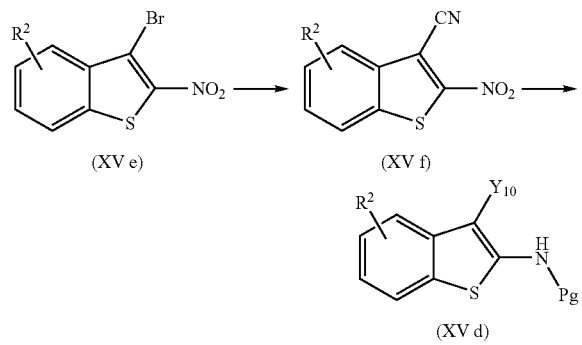

Compounds of formula (V) of this invention may be prepared from compounds of formula (XXIVb), as shown in Scheme 20, in which one of the nitrogens in the piperazine ring may be protected by an amine protecting group, by removal of this protecting group. In this equation, $ProG_2$ represents an amine protecting group. Examples of such $ProG_2$ groups include benzyl, acetyl, t-butoxycarbonyl, methanesulfonyl, and the like. Examples of additional $ProG_2$ groups and methods for the introduction and removal of such groups can be found in T. W. Green, *Protective Groups in Organic Synthesis*, John Wiley and Sons, Inc. (1981). In the subsequent text, $Pg_2$ represents either hydrogen or an amine protecting group $ProG_2$. In the following text, for those intermediates containing a group $Pg_2$ in which $Pg_2$ is an amine protecting group, the protecting group may be removed to give the unprotected amine. Similarly, for those intermediates in which $Pg_2$ is hydrogen, an amine protecting group may be incorporated into the intermediate. The methods for introducing and removing these protecting groups are known in the art.

Scheme 20

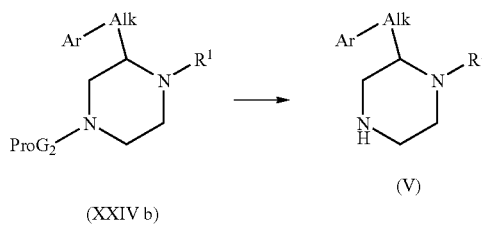

According to Scheme 21, compounds of formula (XXIVa) of this invention may be prepared from compounds of formula (XXVa) by removal of the amine protecting group $ProG_1$. Examples of such $ProG_1$ amine protecting groups include benzyl, acetyl, t-butoxycarbonyl, methanesulfonyl, and the like. Examples of additional $ProG_1$ groups and methods for the introduction and removal of such groups can be found in T. W. Green, *Protective Groups in Organic Synthesis*, John Wiley and Sons, Inc. 1981. It will be recognized that in some instances, in compounds of formula (XXVa), $Pg_2$ and $ProG_1$ may both be protecting groups that are removed under the same reaction conditions. In those cases, deprotection of this compound will yield compounds of formula (V) in which $R^1$ is hydrogen. In compounds of formula (XXIVa), if $Pg_2$ is an amine protecting group, $ProG_2$, then alkylation of formula (XXIVa) will yield compounds of formula (XXIV), in which $R^1$ is ($C_{1-4}$) alkyl optionally substituted with hydroxy, methoxy, ethoxy, or $OCH_2CH_2OH$.

Scheme 21

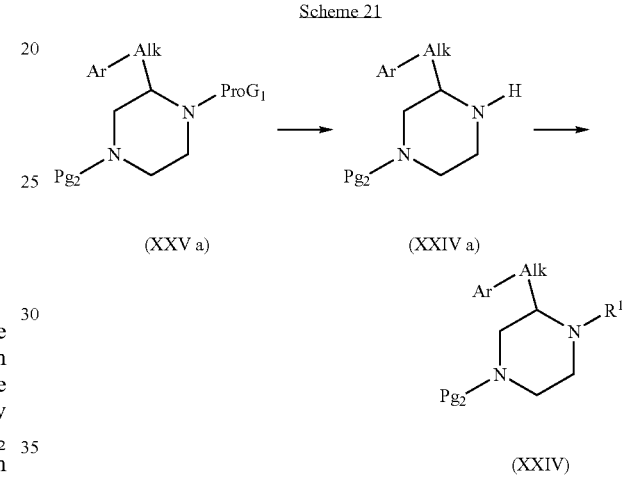

In Scheme 22, compounds of formula (XXV), in which all groups are defined as above, may be prepared by reduction of either a ketopiperazine of formula (XXVI) or a diketopiperazine of formula XVI. $Pg_1$ represents either hydrogen, ($C_{1-4}$) alkyl optionally substituted with hydroxy, methoxy, ethoxy, or $OCH_2CH_2OH$, or an amine protecting group $ProG_1$. Suitable reducing agents for this transformation include lithium aluminum hydride and borane. Methods for the synthesis of ketopiperazines and diketopiperazines are known in the art.

Scheme 22

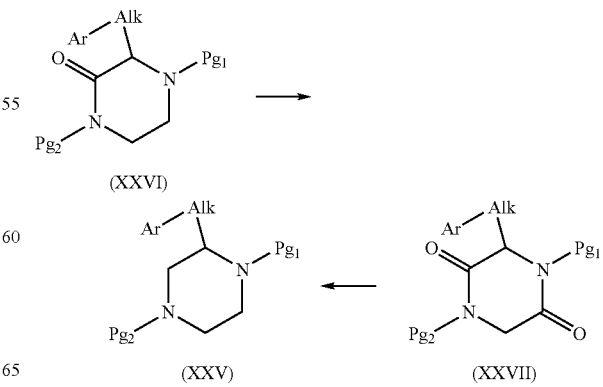

Further, as shown in Scheme 23, compounds of formula (XXVb) in which Alk is —CH$_2$CH$_2$—, —CH$_2$CH$_2$CH$_2$—, and —CH$_2$CH$_2$CH$_2$CH$_2$— may be prepared from a suitably protected 2-substituted piperazine of formula (XXVIII) by employing either a Heck coupling/reduction sequence or a hydroboration/Suzuki coupling sequence. In the Heck coupling/reduction sequence, reaction of formula (XXVIII) with an arylhalide or aryl triflate in the presence of a suitable metal catalyst provides the unsaturated aryl product of formula (XXIX). For a description of the Heck reaction and its application to organic synthesis see, Whitcombe, et al., *Tetrahedron*, 57, 7449–7476, (2001); Herrmann, Wolfgang A., *App. Homogeneous Catal. Organomet. Compd.*, 2, 712–732, VCH, Weinheim, Germany (Editors: Cornils, Boy; Herrmann, Wolfgang A.), (1996); and references cited therein. Reduction of compounds of formula (XXIX) provides compounds of formula (XXVb), m=0–2. Suitable reducing conditions include catalytic hydrogenation.

organoborane of formula (XXX). Suitable boranes HBZZ' include, borane, trisiamylborane, catecholborane, and 9-borabicyclo[3,3,0]nonane (9-BBN). Reaction of formula (XXX) with an arylhalide or aryl triflate in the presence of a suitable catalyst provides compounds of formula (XXVb). For a description of the Suzuki reaction and its application to organic synthesis see, Miyaura and Suzuki, *Chem. Rev.*, 95, 2457–2483, (1995), and references cited therein.

Compounds of formula (XXVIII)(m=0) may be prepared by the method described in Tsuda, et al., *J. Org. Chem.*, 55, 3388–3390, (1990), and Uozumi, et al., *J. Org. Chem.*, 58, 6826–6832, (1993).

In Scheme 24 compounds of formula (XXVIII) (m=1,2) may be prepared by an alkylation of formula (XXXI) with an allyl halide or a homoallyl halide and to give compounds of formula (XXXII) and reduction with lithium aluminum hydride to give compounds of formula (XXVIII) (m=1,2).

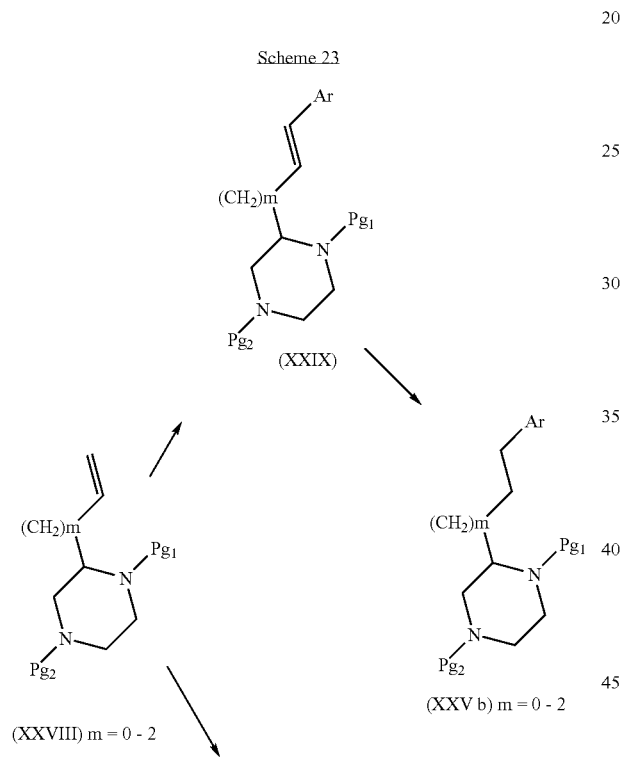

Scheme 23

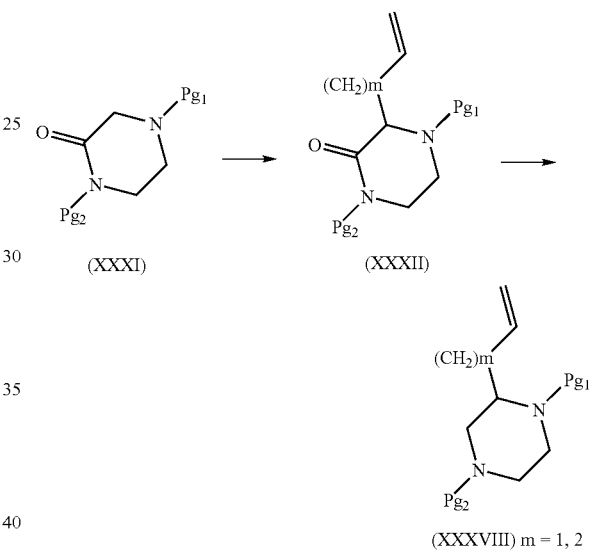

Scheme 24

The hydroboration/Suzuki coupling sequence represents a second method for converting compounds of formula (XXVIII) to compounds of formula (XXVb). Reaction of formula (XXVIII) with a borane HBZZ', in which Z and Z' are independently H, alkyl such as methyl, ethyl, propyl, or alkoxy such as methoxy, ethoxy, or propoxy provides an The skilled artisan will appreciate that many of the aforementioned reactions may be performed in any convenient order. Similarly, for those compounds that contain an asymmetric center, the skilled artisan will recognize that the aforementioned reactions may be performed either on pure isomers or on a mixture of isomers. The isomers may be separated at any convenient stage during the synthesis.

Pharmacological Activity

Compounds of the formula (I) have moderate to high binding affinity for multiple neurotransmitter receptors, and in particular, the dopamine receptors. Those skilled in neuropharmacology and related disciplines have recognized dopamine receptor binding activity as indicative of antipsychotic, in particular, antischizophrenic properties. See P. Seeman, et al., *Nature*, 261, 717–718 (1976); P. Seeman, *Synapse*, 1, 133 (1987); H. Howard, et al., 28, 39 (1993); and J. Schaus. Et al., *Annual Reports in Medicinal Chemistry*, 33, 1 (1998). Cloning studies have currently demonstrated five principal dopamine receptor subtypes that fall into two major classes, $D_1$-like and $D_2$-like. The $D_1$-like class includes the $D_1$ and $D_5$ subtypes, and the $D_2$-like class encompasses the $D_2$, $D_3$, and $D_4$ subtypes. Table 2 shows the relative binding affinity of selected compounds of formula (I) for the $D_2$ receptor. The experimental protocol for the assay generating this data is in the Example section below.

TABLE 3

Relative $D_2$ Receptor Binding Affinity
For Compounds of Formula (I)

| Comp. No. | Affinity $K_i$* |
|---|---|
| 59 | +++ |
| 61 | ++++ |
| 69 | +++ |
| 70 | ++++ |
| 71 | ++++ |
| 72 | +++ |
| 75 | ++++ |
| 76 | ++++ |
| 77 | +++ |
| 80 | ++++ |
| 85 | ++++ |
| 87 | +++ |
| 88 | ++++ |
| 90 | +++ |
| 92 | +++ |
| 103 | +++ |
| 109 | ++++ |
| 119 | +++ |
| 176 | +++ |
| 177 | +++ |
| 178 | +++ |
| 179 | ++++ |
| 180 | ++++ |
| 181 | +++ |
| 182 | +++ |
| 183 | +++ |
| 184 | +++ |
| 185 | +++ |
| 186 | ++++ |
| 187 | +++ |
| 194 | ++++ |
| 195 | +++ |
| 212 | ++++ |
| 219 | +++ |
| 460 | ++++ |
| 461 | +++ |
| 594 | ++++ |
| 595 | +++ |

*$K_i$ is generally defined as the binding affinity constant (i.e., dissociation constant) of an unlabeled ligand in a radioligand-binding assay. See, for example, Neurotransmitter Receptor Binding, Second Edition, Eds H. I. Yamamura, S. J. Enna, and M. J. Kuhar, Raven Press (1985).
*++++ = <10 nM; +++ = 10–100 nM; ++ = 100–1000 nM Using the relative $K_i$ scale of Table 3, clozapine has a ++ affinity and olanzapine has a +++ affinity. Thus, many of the compounds of formula (I) exhibit $D_2$ receptor affinity greater than both clozapine and olanzapine.

Like clozapine and olanzapine, the compounds of formula (I) also exhibit affinity for the 5-$HT_6$ receptor. Because clozapine and olanzapine have greater efficacy in treating the cognitive disturbances of schizophrenia than typical antipsychotics (Purdon, et al., Arch Gen. Psych., 57, 249 (2000)) and selective 5-$HT_6$ antagonists are active in models of cognitive enhancement, this activity is desirable in an antipsychotic drug.

Many atypical antipsychotics have a high affinity for the 5-$HT_{2A}$ receptor. Researchers believe that high affinity for the 5-$HT_{2A}$ receptor helps in treating the negative symptoms of schizophrenia and preventing some of the motor side effects (H Meltzer, et al., J. Pharm. Exp. Ther. 25, 238 (1989)). However, selective 5-$HT_{2A}$ antagonists are not effective antipsychotics as monotherapy. Thus, 5-$HT_{2A}$ antagonism would likely be among the other neuroreceptor affinities of a superior antipsychotic compound. The compounds of formula (I) exhibit a desirable level of 5-$HT_{2A}$ affinity.

The compounds of formula (I) are useful for treating pathologic psychologic conditions, especially psychosis, with minimal detrimental adverse events. Pathologic psychological conditions which are psychosis or may be associated with psychotic features include, but are not limited to the psychotic disorders which have been characterized in the DSM-IV-TR., *Diagnostic and Statistical Manual of Mental Disorders. Revised*, $4^{th}$ Ed., Text Revision (2000). See also DSM-IV, *Diagnostic and Statistical Manual of Mental Disorders* $4^{th}$ Ed., (1994). The DSM-IV and DSM-IV-TR was prepared by the Task Force on Nomenclature and Statistics of the American Psychiatric Association, and provides descriptions of diagnostic categories. The skilled artisan will recognize that there are alternative nomenclatures, nosologies, and classification systems for pathologic psychological conditions and that these systems evolve with medical scientific progress. Examples of pathologic conditions associated with psychosis that may be treated with the compounds of the present invention include, but are not limited to, schizophrenia, schizophreniform disorder, schizoaffective disorder, delusional disorder, brief psychotic disorder, shared psychotic disorder, psychotic disorder due to a general medical condition, substance-induced psychotic disorder, schizotypical, schizoid, paranoid personality disorder, and psychotic disorder-not other specified, see DSM-IV, Section: Schizophrenia and Other Psychotic Disorders, pages 273 to 316.

Compounds of the present invention are useful in treating depression and mood disorders found in the DSM-IV, *Diagnostic and Statistical Manual of Mental Disorders* $4^{th}$ Ed., (1994) Section: Mood Disorders, pages 317 to 392. Disorders include, but are not limited to, mood disorders such as major depressive episodes, manic episode, mixed episode, hypomanic episode; depressive disorders such as major depressive disorder, dysthymic disorder, depressive disorder not otherwise specificed; Bipolar disorders such as bipolar I disorder, bipolar II disorder, cyclothymic disorder, bipolar disorder not otherwise specified; other mood disorders such as mood disorder due to general medical conditions, substance-induced mood disorder, mood disorder not otherwise specified; and mood disorders with mild, moderate, severe without psychotic features, severe with psychotic features, in partial remission, in full remission, with catatonic features, with melancholic features, with atypical features, with postpartum onset.

One of oridinary skilled in the art would appreciate that the compounds of the present invention would be useful in the treatment of depressive episodes associated with bipolar disorders, treatment of manic episodes associated with bipolar disorders such as, but not limited to, the treatment of the acute manic episodes associated with bipolar I disorder.

Compounds of the present invention are useful in treating cognitive disorders, age-related cognitive disorder, mild cognitive impairment, postconcussional disorder, mild neurocognitive disorder, anxiety (particularly including generalized anxiety disorder, panic disorder, and obsessive compulsive disorder), and migraine (including migraine headache). These compounds are also useful in treating substance withdrawal (including substances such as opiates, nicotine, tobacco products, alcohol, benzodiazepines, cocaine, sedatives, hypnotics, caffeine, etc.). Other conditions that may be treated with the compounds of the present invention include, but are not limited to, dementia, dementia with behavioral disturbances, movement disorders, personality disorders, borderline personality disorder, pervasive development disoders, eating disorders, premenstrual dysphoric disorder, tic disorders, sexual dysfunction, delirium, emesis, substance related disorders, impulse-control disorders, postpsychotic depressive disorder of schizophrenia, simple deteriorative disorder (simple schizophrenia), minor depressive disorder, recurrent brief depressive disorder, and mixed anxiety-depresssive disorder Compounds of the present invention are also useful in treating the cognitive deficients associated with the above listed, but not limited to, psychological conditions such as schizophrenia, mood disorders, and other psychotic disorders.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are effective over a wide dosage range, but the actual dose administered being dependent on the condition being treated. While the exact dose is administered according to the discretion of the attending health care professional, typically, in the treatment of adult humans, dosages of from 0.1 to 500 mg, preferably from 0.25 mg to 100 mg, most preferably 0.25 mg to 50 mg per day may be used. A once a day dosage is normally sufficient, although divided doses may be administered. For example, for the treatment of psychotic disorders a dose range of from 0.1 mg to 500 mg, preferably 0.25 mg to 100 mg, per day is suitable.

In choosing a suitable regimen for patients suffering from psychotic conditions, compositions containing compounds of formula (I) as an active ingredient may be formulated to provide quick, sustained or delayed release of the active ingredient after administration to the patient. Depending on the method of administration, compositions may be formulated as tablets, capsules, suspensions, or elixirs for oral use, or injection solutions or suppositories for parental use. Preferably the compositions are formulated in a unit dosage form, each dosage containing from 0.1 mg to 500 mg, more usually 0.25 mg to 100 mg, of the active ingredient.

A preferred formulation of the invention is a capsule or tablet comprising 0.1 to 500 mg of active ingredient together with a pharmaceutically acceptable carrier. A further preferred formulation is an injection which in unit dosage form comprises 0.1 mg to 500 mg of active ingredient together with a pharmaceutically acceptable diluent. A sustained release formulation is also a preferred formulation.

Pharmaceutical Formulations

While it is possible to administer a compound of formula (I) with no additional ingredients to a patient in need thereof, it is far more desirable to administer such a compound in the form of a pharmaceutical composition. Pharmaceutical compositions containing a compound of formula (I) as an active ingredient provides control of the dosage and rate of absorption into the body and stability of the product in shipment and storage. Further, pharmaceutical formulations are more acceptable to the patient being treated, and thus increase compliance with a treatment program. Such compositions, comprising at least one pharmaceutically acceptable carrier, are valuable and novel because of the presence of the compounds of formula (I) therein. Formulation of pharmaceutical compositions is an art unto itself, about which much has been published. The compounds of the present invention may be formulated into pharmaceutical compositions by essentially any suitable method of the art including, but not limited to, the methods discussed hereinbelow.

The usual methods of formulation used in pharmaceutical science and the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% by weight of the compound in total, depending on the desired dose and the type of composition to be used. The amount of the compound, however, is best defined as the effective amount, that is, the amount of each compound which provides the desired dose to the patient in need of such treatment. The compositions may be chosen and formulated for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, naphth and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular in recent years because of technological advances in matrix compositions. Typically they comprise a resinous matrix composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

EXAMPLES

The following examples illustrate aspects of this invention but should not be construed as limitations thereof. The symbols and conventions used in these examples and consistent with those used in the contemporary chemical literature such as the *Journal of the American Chemical Society*, and *Tetrahedron Letters*, and contemporary literature of other scientific disciplines as appropriate.

Chemical Compounds

Example 1

3-(S)-Phenethyl-piperazine-2,5-dione

Add sequentially, glycine methyl ester hydrochloride (4.51 g, 35.9 mmol), 1-ethyl-(3-dimethyl-aminopropyl)carbodiimide hydrochloride (8.23 g, 42.9 mmol), 1-hydroxybenzotriazole monohydrate (5.81 g, 43.0 mmol), and triethylamine (10.0 mL, 71.7 mmol) to a solution of 2-tert-butoxycarbonylamino-4-(S)-phenyl-butyric acid (10.0 g, 35.8 mmol) in methylene chloride (30 mL) at 0° C. Stir the mixture at room temperature overnight and concentrate. Partition the residue between ethyl acetate and aqueous 2N HCl (100 mL). Wash the organic layer with 10% $K_2CO_3$, dry ($MgSO_4$), and concentrate to provide the (2-tert-butoxycarbonylamino-4-(S)-phenyl-butyrylamino)-acetic acid methyl ester as a clear oil (12.3 g, 98%): $^1$H NMR (CDCl$_3$): δ1.45 (s, 9H), 1.95 (m, 1H), 2.20 (m, 1H), 2.71 (t, 2H), 3.76 (s, 3H), 4.04 (d, 2H), 4.16 (m, H), 5.00 (d, 1H), 6.57 (t, 1H), 7.17–7.32 (m, 5H).

Add trifluoroacetic acid (30 mL) to (2-tert-butoxycarbonylamino-4-(S)-phenyl-butyrylamino)-acetic acid methyl ester (14.4 g). Stir one hour at room temperature and concentrate to afford (2-amino-4-(S)-phenyl-butyrylamino)-acetic acid methyl ester trifluoroacetate as an amber oil: $^1$H NMR (D$_2$O): δ2.09 (m, 2H), 2.67 (m, 2H), 3.61 (s, 3H), 3.82 (d, 1H), 3.91 (d, 1H), 3.95 (m, 1H), 7.13–7.28 (m, 5H).

Add methanol (200 mL) and Et$_3$N (30 mL) to the crude trifluoroacetate salt and reflux the solution. At 2 hours, white crystals begin to form. Reflux for an additional 2 hours and cool in an ice bath and filter. Wash the crystals with cold MeOH and hexanes to afford the title compound as white crystals (6.6 g, 74%): $^1$H NMR (DMSO-d6): δ1.97 (m, 2H), 2.63 (m, 2H), 3.70 (d, 1H), 3.75 (m, 1H), 3.81 (d, 1H), 7.13–7.32 (m, 5H), 8.03 (bs, 1H), 8.32 (bs, 1H).

By the method of Example 1, the following compounds were prepared and isolated as the (S) isomer except where noted below:

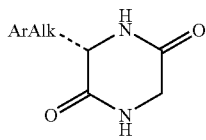

| No: | ArAlk | Data |
|---|---|---|
| 2 | CH$_2$(4-CH$_3$)Ph | mp 252–253° C.; $^1$H NMR(DMSO-d$_6$): δ2.27(s, 3H), 2.77(d, 1H), 2.81(dd, 1H), 3.04(dd, 1H), 3.34(d, 1H), 4.03(m, 1H), 7.04–7.10(m, 4H), 7.86(s, 1H), 8.12(s, 1H); MS(APCI)m/z(rel intensity)219(100). |
| 3 | CH$_2$(3-CH$_3$)Ph | $^1$H NMR(DMSO-d$_6$): δ2.22(s, 3H), 2.76(d, 1H), 2.80(dd, 1H), 3.00(dd, 1H), 3.32(d, 1H), 4.00(m, 1H), 6.91–6.95(m, 2H), 7.03(d, 1H), 7.12(t, 1H), 7.88(s, 1H), 8.11(s, 1H); MS(APCI)m/z(rel intensity)219(100). |
| 4 | CH$_2$(2-F)Ph | mp 227° C.; $^1$H NMR(DMSO-d$_6$): δ2.99(m, 2H), 3.15(d, 1H), 3.36(dd, 1H), 4.00(m, 1H), 6.91–7.36(m, 4H), 7.88(s, 1H), 8.10(s, 1H); MS(APCI)m/z(rel intensity)223 (100). |
| 5 | CH$_2$(3-F)Ph | $^1$H NMR(DMSO-d$_6$): δ2.87(dd, 1H), 2.98(d, 1H), 3.06(dd, 1H), 3.42(d, 1H), 4.06(m, 1H), 6.93–7.04(m, 3H), 7.27(m, 1H), 7.92(s, 1H), 8.12(s, 1H); MS(APCI)m/z (rel intensity)223(100). |
| 6 | CH$_2$(4-F)Ph | $^1$H NMR(DMSO-d$_6$): δ2.87(dd, 1H), 2.88(d, 1H), 3.04(dd, 1H), 3.38(d, 1H), 4.02(m, 1H), 7.07(t, 2H), 7.14(dd, 2H), 7.87(s, 1H), 8.11(s, 1H); MS(APCI)m/z(rel intensity)223(100). |
| 7 | CH$_2$(2-Cl)Ph | $^1$H NMR(DMSO-d$_6$): δ.08(dd, 1H), 3.19(dd, 1H), 3.48(m, 2H), 3.99(m, 1H), 7.27–7.31(m, 3H), 7.43(m, 1H), 8.06(s, 2H); MS(APCI)m/z(rel intensity)239(100), 241 (36). |

-continued

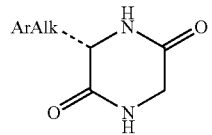

| No: | ArAlk | Data |
|---|---|---|
| 8 | CH$_2$(3-Cl)Ph | $^1$H NMR(DMSO-d$_6$): δ2.90(dd, 1H), 3.06(d, 1H), 3.08 (dd, 1H), 3.49(d, 1H), 4.10(m, 1H), 7.15(m, 1H), 7.25(s, 1H), 7.32(m, 2H), 8.01(s, 1H), 8.22(s, 1H); MS(APCI) m/z(rel intensity)239(100), 241(36). |
| 9 | CH$_2$(4-Cl)Ph | mp 259–262° C.; $^1$H NMR(DMSO-d$_6$): δ2.89(dd, 1H), 3.01(d, 1H), 3.09(dd, 1H), 3.46(d, 1H), 4.08(m, 1H), 7.19(d, 2H), 7.35(d, 2H), 7.94(s, 1H), 8.17(s, 1H); MS (APCI)m/z(rel intensity)239(100), 241(36). |
| 10 | CH$_2$(3-CF$_3$)Ph | $^1$H NMR(DMSO-d$_6$): δ2.98(dd, 1H), 2.99(d, 1H), 3.16(dd, 1H), 3.46(d, 1H), 4.12(m, 1H), 7.43–7.60(m, 4H), 7.96(s, 1H), 8.20(s, 1H): ms(APCI)m/z(rel intensity) 273(100). |
| 11 | CH$_2$(2-CF$_3$)Ph | $^1$H NMR(DMSO-d$_6$): δ3.06(dd, 1H), 3.20(dd, 1H), 3.55(dd, 1H), 3.77(d, 1H), 3.89(m, 1H), 7.41–7.46(m, 2H), 7.59(t, 1H), 7.67(d, 1H), 8.03(s, 1H), 8.09(s, 1H); MS (APCI)m/z(rel intensity)273(100). |
| 12 | CH$_2$(2-OCH$_3$)Ph | mp 222–224° C.; $^1$H NMR(DMSOd$_6$): δ2.90(dd, 1H), 3.06(dd, 1H), 3.21(d, 1H), 3.41(d, 1H), 3.75(s, 3H), 3.93(m, 1H), 6.86(t, 1H), 6.95(d, 1H), 7.09(d, 1H), 7.24(t, 1H), 7.87(s, 1H), 7.92(s, 1H); MS(APCI)m/z(rel intensity)235(100). |
| 13 | CH$_2$(3-OCH$_3$)Ph | mp 204–206° C.; $^1$H NMR(DMSO-d$_6$): δ2.86(dd, 1H), 2.86(d, 1H), 3.07(dd, 1H), 3.38(d, 1H), 3.41(s, 3H), 4.05(m, 1H), 6.73(d, 1H), 6.74(s, 1H), 6.83(d, 1H), 7.19(t, 1H), 7.91(s, 1H), 8.13(s, 1H); MS(APCI)m/z(rel intensity)235(100). |
| 14 | CH$_2$(4-OCH$_3$)Ph | $^1$H NMR(DMSO-d$_6$): δ2.73(d, 1H), 2.75(dd, 1H), 2.97(dd, 1H), 3.31(d, 1H), 3.68(s, 3H), 3.96(m, 1H), 6.79(d, 2H), 7.02(d, 2H), 7.82(s, 1H), 8.06(s, 1H); MS(APCI) m/z(rel intensity)235(100). |
| 15 | CH$_2$(3,5-diCl)Ph | $^1$H NMR(DMSO-d$_6$): δ2.86(dd, 1H), 3.04(dd, 1H), 3.20(d, 1H), 3.50(d, 1H), 4.07(m, 1H), 7.14(d, 1H), 7.39(s, 1H), 7.51(d, 1H), 7.97(s, 1H), 8.15(s, 1H); MS(APCI) m/z(rel intensity)273(100), 275(60). |
| 16 | CH$_2$(indol-3yl) | mp 262–271° C.; $^1$H NMR(DMSO-d$_6$): δ2.74(d, 1H), 2.98(dd, 1H), 3.19(dd, 1H), 3.21(d, 1H), 3.98(m, 1H), 6.93(t, 1H), 7.02(t, 1H), 7.03(s, 1H), 7.29(d, 1H), 7.50(d, 1H), 7.72(s, 1H), 8.05(s, 1H); MS(APCI)m/z(rel intensity)244(100). |
| 17 | CH$_2$(thiophen-2-yl) | $^1$H NMR(DMSO-d$_6$): δ3.00(dd, 1H), 3.07(d, 1H), 3.28(dd, 1H), 3.45(d, 1H), 4.05(t, 1H), 6.80(s, 1H), 6.91(d, 1H), 7.40(d, 1H), 7.91(s, 1H), 8.17(s, 1H); MS(APCI) m/z(rel intensity)211(100). |
| 18 | CH$_2$(benzo(b)thiophen-3-yl) | $^1$H NMR(DMSO-d$_6$): δ3.04(d, 1H), 3.17(dd, 1H), 3.29(dd, 1H), 3.37(d, 1H), 4.08(s, 1H), 7.30–7.36(m, 2H), 7.37(s, 1H), 7.80(d, 1H), 7.87(s, 1H), 7.92(d, 1H), 8.15(s, 1H); MS(APCI)m/z(rel intensity)261(100). |
| 20 | CH$_2$(naphthalene-1-yl) | $^1$H NMR(DMSO-d$_6$): δ3.11(d, 1H), 3.35(d, 1H), 3.44(dd, 1H), 3.50(dd, 1H), 4.07(m, 1H), 7.37(d, 1H), 7.44(t, 1H), 7.48–7.57(m, 2H), 7.84(d, 1H), 7.92(d, 1H), 7.94(s, 1H), 8.10(s, 1H), 8.13(d, 1H); MS(APCI)m/z(rel intensity)255(100). |
| 21 | CH$_2$(naphthalene-2-yl) | $^1$H NMR(DMSO-d$_6$): δ2.83(d, 1H), 3.09(dd, 1H), 3.26(dd, 1H), 3.36(d, 1H), 4.16(m, 1H), 7.36(d, 1H), 7.45–7.52(m, 2H), 7.69(s, 1H), 7.80–7.91(m, 4H), 7.95(s, 1H), 8.27(s, 1H); MS(APCI)m/z(rel intensity)255 (100). |
| 23 | CH$_2$(3,5-Di-F)Ph | $^1$H NMR(DMSO-d$_6$): δ2.90(dd, 1H), 3.23(d, 1H), 3.52(d, 1H), 3.61(dd, 1H), 4.09(m, 1H), 6.86(d, 2H), 7.07(t, 1H), 8.00(s, 1H), 8.13(s, 1H); MS(APCI)m/z(rel intensity)241(100). |
| 23a | CH$_2$(4-Ph)Ph | $^1$H NMR(DMSO-d$_6$)δ2.94(dd, 1H), 3.06–3.18(m, 2H), 3.43(d, 1H), 4.11(m, 1H), 7.23(d, 2H), 7.36(t, 1H), 7.44(t, 2H), 7.61(d, 2H), 7.66(d, 2H), 7.94(bs, 1H), 8.20(bs, 1H). |

Example 24

2-(S)-Phenethyl-piperazine

Add 3-(S)-phenethyl-piperazine-2,5-dione (2.5 g, 11 mmol) portionwise to lithium aluminum hydride (1.75 g, 46 mmol) in THF (46 mL). Reflux the resulting suspension for an hour and cool to 0° C. Add sodium sulfate decahydrate carefully until hydrogen evolution ceases and stir the mixture for an additional three hours at room temperature and filter. Wash the solids with THF several times. Combine the filtrates, concentrate, and recrystallize the residue with THF/pentane to afford 2-(S)-phenethyl-piperazine as white crystals (1.9 g, 90%): mp 114–115° C.; $^1$H NMR (CDCl$_3$): δ1.58–1,70 (m, 2H), 2.41 (dd, 1H), 2.58–3.02 (m, 8H), 7.16–7.30 (m, 5H); MS (APCI) m/z (rel intensity) 191 (100).

By a similar method to Example 24, using the appropriate starting materials, the following piperazines were prepared and isolated as the (S) isomer except where noted below:

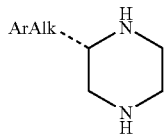

| No: | ArAlk | Data |
|---|---|---|
| 25 | CH$_2$Ph | mp 65–67° C.; $^1$H NMR(CDCl$_3$): δ2.47–2.57(m, 2H), 2.67–3.00(m, 7H), 7.16–7.30(m, 5H); MS(APCI)m/z(rel intensity)177(100). |
| 26 | CH$_2$(4-Ph)Ph | mp 129–134° C.; $^1$H NMR(CDCl$_3$)δ2.51–2.59(m, 2H), 2.68–3.03(m, 7H), 7.23(d, 2H), 7.31(t, 1H), 7.42(t, 2H), 7.57(d, 2H), 7.59(d, 2H); MS(ESIpos)m/z(rel intensity)253.3(100). |
| 33 | CH$_2$(naphthalen-1-yl) | $^1$H NMR(CDCl$_3$): δ2.58–2.67(m, 2H), 2.82(ddd, 1H), 2.85–2.95(m, 3H), 3.02(m, 1H), 3.05(m, 1H), 3.22(dd, 1H), 7.37–7.43(m, 2H), 7.47–7.54(m, 2H), 7.75(d, 1H), 7.86(m, 1H), 8.07(m, 1H); MS(APCI)m/z(rel intensity)227(100). |
| 34 | CH$_2$(naphthalen-2-yl) | $^1$H NMR(CDCl$_3$): δ2.57(dd, 1H), 2.65–2.99(m, 7H), 3.02(dd, 1H), 7.33(d, 1H), 7.42–7.50(m, 2H), 7.66(s, 1H), 7.75–7.83(m, 3H); MS(APCI)m/z(rel intensity)227(100). |
| 35 | CH$_2$(3-F)Ph | $^1$H NMR(CDCl$_3$): δ2.57–2.46(ddd, 1H), 2.81–2.65(m, 4H), 3.02–2.82(m, 4H), 7.00–6.88(m, 3H), 7.29–7.21(m, 1H); MS (APCI)m/z(rel intensity)195.3(100). |
| 36 | CH$_2$(2-F)Ph | $^1$H NMR(CDCl$_3$): δ2.49(dd, 1H), 2.58(dd, 1H), 2.98–2.84(m, 3H), 3.02–2.82(m, 4H), 7.09–6.97(m, 2H), 7.24–7.17(m, 2H); MS(APCI)m/z(rel intensity)195.3(100). |
| 37 | CH$_2$(3-CF$_3$)Ph | $^1$H NMR(CDCl$_3$): δ2.50(dd, 1H), 2.61(dd, 1H), 2.81–2.69(m, 3H), 2.98–2.83(m, 4H), 7.54–7.36(m, 4H); MS(APCI) m/z(rel intensity)245.3(100). |
| 38 | (R)—CH$_2$Ph | $^1$H NMR(CDCl$_3$): δ2.47–2.57(m, 2H), 2.67–3.00(m, 7H), 7.16–7.30(m, 5H); MS(APCI)m/z(rel intensity)177(100). |
| 39 | CH$_2$(3-CH$_3$)Ph | mp 58–63° C.; $^1$H NMR(CDCl$_3$): δ2.33(s, 3H), 2.50(ddd, 2H), 2.67(dd, 1H), 2.94–2.70(m, 5H), 2.98(dd, 1H), 7.06–6.97(m, 3H), 7.19(t, 1H); MS(APCI)m/z(rel intensity)191.3(100). |
| 40 | CH$_2$(indol-3-yl) | mp 45–58° C.; $^1$H NMR(CDCl$_3$): δ2.54(dd, 1H), 3.02–2.63(m, 7H), 3.06(dd, 1H), 7.05(bs, 1H), 7.11(dt, 1H), 7.18(dt, 1H), 7.36(dd, 1H), 7.65(d, 1H), 8.06(bs, 1H) |
| 41 | CH$_2$(benzo(b)thiophen-3-yl) | $^1$H NMR(CDCl$_3$): δ2.57(dd, 1H), 2.99–2.76(m, 7H), 3.08(dd, 1H), 7.15(s, 1H), 7.19(s, 1H), 7.35–7.25(m, 1H), 7.82–7.70(m, 2H), MS(APCI)m/z(rel intensity)233.2(100). |
| 42 | CH$_2$(4-F)Ph | $^1$H NMR(CDCl$_3$): δ2.46(ddd, 1H), 2.63(dd, 1H), 2.84–2.67(m, 3H), 2.95–2.85(m, 3H), 6.98–6.92(m, 2H), 7.14–7.04(m, 2H); MS(APCI)m/z(rel intensity)195.3(100). |
| 43 | CH$_2$(4-OCH$_3$)Ph | mp 76–80° C.; $^1$H NMR(CDCl$_3$): δ2.45(ddd, 2H), 2.61(dd, 1H), 2.82–2.65(m, 3H), 2.91–2.85(m, 2H), 2.94(dd, 1H), 3.76(s, 3H), 6.81(d, 2H), 7.09(d, 2H); MS(APCI)m/z(rel intensity)207.3(100). |
| 46 | CH$_2$(4-CH$_3$)Ph | mp 64–68° C.; $^1$H NMR(CDCl$_3$): δ2.32(s, 3H), 2.47(dd, 1H), 2.49(dd, 1H), 2.65(dd, 1H), 2.68(dd, 1H), 2.73(dd, 1H), 2.80(m, 1H), 2.86–2.93(m, 2H), 7.07–7.13(m, 4H); MS(APCI) m/z(rel intensity)191(100). |
| 47 | CH$_2$(4-Cl)Ph | mp 77–81° C.; $^1$H NMR(CDCl$_3$): δ2.45(ddd, 2H), 2.61(dd, 1H), 2.82–2.65(m, 3H), 2.91–2.85(m, 2H), 2.94(dd, 1H), 6.81(d, 2H), 7.09(d, 2H); MS(APCI)m/z(rel intensity)211.3 (100). |
| 48 | CH$_2$(2-OCH$_3$)Ph | $^1$H NMR(CDCl$_3$): δ2.49(dd, 1H), 2.53(dd, 1H), 2.80–2.68(m, 3H), 2.98–2.87(m, 4H), 3.81(s, 3H), 6.90–6.83(m, 2H), 7.23–7.12(m, 2H); MS(APCI)m/z(rel intensity)207.3(100). |
| 49 | CH$_2$(3-OCH$_3$)Ph | mp 57–61° C.; $^1$H NMR(CDCl$_3$); δ2.49(dd, 1H), 2.52(dd, 1H), 2.78–2.65(m, 3H), 2.94–2.79(m, 3H), 2.97(dd, 1H), 3.80(s, 3H), 6.81–6.74(m, 3H), 7.21(ddd, 1H); MS(APCI)m/z(rel intensity)207.3(100). |

-continued

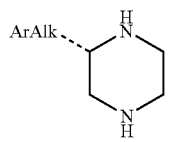

| No: | ArAlk | Data |
|---|---|---|
| 50 | CH$_2$(2-Cl)Ph | $^1$H NMR(CDCl$_3$): δ2.53(dd, 1H), 2.65(dd, 1H), 2.81–2.70(m, 2H), 2.99–2.83(m, 5H), 7.27–7.14(m, 3H), 7.38–7.35(m, 1H); MS(APCI)m/z(rel intensity)211(100), 213(36). |
| 51 | CH$_2$(3-Cl)Ph | $^1$H NMR(CDCl$_3$): δ2.49(dd, 1H), 2.51(dd, 1H), 2.67(m, 1H), 2.77–2.71(m, 2H), 2.99–2.78(m, 4H), 7.10–7.07(m, 1H), 7.26–7.19(m, 3H); MS(APCI)m/z(rel intensity)211(100), 213(38). |
| 52 | CH$_2$(3,4-Di-Cl)Ph | $^1$H NMR(CDCl$_3$): δ2.49(dd, 1H), 2.97–2.73(m, 7H), 3.00(dd, 1H), 6.86–6.83(m, 1H), 6.94(dd, 1H), 7.17(dd, 1H); MS(APCI)m/z(rel intensity)245(100). |
| 53 | CH$_2$(thiophen-2-yl) | $^1$H NMR(CDCl$_3$): δ2.49(dd, 1H), 2.51(dd, 1H), 2.67(m, 1H), 2.77–2.71(m, 2H), 2.99–2.78(m, 4H), 7.10–7.07(m, 1H), 7.26–7.19(m, 2H); MS(APCI)m/z(rel intensity)183(100). |
| 55 | CH$_2$(2-CF$_3$)Ph | $^1$H NMR(CDCl$_3$): δ2.53–2.46(m, 1H), 2.78–2.66(m, 3H), 2.96–2.84(m, 5H), 7.31(t, 1H), 7.37(d, 1H), 7.46(t, 1H), 7.63(d, 1H): MS(APCI)m/z(rel intensity)183(100). |
| 57 | CH$_2$(3,5-Di-F)Ph | $^1$H NMR(CDCl$_3$): δ2.48(ddd, 1H), 2.53(dd, 1H), 2.66(dd, 1H), 2.72–2.78(m, 2H), 2.84(m, 1H), 2.88–2.98(m, 3H), 6.67(t, 1H), 6.73(d, 2H); MS(APCI)m/z(rel intensity)213(100). |

Example 58

2-(S)-(4-Bromo-benzyl)-pipierazine

Add dropwise a 1M solution of BH$_3$.THF (183 mL, 183 mmol) to 3-(S)-(4-bromo-benzyl)-piperazine-2,5-dione (6.5 g, 23 mmol) in 100 mL of dry THF at ambient temperature. Stir for an hour then heat to reflux for two days and cool down to 0° C. Add slowly a 12% hydrobromic acid solution in acetic acid and stir overnight. Isolate the precipitate, wash it with ethyl acetate and hexanes and dry it to yield the di-hydrobromic salt as a white solid. Add to this solid a saturated sodium bicarbonate in water and extract with a solution of dichloromethane and isopropyl alcohol (75/25). Dry over magnesium sulfate and evaporate the solvent to yield the title compound (4.3 g, 73%) as a white powder: mp=91–93° C.; $^1$H NMR (CDCl$_3$): δ2.45–2.52 (m, 2H), 2.64 (dd, 1H), 2.68–2.75 (m, 2H), 2.82 (m, 1H), 2.88–2.97 (m, 3H), 7.08 (d, 2H), 7.42 (d, 2H); MS (APCI) m/z (rel intensity) 255 (100), 257 (100).

Example 59

2-Methyl-10-(S)-(3-phenethyl-piperazin-1-yl)-4H-3-thia-4,9-diazabenzo[f]azulene

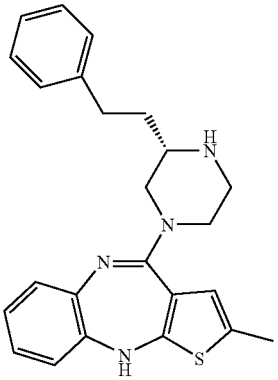

Heat a suspension of 2-methyl-4H-3-thia4,9-diaza-benzo[f]-azulen-10-ylamine hydrochloride (466 mg, 1.75 mmol) and 2-(S)-phenethyl-piperazine (1.0 g, 5.3 mmol) in DMSO (2.5 mL) and toluene (10 mL) at reflux for 48 hours. Evaporate the toluene under vacuo and pour the resulting solution into water (10 mL). Purify the resulting brown solid by flash chromatography eluting with methylene chloride/methanol (95:5) to give 2-methyl-10-(3-(S)-phenethyl-piperazin-1-yl)-4H-3-thia-4,9-diaza-benzo[f]azulene as a yellow solid (478 mg, 65%): mp 75–84° C.; $^1$H NMR(CDCl$_3$): δ1.76 (m, 2H), 2.31 (s, 3H), 2.60 (dd, 1H), 2.71 (m, 2H), 2.80 (m, 1H), 2.92 (m, 2H), 3.04 (m, 1H), 3.96 (m, 1H), 4.12 (m, 1H), 4.91 (s, 1H), 6.29 (s, 1H), 6.60 (d, 1H), 6.89 (t, 1H), 6.96 (t, 1H), 7.03 (d, 1H), 7.15–7.30 (m, 5H); MS (APCI) m/z (rel intensity) 403 (100).

By a method similar to Example 59, using the appropriate starting material, the following compounds were prepared and isolated as the (S) isomer except where noted below:

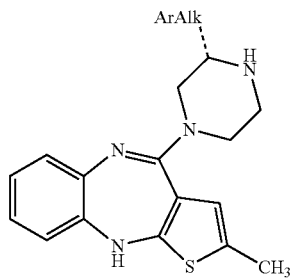

| No: | ArAlk | Data |
|---|---|---|
| 61 | CH$_2$Ph | mp 169–170° C.; $^1$H NMR(CDCl$_3$): δ2.26(s, 3H), 2.61(dd, 1H), 2.68(dd, 1H), 2.71–2.87(m, 2H), 2.92–3.03(m, 3H), 3.99(d, 1H), 4.09(d, 1H), 4.93(s, 1H), 6.20(s, 1H), 6.59(d, 1H), 6.87(t, 1H), 6.96(t, 1H), 7.03(d, 1H), 7.20–7.33(m, 5H); MS (APCI)m/z(rel intensity)389(100). 70% yield. |
| 62 | CH$_2$(4-O—CH$_2$CH=C(CH$_3$)$_2$)Ph | mp 86–97° C.; $^1$H NMR(CDCl$_3$)δ1.74(s, 3H), 1.80(s, 3H), 2.26(s, 3H), 2.57(dd, 1H), 2.67(dd, 1H), 2.74(dd, 1H), 2.84(dd, 1H), 3.04–2.92(m, 3H), 4.00(d, 1H), 4.08(d, 1H), 4.49(d, 2H), 4.95(s, 1H), 5.50(m, 1H), 6.20(d, 1H), 6.60(dd, 1H), 6.89–6.84(m, 3H), 6.96(dt, 1H), 7.02(dd, 1H), 7.13(d, 2H); MS(APCI)m/z(rel intensity)473.5(100). 34% yield. |
| 63 | CH$_2$(3,4-OCH$_2$O—)Ph | mp 123–130° C.; $^1$H NMR(CDCl$_3$)δ2.26(s, 3H), 2.55(dd, 1H), 2.67(dd, 1H), 2.72(dd, 1H), 2.85(dd, 1H), 3.04–2.92(m, 3H), 4.00(d, 1H), 4.08(d, 1H), 4.98(s, 1H), 5.94(d, 2H), 6.21(dd, 1H), 6.61(dt, 1H), 6.68(dt, 1H), 6.77–6.73(m, 2H), 6.87(ddd, 1H), 6.97(ddd, 1H), 7.02(dd, 1H); MS(APCI)m/z(rel intensity)433.5(100). 43% yield. |
| 64 | CH$_2$(3,4-Di-OCH$_3$)Ph | mp 127–139° C.; $^1$H NMR(CDCl$_3$)δ2.26(s, 3H), 2.55(dd, 1H), 2.68(dd, 1H), 2.76(dd, 1H), 2.82(dd, 1H), 3.04–2.92(m, 3H), 3.87(s, 3H), 3.88(s, 3H), 4.00(d, 1H), 4.15(d, 1H), 4.98(s, 1H), 6.22(d, 1H), 6.60(dd, 1H), 6.83–6.73(m, 3H), 6.87(dt, 1H), 6.97(dt, 1H), 7.02(dd, 1H); MS(APCI)m/z(rel intensity) 449.5(100). 47% yield. |
| 65 | CH$_2$(4-iPr)Ph | mp 78–83° C.: $^1$H NMR(CDCl$_3$)δ1.24(d, 6H), 2.27(s, 3H), 2.57(dd, 1H), 2.69(dd, 1H), 2.76(dd, 1H), 2.79–3.02(m, 5H), 3.98(m, 1H), 4.11(m, 1H), 4.97(s, 1H), 6.23(s, 1H), 6.60(d, 1H), 6.86(t, 1H), 6.96(t, 1H), 7.01(d, 1H), 7.14–7.18(m, 4H); MS(APCI)m/z(rel intensity)431(100). 66% yield. |
| 66 | CH$_2$(4-OPh)Ph | $^1$H NMR(CDCl$_3$)δ2.27(s, 3H), 2.61(dd, 1H), 2.67(dd, 1H), 2.76(dd, 1H), 2.86(ddd, 1H), 2.93–3.05(m, 3H), 3.99(m, 1H), 4.09(m, 1H), 4.96(s, 1H), 6.22(s, 1H), 6.59(d, 1H), 6.86(t, 1H), 6.94–7.02(m, 5H), 7.10(t, 1H), 7.19(d, 2H), 7.33(t, 2H); MS(APCI)m/z(rel intensity)481(100). Product isolated as an orange powder. |
| 67 | CH$_2$(naphthalene-2-yl) | mp 101–119° C.; $^1$H NMR(CDCl$_3$): δ2.32(s, 3H), 2.70–2.88(m, 3H), 2.98(m, 3H), 3.10(m, 3H), 4.00(m, 1H), 4.17(m, 1H), 4.93(s, 1H), 6.28(s, 1H), 6.60(d, 1H), 6.86(t, 1H), 6.96(t, 1H), 7.02(d, 1H), 7.39(d, 1H), 7.32(m, 2H), 7.70(s, 1H), 7.81(m, 3H); MS(APCI)m/z(rel intensity)439(100). 27% yield. |
| 68 | CH$_2$(naphthalene-1-yl) | mp 106–116° C.; $^1$H NMR(CDCl$_3$): δ2.30(s, 3H), 2.74–2.83(m, 2H), 2.94–3.06(m, 3H), 3.18(m, 1H), 3.30(dd, 1H), 3.96(m, 1H), 4.15(m, 1H), 4.92(s, 1H), 6.14(s, 1H), 6.60(d, 1H), 6.86(t, 1H), 7.96(t, 1H), 7.03(d, 1H), 7.40(m, 2H), 7.47–7.56(m, 2H), 7.77(d, 1H), 7.88(d, 1H), 8.09(d, 1H); MS(APCI) m/z(rel intensity)439(100). 36% yeild. |
| 69 | CH$_2$(4-CH$_3$)Ph | mp 92–101° C.; $^1$H NMR(CDCl$_3$): δ2.26(d, 3H), 2.33(s, 3H), 2.57(dd, 1H), 2.68(dd, 1H), 2.86–2.74(m, 2H), 3.03–2.91(m, 3H), 4.00(bd, 1H), 4.10(bd, 1H), 4.97(s, 1H), 6.21(d, 1H), 6.60(dd, 1H), 6.87(dt, 1H), 6.96(dt, 1H), 7.02(dd, 1H), 7.12(m, 4H); MS(APCI)m/z(rel intensity)403.3(100). 80% yield. |
| 70 | CH$_2$(3-CH$_3$)Ph | mp 80–97° C.; $^1$H NMR(CDCl$_3$): δ2.26(d, 3H), 2.34(s, 3H), 2.57(dd, 1H), 2.69(dd, 1H), 2.87–2.74(m, 2H), 3.03–2.93(m, 3H), 3.96(bd, 1H), 4.41(bd, 1H), 4.93(s, 1H), 6.21(d, 1H), 6.60(dd, 1H), 6.87(dt, 1H), 6.96(dt, 1H), 7.06–7.00(m, 4H), 7.23–7.17(m, 1H); MS(APCI)m/z(rel intensity)403.3(100). 55% yield. |

-continued

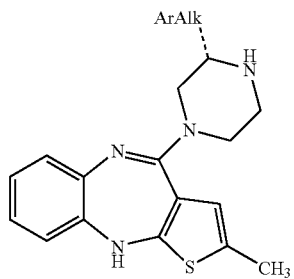

| No: | ArAlk | Data |
|---|---|---|
| 71 | CH$_2$(2-F)Ph | mp 84–102° C.; $^1$H NMR(CDCl$_3$): δ2.24(s, 3H), 2.74–2.65(m, 2H), 2.86–2.79(m, 1H), 2.88(dd, 1H), 3.10–2.92(m, 3H), 4.02(t, 2H), 4.96(s, 1H), 6.19(d, 1H), 6.59(dd, 1H), 6.86(dt, 1H), 6.96(dt, 1H), 7.11–6.99(m, 3H), 7.26–7.19(m, 2H); MS (APCI)m/z(rel intensity)407.4(100). 64% yield. |
| 72 | CH$_2$(3-F)Ph | mp 87–99° C.; $^1$H NMR(CDCl$_3$): δ2.26(s, 3H), 2.70–2.59(m, 2H), 2.90–2.75(m, 2H), 3.05–2.92(m, 3H), 3.98(d, 1H), 4.09(d, 1H), 4.96(s, 1H), 6.21–6.19(m, 1H), 6.60(dd, 1H), 6.87(dt, 1H), 7.04–6.91(m, 5H), 7.30–7.24(m, 1H); MS(APCI)m/z(rel intensity)407.4(100). 54% yield. |
| 73 | CH$_2$(4-F)Ph | mp 86–99° C.; $^1$H NMR(CDCl$_3$): δ2.23(s, 3H), 2.69–2.57(m, 2H), 2.74(dd, 1H), 2.83(dd, 1H), 3.12–2.91(m, 3H), 3.97(d, 1H), 4.05(d, 1H), 4.97(bs, 1H), 6.16(d, 1H), 6.58(dd, 1H), 6.85(dt, 1H), 7.01–6.92(m, 4H), 7.19–7.14(m, 2H); MS (APCI)m/z(rel intensity)407.4(100). 73% yield. |
| 74 | CH$_2$(2-CF$_3$)Ph | mp 103–108° C.; $^1$H NMR(CDCl$_3$): δ2.25(s, 3H), 2.67(dd, 1H), 2.72–2.82(m, 2H), 2.87(dd, 1H), 2.93–3.07(m, 3H), 4.01(m, 2H), 4.93(s, 1H), 6.19(s, 1H), 6.59(d, 1H), 6.86(t, 1H), 6.94–7.01(m, 2H), 7.34(t, 1H), 7.40(d, 1H), 7.49(t, 1H), 7.67(d, 1H); MS(APCI)m/z(rel intensity)457(100). 54% yield. |
| 75 | CH$_2$(2-OCH$_3$)Ph | mp 95–109° C.; $^1$H NMR(CDCl$_3$): δ2.23(s, 3H), 2.66(dd, 1H), 2.71(dd, 1H), 2.90–2.80(m, 2H), 3.09–2.93(m, 3H), 3.83(s, 3H), 4.06–3.98(m, 2H), 4.98(bs, 1H), 6.17(s, 1H), 6.60(dd, 1H), 6.92–6.84(m, 3H), 6.96(dt, 1H), 7.02(dd, 1H), 7.18(dd, 1H), 7.22(dt, 1H); MS(APCI)m/z(rel intensity)419.4(100). 54% yield. |
| 76 | CH$_2$(3-OCH$_3$)Ph | mp 96–109° C.; $^1$H NMR(CDCl$_3$): δ2.24(s, 3H), 2.64–2.91(m, 4H), 3.12–3.01(m, 3H), 3.79(s, 3H), 4.01(bd, 1H), 4.09(bd, 1H), 5.06(bs, 1H), 6.17(s, 1H), 6.60(d, 1H), 6.89–6.75(m, 4H), 6.95(t, 1H), 7.02(d, 1H), 7.21(dt, 1H); MS(APCI)m/z (rel intensity)419.4(100). 25% yield. |
| 77 | CH$_2$(4-OCH$_3$)Ph | mp 85–98° C.: $^1$H NMR(CDCl$_3$): δ2.23(s, 3H), 2.56(dd, 1H), 2.66(dd, 1H), 2.72(dd, 1H), 2.81(dt, 1H), 3.02–2.91(m, 3H), 3.77(s, 3H), 3.98(d, 1H), 4.06(d, 1H), 4.98(bs, 1H), 6.17(s, 1H), 6.58(dd, 1H), 6.87–6.80(m, 3H), 6.94(dt, 1H), 6.99(dd, 1H), 7.15–7.10(m, 2H); MS(APCI)m/z(rel intensity)419.5 (100). 17% yield. |
| 78 | CH$_2$(34,-Di-Cl)Ph | mp 108–114° C.; $^1$H NMR(CDCl$_3$): δ2.26(s, 3H), 2.58(dd, 1H), 2.66(dd, 1H), 2.74(dd, 1H), 2.85(ddd, 1H), 2.93–3.03(m, 3H), 3.96(m, 1H), 4.07(m, 1H), 4.97(s, 1H), 6.19(s, 1H), 6.60(d, 1H), 6.86(t, 1H), 6.94–7.03(m, 2H), 7.07(d, 1H), 7.36–7.42(m, 2H; MS(APCI)m/z(rel intensity)457(100), 457(68). 48% yield. |
| 79 | CH$_2$(indol-3-yl) | mp 146–158° C.; $^1$H NMR(CDCl$_3$): δ2.16(s, 3H), 2.84–2.68(m, 3H), 3.05–2.88(m, 3H), 3.17–3.07(m, 1H), 3.95(d, 1H), 4.14(bs, 1H), 5.07(bs, 1H), 6.15(bs, 1H), 6.57(d, 1H), 6.84(t, 1H), 6.94(t, 1H), 7.06–7.00(m, 2H), 7.09(t, 1H), 7.17(t, 1H), 7.33(d, 1H), 7.63(d, 1H), 8.26(bs, 1H); MS(APCI)m/z (rel intensity)428.4(100). 55% yield. |
| 80 | CH$_2$(thiophen-2-yl) | mp 95–104° C.; $^1$H NMR(CDCl$_3$): δ2.27(s, 3H), 2.68(dd, 1H), 2.84–2.90(m, 2H), 2.94–3.04(m, 4H), 3.98(m, 1H), 4.10(m, 1H), 5.04(bs, 1H), 6.24(s, 1H), 6.59(d, 1H), 6.86(m, 2H), 6.93–6.97(m, 2H), 7.02(d, 1H), 7.17(d, 1H); MS(APCI)m/z (rel intensity)395(100). 10% yield. |

-continued

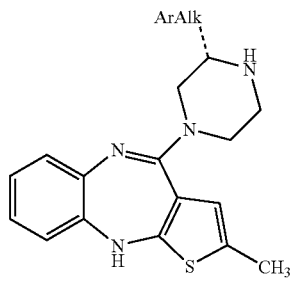

| No: | ArAlk | Data |
|---|---|---|
| 81 | CH$_2$(benzo(b)thiophen-3-yl) | mp 115–124° C.; $^1$H NMR(CDCl$_3$): δ2.20(s, 3H), 2.73(dd, 1H), 2.82(dd, 1H), 3.05–2.85(m, 4H), 3.22–3.14(m, 1H), 3.95(d, 1H), 4.16(d, 1H), 4.97(bs, 1H), 6.14(d, 1H), 6.57(dd, 1H), 6.85(dt, 1H), 6.95(dt, 1H), 7.01(dd, 1H), 7.22(s, 1H), 7.34(dd, 1H), 7.38(dd, 1H), 7.79(dd, 1H), 7.85(dd, 1H); MS (APCI)m/z(rel intensity)445.4(100). 28% yield. |
| 82 | CH$_2$(3-O-i-Pr—Ph) | $^1$H NMR(CDCl$_3$)δ1.33(dd, 6H), 2.26(s, 3H), 2.55–3.01(m, 7H), 3.98(d, 1H), 4.11(d, 1H), 4.55(m, 1H), 4.93(s, 1H), 6.21(s, 1H), 6.59(d, 1H), 6.77(m, 3H), 6.87(t, 1H), 6.98(m, 2H), 7.21(t, 1H); MS(ESI)m/z(rel intensity)447(100). Product isolated as a yellow solid. |
| 83 | (R)CH$_2$Ph | mp 84–98° C.: $^1$H NMR(CDCl$_3$)δ2.26(s, 3H), 2.61(dd, 1H), 2.68(dd, 1H), 2.71–2.87(m, 2H), 2.92–3.03(m, 3H), 3.99(d, 1H), 4.09(d, 1H), 4.93(s, 1H), 6.20(s, 1H), 6.59(d, 1H), 6.87(t, 1H), 6.96(t, 1H), 7.03(d, 1H), 7.20–7.33(m, 5H); MS (APCI)m/z(rel intensity)389(100). 83% yield. |
| 84 | CH$_2$(2,4-di-OCH$_3$)Ph | $^1$H NMR(CDCl$_3$)δ2.24(s, 3H), 2.55(dd, 1H), 2.65(m, 1H), 2.75(dd, 1H), 2.84(ddd, 1H), 2.91–3.04(m, 3H), 3.80(s, 6H), 3.99–4.03(m, 2H), 4.95(s, 1H), 6.19(s, 1H), 6.42(d, 1H), 6.46(s, 1H), 6.60(d, 1H), 6.86(t, 1H), 6.96(t, 1H), 7.02(d, 1H), 7.06(d, 1H); MS(APCI)m/z(rel intensity)449(100). Product isolated as a a yellow solid. |
| 85 | CH$_2$(4-Cl)Ph | mp 91–108° C.; $^1$H NMR(CDCl$_3$): δ2.26(s, 3H), 2.61(dd, 1H), 2.66(dd, 1H), 2.75(dd, 1H), 2.88–2.81(m, 1H), 3.03–2.91(m, 3H), 3.99(bd, 1H), 4.07(bd, 1H), 4.95(bs, 1H), 6.17(d, 1H), 6.60(dd, 1H), 6.87(dt, 1H), 6.97(dt, 1H), 7.01(dd, 1H), 7.19–7.14(m, 2H), 7.30–7.25(m, 2H); MS(APCI)m/z(rel intensity) 423.4(100). 63% yield. |
| 86 | CH$_2$(2-Cl)Ph | $^1$H NMR(CDCl$_3$): δ2.24(s, 3H), 2.65–3.14(m, 7H), 3.99–4.05(m, 2H), 4.96(s, 1H), 6.20(s, 1H), 6.59(d, 1H), 6.87(t, 1H), 6.97(t, 1H), 7.02(d, 1H), 7.18–7.22(m, 2H), 7.27(m, 1H), 7.39(m, 1H); MS(APCI)m/z(rel intensity)423(100), 425(39). 200 mg of product. |
| 87 | CH$_2$(3-Cl)Ph | $^1$H NMR(CDCl$_3$): δ2.28(s, 3H), 2.58–3.04(m, 5H), 3.98(m, 1H), 4.08(m, 1H), 4.96(s, 1H), 6.21(s, 1H), 6.61(d, 1H), 6.88(t, 1H), 6.98(t, 1H), 7.03(d, 1H), 7.11(m, 1H), 7.21–7.28(m, 3H); MS(APCI)m/z(rel intensity)423(100), 425(39). |
| 88 | CH$_2$(3,5-Di-F)Ph | $^1$H NMR(CDCl$_3$): δ2.27(s, 3H), 2.58–2.70(m, 2H), 2.77(dd, 1H), 2.83–3.06(m, 4H), 3.95(m, 1H), 4.07(m, 1H), 4.99(s, 1H), 6.21(s, 1H), 6.60(d, 1H), 6.69(t, 1H), 6.76–6.83(m, 2H), 6.87(t, 1H), 6.96(t, 1H), 7.01(d, 1H); MS(APCI)m/z(rel intensity)425(100). 10 mg of product. |
| 89 | CH$_2$(3-CF$_3$)Ph | mp 105–117° C.: $^1$H NMR(CDCl$_3$): δ2.24(s, 3H), 2.68–2.73(m, 2H), 2.82–2.89(m, 2H), 2.95–3.10(m, 3H), 3.98(m, 1H), 4.11(m, 1H), 5.00(s, 1H), 6.19(s, 1H), 6.60(d, 1H), 6.88(t, 1H), 6.96(t, 1H), 7.01(d, 1H), 7.42–7.50(m, 4H); MS(APCI) m/z(rel intensity)457(100). |

Example 90

2-Methyl-10-(4-methyl-3-(S)-phenethyl-piperazin-1-yl)-4H-3-thia-4,9-diaza-benzo[f]azulene

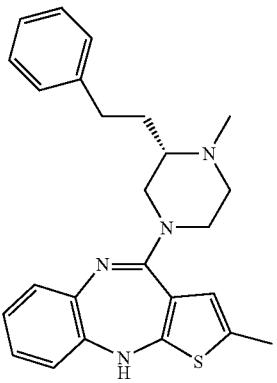

Add aqueous 37% formaldehyde (45 mL, 0.55 mmol) to a solution of 2-methyl-10-(3-(S)-phenethyl-piperazin-1-yl)-4H-3-thia-4,9-diazabenzo[f]azulene (200 mg, 0.5 mmol) in dichloroethane (30 mL). Stir the mixture 2 minutes and add sodium triacetoxyborohydride (159 mg, 0.75 mmol). Stir the suspension for 30 minutes and quench with a saturated aqueous solution of sodium bicarbonate. Extract the aqueous phase 3 times with dichloromethane and combine the organic phases, dry (MgSO$_4$), filter and concentrate. Purify the residue via chromatography eluting with methylene chloride/methanol (90:10) to provide the title compound as a yellow solid (143 mg, 67%): mp 87–91° C.: $^1$H NMR (CDCl$_3$): δ1.78 (m, 1H), 1.96 (m, 1H), 2.22 (m, 1H), 2.32 (s, 3H), 2.35 (s, 3H), 2.38 (ddd, 1H), 2.58 (ddd, 1H), 2.75 (ddd, 1H), 2.86 (ddd, 1H), 2.94 (dd, 1H), 3.16 (ddd, 1H), 3.90 (m, 1H), 4.05 (m, 1H), 4.94 (s, 1H), 6.30 (s, 1H), 6.60 (d, 1H), 6.87 (t, 1H), 6.98 (t, 1H), 7.04 (d, 1H), 7.17–7.32 (m, 5H); MS (APCI) m/z (rel intensity) 417 (100).

Example 91

(S)-2-Methyl-10-(4-methyl-3-phenethyl-piperazin-1-yl)-4H-3-thia-4,9-diaza-benzo[f]azulene dihydrochloride

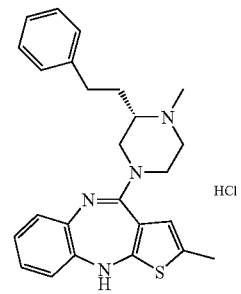

Dissolve (S)-2-methyl-10-(4-methyl-3-phenethyl-piperazin-1-yl)-4H-3-thia-4,9-diaza-benzo[f]azulene in ethyl acetate add hydrochloride acid until the title compound precipitates as the dihydrochloride salt as a yellow solid: mp 225° C.; mass spectrum (ion spray): m/z=417 (M+1); Analysis for C$_{25}$H$_{30}$Cl$_2$N$_4$S(0.3 H$_2$O): calcd: C, 60.67; H, 6.23; N, 11.32; found: C, 60.76; H, 6.17; N, 11.13.

By method similar Example 90, using the appropriate starting materials, the following compounds were prepared and isolated as the free base and as the (S) isomer except where noted:

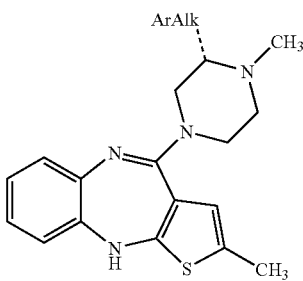

| No: | ArAlk | Data |
|---|---|---|
| 92 | CH$_2$Ph | mp 94–97° C.; $^1$H NMR(CDCl$_3$): δ2.12(s, 3H), 2.36–2.48(m, 3H), 2.49(s, 3H), 2.79(ddd, 1H), 2.92(ddd, 1H), 3.12–3.23(m, 2H), 3.58(m, 1H), 3.94(m, 1H), 4.90(s, 1H), 5.96(s, 1H), 6.57(d, 1H), 6.82–6.86(m, 1H), 6.91–6.96(m, 1H), 7.14–7.29(m, 5H); MS(APCI)m/z(rel intensity)403(100), 346(80). 93% yield. |
| 93 | CH$_2$(4-O—CH$_2$CH=CH$_2$)Ph | mp 97–108° C.; $^1$H NMR(CDCl$_3$)δ2.12(s, 3H), 2.39–2.32(m, 2H), 2.43(dd, 1H), 2.48(s, 3H), 2.78(m, 1H), 2.90(dt, 1H), 3.09(d, 1H), 3.21(m, 1H), 3.60(d, 1H), 3.97(d, 1H), 4.49(dt, 2H), 4.94(bs, 1H), 5.30–5.25(m, 1H), 5.43–5.36(m, 1H), 5.96(s, 1H), 6.10–5.98(m, 1H), 6.56(dd, 1H), 6.86–6.78(m, 3H), 6.95–6.91(m, 2H), 7.05(d, 1H); MS(APCI)m/z(rel intensity) 459.4(39), 665.5(100). 71% yield. |

-continued

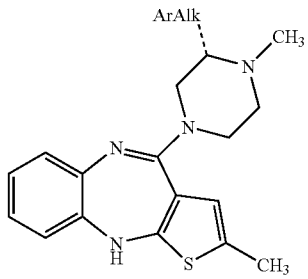

| No: | ArAlk | Data |
|---|---|---|
| 94 | CH₂(pyridin-2-yl) | mp 94–102° C.; ¹H NMR(CDCl₃)δ2.18(s, 3H), 2.44(dd, 1H), 2.49(s, 3H), 2.70(dd, 1H), 2.76(dt, 1H), 2.95–2.84(m, 2H), 3.23(ddd, 1H), 3.30(dd, 1H), 3.58(d, 1H), 3.93(d, 1H), 4.95(bs, 1H), 6.08(s, 1H), 6.57(dd, 1H), 6.84(ddd, 1H), 6.98–6.89(m, 2H), 7.19–7.09(m, 2H), 7.57(dt, 1H), 8.55(m, 1H); MS (APCI)m/z(rel intensity)311.3(100), 404.3(74). 82% yield. |
| 95 | (R)CH₂Ph | mp 64–82° C.; ¹H NMR(CDCl₃)δ2.12(s, 3H), 2.36–2.48(m, 3H), 2.49(s, 3H), 2.79(ddd, 1H), 2.92(ddd, 1H), 3.12–3.23(m, 2H), 3.58(m, 1H), 3.94(m, 1H), 4.90(s, 1H), 5.96(s, 1H), 6.57(d, 1H), 6.82–6.86(m, 1H), 6.91–6.96(m, 2H), 7.14–7.29(m, 5H); MS(APCI)m/z(rel intensity)403(100), 346(80). 87% yield. 89% yield. |
| 100 | CH₂(naphthalen-2-yl) | mp 89–102° C.; ¹H NMR(CDCl₃): δ1.70(bs, 3H), 2.43(m, 1H), 2.50(m, 1H), 2.52(s, 3H), 2.59(m, 1H), 2.86(m, 1H), 2.93(m, 1H), 3.22(m, 1H), 3.34(dd, 1H), 3.62(m, 1H), 4.02(m, 1H), 4.86(s, 1H), 5.83(s, 1H), 6.55(d, 1H), 6.80–6.92(m, 3H), 7.30(d, 1H), 7.44(m, 2H), 7.60(s, 1H), 7.73–7.83(m, 3H); MS (APCI)m/z(rel intensity)453(100). 71% yield. |
| 101 | CH₂(naphthalen-1-yl) | mp 98–116° C.; ¹H NMR(CDCl₃): δ1.87(bs, 3H), 2.47(m, 1H), 2.64(m, 1H), 2.65(s, 3H), 2.80–2.94(m, 2H), 3.00(m, 1H), 3.23(m, 1H), 3.43(m, 1H), 3.77(dd, 1H), 3.97(m, 1H), 4.92(s, 1H), 5.72(bs, 1H), 6.53(d, 1H), 6.80–6.92(m, 3H), 7.28–7.36(m, 2H), 7.45–7.55(m, 2H), 7.71(d, 1H), 7.86(d, 1H), 8.07(d, 1H); MS(APCI)m/z(rel intensity)453(100). 58% yield. |
| 102 | CH₂(4-CH₃)Ph | mp 81–93° C.; ¹H NMR(CDCl₃): δ2.12(s, 3H), 2.31(s, 3H), 2.45–2.35(m, 3H), 2.49(s, 3H), 2.82–2.72(m, 1H), 2.92(dt, 1H), 3.23–3.09(m, 2H), 3.61(d, 1H), 4.00(bd, 1H), 4.90(s, 1H), 5.96(bs, 1H), 6.58–6.55(m, 1H), 6.85(ddd, 1H), 6.96–6.92(m, 2H), 7.09–7.02(m, 4H); MS(APCI)m/z(rel intensity)417.4 (100). 73% yield |
| 103 | CH₂(3-CH₃)Ph | mp 67–83° C.; ¹H NMR(CDCl₃): δ2.31(s, 3H), 2.40(s, 3H), 2.47–2.36(m, 3H), 2.49(s, 3H), 2.86–2.76(m, 1H), 2.91(dt, 1H), 3.25–3.06(m, 2H), 3.61(d, 1H), 3.99–3.88(m, 1H)4.89(s, 1H), 5.97(s, 1H), 6.57(d, 1H), 6.88–6.81(m, 1H), 7.02–6.96(m, 5H), 7.19–7.10(m, 1H); MS(APCI)m/z(rel intensity)417.3 (100). 74% yield. |
| 104 | CH₂(2-F)Ph | mp 69–81° C.; ¹H NMR(CDCl₃): δ2.14(s, 3H), 2.52(s, 3H), 2.53–2.38(m, 3H), 2.95–2.82(m, 2H), 3.26–3.17(m, 2H), 3.58(d, 1H), 3.95(d, 1H), 4.90(s, 1H), 6.03(s, 1H), 6.58–6.54(m, 1H), 6.87–6.82(m, 1H), 7.05–6.90(m, 4H), 7.21–7.14(m, 2H); MS(APCI)m/z(rel intensity)421.3(100). 94% yield. |
| 105 | CH₂(3-F)Ph | mp 74–88° C.; ¹H NMR(CDCl₃): δ2.16(s, 3H), 2.48(s, 3H), 2.52–2.39(m, 3H), 2.82(dd, 1H), 2.91(dt, 1H), 3.17–3.14(m, 1H), 3.26–3.18(m, 1H), 3.57(d, 1H), 3.95(d, 1H), 4.19(s, 1H), 6.02(s, 1H), 6.58–6.55(m, 1H), 6.98–6.82(m, 6H), 7.26–7.18(m, 1H); MS(APCI)m/z(rel intensity)421.3(100). 81% yield. |
| 106 | CH₂(4-F)Ph | mp 76–84° C.; ¹H NMR(CDCl₃): δ2.08(s, 3H), 2.43(s, 3H), 2.45–2.23(m, 3H), 2.76–2.65(m, 1H), 2.86(dt, 1H), 3.07(d, 1H), 3.22–3.07(m, 1H), 3.52(bd, 1H), 3.90(bd, 1H), 5.05–4.79(m, 1H), 5.90(s, 1H), 6.50(d, 1H), 6.81–6.75(m, 1H), 6.92–6.83(m, 4H), 7.08–7.02(m, 2H); MS(APCI)m/z(rel intensity)421.4 (100). 81% yield. |
| 107 | CH₂(3-CF₃)Ph | mp 88–105° C.; ¹H NMR(CDCl₃): δ2.11(s, 3H), 2.51(s, 3H), 2.60–2.38(m, 3H), 2.96–2.78(m, 2H), 3.30–3.16(m, 2H), 3.59(bd, 1H), 3.92(bd, 1H), 4.92(s, 1H), 5.99(s, 1H), 6.57(d, 1H), 6.96–6.82(m, 3H), 7.50–7.36(m, 4H); MS(APCI)m/z(rel intensity)471.3(100). 57% yield. |

-continued

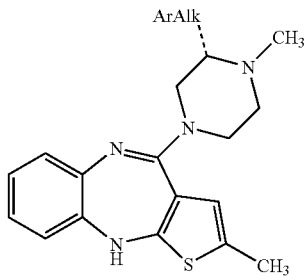

| No: | ArAlk | Data |
|---|---|---|
| 108 | CH₂(2-CF₃)Ph | ¹H NMR(CDCl₃): δ2.14(s, 3H), 2.46(m, 2H), 2.50(s, 3H), 2.62(m, 1H), 2.70(m, 1H), 2.90–2.97(m, 2H), 3.24(m, 1H), 3.42(dd, 1H), 3.46(dd, 1H), 4.93(s, 1H), 6.04(s, 1H), 6.57(d, 1H), 6.86(t, 1H), 6.90–6.97(m, 2H), 7.26–7.40(m, 2H), 7.43(t, 1H), 7.64(d, 1H); MS(APCI)m/z(rel intensity)471(100). 58% yield. |
| 109 | CH₂(2-OCH₃)Ph | mp 81–93° C.; ¹H NMR(CDCl₃): δ2.12(s, 3H), 2.49(m, 3H), 2.51(s, 3H), 2.90–2.83(m, 1H), 2.92(dt, 1H), 3.25–3.16(m, 2H), 3.57(d, 1H), 3.79(s, 3H), 3.96(bd, 1H), 4.89(s, 1H), 5.98(bs, 1H); 6.56(dd, 1H), 6.87–6.81(m, 3H), 6.95–6.91(m, 2H), 7.08(d, 1H), 7.19(dt, 1H); MS(APCI)m/z(rel intensity)433.4 (100). 73% yield. |
| 110 | CH₂(3-OCH₃)Ph | mp 70–82° C.; ¹H NMR(CDCl₃): δ2.13(s, 3H), 2.48–2.37(m, 3H), 2.49(s, 3H), 2.79(dd, 1H), 2.91(dt, 1H), 3.23–3.11(m, 2H), 3.62(d, 1H), 3.77(s, 3H), 3.98(d, 1H), 4.90(bs, 1H), 5.99(s, 1H), 6.57(d, 1H), 6.77–6.69(m, 3H), 6.85(ddd, 1H), 6.95–6.92(m, 2H), 7.18(t, 1H); MS(APCI)m/z(rel intensity)433.3 (100). 68% yield. |
| 111 | CH₂(4-OCH₃)Ph | mp 74–88° C.; ¹H NMR(CDCl₃): δ2.10(s, 3H), 2.44–2.29(m, 3H), 2.46(s, 3H), 2.74(dd, 1H), 2.89(dt, 1H), 3.08(d, 1H), 3.16(ddd, 1H), 3.58(d, 1H), 3.76(s, 3H), 3.97(d, 1H), 4.90(bs, 1H), 5.94(s, 1H), 6.54(d, 1H), 6.84–6.76(m, 3H), 6.93–6.89(m, 2H), 7.06–7.02(m, 2H); MS(APCI)m/z(rel intensity)433.3(50), 242.5(100). 74% yield. |
| 112 | CH₂(3,4-di-Cl)Ph | mp 87–94° C.; ¹H NMR(CDCl₃): δ2.17(s, 3H), 2.38–2.50(m, 3H), 2.47(s, 3H), 2.82–2.93(m, 2H), 3.08(ddd, 1H), 3.24(ddd, 1H), 3.57(d, 1H), 3.91(m, 1H), 4.92(s, 1H), 6.01(s, 1H), 6.57(d, 1H), 6.86(m, 1H), 6.92–6.97(m, 2H), 7.01(dd, 1H), 7.27(d, 1H), 7.32(d, 1H); MS(APCI)m/z(rel intensity)471(100), 473 (62). 54% yield. |
| 113 | CH₂(indol-3-yl) | mp 138–156° C.; ¹H NMR(CDCl₃): δ1.90(s, 3H), 2.43(dt, 1H), 2.55(s, 3H), 2.67–2.51(m, 2H), 2.90–2.78(m, 1H), 2.94(bd, 1H), 3.31–3.17(m, 2H), 3.74(bd, 1H), 3.98(bd, 1H), 4.94(bs, 1H), 5.87(s, 1H), 6.51(d, 1H), 6.83–6.77(m, 1H), 6.93–6.88(m, 2H), 6.96(s, 1H), 7.10(dt, 1H), 7.16(dt, 1H), 7.31(d, 1H), 7.59(d, 1H), 8.18(bs, 1H); MS(APCI)m/z(rel intensity)442.4 (100). 63% yield. |
| 114 | CH₂(thiophen-2-yl) | mp 85–87° C.; ¹H NMR(CDCl₃): δ2.20(s, 3H), 2.39–2.48(m, 2H), 2.47(s, 3H), 2.79–2.85(m, 2H), 2.90(ddd, 1H), 3.18(ddd, 1H), 3.27(dd, 1H), 3.73(m, 1H), 3.97(m, 1H), 4.91(s, 1H), 6.11(s, 1H), 6.57(d, 1H), 6.79–7.00(m, 5H), 7.13(d, 1H); MS (APCI)m/z(rel intensity)409(100). 53% yield. |
| 115 | CH₂(benzo(b)thiophen-3-yl) | mp 84–97° C.; ¹H NMR(CDCl₃): δ1.99(s, 3H), 2.46(dt, 1H), 2.56(s, 3H), 2.70–2.62(m, 1H), 2.76(dd, 1H), 2.97–2.85(m, 2H), 3.26(t, 1H), 3.34(dd, 1H), 3.67(d, 1H), 3.94(d, 1H), 4.88(bs, 1H), 5.88(s, 1H), 6.53(d, 1H), 6.85–6.79(m, 1H), 6.94–6.88(m, 2H), 7.16(s, 1H), 7.33(dd, 1H), 7.37(dd, 1H), 7.74(d, 1H), 7.83(d, 1H); MS(APCI)m/z(rel intensity)459.3(100). 82% yield. |
| 118 | CH₂(2-Cl)Ph | ¹H NMR(CDCl₃): δ2.14(s, 3H), 2.34–2.67(m, 3H), 2.54(s, 3H), 2.91–2.96(m, 2H), 3.22(ddd, 1H), 3.38(m, 1H), 3.52(m, 1H), 3.93(m, 1H), 4.92(s, 1H), 6.04(s, 1H), 6.56(d, 1H), 6.86(t, 1H), 6.92–6.97(m, 2H), 7.12–7.19(m, 3H), 7.36(m, 1H); MS (APCI)m/z(rel intensity)437(100), 439(39). |
| 119 | CH₂(3-Cl)Ph | ¹H NMR(CDCl₃): δ2.16(s, 3H), 2.42–2.48(m, 3H), 2.49(s, 3H), 2.83(m, 1H), 2.90(m, 1H), 3.13(dd, 1H), 3.24(ddd, 1H), 3.57(ddd, 1H), 3.93(m, 1H), 4.92(s, 1H), 6.01(s, 1H), 6.57(d, 1H), 6.85(m, 1H), 6.93–6.96(m, 2H), 7.05(m, 1H), 7.16–7.20(m, 3H); MS(APCI)m/z(rel intensity)437(100), 439(44). |

-continued

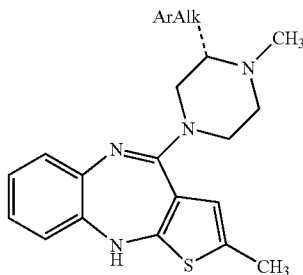

| No: | ArAlk | Data |
|---|---|---|
| 120 | CH₂(4-Cl)Ph | mp 64–77° C.: ¹H NMR(CDCl₃): δ2.16(s, 3H), 2.48(s, 3H), 2.51–2.33(m, 3H), 2.78(dd, 1H), 2.90(dt, (1H), 3.19(ddd, 1H), 3.57(d, 1H), 3.97(bd(1H), 4.91(bs, 1H), 5.96(d, 1H), 6.57(dd, 1H), 6.85(ddd, 1H), 6.96–6.91(m, 2H), 7.12–7.07(m, 2H), 7.27–7.21(m, 2H); MS(APCI)m/z(rel intensity)437(100), 439(44). |
| 121 | CH₂(4-OPh)Ph | mp 94–101° C.; ¹H NMR(CDCl₃)δ2.17(s, 3H), 2.48–2.38(m, 2H), 2.49(s, 3H), 2.81(m, 1H), 2.92(dt, 1H), 3.14(d, 1H), 3.23(t, 1H), 3.61(d, 1H), 3.94(d, 1H), 5.10–4.91(m, 1H), 6.08(bs, 1H), 6.56(d, 1H), 6.83(ddd, 1H), 6.98–6.88(m, 6H), 7.14–7.05(m, 4H), 7.35–7.29(m, 2H); MS(APCI)m/z(rel intensity)495.7 (100). 80% yield. |
| 122 | CH₂(3-OPh)Ph | mp. 89–93° C.; ¹H NMR(CDCl₃)δ2.14(s, 3H), 2.50–2.40(m, 3H), 2.47(s, 3H), 2.80(bs, 1H), 2.93(d, 1H), 3.14(d, 1H), 3.28(bs, 1H), 3.60(d, 1H), 3.96(d, 1H), 4.90(s, 1H), 5.97(s, 1H), 6.56(dd, 1H), 6.90–6.82(m, 3H), 7.01–6.91(m, 5H), 7.09(ddd, 1H), 7.24(t, 1H), 7.36–7.30(m, 2H); MS(APCI)m/z(rel intensity)495.4(100). 94% yield. |
| 123 | CH₂(3-O-i-Pr)Ph | ¹H NMR(CDCl₃)δ1.29(dd, 6H), 2.14(s, 3H), 2.40(m, 3H), 2.48(s, 3H), 2.80(m, 1H), 2.90(dt, 1H), 3.15(m, 2H), 3.61(d, 1H), 3.98(m, 1H), 4.51(m, 1H), 4.89(s, 1H), 5.98(s, 1H), 6.57(d, 1H), 6.72(m, 3H), 6.84(m, 1H), 6.93(d, 12H), 7.16(t, 1H); MS(ESI)m/z(rel intensity)461(100). Product isolated as a yellow solid |
| 124 | CH₂(2,4-di-OCH₃)Ph | ¹H NMR(CDCl₃)δ2.12(s, 3H), 2.31–2.47(m, 3H), 2.49(s, 3H), 2.82(m, 1H), 2.91(ddd, 1H), 3.11(dd, 1H), 3.19(ddd, 1H), 3.58(m, 1H), 3.75(s, 3H), 3.78(s, 3H), 3.97(m, 1H), 4.94(s, 1H), 5.97(s, 1H), 6.36–6.45(m, 2H), 6.56(d, 1H), 6.83(m, 1H), 6.91–6.97(m, 3H); MS(APCI)m/z(rel intensity)463(100). Product isolated as a yellow solid. |

Example 125

2-Methyl-4H-3-thia-4,9-diazabenzo[f]azulen-10-ylamine

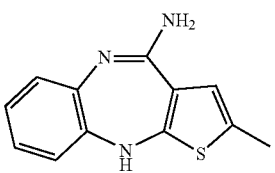

Dissolve 2-methyl-4H-3-thia-4,9-diazabenzo[f]azulen-10-ylamine hydrochloride (6 g, 22.6 mmoles) in a 5:1 mixture of dichloromethane and commercial 7N ammonia-methanol, wash with half a volume of 5N aqueous sodium hydroxide. Separate the organic layer and extract the aqueous layer twice with dichloromethane. Combine all organic extracts, dry over magnesium sulfate, filter and concentrate in vacuo to yield the title free base as an orange solid: ¹H NMR (DMSO-d₆): δ8.10–7.80 (br, 1H), 7.30–6.90 (br, 2H), 6.80–6.65 (m, 3H), 6.59 (br dd, 1H, J=7.6, 1.6 Hz), 6.52 (br s, 1H), 2.22 (br s, 3H).

Example 126

2-Methyl-4H-3-thia-4,9-diaza-benzo[f]azulene-10-ylamine

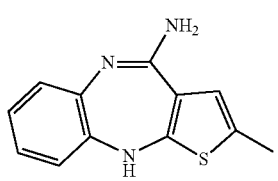

Slurry 2-methyl-4H-3-thia-4,9-diaza-benzo[f]azulene-10-ylamine hydrochloride (5.2 g, 19.5 mmol) in water and add 1N sodium hydroxide (19.5 mL, 19.5 mmol). Add methanol to facilitate stirring and extract with methylene chloride. Purify the methylene chloride extracts by silica gel chromatography using 7N ammonia in methanol-methylene chloride (5%) as the eluent to give (4.13 g, 92%) of the title compound.

Example 127 and Example 127a (S)-1,4-Dibenzyl-2-vinylpiperazine (R)-1,4-Dibenzyl-2-vinylpiperazine Add anhydrous tetrahydrofuran (4.5 L) to a 10 L flange-neck flask equipped with an air stirrer rod and paddle, thermometer, and nitrogen inlet and outlet tubes. Purge with dry nitrogen gas (inlet tube had a sintered end for maximum gas dispersal) the body of the liquid for 1 h, add tris (dibenzylideneacetone)dipalladium(0) chloroform adduct (36.0 g, 34.8 mmol). Add isopropyl phosphite (67.8 mL, 0.275 mol) in one lot to the mixture still under nitrogen and stir. After 5 minutes, the color lightens from purple to amber. Add dibenzylethylenediamine (322.0 g, 1.34 mol) in one lot, followed by the dropwise addition of cis-1,4-diacetoxy-2-butene (214 mL, 1.34 mol) over 15 minutes stir under nitrogen for 18 hours. Remove the solvent in vacuo at 40° C. and dissolve the residual oil in diethyl ether (2.5 L) and extract with 1N aq. sodium hydroxide (2×2 L). Wash the bulked aqueous extracts with diethyl ether (2×) and basify to pH 14 using 5N aq. sodium hydroxide and extract with diethyl ether (3×). Dry the bulked ethereal extracts over magnesium sulphate, filter and evaporate to dryness in vacuo at 40° C. Purification by chromatography on silica (117 kg) using 1% methanol/ether (can also use dichloromethane) gives a pale yellow oil (377.35 g, 96%) 1H NMR and Mass Spec are consistent with product.

Dissolve the mixture of isomers in ethyl acetate (3670 mL) and add portionwise to a hot solution of (S)-(+)-mandelic acid (385 g, 2 eq.) in ethyl acetate (3850 mL), starting at 72° C. Chill the mixture to 0° C. and seed with crystals (which were previously obtained from an earlier resolution). Place the mixture in the freezer (−20° C.) overnight. Scrape the crystalline solid away from the sides of the flask and allow the mixture to warm to 0° C. Isolate the solid dry. Further dry the material in vacuo at room temperature. Yield=252.6 g, white, crystalline solid of the S-mandelic acid salt of the (R)-1,4-dibenzyl-2-vinylpiperazine.

Evaporate the filtrate to dryness in vacuo at 40° C. to leave an amber oil. Dissolve the filtrate in dichloromethane (2 L) and wash the solution with 1N aq. sodium hydroxide (2 L+1 L), brine (1 L) and dry over magnesium sulphate. Filter and evaporate to dryness in vacuo at 45° C. to yield the recovered free base. Further dry by vacuum. Extract the aqueous liquors with dichloromethane to further recover any remaining free base (207.6 g). Chiral HPLC showed the material to consist of a 85:15 ratio of isomers in favour of the required isomer.

Add (R)-(−)-mandelic acid (216 g, 1.42 mol) and ethyl acetate (2.5 L) to a 10 liter flange-neck flask equipped with an air stirrer rod and paddle, thermometer and water condenser and warm the suspension to 60° C. Add a solution of free base (207.6 g, 0.71 mol) in ethyl acetate (500 mL) and allow to cool down to room temperature and place in the freezer overnight (at 35° C. solid starts to precipitate). Isolate the crystalline solid by filtration and pull dry. Further dry in vacuo at room temperature(290.34 g).

Recrystallize from hot ethyl acetate (2.3 L) at 70° C. Allow this solution to cool down to room temperature overnight after seeding. Filtration and drying in vacuo at room temperature gives the R-mandelic acid salt of the (S)-1,4dibenzyl-2-vinylpiperazine from which the free base may be prepared (225.44 g). Chiral HPLC showed: 98.74%+ 1.26%: $^1$H NMR, OMSO $d_6$): δ7.20–7.35 (m, 10H); 5.75–5.90 (m, 1H); 5.15–5.30 (q, 2H); 3.85–3.95 (d, 1H); 3.40–3.45 (s, 2H); 3.00–3.10 (d, 1H); 2.80–2.90 (t, 1H); 2.55–2.60 (d, 3H); 1.95–2.10 (m, 311).

Example 128

(S)-1,4-Dibenzyl-2-(2-pyridin-2-yl-ethyl)-piperazine

Combine 9-borabicyclo[3.3.1]nonane (62.6 mL, 31.3 mmol, 0.5 M in THF) and (S)-1,4-dibenzyl-2-vinyl-piperazine. (2.29 g, 7.83 mmol) and stir at ambient temperature. After 18 hours, add triphenylphosphine (657 mg, 2.50 mmol), tetrakis(triphenylphosphine) palladium(0) (362 mg, 0.31 mmol), and 2-bromopyridine (1.12 mL, 11.7 mmol). Add 3M NaOH (6.4 mL, 19.3 mmol) slowly, and gas evolution will occur. Heat at reflux. After 24 hours, cool to ambient temperature, add 5N HCl (50 mL), and stir 1 hour. Dilute with 0.2 N HCl, extract with diethyl ether, and discard the diethyl ether extracts. Add 5N NaOH to the acidic aqueous solution until pH is 12–14. Extract with diethyl ether. Wash the diethyl ether extracts with water and brine, dry over sodium sulfate, filter and concentrate under reduced pressure. Purify by silica gel chromatography using 2N ammonia in methanol-methylene chloride (0.5%–3%) as the eluent to give the title compound (2.3 g, 79%): mp 83–86° C.; mass spectrum (ion spray): m/z=372 (M+1). Analysis calculated for $C_{25}H_{29}N_3$: C, 80.82; H, 7.87; N, 11.31. Found: C, 80.56; H, 7.60; N, 11.30.

Example 129

(S)-1,4-Dibenzyl-2-(2-pridin-4-yl-ethyl)-piperazine

Prepared by the method in Example 128, using 9-borabicyclo[3.3.1]nonane (71.4 mL, 35.7 mmol, 0.5 M in THF), (S)-1,4-dibenzyl-2-vinyl-piperazine (2.61 g, 8.92 mmol), triphenylphosphine (749 mg, 2.86 mmol), tetrakis(triphenylphosphine)palladium(0) (413 mg, 0.36 mmol), 4-bromopyridine hydrochloride (2.60 g, 13.4 mmol) and 3M NaOH (10.4 mL, 31.2 mmol) to give the title compound (1.87 g, 56%): mp 96–98° C.; mass spectrum (ion spray): m/z=372 (M+1). Analysis calculated for $C_{25}H_{29}N_3$: C, 80.82; H, 7.87; N, 11.31. Found: C, 80.80; H, 7.99; N, 11.18.

Example 130

(S)-2-(2-Pyridin-2-yl-ethyl)-piperazine

Dissolve (S)-1,4-dibenzyl-2-(2-pyridin-2-yl-ethyl)-piperazine (2.86 g, 7.69 mmol) in ethanol (50 mL). Add ammonium formate (2.43 g, 38.5 mmol) and palladium (430 mg, 5 wt. % on carbon) and heat to reflux. After 6 hours 40 minutes, filter the palladium on carbon and concentrate the filtrate. Purify by silica gel chromatography using 7N ammonia in methanol-methylene chloride (5%–15%) as the eluent to give the title compound (1.1 g, 75%): mp 83–87° C.; mass spectrum (ion spray): m/z=192 (M+1). Analysis calculated for $C_{11}H_{17}N_3$: C, 69.07; H, 8.96; N, 21.97. Found: C, 68.84; H, 8.85; N, 21.65.

Example 131

(S)-2-(2-Pyridin-4-yl-ethyl)-piperazine

Dissolve (S)-1,4-dibenzyl-2-(2-pyridinyl-ethyl)-piperazine (2.14 g, 5.76 mmol) in ethanol (40 mL). Add ammonium formate (2.18 g, 34.6 mmol) and palladium (430 mg, 5 wt. % on carbon) and heat to reflux. After 6 hours 30 minutes, filter the palladium on carbon and concentrate the filtrate. Purify by silica gel chromatography using 7N ammonia in methanol-methylene chloride (5%–15%) as the eluent to give 945 mg (86%) of the title compound: mp 113–116° C.; mass spectrum (ion spray): m/z=192 (M+1). Analysis calculated for $C_{11}H_{17}N_3$: C, 69.07; H, 8.96; N, 21.97. Found: C, 69.08; H, 8.77; N, 21.81.

Example 132

(S)-2-Methyl-10-(3-(2-pyridin-2-yl-ethyl)-piperazin-1-yl)-4H-3-thia-4,9-diaza-benzo[f]azulene trihydrochloride

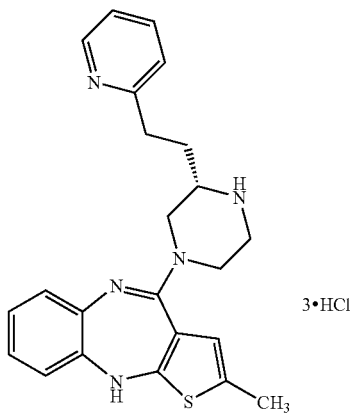

Combine (S)-2-(2-pyridin-2-yl-ethyl)-piperazine (470 mg, 2.46 mmol), 2-methyl-4H-3-thia-4,9-diaza-benzo[f]azulen-10-ylamine (282 mg, 1.23 mmol), toluene (8 mL), and DMSO (2 mL). Heat at 110° C. After 41 hours, cool to ambient temperature and dilute with ethyl acetate and water. Extract with ethyl acetate. Wash the extracts with water and brine, dry over sodium sulfate, filter and concentrate the filtrate. Purify by silica gel chromatography using 7N ammonia in methanol-methylene chloride (2.5%) as the eluent to give 270 mg. Purify again by silica gel chromatography using 2N ammonia in methanol-methylene chloride (2%–5%) as the eluent to give the free base. Crystallize as the trihydrochloride salt from ethyl acetate and ethanol to give the title compound (20 g, 40%): mp 220–224° C. dec.; mass spectrum (ion spray): m/z=404 (M+1). Analysis calculated for $C_{23}H_{25}N_5S.2.7HCl$: C, 55.03; H, 5.56; N, 13.95. Found: C, 55.22; H, 5.59; N, 13.81.

Example 133

(S)-2-Methyl-10-(3-(2-pyridin-4-yl-ethyl)-piperazin-1-yl)-4H-3-thia-49-diaza-benzo[f]azulene trihydrochloride

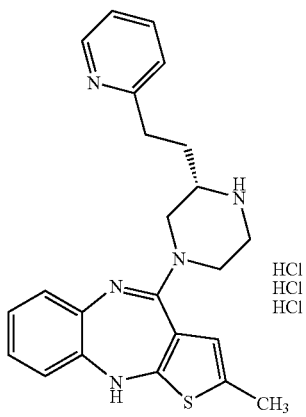

Combine (S)-2-(2-pyridin-4-yl-ethyl)-piperazine (889 mg, 4.65 mmol), 2-methyl-4H-3-thia-4,9-diaza-benzo[f]azulen-10-ylamine (533 mg, 2.32 mmol), toluene (12 mL), and DMSO (3 mL). Heat at 110° C. After 72 hours, cool to ambient temperature and dilute with ethyl acetate and water. Extract with ethyl acetate. Wash the extracts with water and brine, dry over sodium sulfate, filter and concentrate the filtrate. Purify by silica gel chromatography using 2N ammonia in methanol-methylene chloride (2%–4%) as the eluent to give the free base. Crystallize as the trihydrochloride salt from ethyl acetate and ethanol to give the title compound (486 mg, 52%): mp 234–239° C. dec.; mass spectrum (ion spray): m/z=404 (M+1). Analysis calculated for $C_{23}H_{25}N_5S.3HCl$: C, 53.86; H, 5.50; N, 13.65. Found: C, 53.71; H, 5.79; N, 13.37.

Example 134

(S)-1,4-Dibenzyl-2-(2-(4-fluoro-phenyl-ethyl)-piperazine

Combine (S)-1,4-dibenzyl-2-vinyl-piperazine (2.0 g, 6.84 mmol) and 9-borabicyclo[3.3.1]nonane (82.1 mL, 41.04 mmol, 0.5 M in THF) and stir at ambient temperature. After 6 hours 30 minutes, add 1-fluoro-4-iodo-benzene (2.3 g, 10.26 mmol), triphenylphosphine (287.0 mg, 1.09 mmol), tetrakis(triphenylphosphine) palladium(0)(158.0 mg, 0.14 mmol), and 3N NaOH (5.6 ml) and stir at 60° C. After 22 hours, add ethanolamine (10.0 mL) and dilute the mixture with water. Extract with ethyl acetate and combine, wash (brine), dry (sodium sulfate), and reduce the extracts to residue. Purify the residue on silica gel using ethyl acetate/hexanes (5:95) to give a yellow oil. Dissolve the yellow oil in acetic acid/methanol (1:9) and apply to an SCX column. Wash the column with methanol followed by 2N ammonia in methanol to give the title compound: mp 79–82° C.; mass spectrum (ion spray): m/z=389.4 (M+1).

Example 135

(S)-1,4-Dibenzyl-2-(2-(3-fluoro-phenyl)-ethyl)-piperazine

Combine (S)-1,4-dibenzyl-2-vinyl-piperazine (2.0 g, 6.84 mmol) and 9-borabicyclo[3.3.1]nonane (82.1 mL, 41.04 mmol, 0.5 M in THF) and stir at ambient temperature. After 24 hours, add 1-fluoro-3-iodo-benzene (2.3 g, 10.26 mmol), triphenylphosphine (287.0 mg, 1.09 mmol), tetrakis(triphenylphosphine) palladium(0)(158.0 mg, 0.14 mmol), and 3N NaOH (5.6 mL) and stir at 60° C. After 22 hours, add ethanolamine (10.0 mL) and dilute the mixture with water. Extract with ethyl acetate and combine, wash (brine), dry (sodium sulfate), and reduce the extracts to residue. Purify the residue on silica gel using ethyl acetate/hexanes (5:95) to give a yellow oil. Dissolve the yellow oil in acetic acid/methanol (1:9) and apply to an SCX column. Wash the column with methanol followed by 2N ammonia in methanol to give the title compound: mp 69–71° C.; mass spectrum (ion spray): m/z=389.4 (M+1).

Example 136

(S)-1,4-Dibenyl-2-(2-(2-fluoro-phenyl)-ethyl)-piperazine

Combine (S)-1,4-dibenzyl-2-vinyl-piperazine (2.0 g, 6.84 mmol) and 9-borabicyclo[3.3.1]nonane (82.1 mL, 41.04 mmol, 0.5 M in THF) and stir at ambient temperature. After 24 hours, add 1-fluoro-2-iodo-benzene (2.3 g, 10.26 mmol), triphenylphosphine (287.0 mg, 1.09 mmol), tetrakis(triphenylphosphine) palladium(0)(158.0 mg, 0.14 mmol), and 3N NaOH (5.6 mL) and stir at 60° C. After 22 hours, add ethanolamine (10.0 mL) and dilute the mixture with water. Extract with ethyl acetate and combine, wash (brine), dry (sodium sulfate), and reduce the extracts to residue Purify the residue on silica gel using ethyl acetate/hexanes (5:95) to give a yellow oil. Dissolve the yellow oil in acetic acid/methanol (1:9) and apply to an SCX column. Wash the column with methanol followed by 2N ammonia in methanol to give the title compound: mp 62–66° C.; mass spectrum (ion spray): m/z=389.4 (M+1).

Example 137

(S)-2-(2-(4-Fluoro-phenyl)-ethyl)-piperazine

Combine (S)-1,4-dibenzyl-2-(2-(4-fluoro-phenyl)-ethyl)-piperazine (1.94 g, 4.99 mmol), ammonium formate (1.57 g, 24.95 mmol), 5% Pd/C (241.1 mg), and ethanol (50 mL) and stir and heat the mixture at reflux. After 4 hours 30 minutes, cool to ambient temperature and remove the catalyst by vacuum filtration through celite. Reduce the filtrate to residue and dissolve it in 1N NaOH. Extract with dichloromethane and combine, wash (brine), dry (sodium sulfate), and reduce the extracts to residue. Purify the residue on silica gel using dichloromethane/2N ammonia in methanol (80:20) to give the title compound as a white solid: mp 112–114° C.; mass spectrum (ion spray): m/z=209.3 (M+1); Analysis for $C_{12}H_{17}FN_2$: calcd: C, 69.20; H, 8.23; N, 13.45; found: C, 68.97; H, 8.14; N, 13.21.

Example 138

(S)-2-(2-(3-Fluoro-phenyl)-ethyl)-piperazine

Combine (S)-1,4-dibenzyl-2-(2-(3-fluoro-phenyl)-ethyl)-piperazine (1.96 g, 5.04 mmol), ammonium formate (1.59 g, 25.18 mmol), 5% Pd/C (243.3 mg), and ethanol (50 mL). Stir and heat the mixture at reflux. After 4 hours 30 minutes, cool to ambient temperature and remove the catalyst by vacuum filtration through celite. Reduce the filtrate to residue and purify it on silica gel using dichloromethane/2N ammonia in methanol (80:20) to give the title compound as a white solid: mp 95–99° C.; mass spectrum (ion spray): m/z=209.3 (M+1); Analysis for $C_{12}H_{17}FN_2$: calcd: C, 69.20; H, 8.23; N, 13.45; found: C, 69.13; H, 8.40; N, 13.28.

Example 139

(S)-2-(2-(2-Fluoro-phenyl)-ethyl)-piperazine

Combine (S)-1,4-dibenzyl-2-(2-(2-fluoro-phenyl)-ethyl)-piperazine (1.06 g, 2.73 mmol), ammonium formate (861.0 mg, 13.66 mmol), 5% Pd/C (132.0 mg), and ethanol (50 mL). Stir and heat the mixture at reflux. After 4 hours 30 minutes, cool to ambient temperature and remove the catalyst by vacuum filtration through celite. Reduce the filtrate to residue and purify it on silica gel using dichloromethane/2N ammonia in methanol (80:20) to give (443.8 mg, 78%) of the title compound as a white solid: mp 94–99° C.; mass spectrum (ion spray): m/z=209.3 (M+1); Analysis for $C_{12}H_{17}FN_2$: calcd: C, 69.20; H, 8.23; N, 13.45; found: C, 69.20; H, 8.26; N, 13.57.

Example 140

(S)-2-Phenethyl-piperazine

Combine (S)-1,4-dibenzyl-2-phenethyl-piperazine (5.15 g, 13.90 mmol), ammonium formate (4.38 g, 69.49 mmol), 5% Pd/C (672.5 mg), and ethanol (100 mL). Stir and heat the mixture at reflux. After 3 hours, cool to ambient temperature and remove the catalyst by vacuum filtration through celite. Reduce the filtrate to residue and purify by silica gel chromatography using dichloromethane/7N ammonia in methanol (90:10) to give the title compound as a white solid: mp 116–119° C.; mass spectrum (ion spray): m/z=191.2 (M+1); Analysis for $C_{12}H_{18}N_2$: calcd: C, 75.74; H, 9.53; N, 14.72; found: C, 75.90; H, 9.57; N, 14.59.

Example 141

(S)-1,4-Dibenyl-2-(2-(4-methoxy-phenyl)-ethyl)-piperazine

Combine (S)-1,4-dibenzyl-2-vinyl-piperazine (2.0 g, 6.84 mmol) and 9-borabicyclo[3.3.1]nonane (82.1 mL, 41.04 mmol, 0.5 M in THF) and stir at ambient temperature. After 6 hours and 30 minutes, add 1-iodo-4-methoxy-benzene (2.4 g, 10.26 mmol), triphenylphosphine (287.0 mg, 1.09 mmol), tetrakis(triphenylphosphine) palladium(0)(158.0 mg, 0.14 mmol), and 3N NaOH (5.6 mL) and stir at 60° C. After 22 hours, add ethanolamine (10.0 ml) and dilute the mixture with water. Extract with ethyl acetate and combine, wash (brine), dry (sodium sulfate), and reduce the extracts to residue. Purify the residue on silica gel using ethyl acetate/hexanes (5:95) to give a yellow oil. Dissolve the yellow oil in acetic acid/methanol (1:9) and apply to an SCX column. Wash the column with methanol followed by 7N ammonia in methanol to give the title compound: mp 88–91° C.; mass spectrum (ion spray): m/z=401.4 (M+1).

Example 142

(S)-1,4-Dibenzyl-2-(2-(3-methoxy-phenyl)-ethyl)-piperazine

Combine (S)-1,4-dibenzyl-2-vinyl-piperazine (2.0 g, 6.84 mmol) and 9-borabicyclo[3.3.1]nonane (82.1 mL, 41.04 mmol, 0.5 M in THF) and stir at ambient temperature. After 6 hours and 30 minutes, add 1-iodo-3-methoxy-benzene (2.4 g, 10.26 mmol), triphenylphosphine (287.0 mg, 1.09 mmol), tetrakis(triphenylphosphine) palladium(0)(158.0 mg, 0.14 mmol), and 3N NaOH (5.6 mL) and stir at 60° C. After 22 hours, add ethanolamine (10.0 ml) and dilute the mixture with water. Extract with ethyl acetate and combine, wash (brine), dry (sodium sulfate), and reduce the extracts to residue. Purify the residue on silica gel using ethyl acetate/hexanes (5:95) to give a yellow oil. Dissolve the yellow oil in acetic acid/methanol (1:9) and apply to an SCX column. Wash the column with methanol followed by 7N ammonia in methanol to give the title compound: mp 73–75° C.; mass spectrum (ion spray): m/z=401.4 (M+1).

Example 143

1,4-Dibenzyl-2-styryl-piperazine

Combine 1,4-dibenzyl-2-vinyl-piperazine (200.0 mg, 0.68 mmol), styrene (142.5 mg, 1.37 mmol), bis(tricyclohexylphosphine)benzylidine ruthenium (IV) dichloride (168.8 mg, 0.21 mmol), and dichloromethane (8 mL) and stir at reflux. After 24 hours, the reaction mixture was filtered and reduced to residue. The title compound was observed by LC/MS: mass spectrum (ion spray): m/z=369.1 (M+1); $R_f$=0.49 (hexanes/ethyl acetate (40:60)).

Example 144

1,4-Dibenzyl-2-styryl-piperazine

Combine tri-o-tolylphosphine (1.05 g, 3.46 mmol), palladium acetate (175 mg, 0.78 mmol), triethylamine (3.26 mL, 23.4 mmol), iodobenzene (2.74 mL, 24.5 mmol), 1,4-dibenzyl-2-vinyl-piperazine (3.26 g, 11.1 mmol) and acetonitrile (50 mL) in a sealable vessel and purge with nitrogen. Seal the vessel and heat at 110° C. After 20 hours 45 minutes, cool to ambient temperature and dilute with ethyl acetate. Filter and discard the solids. Concentrate the filtrate and purify by silica gel chromatography using ethyl acetate-hexanes (0–100%) as the eluent to give the title compound: mass spectrum (ion spray): m/z=369 (M+1); $^1$H NMR (DMSO-$d_6$): δ7.41 (d, 2H), 7.18–7.34 (m, 13H), 6.64 (d, 1H), 6.27 (dd, 1H), 3.94 (d, 1H), 3.46 (dd, 2H), 3.10 (d, 1H), 3.02 (dt, 1H), 2.56–2.70 (m, 3H), 2.05–2.19 (m, 3H).

Example 145

1,4-Bis-(toluene-4-sulfonyl)-2-vinyl-piperazine

Combine tris(dibenzylideneacetone)dipalladium(0)-chloroform adduct (503 mg, 0.49 mmol), racemic 2,2'-bis(diphenylphosphino)-1,1'-binaphthyl (606 mg, 0.97 mmol) and tetrahydrofuran (100 mL) and stir at ambient temperature. After 1 hour 30 minutes, add 1,4-bis-(toluene-4-sulfonyl)-ethane (7.17 g, 19.5 mmol), cis-2-butene-1,4-diol diacetate (3.10 mL, 19.5 mmol) and tetrahydrofuran (100 mL) and heat at 40° C. After 18 hours, cool to ambient temperature and concentrate under vacuum. Purify by silica gel chromatography using ethyl acetate-hexanes (20–60%) as the eluent. Recrystallize from ethyl acetate-hexanes to give the title compound: mp 177–178° C.; mass spectrum (ion spray): m/z=421 (M+1). Analysis calculated for $C_{20}H_{24}N_2O_4S_2$: C, 57.12; H, 5.75; N, 6.66. Found: C, 56.83; H, 5.26; N, 6.62.

Example 146

2-Styryl-1,4-bis-(toluene-4-sulfonyl)-piperazine

Combine tri-o-tolylphosphine (72 mg, 0.24 mmol), palladium acetate (12 mg, 0.05 mmol), triethylamine (0.22 mL, 1.6 mmol), iodobenzene (0.20 mL, 1.83 mmol), 1,4-bis-(toluene-4-sulfonyl)-2-vinyl-piperazine (320 mg, 0.76 mmol) and acetonitrile (8 mL) in a sealable vessel and purge with nitrogen. Seal the vessel and heat at 110° C. After 21 hours 45 minutes, cool to ambient temperature and dilute with ethyl acetate. Filter and discard the solids. Concentrate the filtrate and purify by silica gel chromatography using ethyl acetate-hexanes (0–30%) as the eluent to give a 8:1 ratio of the title compound to 1,4-bis-(toluene-4-sulfonyl)-2-vinyl-piperazine: mass spectrum (ion spray): m/z=497 (M+1); $^1$H NMR(DMSO-$d_6$): δ7.59 (d, 2H), 7.53 (d, 2H), 7.42 (d, 2H), 7.19–7.36 (m, 7H), 6.48 (d, 1H), 6.08 (dd, 1H), 4.62 (m, 1H), 3.70 (br d, 1H), 3.52 (m, 2H), 3.29 (dd, 1H), 2.41 (s, 3H), 2.29–2.32 (m, 1H), 2.26 (s, 3H), 2.12 (dd, 1H).

Example 147

2-Phenethyl-piperazine

Combine 1,4-dibenzyl-2-styryl-piperazine (289 mg, 0.78 mmol), palladium hydroxide (36 mg, 20 wt. % on carbon), and ethanol (100 mL) in a hydrogenation vessel. Shake and heat at 60° C. under a hydrogen atmosphere (60 psi). After 24 hours, cool to ambient temperature and filter the palladium hydroxide. Concentrate the filtrate and purify by silica gel chromatography using 2N ammonia in methanol-methylene chloride (20%) as the eluent to give the title compound: mass spectrum (ion spray): m/z=191 (M+1); $^1$H NMR (DMSO-$d_6$): δ7.11–7.31 (m, 5H), 2.82–2.39 (m, 8H), 2.18 (dd, 1H), 1.48 (dd, 2H).

Example 148

(S)-1,4-Dibenzyl-2-(2-pyridin-3-yl-ethyl)-piperazine

Prepared by the method in Example 128, using 9-borabicyclo[3.3.1]nonane (68.4 mL, 34.2 mmol, 0.5 M in THF), (S)-1,4-dibenzyl-2-vinyl-piperazine (2.5 g, 8.55 mmol), triphenylphosphine (718 mg, 2.74 mmol), tetrakis(triphenylphosphine) palladium(0)(395 mg, 0.34 mmol), 3-iodopyridine (2.63 g, 12.8 mmol) and 3M NaOH (7.0 mL, 21.0 mmol) to give title compound (1.28 g, 40%): mp 94–95.5° C.; mass spectrum (ion spray): m/z=372 (M+1). Analysis calculated for $C_{25}H_{29}N_3$: C, 80.82; H, 7.87; N, 11.31. Found: C, 80.54; H, 7.76; N, 11.32.

Example 149

(S)-2-(2-Pyridin-3-yl-ethyl)-piperazine

Dissolve (S)-1,4-dibenzyl-2-(2-pyridin-3-yl-ethyl)-piperazine (1.6 g, 4.31 mmol) in ethanol (30 mL). Add ammonium formate (1.63 g, 25.8 mmol) and palladium (240 mg, 5 wt. % on carbon) and heat to reflux. After 3 hours 30 minutes, add additional ammonium formate (1.63 g, 25.8 mmol). After 3 hours, filter the palladium on carbon and concentrate the filtrate. Slurry the residue in water and methylene chloride, basify with 5N NaOH, and extract with methylene chloride and chloroform-isopropanol (3:1 mixture). Dry the extracts over sodium sulfate, filter and concentrate the filtrate. Purify by silica gel chromatography using 7N ammonia in methanol-methylene chloride (2.5%–15%) as the eluent to give (261 mg, 32%) of the title compound: mp 104–110° C.; mass spectrum (ion spray): m/z=192 (M+1). $^1$H NMR (DMSO-$d_6$, $D_2O$): δ8.42 (d, 1H), 8.38 (dd, 1H), 7.63 (dt, 1H), 7.31 (dd, 1H), 2.38–2.83 (m, 8H), 2.18 (dd, 1H), 1.50 (dd, 2H).

Example 150

Carbonic acid 4-methoxycarbonyloxy-but-2-enyl ester methyl ester

Combine methyl chloroformate (7.04 g, 80.0 mmol) in THF (70 mL) and add dropwise to a ice-water cold solution of 2-buten-1,4-diol (majority Z form) (19.7 g, 208 mmol) and pyridine (16.5 g, 208 mmol) in THF (150 mL). Warm the mixture to room temperature and stir for 20 hours. Remove the pyridine salt by filtration and concentrate the filtrate to a residue. Dissolve the residue with $CH_2Cl_2$ and wash sequentially with 1 N HCl and brine. Dry the organic layer over $Na_2SO_4$ and concentrate the solvent in vacuo to give a residue. Purification by chromatography using hexanes:EtOAc=12:1 as the eluents give the title compound: $^1$H NMR (CDCl$_3$): δ5.82–5.79 (m, 2H), 4.75 (d, J=4.8 Hz, 4H), 3.79 (s, 6H).

Example 151

1,2-Bis(p-tolylsulfonylamino)ethane

Using ethylenediamine (72 g, 1.2 mol), p-toluenesulfonyl chloride (500 g, 2.6 mol), sodium hydroxide (330 g, 8.25 mol), 6 N HCl (400 mL) and following the procedure described in *Caribb. J. Sci.*, 14, 77 (1974), gives the title compound as white solid.

Example 152

1,2-Bis(p-methoxybenzenesulfonylamino)ethane

Combine ethylenediamine (0.9 g, 15 mmol) in $CH_2Cl_2$ (50 mL) and mix with triethylamine (3.03 g, 30 mmol). Cool the mixture on a ice-water bath and add dropwise 4-methoxybenzenesulfonyl chloride (6.2 g, 30 mmol) in $CH_2Cl_2$ (50 mL). Warm the reaction to room temperature and stir overnight. Wash the reaction with 1N HCl (100 mL), sat. $NaHCO_3$, brine, dry over $Na_2SO_4$, and concentrate the crude product in vacuo. Purification by flash chromatography ($CH_2Cl_2$/EtOAc=5:1) gives the title compound: Mass spectrum (electrospray): (m/z)=401.1 (M+1); $^1$H NMR ($CDCl_3$): δ7.77–7.74 (m, 4H), 6.99–6.96 (m, 4H), 4.95 (br, 2H), 3.87 (s, 6H), 3.06–3.04 (m, 4H).

Example 153

1,2-Bis(o-nitrobenzenesulfonylamino)ethane

By a method similar to Example 152, using ethylenediamine (0.9 g, 15 mmol), triethylamine (3.03 g, 30 mmol), 2-nitrophenyl sulfonyl chloride 6.63 g, 30 mmol) gives the title compound: Mass spectrum (electrospray): (m/z)=431.1 (M+1); $^1$H NMR (DMSO-$d_6$): δ8.19 (br, 2H), 8.017.86 (m, 8H), 3.00–2.99 (m, 4H).

Example 154

1.2-Bis(2,4,6-trimethylbenzenesulfonylamino)ethane

By a method similar to Example 152, using ethylenediamine (0.9 g, 15 mmol), triethylamine (3.03 g, 30 mmol), 2-mesitylenesulfonyl chloride (6.56 g, 30 mmol) gives the title compound. Mass spectrum (electrospray): (m/z)=425.2 (M+1); $^1$H NMR (DMSO-$d_6$): δ7.28 (br, 2H), 7.01 (s, 4H), 2.69–2.68 (m, 4H), 2.47 (s, 12H), 2.28 (s, 6H).

Example 155

1,4-Bis(toluene-4-sulfonyl)-2-vinyl-piperazine

Combine tris(dibenzylideneacetone)dipalladium chloroform (($dba)_3Pd_2$ $CHCl_3$)(13 mg, "pd" 0.025 mmol) and racemic 2,2'-bis(diphenylphosphino)-1,1'-binaphthyl (BINAP, 15.6 mg, 0.025 mmol) in THF (2.5 mL) under $N_2$ and stir at room temperature. After 1 hour, add 1,2-bis(p-toylsulfonylamine) ethane (184 mg, 0.5 mmol),(Z)-1,4-bis(methoxycarbonyloxy)but-2-ene (102 mg, 0.5 mmol), and THF (2.5 mL) and heat to 40° C. After 24 hours, cool to room temperature and concentrate the reaction under reduced pressure to give a brown solid. Wash the solid with ether (3×5 mL), dissolve in $CH_2Cl_2$, pass through a plug of silica gel to remove insoluble material and concentrate the filtrate. Purification by Chiral HPLC: Chiralpak AD(0.46× 25 cm), IPA:Heptane 40:60, 1 mL/min, Retention Time: 14.53, 18.01 min or by flash chromatography on silica gel, gradient: $CH_2Cl_2$ to 2.5% EtOAc in $CH_2Cl_2$ to give the title compound: $^1$H NMR ($CDCl_3$): δ7.60–7.56 (m, 4H), 7.35–7.32 (m, 2H), 7.26–7.23 (m, 2H), 5.7 (ddd, 1H, J=6.4 Hz, J=10.1 Hz, J=17.2 Hz), 5.30–5.17 (m, 2H), 4.45 (br, 1H), 3.66–3.55 (m, 3H), 3.23 (dt, 1H, J=3.1 Hz, J=11.9 Hz), 2.57 (dd, 1H, J=3.1 Hz, J=11.5 Hz), 2.47–2.43, (m, 1H), 2.47 (s, 3H), 2.40 (s, 3H).

By a method similar to Example 155, the following examples were prepared:

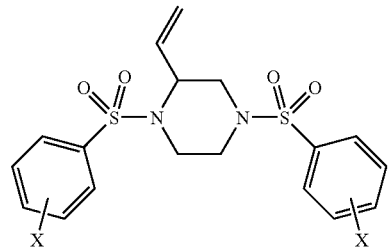

| No.: | X | Data |
|---|---|---|
| 156 | 4-$OCH_3$ | Mass spectrum(electrospray): (m/z)=453.2(M+1); $^1$H NMR: δ7.65–7.60(m, 4H), 7.00–6.89(m, 4H), 5.75(ddd, 1H, J=6.3Hz, J=10.5Hz, J=17.4Hz), 5.30–5.19(m, 2H), 4.44(br, 1H), 3.89(s, 3H), 3.85(s, 3H), 3.63–3.53(m, 3H), 3.23(dt, 1H, J=3.0Hz, J=12.0Hz), 2.56(dd, 1H), J=3.7Hz, J=11.5Hz), 2.40(dt, 1H, J=3.1Hz, J=11.3Hz). Chiral HPLC: Chiralpak AD (0.46 × 25 cm), IPA:Heptane = 40:60, 1 mL/min, Retention Time: 21.00, 25.9 min. |
| 157 | 2,4,6-tri-methyl | Mass spectrum(electrospray): (m/z)=477.3(M+1); $^1$H NMR ($CDCl_3$): δ6.95(s, 4H), 5.83–5.72(m, 1H), 5.16–5.00(m, 2H), 4.40(br, 1H), 3.47–3.28(m, 4H), 3.14(dd, 1H, J=3.5Hz, J=11.9Hz), 2.83(dt, 1H, J=3.8Hz, J=11.1Hz), 2.59(s, 12H), 2.30(s, 6H). Chiral HPLC: Chiralpak AD(0.46 × 25 cm), IPA:Heptane = 20:80, 1 mL/min, Retention Time: 8.43, 9.05 min. |
| 158 | 2-$NO_2$ | Mass spectrum(electrospray): (m/z)=483.1(M+1; $^1$H NMR ($CDCl_3$): δ8.07–8.04(m, 1H), 7.94–7.91(m, 1H), 7.74–7.60(m, 6H), 5.83(m, 1H), 5.32–5.22(m, 2H), 4.63(br, 1H), 3.95–3.71(m, 3H), 3.49(dt, 1H, J=3.2Hz, J=11.9Hz), 3.15(dt, 1H, J=3.7Hz, J=12.7Hz), 2.86(dt, 1H, J=3.4Hz, J=12.2Hz). Chiral HPLC: Chiralpak AD(0.46 × 25 cm), 100% EtOH, 1 mL/min, Retention Time: 8.92, 10.67 min. |

By a method similar to Example 155, the following asymmetric products were obtained using $(dba)_3Pd_2CHCl_3$, (26 mg, "Pd":0.05 mmol), (R)-BINAP (31.2 mg, 0.05 mmol), 1,2-bis(p-toylsulfonylamini)ethane(368 mg, 1.0 mmol) and (Z)-1,4-bis(methoxycarbonyloxy)but-2-ene (204 mg, 1.0 mmol).

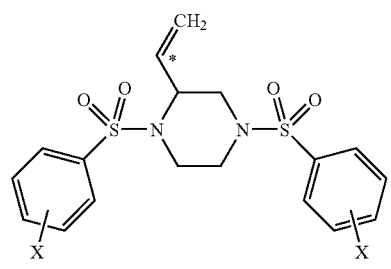

| No.: | X | Yield % | ee % |
|---|---|---|---|
| 159 | p-Me | 84 | 74.9(S) |
| 160 | p-OMe | 85 | 73.9 |
| 161 | 2,4,6-TriMe | 70 | 77.0 |
| 162 | 2-$NO_2$ | 39 | 65.3 |

Example 163

2-Phenethyl-1,4-bis-(toluene-4-sulfonyl)-piperazine

Add 9-BBN (0.5 M THF solution, 13.7 mL, 6.85 mmol) to a 100 mL schlenk flask containing (S)-1,4-bis(toluene-4-sulfonyl)-2-vinyl-piperazine(0.96 g, 2.3 mmol) in THF (5 mL), at room temperature under nitrogen and stir. After 18 hours, treat the reaction with tetrakis(triphenylphosphine) palladium (53 mg, 0.046 mmol), triphenyl phosphine (94.6 mg, 0.36 mmol), iodobenzene (0.703 g, 3.4 mmol) and 3N NaOH (2.8 mL, 8.4 mmol) and heat to reflux. After 24 hours, cool the reaction to room temperature, remove in vacuo the THF solvent, dilute the residue with $CH_2Cl_2$, wash with 1N HCl, brine, and dry over $Na_2SO_4$. Purification by flash chromatography twice (Gradient: Hexanes/$CH_2Cl_2$=50/50, to Hexanes/$CH_2Cl_2$/EtOAc=40/40/10), and recrystallization in MeOH gives 860 mg (75%) of the title compound: mass spectrum (electrospray): (m/z)=499.2 (M+1); $^1$H NMR ($CDCl_3$): δ7.58–7.54 (m, 4H), 7.33–7.20 (m, 7H), 7.19–7.07 (m, 2H), 3.99 (m, 1H), 3.81–3.78 (m, 1H), 3.64–3.60 (m, 2H), 3.22 (dt, 1H, J=3.2 Hz, J=12.4 Hz), 2.57–2.41 (m, 2H), 2.41 (s, 3H), 2.33 (s, 3H), 2.33–2.20 (m, 2H), 2.03–1.98 (m, 1H), 1.75–1.63 (m, 1H).

Example 164

2-Phenethyl-piperazine

Add 2-phenethyl-1,4-bis-(toluene-4-sulfonyl)-piperazine (100 mg, 0.2 mmol) in THF (2 mL) to a cooled (−78° C.) suspension of metallic Na (36.8 mg, 1.6 mmol) and naphthalene (230.4 mg, 1.8 mmol) in fresh distilled THF(4 mL) was under nitrogen and stir at −78° C. After 1 hour, TLC indicated the reaction is complete. Hydrolyze the reaction with brine (10 mL) and extract with $CH_2Cl_2$ (3×10 mL). Combine the organic layers and dry over $Na_2SO_4$ and evaporate. Pass the resulting residue through a SCX column to obtain the title compound as a solid: mass spectrum (electrospray): (m/z)=191.2 (M+1); $^1$H NMR ($CDCl_3$): δ7.30–7.25 (m, 2H), 7.20–7.15 (m, 3H), 3.00–2.61 (m, 8H), 2.40 (t, 1H, J=11.7 Hz), 1.70 (br, 2H), 1.67–1.60 (m, 2H).

Example 171

(S)-1,4-Dibenzyl-2-phenethyl-piperazine

Combine (S)-1,4-dibenzyl-2-vinyl-piperazine (4.9 g, 16.63 mmol) and 9-borabicyclo[3.3.1]nonane (199.6 ml, 99.78 mmol, 0.5 M in THF) and stir at ambient temperature. After 24 hours, add iodo-benzene (5.1 g, 24.95 mmol), triphenylphosphine (697.9 mg, 2.66 mmol), tetrakis(triphenylphosphine) palladium(0)(384.3 mg, 0.33 mmol), and 3N NaOH (13.7 mL) and stir at 60° C. After 22 hours, dilute the mixture with ethyl acetate and wash it with 1N sulfuric acid. Adjust the pH to 14, extract with ethyl acetate, and combine, wash (brine), dry (sodium sulfate), and reduce the extracts to residue. Purify the residue on silica gel using a ethyl acetate/hexanes gradient (5:95 to 10:90) to give (5.15 g, 84%) of the title compound as a white solid: mp 86–90° C.; mass spectrum (ion spray): m/z=371.3 (M+1).

Example 172

(S)-1,4-Dibenzyl-2-(2-(2-methoxy-phenyl)-ethyl)-piperazine

Combine (S)-1,4-dibenzyl-2-vinyl-piperazine (2.5 g, 8.55 mmol) and 9-borabicyclo[3.3.1]nonane (68.4 mL, 34.20 mmol, 0.5 M in THF) and stir at ambient temperature. After 24 hours, add 1-iodo-2-methoxy-benzene (3.0 g, 12.82 mmol), triphenylphosphine (358.8 mg, 1.37 mmol), tetrakis (triphenylphosphine) palladium(0) (197.5 mg, 0.17 mmol), and 3N NaOH (7.0 mL) and stir at 60° C. After 22 hours, remove the THF under vacuum, stir the residue in 2N NaOH, and extract with diethyl ether. Wash the organic with 1N $H_2SO_4$ then adjust the aqueous to pH 14. Extract the aqueous with diethyl ether and combine, wash (brine), dry (sodium sulfate), and reduce the extracts to residue. Purify the residue on silica gel using ethyl acetate/hexanes (5:95) to give (2.21 g, 65%) of the title compound: mp 58–61 C°; mass spectrum (ion spray): m/z=401.3 (M+1); Analysis for $C_{27}H_{32}N_2O$: calcd: C, 80.96; H, 8.05; N, 6.99; found: C, 81.08; H, 7.99; N, 7.10.

Example 173

(S)-2-(2-(4-Methoxy-phenyl)-ethyl)-piperazine

Combine (S)-1,4-dibenzyl-2-(2-(4-methoxy-phenyl)-ethyl)-piperazine (1.34 g, 3.33 mmol), ammonium formate (1.05 g, 16.67 mmol), 5% Pd/C (161.2 mg), and ethanol (100 mL). Stir and heat the mixture at reflux. After 3 hours, cool to ambient temperature and remove the catalyst by vacuum filtration through celite. Reduce the filtrate to residue and purify it on silica gel using dichloromethane/2N ammonia in methanol (80:20) to give (689.3 mg, 94%) of the title compound as a white solid: mp 125–130° C.; mass spectrum (ion spray): m/z=221.1 (M+1); Analysis for $C_{13}H_{20}N_2O$: calcd: C, 70.87; H, 9.15; N, 12.72; found: C, 70.58; H, 9.05; N, 12.61.

Example 174

(S)-2-(2-(3-Methoxy-phenyl)-ethyl)-piperazine

Combine (S)-1,4-dibenzyl-2-(2-(3-methoxy-phenyl)-ethyl)-piperazine (2.15 g, 5.37 mmol), ammonium formate (1.69 g, 26.84 mmol), 5% Pd/C (259.7 mg), and ethanol (100 mL). Stir and heat the mixture at reflux. After 3 hours, cool to ambient temperature and remove the catalyst by vacuum filtration through celite. Reduce the filtrate to residue and purify it on silica gel using dichloromethane/7N ammonia in methanol (90:10) to give (1.11 g, 94%) of the title compound as a white solid: mp 53–57° C.; mass spectrum (ion spray): m/z=221.1 (M+1); Analysis for $C_{13}H_{20}N_2O$: calcd: C, 70.87; H, 9.15; N, 12.72; found: C, 70.52; H, 9.06; N, 12.74.

Example 175

(S)-2-(2-(2-methoxy-phenyl)-ethyl)-piperazine

Combine (S)-1,4-dibenzyl-2-(2-(2-methoxy-phenyl)-ethyl)-piperazine (2.10 g, 5.24 mmol), ammonium formate (1.65 g, 26.19 mmol), 5% Pd/C (253.6 mg), and ethanol (100 mL). Stir and heat the mixture at reflux. After 3 hours, cool to ambient temperature and remove the catalyst by vacuum filtration through celite. Reduce the filtrate to residue and purify it on silica gel using dichloromethane/2N ammonia in methanol (80:20) to give (1.00 g, 87%) of the title compound: mass spectrum (ion spray): m/z=221.1 (M+1).

Example 176

10-((S)-3-(2-(4-Fluorophenyl)-ethyl)-piperazin-1-yl)-2-methyl-4H-3-thia-4,9-diaza-benzo[f]azulene dihydrochloride

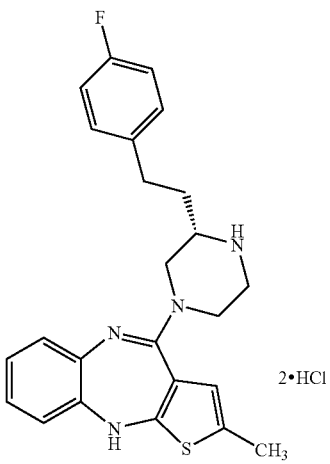

Combine 2-methyl-4H-3-thia-4,9-diaza-benzo[f]azulen-10-ylamine hydrochloride (492.9 mg, 1.85 mmol), (S)-2-(2-(4-fluoro-phenyl)-ethyl)-piperazine (772.6 mg, 3.71 mmol), N,N-diisopropylethylamine (239.7 mg, 1.85 mmol), DMSO (0.82 ml), and toluene (3.3 mL). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give (376.0 mg, 48%) of a brown foam. Prepare the dihydrochloride salt in ethyl acetate: mp 236° C., dec; mass spectrum (ion spray): m/z=421.2 (M+1).

Example 177

10-((S)-3-(2-(3-Fluoro-phenyl)-ethyl)-piperazin-1-yl))-2-methyl-4H-3-thia-4,9-diaza-benzo[f]azulene dihydrochloride

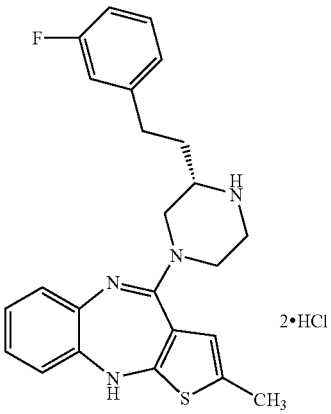

Combine 2-methyl-4H-3-thia-4,9-diaza-benzo[f]azulen-10-ylamine hydrochloride (696.7 mg, 2.62 mmol), (S)-2-(2-(3-fluoro-phenyl)-ethyl)-piperazine (1.09 g, 5.24 mmol), N,N-diisopropylethylamine (338.8 mg, 2.62 mmol), DMSO (1.2 ml), and toluene (4.6 mL). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give (526.8 mg, 48%) of a dark brown oil. Prepare the dihydrochloride salt in ethyl acetate: mp 211° C., dec; mass spectrum (ion spray): m/z=421.2 (M+1).

Example 178

10-((S)-3-(2-(2-Fluoro-phenyl)-ethyl)-piperazin-1-yl)-2-methyl-4H-3-thia-4,9-diaza-benzo[f]azulene dihydrochloride

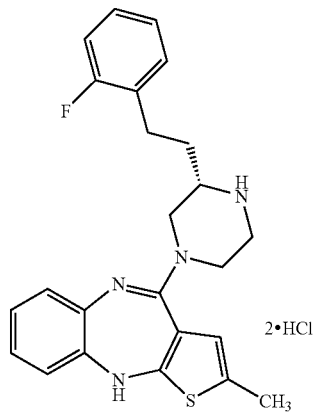

Combine 2-methyl-4H-3-thia-4,9-diaza-benzo[f]azulen-10-ylamine hydrochloride (645.8 mg, 2.43 mmol), (S)-2-(2-(2-fluoro-phenyl)-ethyl)-piperazine (1.01 g, 4.86 mmol), N,N-diisopropylethylamine (314.1 mg, 2.43 mmol), DMSO (1.1 ml), and toluene (4.3 mL). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give (481.7 mg, 47%) of a brown foam. Prepare the dihydrochloride salt in ethyl acetate: mp 209°, dec; mass spectrum (ion spray): m/z=421.2 (M+1).

Example 179

10-((S)-3-(2-(4-methoxy-phenyl)-ethyl)-piperazin-1-yl)-2-methyl-4H-3-thia-4,9-diaza-benzo[f]azulene dihydrochloride

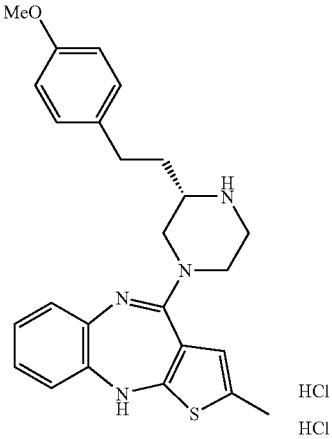

Combine 2-methyl-4H-3-thia-4,9-diaza-benzo[f]azulen-10-ylamine hydrochloride (620.0 mg, 2.33 mmol), (S)-2-(2-(4-methoxy-phenyl)-ethyl)-piperazine (1.03 g, 4.67 mmol), N,N-diisopropylethylamine (301.5 mg, 2.33 mmol), DMSO (1.0 mL), and toluene (4.0 mL). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give (703.8 mg, 70%) of a brown oil. Prepare the dihydrochloride salt in ethyl acetate: mp 213° C., dec; mass spectrum (ion spray): m/z=433.1 (M+1).

Example 180

10-((S)-3-(2-(3-Methoxy-phenyl)-ethyl)-piperazin-1-yl)-2-methyl-4H-3-thia-4,9-diaza-benzo[f]azulene dihydrochloride

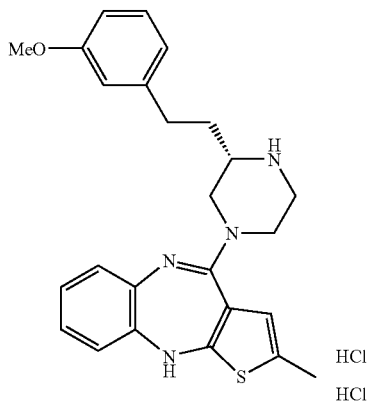

Combine 2-methyl-4H-3-thia-4,9-diaza-benzo[f]azulen-10-ylamine hydrochloride (301.6 mg, 1.13 mmol), (S)-2-(2-(3-methoxy-phenyl)-ethyl)-piperazine (500.0 mg, 2.27 mmol), N,N-diisopropylethylamine (146.7 mg, 1.13 mmol), DMSO (0.5 mL), and toluene (2.0 mL). Stir and heat the mixture at 105° C. After 64 hours, cool the mixture to ambient temperature and then dilute it with acetic acid/methanol (1:9) and apply it to an SCX column. Wash the column with methanol to remove impurities. Treat the column with 7N ammonia in methanol to elude the product. Evaporate the solvent to residue. Purify the residue on silica gel using dichloromethane/methanol (95:5) to give (279.0 mg, 57%) of a brown foam. Prepare the dihydrochloride salt in ethyl acetate: mp 201° C., dec; mass spectrum (ion spray): m/z=433.3 (M+1).

Example 181

10-((S)-3-(2-(2-Methoxy-phenyl)-ethyl)-piperazin-1-yl)-2-methyl-4H-3-thia-4,9-diaza-benzo[f]azulene dihydrochloride

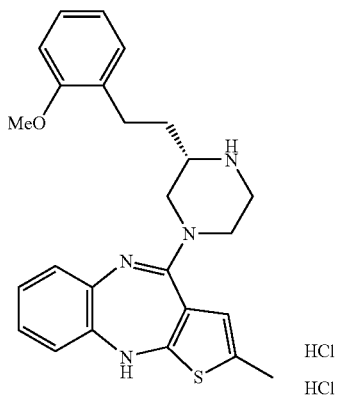

Combine 2-methyl-4H-3-thia-4,9-diaza-benzo[f]azulen-10-ylamine hydrochloride (1.17 g, 4.42 mmol), (S)-2-(2-(2-methoxy-phenyl)-ethyl)-piperazine (973.5 mg, 4.42 mmol), N,N-diisopropylethylamine (571.1 mg, 4.42 mmol), DMSO (2.0 mL), and toluene (8.0 mL). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give (473.9 mg, 25%) of a brown foam. Prepare the dihydrochloride salt in ethyl acetate: mp 202° C., dec; mass spectrum (ion spray): m/z=433.1 (M+1).

Example 182

10-((S)-3-(2-(4-Fluoro-phenyl)-ethyl]-4-methyl-piperazin-1-yl)-2-methyl-4H-3-thia-4,9-diaza-benzo[f]azulene dihydrochloride

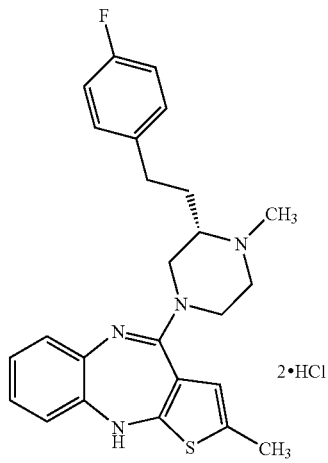

Combine 10-((S)-3-(2-(4-fluoro-phenyl)-ethyl)-piperazin-1-yl)-2-methyl-4H-3-thia-4,9-diaza-benzo[f]azulene (259.0 mg, 0.62 mmol), formaldehyde (55.0 μL, 0.68 mmol, 37% in water), and 1,2-dichloroethane (20.0 mL). Stir the mixture at ambient temperature for 5 minutes and then add sodium triacetoxyborohydride (195.8 mg, 0.92 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give (236.7 mg, 89%) of a brown foam. Prepare the dihydrochloride salt in ethyl acetate: mp 253° C., dec; mass spectrum (ion spray): m/z=435.1 (M+1).

Example 183

10-((S)-3-(2-(3-Fluoro-phenyl)-ethyl)-4-methyl-piperazin-1-yl)-2-methyl-4H-3-thia-4,9-diaza-benzo[f]azulene dihydrochloride

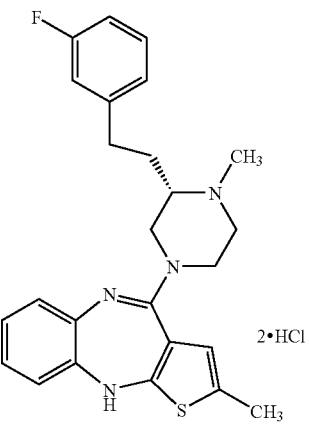

Combine 10-((S)-3-(2-(3-fluoro-phenyl)-ethyl)-piperazin-1-yl)-2-methyl-4H-3-thia-4,9-diaza-benzo[f]azulene (265.6 mg, 0.63 mmol), formaldehyde (56.4 µL, 0.69 mmol, 37% in water), and 1,2-dichloroethane (20.0 mL). Stir the mixture at ambient temperature for 5 minutes and then add sodium triacetoxyborohydride (200.7 mg, 0.95 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give (215.4 mg, 79%) of a brown oil. Prepare the dihydrochloride salt in ethyl acetate: mp 225° C., dec; mass spectrum (ion spray): m/z=435.1 (M+1).

Example 184

10-((S)-3-(2-(2-Fluoro-phenyl)-ethyl)-4-methyl-piperazin-1-yl)-2-methyl-4H-3-thia-4,9-diaza-benzo[f]azulene dihydrochloride

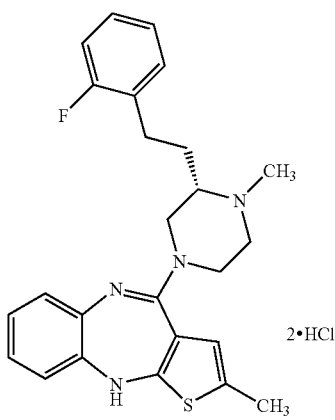

Combine 10-((S)-3-(2-(2-fluoro-phenyl)-ethyl)-piperazin-1-yl)-2-methyl-4H-3-thia-4,9-diaza-benzo[f]azulene (240.0 mg, 0.57 mmol), formaldehyde (50.9 µL, 0.63 mmol, 37% in water), and 1,2-dichloroethane (20.0 mL). Stir the mixture at ambient temperature for 5 minutes and then add sodium triacetoxyborohydride (181.4 mg, 0.86 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give (247.9 mg, 100%) of a brown oil. Prepare the dihydrochloride salt in ethyl acetate: mp 203° C., dec; mass spectrum (ion spray): m/z=435.3 (M+1).

Example 185

10-((S)-3-(2-(4-Methoxy-phenyl)-ethyl)-4-methyl-piperazin-1-yl)-2-methyl-4H-3-thia-4,9-diaza-benzo[f]azulene dihydrochloride

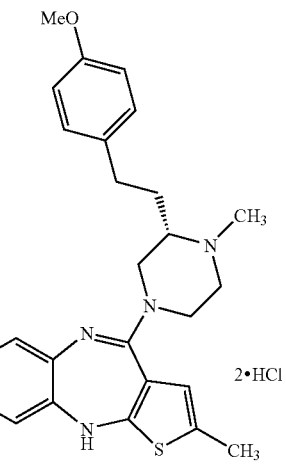

Combine 10-((S)-3-(2-(4-methoxy-phenyl)-ethyl)-piperazin-1-yl)-2-methyl-4H-3-thia-4,9-diaza-benzo[f]azulene (159.2 mg, 0.37 mmol), formaldehyde (32.9 µL, 0.41 mmol, 37% in water), and 1,2-dichloroethane (20.0 mL). Stir the mixture at ambient temperature for 5 minutes and then add sodium triacetoxyborohydride (117.0 mg, 0.55 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give (158.4 mg, 96%) of a brown foam. Prepare the dihydrochloride salt in ethyl acetate: mp 239° C., dec; mass spectrum (ion spray): m/z=447.2 (M+1).

Example 186

10-((S)-3-(2-(3-Methoxy-phenyl)-ethyl)-4-methyl-piperazin-1-yl)-2-methyl-4H-3-thia-4,9-diaza-benzo[f]azulene dihydrochloride

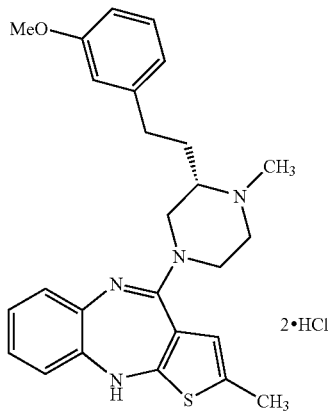

Combine 10-((S)-3-(2-(3-methoxy-phenyl)-ethyl)-piperazin-1-yl)-2-methyl-4H-3-thia-4,9-diaza-benzo[f]azulene (279.0 mg, 0.65 mmol), formaldehyde (57.6 µL, 0.71 mmol, 37% in water), and 1,2-dichloroethane (20.0 mL). Stir the mixture at ambient temperature for 5 minutes and then add sodium triacetoxyborohydride (205.0 mg, 0.97 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give (278.7 mg, 97%) of a brown oil. Prepare the dihydrochloride salt in ethyl acetate:mp 200° C., dec; mass spectrum (ion spray): m/z=447.1 (M+1).

Example 187

10-((S)-3-(2-(2-Methoxy-phenyl)-ethyl)-4-methyl-piperazin-1-yl)-2-methyl-4H-3-thia-4,9-diaza-benzo[f]azulene dihydrochloride

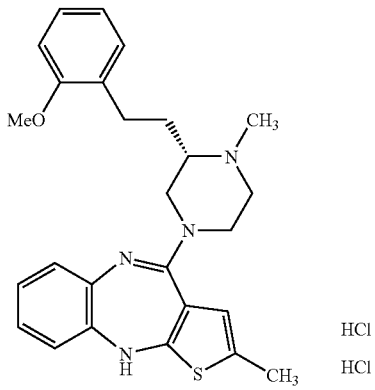

Combine 10-((S)-3-(2-(2-methoxy-phenyl)-ethyl)-piperazin-1-yl)-2-methyl-4H-3-thia-4,9-diaza-benzo[f]azulene (209.2 mg, 0.48 mmol), formaldehyde (43.2 µL, 0.53 mmol, 37% in water), and 1,2-dichloroethane (20.0 mL). Stir the mixture at ambient temperature for 5 minutes and then add sodium triacetoxyborohydride (153.7 mg, 0.73 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give (191.6 mg, 89%) of a brown foam. Prepare the dihydrochloride salt in ethyl acetate: mp 213° C., dec; mass spectrum (ion spray): m/z=447.2 (M+1).

Example 188

2-Methyl-10-(4-methyl-(S)-3-(2-pyridin-4-yl-ethyl)-piperazin-1-yl)-4H-3-thia-4,9-diaza-benzo[f]azulene trihydrochloride hydrate

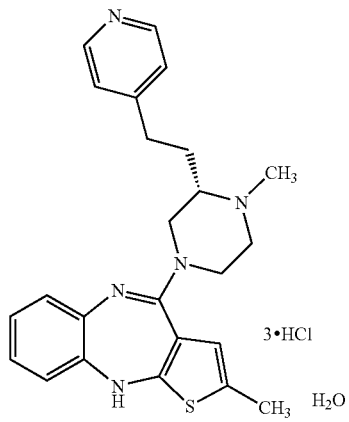

Combine 2-methyl-10-((S)-3-(2-pyridin-4-yl-ethyl)-piperazin-1-yl)-4H-3-thia-4,9-diaza-benzo[f]azulene (380 mg, 0.94 mmol) and formaldehyde (82 µL, 1.04 mmol, 37% in water), and methylene chloride (10 mL). Stir 5 minutes at ambient temperature. Add sodium triacetoxyborohydride (300 mg, 1.41 mmol) and stir 30 minutes at ambient temperature. Dilute with saturated sodium bicarbonate solution and extract with methylene chloride. Dry the extracts with sodium sulfate, filter and concentrate the filtrate. Purify by silica gel chromatography using 2N ammonia in methanol-methylene chloride (1%–3%) as the eluent to give 345 mg of a brown foam. Purify again by silica gel chromatography using 2N ammonia in methanol-methylene chloride (0%–6.5%) as the eluent to give the free base. Crystallize as the trihydrochloride salt from ethyl acetate and ethanol to give the title compound (244 mg, 62%): mp 214–217° C. dec.; mass spectrum (ion spray): m/z=418 (M+1), 416 (M−1). Analysis calculated for $C_{24}H_{27}N_5S \cdot 3HCl \cdot 0.9H_2O$: C, 53.07; H, 5.90; N, 12.89. Found: C, 53.31; H, 5.54; N, 12.75.

Example 189

2-Methyl-10-((S)-3-(2-pyridin-3-yl-ethyl)-piperazin-1-yl)-4H-3-thia-4,9-diaza-benzo[f]azulene trihydrochloride dihydrate

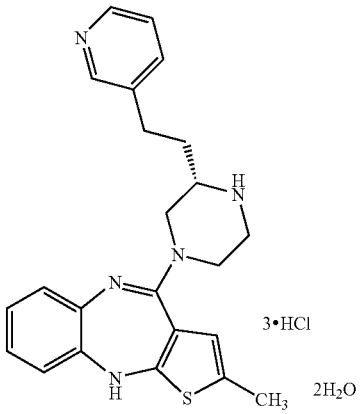

Combine (S)-2-(2-pyridin-3-yl-ethyl)-piperazine (2.0 g, 10.5 mmol), 2-methyl-4H-3-thia-4,9-diaza-benzo[f]azulen-10-ylamine (2.4 g, 10.5 mmol), acetic acid (0.1 mL), toluene (21 mL), and DMSO (5 mL). Heat at 110° C. Purge periodically with nitrogen and replace condensor after 4 hours. After 41 hours 30 minutes, cool to ambient temperature and dilute with ethyl acetate and water. Extract with ethyl acetate. Wash the extracts with water and brine, dry over sodium sulfate, filter and concentrate the filtrate. Purify by silica gel chromatography using 2N ammonia in methanol-methylene chloride (0%–5%) as the eluent to give the free base. Purify 600 mg by radial silica gel chromatography using a 2 mm plate and 2N ammonia in methanol-methylene chloride (1%–4%) as the eluent to give the free base. Crystallize as the trihydrochloride salt from ethyl acetate and ethanol to give the title compound: mp 226–229° C. dec.; mass spectrum (ion spray): m/z=404 (M+1), 402 (M–1). Analysis calculated for $C_{23}H_{25}N_5S \cdot 3HCl \cdot 2H_2O$: C, 50.32; H, 5.88; N, 12.76. Found: C, 50.32; H, 5.97; N, 12.71.

Example 190

2-Methyl-10-(4-methyl-(S)-3-(2-pyridin-3-yl-ethyl)-piperazin-1-yl)-4H-3-thia-4,9-diaza-benzo[f]azulene

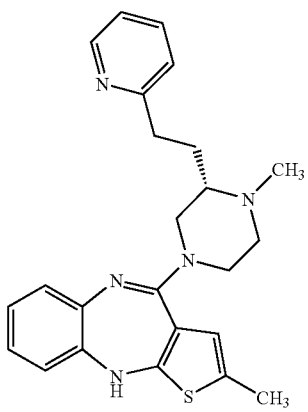

Combine 2-methyl-10-((S)-3-(2-pyridin-3-yl-ethyl)-piperazin-1-yl)-4H-3-thia-4,9-diaza-benzo[f]azulene (728 mg, 1.80 mmol) and formaldehyde (158 μL, 1.98 mmol, 37% in water), and methylene chloride (30 mL). Stir 10 minutes at ambient temperature. Add sodium triacetoxyborohydride (573 mg, 2.70 mmol) and stir 1 hour at ambient temperature. Dilute with saturated sodium bicarbonate solution and extract with methylene chloride. Dry the extracts with sodium sulfate, filter and concentrate the filtrate. Purify by silica gel chromatography using 2N ammonia in methanol-methylene chloride (0%–4%) as the eluent to give the title compound (595 mg, 79%): Mass spectrum (ion spray): m/z=418 (M+1), 416 (M–1). Analysis calculated for $C_{24}H_{27}N_5S$: C, 69.03; H, 6.52; N, 16.77. Found: C, 68.92; H, 6.60; N, 16.65.

Example 191

2-Methyl-10-(4-methyl-(S)-3-(2-pyridin-2-yl-ethyl)-piperazin-1-yl)-4H-3-thia-4,9-diaza-benzo[f]azulene trihydrochloride

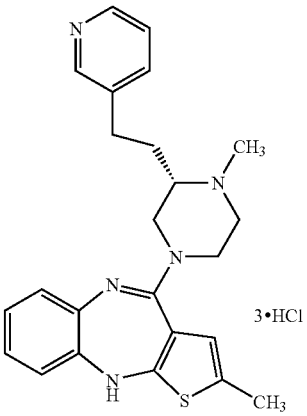

Combine 2-methyl-10-((S)-3-(2-pyridin-2-yl-ethyl)-piperazin-1-yl)-4H-3-thia-4,9-diaza-benzo[f]azulene (200 mg, 0.50 mmol) and formaldehyde (43 μL, 0.54 mmol, 37% in water), and methylene chloride (5 mL). Stir 10 minutes at ambient temperature. Add sodium triacetoxyborohydride (158 mg, 0.74 mmol) and stir 1 hour at ambient temperature. Dilute with saturated sodium bicarbonate solution and extract with methylene chloride. Dry the extracts with sodium sulfate, filter and concentrate the filtrate. Purify by silica gel chromatography using 2N ammonia in methanol-methylene chloride (0%–4%) as the eluent to give the free base. Crystallize as the trihydrochloride salt from ethyl acetate and ethanol to give the title compound (161 mg, 78%): Mass spectrum (ion spray): m/z=418 (M+1), 416 (M–1). Analysis calculated for $C_{24}H_{27}N_5S \cdot 3HCl$: C, 54.70; H, 5.74; N, 13.29. Found: C, 54.88; H, 6.02; N, 12.96.

Example 192

(S)-1,4-Dibenzyl-2-(4-phenyl-but-3-enyl)-piperazine

Combine 9-borabicyclo[3.3.1]nonane (81.6 mL, 40.3 mmol, 0.5 M in THF) and (S)-1,4-dibenzyl-2-vinyl-piperazine (2.0 g, 6.8 mmol) and stir at ambient temperature. After 16 hours, take half volume of it, add triphenylphosphine (143 mg, 0.55 mmol), tetrakis(triphenylphosphine)palladium(0) (78.5 mg, 0.068 mmol), and beta-bromostyrene (0.93 g, 5.08 mmol). Add 3N NaOH (2.8 mL, 8.8 mmol) slowly, gas evolution will occur. Heat to reflux. After 24 hours, cool to ambient temperature. Remove the solvent under reduced pressure, dilute with diethyl ether, wash with 1N HCl, 1N NaOH, H₂O and brine, dry the organic layer over Na₂SO₄, filter and concentrate under reduced pressure. Purification by flash chromatography on silica gel using 2N ammonia in methanol-methylene chloride (0.5%–3%) as the eluent, collect compound and pass through 10 g SCX column, using MeOH, 0.2 N NH₃ in MeOH as eluent to give the title compound (750 mg, 56%): mass spectrum (electrospray): m/z=397.3 (M+1); ¹H NMR (300 MHz, CDCl₃): δ7.35–7.16 (m, 15H), 6.36–6.12 (m, 2H), 4.01 (d, 1H, J=13.2), 3.56–3.43 (m, 2H), 3.25 (d, 1H, J=13.4 Hz), 2.75–2.68 (m, 2H), 2.56–2.48 (m, 2H), 2.29–2.13 (m, 5H), 1.82–1.76 (m, 2H).

Example 193

(S)-2-(4-Phenyl-butyl)-piperazine

Combine (S)-1,4-dibenzyl-2-(4-phenyl-but-3-enyl)-piperazine (2.12 g, 5.3 mmol), 10% Pd/C (300 mg, 0.027 mmol) and ammonia formate (1.67 g, 26.5 mmol) in EtOH (50 mL), heat to reflux for 3 hours 30 minutes, and cool to room temperature. Remove the catalyst via filtration, and concentrate the filtrate to a residue. Purification by flash chromatography on silica gel using 2N NH₃ in MeOH and dichloromethane (5%–15%) to give the title compound (780 mg, yield 67%): mass spectrum (Electrospray): m/z=219.2 (M+1); ¹H NMR (CDCl₃): δ7.30–7.15 (m, 5H), 2.96–2.55 (m, 8H), 2.37–2.30 (m, 1H), 1.64–1.60 (m, 2H), 1.39–1.29 (m, 4H).

Example 194

(S)-2-Methyl-10-(3-(4-phenyl-butyl-piperazin-1-yl)-4H-3-thia-4,9-diaza-benzo[f]azulene, dihydrochloric acid

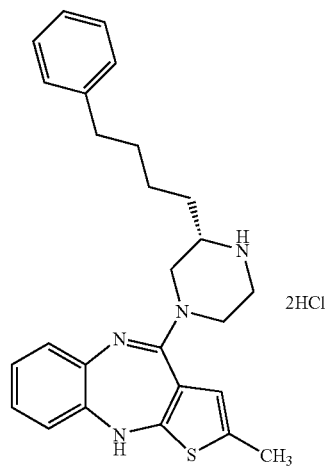

Combine (S)-2-(4-phenyl-butyl)-piperazine (820 mg, 3.76 mmol), 2-methyl-4H-3-thia-4,9-diaza-benzo[f]azulen-10-ylamine (861 mg, 3.76 mmol), 1-methyl-2-pyrrolidinone (7 mL), and heat at 220° C. After 4 hours, cool to ambient temperature, pass through SCX column (10 G), and collect the fraction of 0.2 NH₃ in methanol. Purification by silica gel chromatography of the crude product using 2N ammonia in methanol-dichloromethane (2%–4%) as the eluent to give 310 mg brown foam of the free base: mass spectrum (Electronspray): m/z=431.3 (M+1); ¹H NMR (300 MHz, CDCl₃): δ7.30–7.15 (m, 5H), 7.04–6.84 (m, 3H), 6.60 (dd, 1H, J=1.3, J=7.7 Hz), 6.28 (d, 1H, J=1.2 Hz), 4.95 (s, 1H), 4.06–3.96 (m, 2H), 3.05–2.89 (m, 2H), 2.77–2.74 (m, 1H), 2.65–2.49 (m, 3H), 2.30 (d, 3H, J=1.1 Hz), 1.64 (m, 2H), 1.45–1.37 (m, 4H). Pass this product through a SCX column (5 g), eluent with 0.6 M CH₃COCl/EtOH, concentrate to give yellow foam, treat with 15 mL of CH₃CN/H₂O=50/50, and lyophilize overnight to give yellow gold solid of title compound: mass spectrum (Electrospray): m/z=431.1 (M+1–2HCl, 429.1 (M–1–2HCl); Analysis calculated for C₂₆H₃₀N₄S.2HCl.1.6 H₂O: C, 58.66; H, 6.66; N, 10.52. Found: C, 58.34; H, 6.47; N, 10.16.

Example 195

(S)-2-Methyl-10-(3-(4-phenyl-butyl)-4-methyl-piperazin-1-yl)-4H-3-thia-4,9-diaza-benzo[f]azulene, dihydrochloric acid

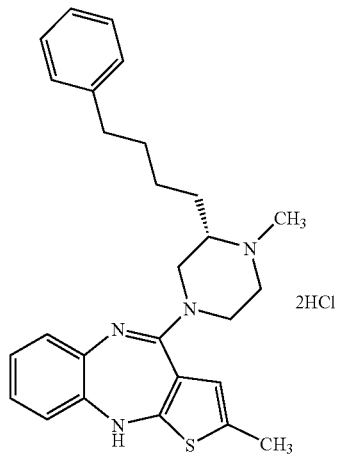

Combine (S)-2-methyl-10-3-(4-phenyl-butyl)-piperazin-1-yl]-4H-3-thia-4,9-diaza-benzo[f]azulene (230 mg, 0.53 mmol), formaldehyde (37% aq, 47 mg, 0.58 mmol) and sodium triacetoxyborohydride (168.5 mg, 0.795 mmol) in 1,2-dichloroethane (15 mL) and stir at room temperature. After 2 hours, quench the reaction by adding sat. NaHCO₃, extract the aqueous solution with CH₂Cl₂ (3×10 mL), wash the organic solvent with brine and dry over Na₂SO₄. Concentrate the solvent in vaccuo to give a residue and purify by silica gel chromatography using 2N ammonia in methanol-dichloromethane (2%–4%) as the eluent to give (170 mg, 72%) light brown foam of the free base: mass spectrum (Electrospray): m/z=445.2 (M+1); ¹H NMR (400 MHz, CDCl₃): δ7.29–7.15 (m, 5H), 7.03–6.85 (m, 3H), 6.60 (dd, 1H, J=1.5, J=7.8 Hz), 6.28 (d, 1H, J=1.0 Hz), 4.95 (s, 1H), 3.98–3.85 (m, 2H), 3.15–3.08 (m, 1H), 2.86–2.75 (m, 3H), 2.64–2.59 (m, 2H), 2.36–28 (m, 8H), 2.10–2.04 (m, 1H), 1.66–1.35 (m, 4H). Treat the free base with acetyl chloride (2.2 eq) in ethanol for 1hour 30 minutes at room temperature, remove the solvent, dissolve in solvent (15 mL) CH₃CN/H₂O=50/50, lyophilize overnight to give yellow solid of title compound: mass spectrum (Electrospray): m/z=445.2 (M+1–2HCl), 443.2 (M–1–2HCl). Analysis calculated for C₂₇H₃₂N₄S.2HCl.0.6 H₂O: C, 61.38; H, 6.71; N, 10.60. Found: C, 61.38; H, 6.44; N, 10.54.

Example 196

(S)-4-Benzyl-2-(2-hydroxy-ethyl)-piperazine-1-carboxylic acid tert-butyl ester Dissolve commercial N-tBoc-L-aspartic acid beta-methyl ester (40 g, 0.16 moles) in dichloromethane (800 mL); cool to 0° C. and add N-benzylglycine methyl ester (28 g, 0.15 moles) as a solution in 100 mL of dichloromethane, followed sequentially by N,N-diisopropylethylamine (28 mL, 0.16 moles), 1-ethyl-3-(3-dimethylaminopropyl)carbodiimide hydrochloride (EDAC, 31 g, 0.16 moles), and 1-hydroxybenzotriazole (22 g, 0.16 moles). Stir at room temperature over the weekend; then concentrate in vacuo to an orange oil. Partition the oil between 2N hydrochloric acid and ethyl acetate; separate aqueous layer and extract with a second portion of ethyl acetate. Combine organic extracts, concentrate in vacuo, and wash with 10% aqueous potassium carbonate. Dry organic layer over magnesium sulfate, filter and concentrate in vacuo to yield 64 g (95%) of the desired dipeptide as an oily residue. Dissolve the crude dipeptide in 150 mL of trifluoroacetic acid, stir at room temperature for 1 h; then remove the solvent in vacuo. Take up the resulting residue on 800 mL of commercial 2N ammonia in methanol solution, and stir at room temperature overnight. Heat the mixture at 70° C. for several hours; then cool to room temperature and remove the solvent in vacuo. Redissolve the residue in dichloromethane, filter off the resulting precipitate, and concentrate the filtrate in vacuo. Apply the residue to a silica gel column. Elute with a 2% mixture of 2N ammonia-methanol in dichloromethane to obtain 31.9 g (72%) of S-(4-benzyl-3,6-dioxopiperazin-2-yl)acetic acid methyl as a yellow oil.

To a 0° C. solution of S-(4-benzyl-3,6-dioxopiperazin-2-yl)acetic acid methyl ester (31.9 g, 0.12 moles) in tetrahydrofuran (1 L), add lithium aluminum hydride via slow cannulation (350 mL of a commercial 1.0 M solution in tetrahydrofuran). Stir at room temperature overnight, quench by successive careful addition of 13.3 mL of water, 13.3 mL of 15% aqueous sodium hydroxide, and 39.9 mL of water, all the while with vigourous stirring to ensure formation of a fine precipitate. Filter through a fritted funnel, washing the solids well with tetrahydrofuran and dichloromethane. Concentrate in vacuo to provide 26.5 g of an oily residue, apply directly to a silica gel column. Elute with a 5% mixture of 7N ammonia-methanol in dichloromethane, to obtain the desired product as an orange oil which solidifies under vacuum. Take up the solid in acetonitrile and sonicate for a few minutes. Filter the resulting precipitate to obtain 7.5 g (25%) of S-(−)-2-(4-benzylpiperazin-2-yl)ethanol as an off-white crystalline solid, mp 78.9–80.4° C. Concentrate the mother liquor to obtain 6.8 g (23%) of slightly less pure material as an amorphous solid Combine (S)-2-(4-benzylpiperazin-2-yl)ethanol (3.08 g, 14.0 mmol) in methylenechloride (30 mL) and di-tert-butyl dicarbonate (3.2 g, 14.7 mmol) in 5 mL $CH_2Cl_2$ and add dropwise at room temperature. After 1 hour, quench the reaction mixture by adding water, extract with $CH_2Cl_2$, wash with water and brine, and dry over $Na_2SO_4$. Purification by silica gel chromatography of the crude product by using MeOH/$CH_2Cl_2$ (5% to 10%) as the eluent, gives 3.17 g (Yield 71%) of title compound: $^1$H NMR (400 MHz, $CDCl_3$): δ7.37–7.23 (m, 5H), 4.27–4.10 (m, 1H), 4.02–3.80 (m, 2H), 3.61–3.23 (m, 4H), 3.00 (t, 1H, J=10 Hz), 2.71–2.56 (m, 2H), 2.24–2.22 (m, 2H), 2.01 (dt, 1H, J=3.4, 12.2 Hz), 1.46 (s, 9H).

Example 197

(S)-4-Benzyl-2-(2-oxo-ethyl)-piperazine-1-carboxylic acid tert-butyl ester

Add dichloromethane (3 mL) to a 50 mL dry schlenk flask, followed by oxalyl chloride (0.178 g, 1.4 mmol) and cool the solution to −78° C. and treat with dimethyl sulfoxide (0.171 g, 2.2 mmol) and triethylamine (0.505 g, 5.0 mmol). After 10 min, add a solution of (S)-4-benzyl-2-(2-hydroxy-ethyl)-piperazine-1-carboxylic acid tert-butyl ester (0.320 g, 1.0 mmol) in dichloromethane (5 mL) and stir the resulting mixture at −78° C. for 1 hour. Quench the reaction mixture by adding sat. $NaHCO_3$, extract the aqueous solution with $CH_2Cl_2$, wash the organic solvent with brine, and dry over $Na_2SO_4$. Purification by silica gel chromatography of the crude product using MeOH/$CH_2Cl_2$ (5% to 10%) as eluent to give the title compound (160 g, 50%) as a light yellow oil: mass spectrum (Electrospray): m/z=319.2 (M+1); $^1$H NMR (400 MHz, $CDCl_3$): δ9.74 (t, 1H, J=2.0 Hz), 7.33–7.21 (m, 5H), 4.57 (br, 1H), 3.88 (m, 2H), 33.52–3.40 (m, 21H), 3.15–3.05 (m, 1H), 2.83–2.66 (m, 4H), 2.22–2.18 (m, 1H), 2.03 (dt, 1H, J=3.4, 11.8 Hz), 1.44 (s, 9H).

Example 198

(S)-4-Benzyl-2-(3-phenyl-allyl)-piperazine-1-carboxylic acid tert-butyl ester Combine and cool to 0° C. a solution of (S)-4-benzyl-2-(2-oxo-ethyl)-piperazine-1-carboxylic acid tert-butyl ester (1.95 g, 6.13 mmol) and diethyl benzyl phosphonate (4.23 g, 18.55 mmol) in dry DMF (25 mL), and add solid sodium methoxide (95%, 1.15 g, 21.3 mmol) in a single portion, and stir at 0° C. for 30 minutes. Dilute the mixture with $CH_2Cl_2$, wash with brine and dry the organic layer over $Na_2SO_4$. Purification by silica gel chromatography of the crude product using EtOAC/$CH_2Cl_2$ (2% to 10%) as eluent gives the title compound (2.37 g) as a white solid: mass spectrum (Electrospray): m/z=393.3 (M+1); $^1$H NMR (400 MHz, $CDCl_3$): δ7.37–7.21 (m, 10H), 6.34–6.30 (m, 1H), 6.12–6.02 (m, 1H), 4.10 (br, 1H), 3.87 (br, 1H), 3.59–3.52 (m, 1H), 3.41–3.35 (m, 1H), 3.13 (m, 1H), 2.82–2.59 (m, 4H), 2.18–2.04 (m, 2H), 1.39 (s, 9H).

Example 199

(S)-1-Benzyl-3-(3-phenyl-allyl)-piperazine

Dissolve (S)-4-benzyl-2-(3-phenyl-allyl)-piperazine-1-carboxylic acid tert-butyl ester (2.37 g, 6.04 mmol) in toluene (50 mL) and treat with trifluoroacetic acid (10.3 g, 90.5 mmol) at room temperature, and stir the reaction mixture. After overnight, dilute the reaction with $CH_2Cl_2$, and basify with 2N NaOH (50 mL), extract the aqueous solution with $CH_2Cl_2$, wash the combined organic layers brine, dry over $Na_2SO_4$. Pass the crude product through a SCX column (10 g), collect the 0.2N $NH_3$/MeOH eluent and concentrate to give 1.46 g of the title compound: mass spectrum (Electrospray): m/z=293.3 (M+1). $^1$H NMR (400 MHz, $CDCl_3$): δ7.35–7.19 (m, 10H), 6.54–6.47 (m, 1H) 6.18–6.11, 5.70–5.60 (m, 1H), 3.70 (s, 2H), 2.97–2.73 (m, 5H), 2.40–2.18 (m, 2H), 2.09–2.00 (m, 1H), 1.83 (t, 1H, J=9.8 Hz).

Example 200

(S)-2-(3-Phenyl-propyl)-piperazine

Combine (S)-1-benzyl-3-(3-phenyl-allyl)-piperazine (1.45 g, 5.0 mmol), 10% Pd/C (265 mg, 0.025 mmol) and ammonia formate (1.57 g, 25.0 mmol) in EtOH (90 mL) and heat to reflux for 3 hours, cool to room temperature, remove the catalyst by filtration. Concentrate the solvent to a residue, which $^1$H NMR shows that the carbon-carbon double bond has been reduced, but the benzyl group remains. Subject the residue to the reaction with 10% Pd(OH)$_2$/C (350 mg, 0.5 mmol) in EtOH with a balloon of hydrogen under reflux conditions. After refluxing for 3 hours, cool the reaction to room temperature, remove the catalyst, concentrate to a residue, and purification by silica gel chromatography using 2N NH$_3$ in MeOH and dichloromethane (5%–15%) to give the title compound (950 mg, 93%): mass spectrum (Electrospray): m/z=205.2 (M+1); $^1$H NMR (CDCl$_3$): δ7.29–7.15 (m, 5H), 2.97–2.59 (m, 6H), 2.35 (t, 1H, J=9.8 Hz), 1.70–1.45 (m, 6H), 1.38–1.25 (m, 2H).

Example 201

(S)-2-Methyl-10-(3-(3-phenyl-propyl)-piperazin-1-yl)-4H-3-thia-4,9-diaza-benzo[f]azulene, dihydrochloric acid

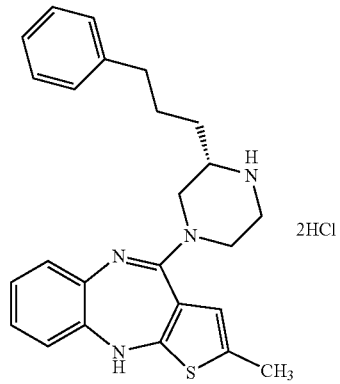

Combine (S)-2-(3-phenyl-propyl)-piperazine (510 mg, 2.50 mmol), 2-methyl-4H-3-thia-4,9-diaza-benzo[f]azulen-10-ylamine (663 mg, 2.50 mmol), diisopropylethylamine (4 mL), DMSO/Toluent (1.25/2.5 mL), heat at 110° C. After 24 hours, cool to ambient temperature, remove the solvent, dilute with CH$_2$Cl$_2$, wash with water, brine, and dry over with Na$_2$SO$_4$. Purification by silica gel chromatography of the crude product using 2N ammonia in methanol-methylene chloride (2–4%) as the eluent gives 310 mg brown foam of the free base: mass spectrum (Electrospray): m/z=417.3 (M+1). $^1$H NMR (400 MHz, CDCl$_3$): δ7.31–7.23 (m, 2H), 7.20–7.15 (m, 3H), 7.04–6.85 (m, 3H), 6.60 (dd, 1H, J=1.5, J=7.8 Hz), 6.28 (d, 1H, J=1.5 Hz), 4.94 (s, 1H), 4.07–3.96 (m, 2H), 3.05–2.89 (m, 3H), 2.79–2.77 (m, 1H), 2.64 (t, 2H, J=7.3 Hz), 2.57–2.51 (m, 1H), 2.29 (d, 3H, J=1.0 Hz), 1.76–1.40 (m, 5H). Treat the free base with NH$_4$Cl (2.0 eq.) in MeOH, remove the solvent, dissolve in CH$_3$CN/H$_2$O=50/50, lyophilize overnight to give the title compound as a yellow solid: mass spectrum (Electrospray): m/z=417.1 (M+1–2HCl), 416.1 (M–1–2HCl).

Example 202

(S)-2-Methyl-10-(3-(3-phenyl-propyl)-4-methyl-piperazin-1-yl)-4H-3-thia-4,9-diaza-benzo[f]azulene, dihydrochloric acid

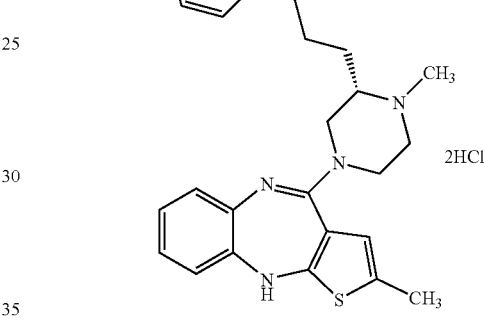

Combine (S)-2-methyl-10-3-(3-phenyl-propyl)-piperazin-1-yl]-4H-3-thia-4,9-diaza-benzo[f]azulene (320 mg, 0.77 mmol), formaldehyde (37% aq, 68.6 mg, 0.85 mmol) and sodium triacetoxyborohydride (244.7 mg, 1.15 mmol) in 1,2-dichloroethane (15 mL) and stir at room temperature. After 4 hours, quench the reaction adding sat. NaHCO$_3$, extract the aqueous solution with CH$_2$Cl$_2$ (3×10 mL), wash the organic solvent with brine, and dry over Na$_2$SO$_4$. Concentrate the solvent in vaccuo to give a residue and purify by silica gel chromatography using 2N ammonia in methanol-methylene chloride (2–4%) as the eluent to give 285 mg (yield 86%) light brown foam of the free base: mass spectrum (Electrospray): m/z=431.3 (M+1); $^1$H NMR (400 MHz, CDCl$_3$): δ7.29–7.16 (m, 5H), 7.03–6.85 (m, 3H), 6.59 (dd, 1H, J=1.5, J=7.8 Hz), 6.28 (d, 1H, J=1.0 Hz), 4.94 (s, 1H), 3.99–3.89 (m, 2H), 3.14–3.09 (m, 1H), 2.85–2.77 (m, 2H), 2.68–2.56 (m, 2H), 2.35–2.14 (m, 8H), 1.74–1.42 (m, 4H). Analysis calculated for C$_{26}$H$_{30}$N$_4$S.0.3H$_2$O: C, 71.62; H, 7.07; N, 12.86. Found: C, 71.69; H, 6.94; N, 12.48. Treat the free base with ammonia chloride (2.0 eq.) in MeOH at 45° C. for 1 hour, remove the solvent, dissolve in a mix solvent (15 mL) CH$_3$CN/H$_2$O=50/50, lyophilize overnight to give the title compound as a yellow solid.

By a method similar to Example 59, using the appropriate starting materials, the following compounds were prepared and isolated as the (S) isomer except where noted below:

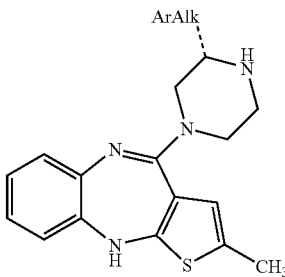

| No: | ArAlk | Data |
|---|---|---|
| 209 | CH$_2$(4-Br)Ph | mp 97–112° C.: $^1$H NMR(CDCl$_3$): δ2.26(s, 3H), 2.59(dd, 1H), 2.65(dd, 1H), 2.74(dd, 1H), 2.88–2.80(m, 1H), 3.03–2.91(m, 3H), 3.99(d, 1H), 4.07(d, 1H), 4.97(s, 1H), 6.17(t, 1H), 6.59(dt, 1H), 6.87(ddd, 1H), 6.97(ddd, 1H), 7.11(d, 2H), 7.43(d, 2H); MS(APCI)m/z(rel intensity)468.3(96), 469.3(100). 57% yield. |
| 210 | CH$_2$(4-I)Ph | mp 105–121° C.: $^1$H NMR(CDCl$_3$): δ2.26(s, 3H), 2.58(dd, 1H), 2.66(dd, 1H), 2.73(dd, 1H), 2.88–2.80(m, 1H), 3.03–2.91(m, 3H), 3.99(d, 1H), 4.07(d, 1H), 4.97(s, 1H), 6.17(d, 1H), 6.60(dd, 1H), 6.87(dt, 1H), 7.03–6.94(m, 4H), 7.63(d, 2H); MS(APCI)m/z(rel intensity)515.4(100). 47% yield. |
| 211 | CH$_2$(4-O—CH$_2$CH$_2$=CH$_2$)Ph | $^1$H NMR(CD$_3$OH): δ2.17(bs, 3H), 2.87(m, 1H), 3.05(m, 1H), 3.39–3.50(m, 2H), 3.63–3.86(m, 3H), 4.07(m, 1H), 4.29(m, 1H), 4.55(m, 2H), 5.26(m, 1H), 5.40(m, 1H), 6.07(m, 1H), 6.25(bs, 1H), 6.88(d, 1H), 6.95(d, 2H), 7.12–7.28(m, 5H); MS(APCI)m/z(rel intensity)445(100). 10 mg product. |
| 212 | CH$_2$(thiophen-3-yl) | mp 82–94° C.: $^1$H NMR(CDCl$_3$): δ2.28(s, 3H), 2.67(dd, 1H), 2.70(dd, 1H), 2.81(dd, 1H), 2.87(dd, 1H), 3.06–2.93(m, 3H), 3.99(d, 1H), 4.11(d, 1H), 4.98(s, 1H), 6.23(d, 1H), 6.60(dd, 1H), 6.87(dt, 1H), 6.97(dt, 1H), 6.99(dd, 1H), 7.02(dd, 1H), 7.05(m, 1H), 7.29(dd, 1H); MS(APCI)m/z(rel intensity 395.4(100). 47% yield. |
| 213 | CH$_2$(4-OiPr)Ph | mp 106–119° C.: $^1$H NMR(CDCl$_3$): δ1.32(d, 3H), 1.34(d, 3H), 2.26(d, 3H), 2.55(dd, 1H), 2.67(dd, 1H), 2.73(dd, 1H), 2.84(dd, 1H), 3.04–2.92(m, 3H), 4.00(d, 1H), 4.09(d, 1H), 4.51(qt, 1H), 4.94(s, 1H), 6.21(d, 1H), 6.60(dd, 1H), 6.84–6.80(m, 2H), 6.87(dt, 1H), 6.96(dt, 1H), 7.01(dd, 1H), 7.14–7.10(m, 2H); MS(APCI)m/z(rel intensity)447.5(100). 44% yield. |

By a method similar to Example 1, using the appropriate starting materials, the following compounds were prepared and isolated as the(S) isomer except where noted below:

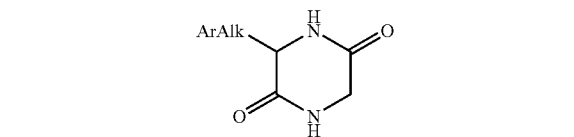

| No.: | ArAlk | Data |
|---|---|---|
| 214 | CH$_2$(4-Br)Ph | $^1$H NMR(DMSO-d$_6$): δ2.87(dd, 1H), 3.01(d, 1H), 3.07(dd, 1H), 3.46(d, 1H), 4.08(m, 1H), 7.13(d, 2H), 7.48(d, 2H), 7.94(s, 1H), 8.17(s, 1H); MS(APCI)m/z (rel intensity)283(100). 285(100). |
| 215 | CH$_2$(4-I)Ph | $^1$H NMR(DMSO-d$_6$): δ2.84(dd, 1H), 2.97(d, 1H), 3.04(dd, 1H), 3.45(d, 1H), 4.06(m, 1H), 6.99(d, 2H), 7.64(2H, 1H), 7.93(s, 1H), 8.16(s, 1H); MS(APCI)m/z (rel intensity)331(100). |
| 216 | CH$_2$(thiophen-3-yl) | mp 248–249° C.: $^1$H NMR(DMSO-d$_6$): δ2.87(dd, 1H), 2.92(d, 1H), 3.09(dd, 1H), 3.42(dd, 1H), 4.01(m, 1H), 6.88(dd, 1H), 7.12(m, 1H), 7.42(m, 1H), 7.87(s, 1H), 8.10(s, 1H). |
| 217 | CH$_2$(4-iPrO)Ph | mp 242° C.: $^1$ H NMR(DMSO-d$_6$): δ1.24(d, 6H), 2.74(d, 1H), 2.80(dd, 1H), 3.03(dd, 1H), 3.34(d, 1H), 4.02(m, 1H), 4.57(septet, 1H), 6.81(d, 1H), 7.04(d, 1H), 7.87(s, 1H), 8.12(s, 1H). |
| 217a | CH$_2$(3,4-OCH$_2$O—)Ph | mp 255–257° C.: $^1$H NMR(DMSO-d$_6$) δ2.80(dd, 1H), 3.01(dd, 2H), 3.43(dd, 1H), 4.01(m, 1H), 5.98(s, 2H), 6.63(dd, 1H), 6.70(s, 1H), 6.83(d, 1H), 7.92(s, 1H), 8.09(d, 1H). |
| 217b | CH$_2$(3,4-Di-OCH$_3$)Ph | mp 254–255° C.: $^1$H NMR(DMSO-d$_6$) δ2.72(d, 1H), 2.78(dd, 1H), 2.98(dd, 1H), 3.33(dd, 1H), 3.65(s, 3H), 3.67(s, 3H), 3.99(m, 1H), 6.63(d, 1H), 6.71(s, 1H), 6.81(d, 1H), 7.82(s, 1H), 8.06(d, 1H). |

By a method similar to Example 90, using the appropriate starting materials, the following compounds were prepared and isolated as the free base and as the (S) isomer except where noted:

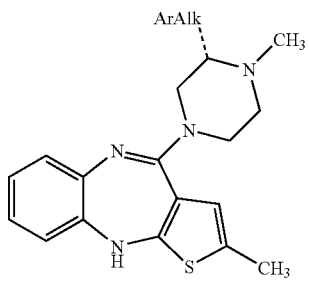

| No: | ArAlk | Data |
|---|---|---|
| 218 | CH$_2$(4-Br)Ph | mp 68–79° C.: $^1$H NMR(CDCl$_3$): δ2.17(s, 3H), 2.46–2.34(m, 3H), 2.48(s, 3H), 2.78(dd, 1H), 2.90(dt, 1H), 3.11(dd, 1H), 3.19(ddd, 1H), 3.56(d, 1H), 3.96(d, 1H), 4.91(s, 1H), 5.96(s, 1H), 6.57(dd, 1H), 6.85(ddd, 1H), 6.98–6.91(m, 2H), 7.06–7.02(m, 2H), 7.41–7.36(m, 2H); MS(APCI)m/z(rel intensity)482.3 (96), 483.3(100). 92% yield. |
| 219 | CH$_2$(thiophen-3-yl) | mp 58–72° C.: $^1$H NMR(CDCl$_3$): δ2.20(s, 3H), 2.48–2.37(m, 2H), 2.46(s, 3H), 2.58(dd, 1H), 2.78(dd, 1H), 2.89(dt, 1H), 3.11(dd, 1H), 3.19(ddd, 1H), 3.69(d, 1H), 3.97(d, 1H), 4.92(s, 1H), 6.06(s, 1H), 6.57(dd, 1H), 6.85(ddd, 1H), 7.00–6.92(m, 4H), 6.25(dd, 1H); MS(APCI)m/z(rel intensity)409.3(100). 95% yield. |
| 220 | CH$_2$(4-I)Ph | mp 76–94° C.: $^1$H NMR(CDCl$_3$): δ2.18(s, 3H), 2.46–2.36(m, 3H), 2.47(s, 3H), 2.78(dd, 1H), 2.90(dt, 1H), 3.09(d, 1H), 3.20(ddd, 1H), 3.56(d, 1H), 3.96(d, 1H), 4.91(s, 1H), 5.97(s, 1H), 6.57(dd, 1H), 6.85(ddd, 1H), 6.97–6.89(m, 4H), 7.60–7.56(m, 2H); MS(APCI)m/z(rel intensity)529.3(100). 87% yield. |
| 221 | CH$_2$(4-OiPr)Ph | mp 92–98° C.: $^1$H NMR(CDCl$_3$): δ1.32(d, 3H), 1.33(d, 3H), 2.14(s, 3H), 2.39–2.32(m, 2H), 2.42(dd, 1H), 2.48(s, 3H), 2.77(dd, 1H), 2.91(dt, 1H), 3.10(d, 1H), 3.18(dd, 1H), 3.62(d, 1H), 3.98(d, 1H), 4.49(qt, 1H), 4.89(s, 1H), 5.99(s, 1H), 6.56(d, 1H), 6.81–6.76(m, 2H), 6.84(dd, 1H), 6.93(d, 2H), 7.04(d, 2H); MS(APCI)m/z(rel intensity)461.5(100). 96% yield. |

By a method similar to Example 58, using the appropriate starting materials, the following piperazine were prepared and isolated.

| No: | ArAlk | Data |
|---|---|---|
| 222 | CH$_2$(4-I)Ph | $^1$H NMR(CDCl$_3$): δ2.52–2.60(m, 2H), 2.69(dd, 1H), 2.81–2.93(m, 2H), 2.99–3.10(m, 4H), 6.95(d, 2H), 7.63(d, 2H); MS(APCI)m/z(rel intensity)303(100). |

Example 223

3-(S)-(4-(3-Methyl-but-2-enyloxy)-benzyl-piperazine-2,5-dione

To a suspension of 3-(S)-(4-hydroxy-benzyl)-piperazine-2,5-dione (15 g, 68.2 mmol), cesium carbonate (111 g, 340 mmol), and tetrabutylammonium iodide (1.25 g, 3.4 mmol) in anhydrous DMF. (500 mL), add at once, at ambient temperature, 1-bromo-3-methyl-but-2-ene (51 g, 340 mmol). Stir 12 hours then add water (300 mL). Concentrate to dryness then add water (500 mL) and extract with a dichloromethane/isopropyl alcohol (3/1) mixture. Wash the organic phases with 10% aqueous potassium carbonate and water then dry over magnesium sulfate. Evaporate the solvent, then triturate the resulting solid with chloroform. Filter and dry to yield (14.3 g, 73%) of the title compound as a white solid: mp 217–220° C.: $^1$H NMR (DMSO-d$_6$): δ 1.69 (s, 3H), 1.74 (s, 3H), 2.84–2.76 (m, 2H), 3.02 (dd, 1H), 3.36 (dd, 1), 4.01 (m, 1H), 4.48 (d, 2H), 5.41 (m, 1H), 6.84 (d, 2H), 7.05 (d, 2H), 7.86 (s, 1H), 8.12 (d, 1H).

By a method similar to Example 223, using the appropriate starting materials, the following compounds were prepared and isolated.

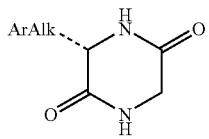

| No: | ArAlk | Data |
|---|---|---|
| 224 | CH$_2$(4-OCH$_2$CH=CH$_2$)Ph | mp 258° C.: $^1$H NMR(DMSO-d$_6$): δ2.78(d, 1H), 2.81(dd, 1H), 3.03(dd, 1H), 3.35(dd, 1H), 4.01(m, 1H), 4.53(d, 2H), 5.24(dd, 1H), 5.38(dd, 1H), 6.07–5.96(m, 1H), 6.86(d, 2H), 7.06(d, 2H), 7.87(s, 1H), 8.11(d, 1H). |
| 224a | CH$_2$-(4-OCH$_2$C(=CH$_2$)CH$_3$Ph | mp 248–249° C.: $^1$H NMR(DMSO-d$_6$) δ1.75(s, 3H), 2.78(d, 1H), 2.81(dd, 1H), 3.03(dd, 1H), 3.35(dd, 1H), 4.01(m, 1H), 4.43(s, 2H), 4.94(s, 1H), 5.04(s, 1H), 6.86(d, 2H), 7.06(d, 2H), 7.87(s, 1H), 8.11(d, 1H). |

By a method similar to Example 24, using the appropriate starting materials, the following piperazines were prepared and isolated were prepared and isolated as the (S) isomer except where noted below.

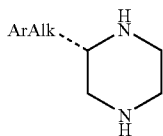

| No: | ArAlk | Data |
|---|---|---|
| 225 | CH$_2$(4-O—CH$_2$CH=CH$_2$)Ph | mp 89–90° C.: $^1$H NMR(CDCl$_3$): δ2.45(dd, 1H), 2.48(dd, 1H), 2.63(dd, 1H), 2.82–2.67(m, 3H), 2.90(dd, 2H), 2.96(dd, 1H), 4.51(t, 1H), 4.52(t, 1H), 5.28(dq, 1H), 5.41(dq, 1H), 6.11–6.00(m, 1H), 6.86(d, 2H), 7.11(d, 2H); MS (APCI)m/z(rel intensity)233.3(100). |
| 226 | CH$_2$(thiophen-3-yl) | mp 75–77° C.: $^1$H NMR(CDCl$_3$): δ2.48(dd, 1H), 2.59(dd, 1H), 2.95–2.66(m, 6H), 2.98(dd, 1H), 6.95(dd, 1H), 7.02(m, 1H), 7.28(m, 1H); MS(APCI)m/z(rel intensity)183.2 (100). |
| 227 | CH$_2$(4-OiPr)Ph | $^1$H NMR(CDCl$_3$)δ1.31(s, 3H), 1.33(s, 3H), 2.45(dd, 1H), 2.48(dd, 1H), 2.63(dd, 1H), 2.82–2.67(m, 3H), 2.90(dd, 2H), 2.96(dd, 1H), 4.45(qt, 1H), 6.81(d, 2H), 7.15(d, 2H); MS(APCI)m/z(rel intensity)235.3(100). |
| 228 | CH$_2$(4-OPh)Ph | $^1$H NMR(CDCl$_3$)δ2.48(dd, 1H), 2.52(dd, 1H), 2.67(dd, 1H), 2.70–2.96(m, 5H), 2.98(dd, 1H), 6.95(d, 2H), 7.01(d, 2H), 7.10(t, 1H), 7.16(d, 2H), 7.32(t, 2H); MS(APCI)m/z (rel intensity)269(100). |
| 229 | CH$_2$(4-i-Pr)Ph | $^1$H NMR(CDCl$_3$)δ1.24(d, 6H), 2.47(dd, 1H), 2.50(dd, 1H), 2.63–2.92(m, 7H), 2.96(dd, 1H), 7.09–7.17(m, 4H); MS(APCI)m/z(rel intensity)219(100). |
| 230 | CH$_2$(3,5-DiCH$_3$)Ph | $^1$H NMR(CDCl$_3$)δ2.28(s, 6H), 2.43(dd, 1H), 2.49(dd, 1H), 2.62(dd, 1H), 2.66–2.99(m, 6H), 6.82(s, 2H), 6.86(s, 1H); MS(APCI)m/z(rel intensity)205(100). |
| 231 | CH$_2$(3,4-OCH$_2$O—)Ph | mp 80–84° C.; $^1$H NMR(CDCl$_3$)δ2.40(dd, 1H), 2.70(dd, 1H), 2.61(dd, 1H), 2.82–2.71(m, 3H), 2.99–2.87(m, 3H), 5.93(s, 2H), 6.76–6.62(m, 3H); MS(APCI)m/z(rel intensity)221.3(100). |
| 232 | CH$_2$(4-O—CH$_2$CH=C(CH$_3$)$_2$)Ph | mp 43–47° C.: $^1$H NMR(CDCl$_3$)δ1.77(s, 3H), 1.89(s, 3H), 2.45(dd, 1H), 2.48(dd, 1H), 2.63(dd, 1H), 2.82–2.67(m, 3H), 2.90(dd, 2H), 2.96(dd, 1H), 4.48(s, 2H), 5.49(ddd, 1H), 6.85(d, 2H), 7.10(d, 2H); MS(APCI)m/z(rel intensity)261.5(100). |
| 233 | CH$_2$(4-O—CH$_2$C(=CH$_2$)CH$_3$)Ph | mp 73–75° C.: $^1$H NMR(CDCl$_3$)δ1.83(s, 3H), 2.45(dd, 1H), 2.48(dd, 1H), 2.63(dd, 1H), 2.82–2.67(m, 3H), 2.90 (dd, 2H), 2.96(dd, 1H), 4.41(s, 2H), 4.98(s, 1H), 5.09(s, 1H), 6.85(d, 2H), 7.09(d, 2H); MS(APCI)m/z(rel intensity)247.4(100). |

-continued

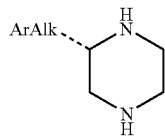

| No: | ArAlk | Data |
|---|---|---|
| 234 | CH$_2$(3,4-DiO—CH$_3$)Ph | $^1$H NMR(CDCl$_3$)δ2.45(dd, 1H), 2.50(dd, 1H), 2.65(dd, 1H), 2.82–2.71(m, 3H), 2.96–2.87(m, 2H), 2.98(dd, 1H), 3.86(s, 3H), 3.87(s, 3H), 6.83–6.72(m, 3H); MS(APCI)m/z (rel intensity)237.3(100). |
| 235 | CH$_2$(2-OCH$_2$CH$_3$)Ph | $^1$H NMR(CDCl$_3$)δ1.43(t, 3H), 2.45–2.53(m, 2H), 2.71–2.79(m, 3H), 2.86–2.95(m, 4H), 4.03(q, 2H), 6.82–6.87(m, 2H), 7.12–7.28(m, 2H); MS(APCI)m/z(rel intensity)221 (100). |
| 235a | CH$_2$(3-OPh)Ph | $^1$H NMR(CDCl$_3$)δ2.47(dd, 1H), 2.49(dd, 1H), 2.64(dd, 1H), 2.67–2.96(m, 6H), 6.86(d, 1H), 6.88(s, 1H), 6.93(d, 1H), 7.01(d, 2H), 7.10(t, 1H), 7.24(t, 1H), 7.33(t, 2H); MS (APCI)m/z(rel intensity)269(100). |
| 235b | CH$_2$(2,4-Di-OCH$_3$)Ph | $^1$H NMR(CDCl$_3$)δ2.43(dd, 1H), 2.47(dd, 1H), 2.66(dd, 1H), 2.69–2.96(m, 6H), 3.78(s, 3H), 3.79(s, 3H), 6.41(d, 1H), 6.44(s, 1H), 7.03(d, 1H); MS(APCI)m/z(rel intensity)237(100). |

25

By a method similar to Example 59, using the appropriate starting materials, the following compounds were prepared and isolated as the (S) isomer except where noted below:

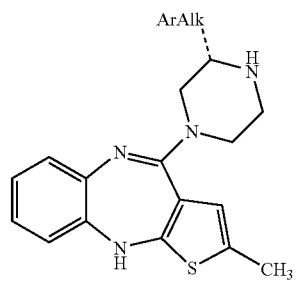

| No: | ArAlk | Data |
|---|---|---|
| 236 | CH$_2$(3,5-DiCH$_3$)Ph | $^1$H NMR(CDCl$_3$)δ2.27(s, 3H), 2.29(s, 6H), 2.51(dd, 1H), 2.69(dd, 1H), 2.74(dd, 1H), 2.82(ddd, 1H), 2.93–3.02(m, 3H), 3.99(m, 1H), 4.12(m, 1H), 4.96(s, 1H), 6.23(s, 1H), 6.60(d, 1H), 6.85(s, 2H), 6.86(s, 1H), 6.86(t, 1H), 6.96(t, 1H), 7.02(d, 1H); MS(APCI)m/z(rel intensity)417(100). 35% yield. |
| 237 | CH$_2$(4-O—CH$_2$C(=CH$_2$)CH$_3$)Ph | mp 106–113° C.; $^1$H NMR(CDCl$_3$)δ1.83(s, 3H), 2.26(s, 3H), 2.56(dd, 1H), 2.66(dd, 1H), 2.73(dd, 1H), 2.84(dd, 1H), 3.04–2.92(m, 3H), 4.00(d, 1H), 4.08(d, 1H), 4.41(s, 2H), 4.95(s, 1H), 4.99(m, 1H), 5.09(m, 1H), 6.20(d, 1H), 6.60(dd, 1H), 6.89–6.84(m, 3H), 6.96(dt, 1H), 7.02(dd, 1H), 7.15–7.01(m, 2H); MS(APCI)m/z(rel intensity)459.5 (100). 41% yield. |
| 238 | CH$_2$(2-OCH$_2$CH$_3$)Ph | $^1$H NMR(CDCl$_3$)δ1.42(t, 3H), 2.22(s, 3H), 2.62(dd, 1H), 2.68(dd, 1H), 2.83–2.90(m, 2H), 2.97(ddd, 1H), 3.02–3.11(m, 2H), 3.97(m, 1H), 4.02(q, 2H), 4.03(m, 1H), 4.99(s, 1H), 6.18(s, 1H), 6.59(d, 1H), 6.82–6.89(m, 3H), 6.95(t, 1H), 7.01(d, 1H), 7.16–7.21(m, 2H); MS(APCI)m/z(rel intensity)433(100). 50 mg of product. |
| 239 | CH$_2$(2-O-i-Pr)Ph | $^1$H NMR(CDCl$_3$)δ1.33(dd, 6H), 2.22(s, 3H), 2.55(m, 1H), 2.65(m, 1H), 2.81–3.20(m, 5H), 3.92(d, 1H), 4.07(d, 1H), 4.51(m, 1H), 4.91(s, 1H), 6.16(s, 1H), 6.58(d, 1H), 6.85(m, 3H), 6.95(t, 1H), 6.99(d, 1H), 7.15(d, 2H); MS(ESI) m/z(rel intensity)447(100). 1.0 g of product. |

-continued

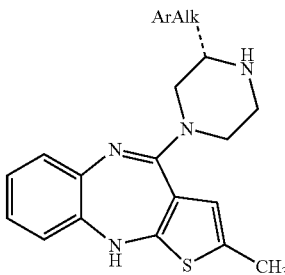

| No: | ArAlk | Data |
|---|---|---|
| 240 | CH₂(pyridin-2-yl) | mp 115–117° C.(decomp); ¹H NMR(CDCl₃)δ2.25(s, 3H), 2.90–2.96(m, 4H), 3.10–3.20(m, 2H), 3.40(m, 1H), 4.05(m, 2H), 5.09(bs, 1H), 6.22(s, 1H), 6.60(d, 1H), 6.85(t, 1H), 6.96(t, 1H), 6.99(d, 1H), 7.12–7.20(m, 2H), 7.60(t, 1H), 8.52(d, 1H); MS(es)m/z(rel intensity)390(100). 50 mg of product. |
| 240a | CH₂(3-OPh)Ph | mp 97–103° C.; ¹H NMR(CDCl₃)δ2.26(s, 3H), 2.62(dd, 1H), 2.65(dd, 1H), 2.75(dd, 1H), 2.86(dd, 1H), 2.94(dd, 1H), 3.05–2.97(m, 2H), 3.99(d, 1H), 4.06(d, 1H), 4.94(s, 1H), 6.20(s, 1H), 6.59(dd, 1H), 6.90–6.84(m, 3H), 7.04–6.93(m, 5H), 7.11(ddd, 1H), 7.27(t, 1H), 7.36–7.31(m, 2H); MS(APCI)m/z(rel intensity)481.5(100). 43% yield. |

By a method similar to Example 90, using the appropriate starting materials, the following compounds were prepared and isolated as the free base and as the (S) isomer except where noted:

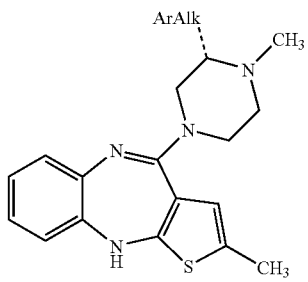

| No: | ArAlk | Data |
|---|---|---|
| 241 | CH₂(4-O—CH₂CH=C(CH₃)₂)Ph | mp 74–78° C.; ¹H NMR(CDCl₃)δ1.75(s, 3H), 1.81(s, 3H), 2.13(s, 3H), 2.39–2.32(m, 2H), 2.42(dd, 1H), 2.48(s, 3H), 2.76(dd, 1H), 2.91(dt, 1H), 3.11(d, 1H), 3.18(dd, 1H), 3.61(d, 1H), 3.99(d, 1H), 4.47(d, 2H), 4.91(s, 1H), 5.50(m, 1H), 5.97(bs, 1H), 6.56(dd, 1H), 6.87–6.79(m, 3H), 6.95–6.91(m, 2H), 7.05(d, 2H); MS(APCI)m/z(rel intensity) 487.5(100). 93% yield. |
| 242 | CH₂(3,4-OCH₂O—)Ph | mp 105–108° C.; ¹H NMR(CDCl₃)δ2.18(d, 3H), 2.39–2.32(m, 2H), 2.43(dd, 1H), 2.47(s, 3H), 2.78(dd, 1H), 2.90(dt, 1H), 3.08(d, 1H), 3.20(dd, 1H), 3.61(d, 1H), 3.97(d, 1H), 4.91(s, 1H), 5.92(dd, 2H), 6.02(bs, 1H), 6.57(dd, 1H), 6.60(dd, 1H), 6.72–6.66(m, 2H), 6.85(ddd, 1H), 6.96–6.92(m, 2H); MS(APCI)m/z(rel intensity)447.4(100). 90% yield. |
| 243 | CH₂(3,4-di-OCH₃)Ph | mp 103–108° C.; ¹H NMR(CDCl₃)δ2.13(s, 3H), 2.39–2.32(m, 2H), 2.43(dd, 1H), 2.49(s, 3H), 2.76(dd, 1H), 2.91(dt, 1H), 3.15–3.08(m, 1H), 3.18(dd, 1H), 3.67(d, 1H), 3.83(s, 3H), 3.86(s, 3H), 4.00(d, 1H), 4.91(s, 1H), 5.96(bs, 1H), 6.57(dd, 1H), 6.65(d, 1H), 6.70(dd, 1H), 6.77(d, 1H), 6.85(ddd, 1H), 6.95–6.91(m, 2H); MS(APCI)m/z(rel intensity) 463.4(100). 90% yield. |

-continued

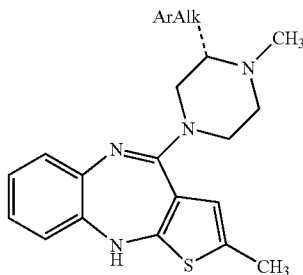

| No: | ArAlk | Data |
|---|---|---|
| 244 | CH₂(4-O—CH₂C(=CH₂)CH₃)Ph | mp 93–100° C.; ¹H NMR(CDCl₃)δ1.83(s, 3H), 2.14(s, 3H), 2.44–2.32(m, 3H), 2.48(s, 3H), 2.76(dd, 1H), 2.91(dt, 1H), 3.11(d, 1H), 3.18(dd, 1H), 3.61(d, 1H), 3.98(d, 1H), 4.40(s, 2H), 4.90(s, 1H), 4.99(m, 1H), 5.09(m, 1H), 5.98 (bs, 1H), 6.56(dd, 1H), 6.87–6.79(m, 3H), 6.95–6.91(m, 2H), 7.05(d, 2H); MS(APCI)m/z(rel intensity)473.5(100). 94% yield. |
| 245 | CH₂(4-iPr—Ph) | mp 94–99° C.; ¹H NMR(CDCl₃)δ1.23(d, 3H), 1.25(d, 3H), 2.16(s, 3H), 2.46–2.38(m, 3H), 2.49(s, 3H), 2.93–2.79(m, 3H), 3.12(d, 1H), 3.22(dd, 1H), 3.6(d, 1H), 3.92(d, 1H), 4.91(s, 1H), 6.07(bs, 1H), 6.84(ddd, 1H), 6.96–6.88(m, 2H), 7.16–6.04(m, 5H); MS(APCI)m/z(rel intensity)445.6 (100). 77% yield. |
| 246 | CH₂(3,5-DiCH₃)Ph | mp 96–103° C.; ¹H NMR(CDCl₃)δ2.10(s, 3H), 2.25(s, 6H), 2.48–2.32(m, 3H), 2.49(s, 3H), 2.87(dd, 1H), 2.91(dt, 1H), 3.10–3.05(m, 1H), 3.26(dd, 1H), 3.62(d, 1H), 3.94(d, 1H), 5.00(m, 1H), 5.96(bs, 1H), 6.56(d, 1H), 6.74(d, 2H), 6.81(s, 1H), 6.83(dd, 1H), 6.94–6.90(m, 2H); MS(APCI) mz/(rel intensity)431.5(100). 82% yield. |
| 247 | CH₂(2-OCH₂CH₃)Ph | mp 135–137° C.; ¹H NMR(CDCl₃)δ1.41(t, 3H), 2.10(s, 3H), 2.42(d, 3H), 2.53(s, 3H), 2.86–2.95(m, 2H), 3.20(m, 2H), 3.61(d, 1H), 4.02(m, 3H), 4.89(s, 1H), 5.96(s, 1H), 6.56(d, 1H), 6.84(m, 3H), 6.92(d, 2H), 7.08(d, 1H), 7.15 (t, 1H); MS(ESI)m/z(rel intensity)447(100). 278 mg of product. |
| 248 | CH₂(4-Ph)Ph | ¹H NMR(CDCl₃)δ2.03(s, 3H), 2.42–2.53(m, 3H), 2.52(s, 3H), 2.87(m, 1H), 2.95(ddd, 1H), 3.21(m, 2H), 3.63(m, 1H), 3.96(m, 1H), 4.89(s, 1H), 6.01(s, 1H), 6.56(d, 1H), 6.84(m, 1H), 6.92(m, 2H), 7.25(d, 2H), 7.34(t, 1H), 7.43(t, 2H), 7.50(d, 2H), 7.58(d, 2H); MS(APCI)m/z(rel intensity)479(100). 421 mg of product. |
| 249 | CH₂(2-O—iPr)Ph | mp 184–186° C.; ¹H NMR(CDCl₃)δ1.21(d, 3H), 1.35(d, 3H), 2.07(s, 3H), 2.41(m, 3H), 2.53(s, 3H), 2.83–2.96(m, 2H), 3.19(m, 2H)3.59(d, 1H), 4.00(d, 1H), 4.55(m, 1H), 4.87(s, 1H), 5.92(s, 1H), 6.55(d, 1H), 6.81(m, 3H), 6.92(d, 2H), 7.08(d, 1H), 7.13(t, 1H); MS(ESI)m/z(rel intensity)461(100). 378 mg of product. |

Example 255

1-Acetyl-3-(pyridin-3-yl)methylene-piperazine-2,5-dione

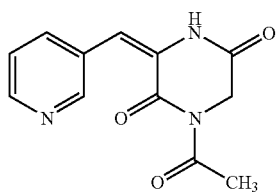

Add DMF (60 mL) to a mixture of 1,4-diacetyl-piperazine-2,5-dione (5.94 g, 30 mmol) and 3-pyridinecarboxaldehyde (12.84 g, 120 mmol). Cool to 0° C. Add portionwise over 20 min a solution of potassium tert-butoxide (3.36 g, 30 mmol) in tert-butanol (60 mL) to this solution. Warm to room temperature and stir for 2 h. Pour the mixture into water (400 mL) and filter. Wash with water three times, then with hexanes to obtain the title compound as a yellow powder (4.0 g, 54%): ¹H NMR (DMSO-d₆) δ 2.51 (s, 3H), 4.37 (s, 2H), 6.95 (s, 1H), 7.43 (dd, 1H), 7.96 (d, 1H1), 8.50 (d, 1H), 8.73 (s, 1H), 10.64 (bs, 1H).

By the method of example 255, the following compounds were prepared and isolated:

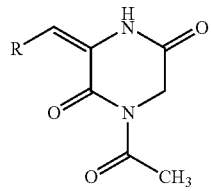

| No: | R | Data |
|---|---|---|
| 256 | 2-pyridyl | $^1$H NMR(DMSO-d$_6$)δ2.49(s, 3H), 4.32(s, 2H), 6.85(s, 1H), 7.36(dd, 1H), 7.67(d, 1H), 7.90(t, 1H), 8.70(d, 1H), 12.43(bs, 1H). 78% yield, 36 g. |
| 257 | (3,5-Di-OCH$_3$)Ph | $^1$H NMR(CDCl$_3$)δ2.61(s, 3H), 3.73(s, 6H), 4.56(s, 2H), 6.43(s, 1H), 6.45(s, 2H), 7.06(s, 1H), 8.09(bs, 1H). 98% yield 17.8 g gave 26.8 g. |
| 258 | (3,5-Di-CH$_3$)Ph | mp 172–174° C.: $^1$H NMR(CDCl$_3$)δ2.30(s, 6H), 2.61(s, 3H), 4.46(s, 2H), 6.95(s, 2H), 6.98(s, 1H), 7.08(s, 1H), 7.99(bs, 1H). 64% yield, 17.8 g gave 15.8 g. |
| 259 | (2-OEt)Ph | mp 142–145° C.: $^1$H NMR(CDCl$_3$)δ1.48(t, 3H), 2.63(t, 3H), 4.17(q, 2H), 4.45(s, 2H), 6.96(d, 1H), 7.01(t, 1H), 7.11(s, 1H), 7.30(d, 1H), 7.34(t, 1H), 8.80(bs, 1H). 64% yield, from 17.8 g gave 16.5 g. |
| 260 | (4-OPh)Ph | mp 165–167° C.: $^1$H NMR(CDCl$_3$)δ2.62(s, 3H), 4.48(s, 2H), 7.01–7.03(m, 4H), 7.11(s, 1H), 7.15(t, 1H), 7.33–7.38(m, 4H), 7.97(bs, 1H). 92% yield, 23.8 g gave 37.0 g |
| 261 | (4-i-Pr)Ph | mp 155–168° C.: $^1$H NMR(CDCl$_3$)δ1.24(d, 6H), 2.62(s, 3H), 2.90(septet, 1H), 4.48(s, 2H), 7.13(s, 1H), 7.27–7.31(m, 4H), 7.91(bs, 1H). 83% yield, 23.8 g gave 32.7 g |
| 262 | (2-OiPr)Ph | mp 187–192° C.; $^1$H NMR(CDCl$_3$)δ1.41(d, 6H), 2.67(s, 3H), 4.47(s, 2H), 4.71(m, 1H), 7.00(m, 2H), 7.11(s, 1H), 7.31(m, 2H). |
| 263 | (2,4-Di-OCH$_3$)Ph | $^1$H NMR(DMSO-d$_6$)δ2.42(s, 3H), 3.75(s, 3H), 3.78(s, 3H), 4.26(s, 2H), 6.54(d, 1H), 6.55(s, 1H), 6.99(s, 1H), 7.49(d, 1H), 10.01(bs, 1H). |

Example 266

(S)-1-Acetyl-3-(3-phenoxy-benzyl)-piperazine-2,5-dione

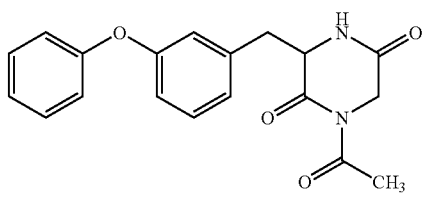

Add EtOH (60 mL) and DMF (15 mL) to the dehydrodiketopiperazine (15–50 g). Exchange the atmosphere to nitrogen with a Parr shaker. Add a catalytic amount of Pd/C (DeGaussa type from Aldrich, 50% water, 100 mg). Exchange the atmosphere three times with hydrogen to a pressure of 30 psi. During the reaction, the mixture will form a solution (except for the catalyst) and shake for an additional 30 minutes or until no more hydrogen uptake is observed. Filter the catalyst through celite, and concentrate to dryness to obtain the title compound as a white solid Separation of the S-isomers occurs via resolution of the piperazines. In all other examples, only the ethanol was removed and the crude product was used as is in a solution in DMF for treatment with hydrazine as in example 267. $^1$H NMR (CDCl$_3$) δ 2.54 (s, 3H), 3.11 (dd, 1H), 3.18 (dd, 1H), 3.50 (d, 1H), 4.22 (d, 1H), 4.36 (m, 1H), 6.82 (s, 1H), 6.90–6.93 (m, 2H), 6.96 (d, 2H), 7.12 (t, 1H), 7.18 (bs, 1H), 7.27 (t, 1H), 7.34 (t, 2H).

Example 267

3-(3-Phenoxy-benzyl)-piperazine-2,5-dione

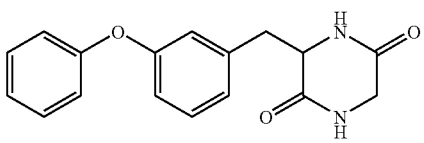

Add hydrazine hydrate (0.7 mL, 14.2 mmol) to a solution of 1-acetyl-3-(3-phenoxy-benzyl)-piperazine-2,5-dione (4.8 g, 14.2 mmol) in DMF (10 mL). Stir 2 h, dilute with water (50 mL) and stir an additional 30 minutes. Filter, wash with water, then cold methanol to obtain the title compound as a white powder (2.8 g, 67%): $^1$H NMR (CDCl$_3$) δ 2.84 (dd, 1H), 2.96 (d, 1H), 3.05 (dd, 1H), 3.42 (d, 1H), 4.03 (m, 1H), 6.83–6.97 (m, 5H), 7.09 (t, 1H), 7.27 (t, 1H), 7.34 (t, 2H), 7.92 (bs, 1H), 8.12 (s, 1H).

By the method of example 266 and 267, the following compounds were prepared and isolated: Separation of the S-isomers occurs via resolution of the piperazines with the use of tartartic acid.

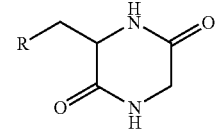

| No: | R | Data |
|---|---|---|
| 269 | (3,5-Di-OCH$_3$)Ph | mp 212–213° C.: $^1$H NMR(DMSO-d$_6$) δ2.76(dd, 1H), 2.87(d, 1H), 2.93(dd, 1H), 3.34(d, 1H), 3.63(s, 6H), 3.99(m, 1H), 6.28(s, 2H), 6.32(s, 1H), 7.87(bs, 1H), 8.05(bs, 1H). 48% yield, 11.1 g from 26.8 g. |
| 270 | (2-OEt)Ph | mp 180–181° C.: $^1$H NMR(DMSO-d$_6$)δ1.30(t, 3H), 2.90(dd, 1H), 2.99(dd, 1H), 3.12(d, 1H), 3.35(d, 1H), 3.91(m, 1H), 3.93(q, 2H), 6.79(t, 1H), 6.88(d, 1H), 7.05(d, 1H), 7.18(t, 1H), 7.79(bs, 1H), 7.86(bs, 1H). 65% yield, 16.5 g gave 9.2 g. |
| 271 | (2-O-i-Pr)Ph | mp 217–218° C.; $^1$H NMR(DMSO-d$_6$)δ1.24(d, 6H), 2.6–3.4(m, 4H), 3.89(m, 1H), 4.52(m, 1H), 6.78(t, 1H), 6.88(d, 1H), 7.06(d, 1H), 7.16(d, 1H), 7.77(s, 1H), 7.88(s, 1H). |
| 272 | (4-i-Pr)Ph | mp > 250° C.: $^1$H NMR(DMSO-d$_6$)δ1.14(d, 6H), 2.71(d, 1H), 2.81(septet, 1H), 2.82(dd, 1H), 3.01(dd, 1H), 3.30(d, 1H), 4.00(m, 1H), 7.04(d, 2H), 7.10(d, 2H), 7.83(bs, 1H), 8.09(bs, 1H). 78% yield, 32.6 g gave 22.4 g. |
| 273 | (3,5-Di-CH$_3$)Ph | mp 210–211° C.: $^1$H NMR(DMSO-d$_6$)δ2.16(s, 6H), 2.77(dd, 1H), 2.79(d, 1H), 2.94(dd, 1H), 3.32(d, 1H), 3.98(m, 1H), 6.73(s, 2H), 6.84(s, 1H), 7.86(bs, 1H), 8.07(bs, 1H). 90% yield, 15.8 g gave 12.2 g. |

-continued

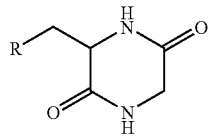

| No: | R | Data |
|---|---|---|
| 274 | (4-OPh)Ph | mp 226–228° C.: $^1$H NMR(DMSO-d$_6$) δ2.85(dd, 1H), 2.91(d, 1H), 3.02(dd, 1H), 3.40(d, 1H), 4.02(m, 1H), (6.93(d, 2H), 6.94(d, 1H), 7.09(t, 1H), 7.14(d, 1H), 7.35(t, 2H), 7.89(bs, 1H), 8.12(bs, 1H). 98% yield, 37.0 g gave 32.1 g. |
| 275 | (Pyrid-2-yl) | $^1$H NMR(DMSO-d$_6$)δ3.14(m, 2H), 3.41(d, 1H), 3.54(d, 2H), 4.17(m, 1H), 7.19–7.23(m, 2H), 7.68(t, 1H), 7.93(bs, 1H), 8.01(bs, 1H), 8.45(d, 1H). |
| 276 | (2,4-Di-OCH$_3$)Ph | mp 221–223° C.: $^1$H NMR(DMSO-d$_6$) δ2.77(dd, 1H), 2.90(dd, 1H), 3.14(d, 1H), 3.33(d, 1H), 3.79(m, 1H), 6.38(d, 1H), 6.45(s, 1H), 6.91(d, 1H), 7.75(bs, 1H), 7.83(bs, 1H). |

Example 280

(S)-1,4-Dibenzyl-2-[2-(4-chloro-phenyl)-ethyl]-piperazine

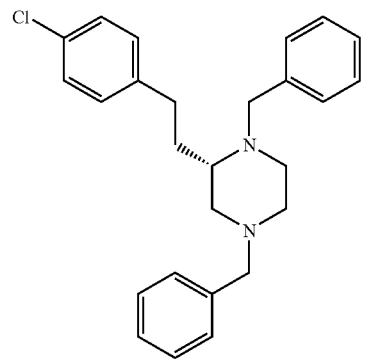

Combine (S)-1,4-dibenzyl-2-vinyl-piperazine (5.0 g, 17.10 mmol) and 9-borabicyclo[3.3.1]nonane (136.8 ml, 68.39 mmol, 0.5 M in THF) and stir at ambient temperature. After 24 hrs, add 1-iodo-4-chloro-benzene (6.12 g, 25.65 mmol), triphenylphosphine (717.5 mg, 2.74 mmol), tetrakis (triphenylphosphine) palladium(0)(395.1 mg, 0.34 mmol), and 3N NaOH (14.0 ml) and stir at 60°. After 22 hrs, remove the THF under vacuum, stir the residue in 2N NaOH, and extract with diethyl ether. Wash the organic with 1N H$_2$SO$_4$ then adjust the aqueous to pH 14. Extract the aqueous with diethyl ether and combine, wash (brine), dry (sodium sulfate), and reduce the extracts to residue. Recrystallize the residue in warm ethanol to give 4.76 g (69%) of the title compound: mp 87°–90°; mass spectrum (ion spray): m/z=405.4 (M+1); Analysis for C$_{26}$H$_{29}$ClN$_2$: calcd: C, 77.11; H, 7.22; N, 6.92; found: C, 76.93; H, 7.06; N, 7.01.

Example 281

(S)-1,4-Dibenzyl-2-[2-(3-chloro-phenyl)-ethyl]-piperazine

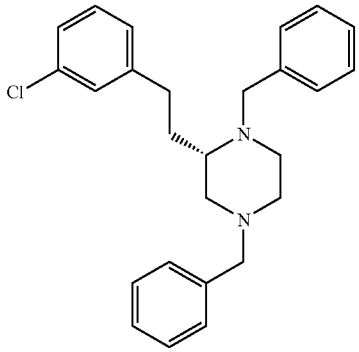

Combine (S)-1,4-dibenzyl-2-vinyl-piperazine (5.0 g, 17.10 mmol) and 9-borabicyclo[3.3.1]nonane (136.8 ml, 68.39 mmol, 0.5 M in THF) and stir at ambient temperature. After 24 hrs, add 1-iodo-3-chloro-benzene (6.12 g, 25.65 mmol), triphenylphosphine (717.5 mg, 2.74 mmol), tetrakis (triphenylphosphine)palladium(0)(395.1 mg, 0.34 mmol), and 3N NaOH (14.0 ml) and stir at 60°. After 22 hrs, remove the THF under vacuum, stir the residue in 2N NaOH, and extract with diethyl ether. Wash the organic with 1N H$_2$SO$_4$ then adjust the aqueous to pH 14. Extract the aqueous with diethyl ether and combine, wash (brine), dry (sodium sulfate), and reduce the extracts to residue. Recrystallize the residue in warm ethanol to give 5.01 g (72%) of the title compound: mp 56°–60°; mass spectrum (ion spray): m/z=405.4 (M+1).

Example 282

(S)-1,4-Dibenzyl-2-[2-(2-chloro-phenyl)-ethyl]-piperazine

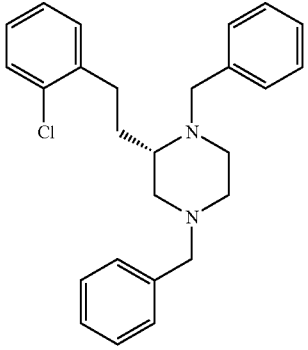

Combine (S)-1,4-dibenzyl-2-vinyl-piperazine (6.0 g, 20.52 mmol) and 9-borabicyclo[3.3.1]nonane (164.1 ml, 82.07 mmol, 0.5 M in THF) and stir at ambient temperature. After 24 hrs, add 1-iodo-2-chloro-benzene (7.34 g, 30.78 mmol), triphenylphosphine (861.0 mg, 3.28 mmol), tetrakis (triphenylphosphine)palladium(0)(474.1 mg, 0.41 mmol), and 3N NaOH (16.8 ml) and stir at 60°. After 22 hrs, remove the THF under vacuum, stir the residue in 2N NaOH, and extract with diethyl ether. Wash the organic with 1N H$_2$SO$_4$ then adjust the aqueous to pH 14. Extract the aqueous with diethyl ether and combine, wash (brine), dry (sodium sulfate), and reduce the extracts to residue. Recrystallize the residue in warm ethanol to give 2.59 g (31%) of the title compound: mass spectrum (ion spray): m/z=405.4 (M+1);

Analysis for $C_{26}H_{29}ClN_2$: calcd: C, 77.11; H, 7.22; N, 6.92; found: C, 77.12; H, 7.13; N, 7.07.

Example 283

(S)-1,4-Dibenzyl-2-[2-(4-trifluoromethyl-phenyl)-ethyl]-piperazine

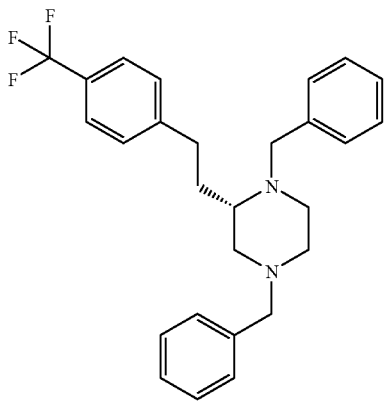

Combine (S)-1,4-dibenzyl-2-vinyl-piperazine (6.0 g, 20.52 mmol) and 9-borabicyclo[3.3.1]nonane (164.1 ml, 82.07 mmol, 0.5 M in THF) and stir at ambient temperature. After 24 hrs, add 1-iodo-4-trifluoromethyl-benzene (8.37 g, 30.78 mmol), triphenylphosphine (861.0 mg, 3.28 mmol), tetrakis(triphenylphosphine)palladium(0 )(474.1 mg, 0.41 mmol), and 3N NaOH (16.8 ml) and stir at 60°. After 22 hrs, remove the THF under vacuum, stir the residue in 2N NaOH, and extract with diethyl ether. Wash the organic with 1N $H_2SO_4$ then adjust the aqueous to pH 14. Extract the aqueous with diethyl ether and combine, wash (brine), dry (sodium sulfate), and reduce the extracts to residue. Recrystallize the residue in warm ethanol to give 3.34 g (37%) of the title compound: mass spectrum (ion spray): mp 71°–75°; m/z=439.2 (M+1); Analysis for $C_{27}H_{29}F_3N_2$: calcd: C, 73.95; H, 6.67; N, 6.39; found: C, 74.15; H, 6.72; N, 6.52.

Example 284

(S)-1,4-Dibenzyl-2-[2-(2-trifluoromethyl-phenyl)-ethyl]-piperazine

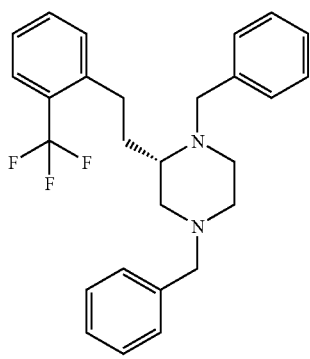

Combine (S)-1,4-dibenzyl-2-vinyl-piperazine (6.0 g, 20.52 mmol) and 9-borabicyclo[3.3.1]nonane (164.1 ml, 82.07 mmol, 0.5 M in THF) and stir at ambient temperature. After 24 hrs, add 1-iodo-2-trifluoromethyl-benzene (8.37 g, 30.78 mmol), triphenylphosphine (861.0 mg, 3.28 mmol), tetrakis(triphenylphosphine)palladium(0)(474.1 mg, 0.41 mmol), and 3N NaOH (16.8 ml) and stir at 60°. After 22 hrs, remove the THF under vacuum and dissolve the residue in ethyl acetate. Wash the organic layer with 1N NaOH then combine, wash (brine), dry (sodium sulfate), and reduce the extracts to residue. Purify the residue using ethyl acetate/hexanes (5:95) and reduce the appropriate fractions to residue. Stir the residue in 2N NaOH, and extract with diethyl ether. Wash the organic with 1N $H_2SO_4$ then adjust the aqueous to pH 14. Extract the aqueous with diethyl ether and combine, wash (brine), dry (sodium sulfate), and reduce the extracts to residue. Recrystallize the residue in warm ethanol to give 2.67 g (30%) of the title compound: mass spectrum (ion spray): mp 77°–82°; m/z=439.2 (M+1); Analysis for $C_{27}H_{29}F_3N_2$: calcd: C, 73.95; H, 6.67; N, 6.39; found: C, 74.11; H, 6.68; N, 6.50.

Example 285

(S)-2-[2-(4-Trifluoromethyl-phenyl)-ethyl]-piperazine

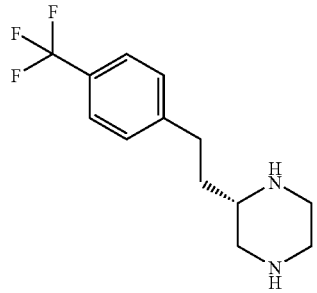

Combine (S)-1,4-dibenzyl-2-[2-(4-trifluoromethyl-phenyl)-ethyl]-piperazine (3.34 g, 7.62 mmol), ammonium formate (2.40 g, 38.09 mmol), 5% Pd/C (368.7 mg), and ethanol (100 ml). Stir and heat the mixture at reflux. After 3 hrs, cool to ambient temperature and remove the catalyst by vacuum filtration through celite. Reduce the filtrate to residue and then dissolve it in dichloromethane. Wash the organic with 1N NaOH and then combine, wash (brine), dry (sodium sulfate), and reduce the extracts to residue to give 1.83 g (93%) of the title compound as an off-white solid: mp 135°–141°; mass spectrum (ion spray): m/z=259.2 (M+1).

Example 286

(S)-2-[2-(2-Trifluoromethyl-phenyl)-ethyl]-piperazine

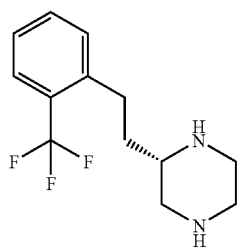

Combine (S)-1,4-dibenzyl-2-[2-(2-trifluoromethyl-phenyl)-ethyl]-piperazine (2.66 g, 6.06 mmol), ammonium formate (1.91 g, 30.31 mmol), 5% Pd/C (293.3 mg), and ethanol (100 ml). Stir and heat the mixture at reflux. After 3 hrs, cool to ambient temperature and remove the catalyst by vacuum filtration through celite. Reduce the filtrate to residue. Purify the residue on silica gel using dichloromethane/2N ammonia in methanol (90:10) to give 1.46 g (93%) of the title compound as a white solid: mp 43°–47°; mass spectrum (ion spray): m/z=259.2 (M+1).

Example 287

(S)-2-[2-(2-chloro-phenyl)-ethyl]-piperazine

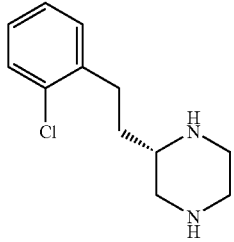

Dissolve (S)-1,4-dibenzyl-2-[2-(2-chloro-phenyl)-ethyl]-piperazine (2.59 g, 6.38 mmol) in dichloroethane (30 ml). Cool the solution to 0° and then add 1-chloroethyl chloroformate (2.74 g, 19.15 mmol) dropwise. Warm the solution to ambient temperature and then heat it at reflux for 15 hours. Remove the dichloroethane under vacuum and reflux the resulting residue in methanol for 1 hour. Remove the methanol under vacuum and dissolve the resulting precipitate in 1N NaOH. Extract the aqueous layer with dichloromethane and then combine, wash (brine), dry (sodium sulfate), and reduce the extracts to residue. Purify the residue on silica gel using dichloromethane/2N ammonia in methanol (90:10) to give 482.4 mg (34%) of the title compound: mass spectrum (ion spray): m/z=225.3 (M+1).

Example 288

(S)-2-[2-(4-chloro-phenyl)-ethyl]-piperazine

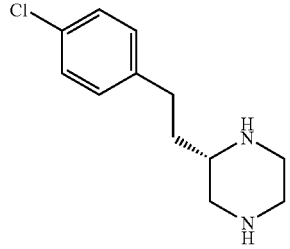

Dissolve (S)-1,4-dibenzyl-2-[2-(4-chloro-phenyl)-ethyl]-piperazine (4.74 g, 11.71 mmol) in dichloroethane (80 ml). Cool the solution to 0° and then add 1-chloroethyl chloroformate (7.95 g, 55.61 mmol) dropwise. Warm the solution to ambient temperature and then heat it at reflux for 15 hours. Remove the dichloroethane under vacuum and reflux the resulting residue in methanol for 1 hour. Remove the methanol under vacuum and dissolve the resulting precipitate in 1N NaOH. Extract the aqueous layer with dichloromethane and then combine, wash (brine), dry (sodium sulfate), and reduce the extracts to residue. Purify the residue on silica gel using dichloromethane/2N ammonia in methanol (90:10) to give 459.0 mg (18%) of the title compound: mp 140°–144°; mass spectrum (ion spray): m/z=225.3 (M+1).

Example 289

(S)-2-[2-(3-chloro-phenyl)-ethyl]-piperazine

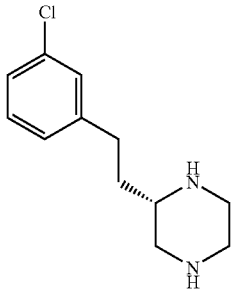

Dissolve (S)-1,4-dibenzyl-2-[2-(3-chloro-phenyl)-ethyl]-piperazine (4.48 g, 11.07 mmol) in dichloroethane (40 ml). Cool the solution to 0° and then add 1-chloroethyl chloroformate (4.75 g, 33.21 mmol) dropwise. Warm the solution to ambient temperature and then heat it at reflux for 42 hours. Remove the dichloroethane under vacuum and reflux the resulting residue in methanol (100 ml) for 1 hour. Remove the methanol under vacuum and dissolve the resulting precipitate in 1N NaOH. Extract the aqueous layer with dichloromethane and then combine, wash (brine), dry (sodium sulfate), and reduce the extracts to residue. Purify the residue on silica gel using dichloromethane/2N ammonia in methanol (90:10) to give 407.6 mg (16%) of the title compound: mp 93°–97°; mass spectrum (ion spray): m/z=225.3 (M+1).

Example 290

1,4-Dibenzyl-2-[2-(2,5-difluoro-phenyl)-ethyl]-piperazine

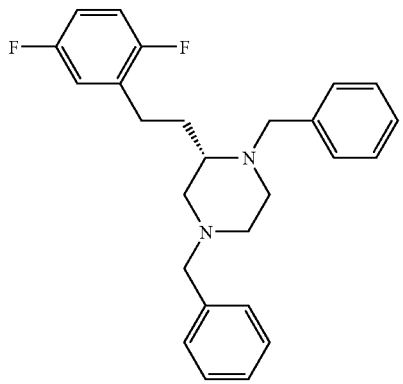

Prepared in a similar fashion to Example 284, Yield 23%, mass spectrum (m/e): 407.3 (M+1)

Example 291

2-[2-(2,5-Difluoro-phenyl)-ethyl]-piperazine

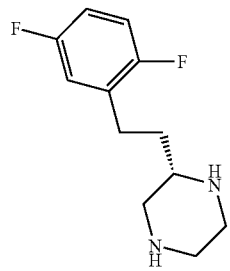

Dissolve 1,4-dibenzyl-2-[2-(2,5-difluoro-phenyl)-ethyl]-piperazine (2.7 g, 6.6 mmol) in methanol (25 ml) and add 10% palladium on carbon (wet, 1.0 g). Carry out the hydrogenation with a hydrogen balloon at room temperature for 16 hours. Filter the reaction mixture, concentrate the filtrate under reduced pressure to give 2-[2-(2,5-difluoro-phenyl)-ethyl]-piperazine as an oil (1.5 g, 100%). mass spectrum (m/e): 227.0 (M+1).

Example 292

1,4-Dibenzyl-2-[2-(3-trifluoromethyl-phenyl)-ethyl]-piperazine

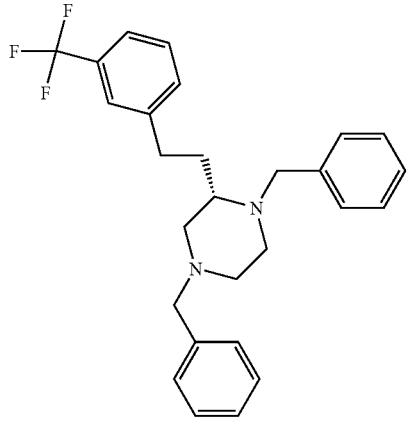

Prepared in a similar fashion to Example 284: Yield 73%, mass spectrum (m/e): 439.3 (M+1)

Example 293

2-[2-(3-Trifluoromethyl-phenyl)-ethyl]-piperazine

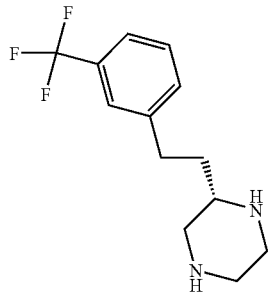

Prepared in a similar fashion to Example 286. Yield 100%, mass spectrum (m/e): 259.1 (M+1).

Example 373

2-Methyl-4,9-dihydro-3-thia-6-fluoro-4,9-diaza-benzo[f]azulene-10-thione

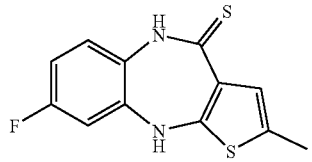

Suspend 2-methyl-4,9-dihydro-3-thia-6-fluoro-4,9-diaza-benzo[f]azulene-10-one (1.2 g, 4.8 mmol) in dry toluene and add Lawesson's reagent (1.1 g, 2.7 mmol) under nitrogen. Heat the reaction mixture under reflux for one hour and cool overnight. Precipate the desired material and collect by filtration, air-dry for several minutes to give 529 mg of yellow solid which can be used in the next step without further purification. Mass Spectrum (FIA) 265 (M+1); $^1$H NMR (300 MHz, CDCl$_3$): 6.98 (s, 1H), 6.75 (t, 1H), 6.6 (t, 1H), 6.43 (d, 1H), 3.29 (s, 1H), 2.21 (s, 3H)

Example 374

2-Amino-5-tert-butyl-thiophene-3-carbonitrile

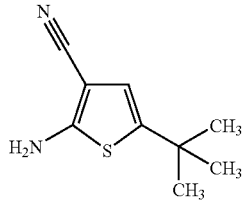

Add a solution of 3,3-dimethyl-butyraldehyde (20 g, 200 mmol) in EtOH (40 mL) dropwise a mixture of sulfur (6.4 g, 200 mmol), malononitrile (13.2 g, 200 mmol) and tri-ethylamine (14.3 mL, 100 mmol) in EtOH (400 mL) at 0° C. Stir the mixture at room temperature for 20 minutes after the addition is complete, then reflux for 2 hours. Cool, concentrate to a paste. Add diethyl ether (200 mL) and 2N HCl (200 mL). Wash the organic layer again with 2N HCl, dry (Na$_2$SO$_4$), and concentrate. Purify the residue via column chromatography eluting with methylene chloride to afford the title compound as tan crystals (16.9 g, 47%): $^1$H NMR (CDCl$_3$) δ 1.27 (s, 9H), 4.60 (bs, 2H), 6.36 (s, 1H).

Example 375

2-Amino-5-iso-propyl-thiophene-3-carbonitrile

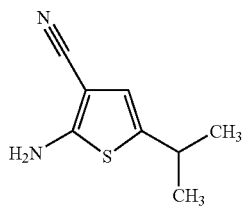

Substitute isovaleraldehyde for 3,3-dimethyl-butyraldehyde and use the method of Example 374 to obtain the title compound as a brown solid: $^1$H NMR (CDCl$_3$) δ1.24 (d, 6H), 2.93 (septet, 1H), 6.37 (s, 1H).

Example 376

2-Amino-5-cyclopentyl-thiophene-3-carbonitrile

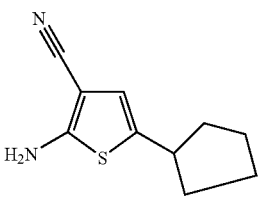

Substitute 2-cyclopentylacetaldehyde for 3,3-dimethyl-butyraldehyde and substitute DMF for EtOH and use the method of Example 374 to obtain the title compound (16.1 g, 57%) as a yellow solid: $^1$H NMR (CDCl$_3$) δ 1.48–1.58 (m, 2H), 1.61–1.69 (m, 2H), 1.72–1.78 (m, 2H), 1.98–2.07 (m, 2H), 3.01 (m, 1H), 4.58 (bs, 2H), 6.38 (s, 1H).

Example 378

5-tert-Butyl-2-(2-nitro-phenylamino)-thiophene-3-carbonitrile

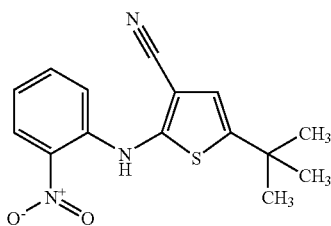

Add a solution of 2-amino-5-tert-butyl-thiophene-3-carbonitrile (16.9 g, 94 mmol) in THF (50 mL) to a mixture of washed NaH (from 6.76 g of 60% mineral oil dispersion) in THF (200 mL) in a water bath at room temperature. Stir 15 minutes, then add a solution of 2-fluoro-nitrobenzene (13.2 g, 94 mmol) in THF (50 mL) dropwise. Stir overnight. Pour the purple reaction mixture unto 6 N HCl (400 mL). Extract the mixture with diethyl ether (400 mL). Wash the ether layer with 2 N HCl (400 mL), brine (250 mL), dry ($Na_2SO_4$), and concentrate to afford a mixture of crystals in a dark oily residue. Triturate the crystals with hexanes and filter to afford the title compound as a red powder (21.2 g, 75%) mp 85–90° C.: $^1$H NMR (CDCl$_3$) δ 1.39 (s, 9H), 6.81 (s, 1H), 6.97 (t, 1H), 7.23 (d, 1H), 7.53 (t, 1H), 8.25 (d, 1H), 9.66 (bs, 1H).

By the method of example 378, the following compounds were prepared and isolated as the free base:

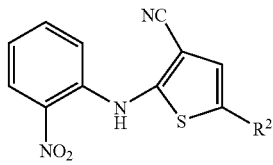

| No: | R$^1$ | Data |
|---|---|---|
| 379 | i-Pr | $^1$H NMR(CDCl$_3$)δ1.35(d, 6H), 3.13(septet, 1H), 6.80(s, 1H), 6.96(t, 1H), 7.22(d, 1H), 7.54(t, 1H), 8.24(d, 1H), 9.65(s, 1H). |
| 380 | c-Pentyl | $^1$H NMR(CDCl$_3$)δ1.56–1.84(m, 6H), 2.11–2.19(m, 2H), 3.18(pentet, 1H), 6.80(s, 1H), 6.96(t, 1H), 7.21(d, 1H), 7.53(t, 1H), 8.25(d, 1H), 9.64(s, 1H). |

Example 381

2-tert-Butyl-4H-3-thia-4,9-diaza-benzo[f]azulen-10-ylamine hydrochloride

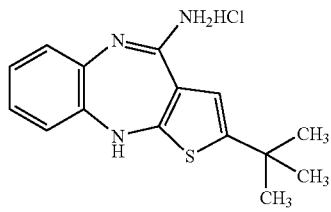

Add 5-tert-butyl-2-(2-nitro-phenylamino)-thiophene-3-carbonitrile (21.2 g, 70 mmol) to a solution of tin(II)chloride dihydrate (46.1 g, 209 mmol) in conc. HCl (200 mL) and ethanol (600 mL). Reflux the mixture for 2 hours. Concentrate the solution to 200 mL and add to water (1 L). Filter and wash with water then hexanes to obtain the title compound as an orange powder (19.4 g): $^1$H NMR (DMSO-d$_6$) δ 1.27 (s, 9H), 6.86 (d, 1H), 6.89 (s, 1H), 6.95 (d, 1H), 7.03 (t, 1H), 7.11 (t, 1H), 8.69 (s, 1H) 9.11 (s, 1), 9.52 (s, 1H), 10.88 (s, 1H); MS (APCI) m/z (rel intensity) 272 (100).

By the method of example 381, the following compounds were prepared and isolated as the free base:

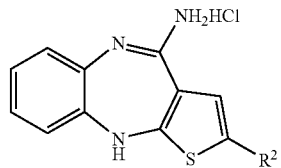

| No. | R | Data |
|---|---|---|
| 382 | i-Pr | $^1$H NMR(DMSO-d$_6$)δ1.16(d, 6H), 2.88(septet, 1H), 6.82(s, 1H), 6.83(d, 1H), 6.91(d, 1H), 6.99(t, 1H), 7.07(t, 1H), 8.71(s, 1H), 9.09(s, 1H), 9.54(s, 1H), 10.94(s, 1H). |
| 383 | c-Pentyl | $^1$H NMR(DMSO-d$_6$)δ1.42–1.70(m, 6H), 1.92–2.00(m, 2H), 2.99(pentet, 1H), 6.81(s, 1H), 6.82(d, 1H), 6.91(d, 1H), 6.99(t, 1H), 7.07(t, 1H), 8.63(bs, 1H), 9.05(bs, 1H), 9.50(bs, 1H), 10.79(bs, 1H). |

Example 384

2-tert-Butyl-10-(4-methyl-piperazin-1-yl)-4H-3-thia-4,9-diaza-benzo[f]azulene

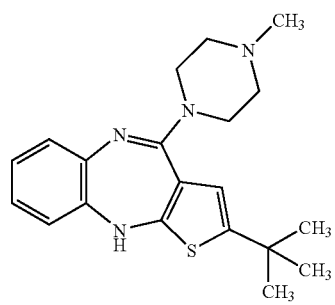

By a method similar to Example 59, using 2-tert-butyl-4H-3-thia-4,9-diaza-benzo[f]azulen-10-ylamine hydrochloride (1.00 g, 3.26 mmol) and N-methyl-piperazine (1.9 g, 19 mmol) to obtain the title compound (904 mg, 78%) as a yellow powder: mp 125–130° C. (dec): $^1$H NMR (CDCl$_3$) δ 1.29 (s, 9H), 2.35 (s, 3H), 2.50 (m, 4H), 3.53 (m, 4H), 4.96 (s, 1H), 6.33 (s, 1H), 6.60 (d, 1H), 6.87 (t, 1H), 6.96 (t, 1H), 7.02 (d, 1).

By a method similar to Example 59, the following compounds were prepared and isolated as the free base:

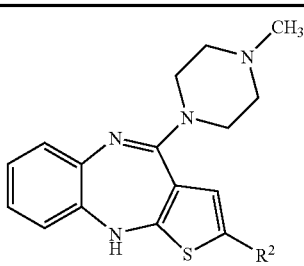

| No: | R² | Data |
|---|---|---|
| 385 | i-Pr | ¹H NMR(CDCl₃)δ1.23(d, 6H), 2.34(s, 3H), 2.50(m, 4H), 2.95(septet, 1H), 3.53(m, 4H), 5.00(s, 1H), 6.32(s, 1H), 6.60(d, 1H), 6.87(t, 1H), 6.97(t, 1H), 7.02(d, 1H); MS(APCI)m/z(rel intensity)581(100), 341(80). |
| 386 | c-Pentyl | ¹H NMR(CDCl₃)δ1.48–1.79(m, 6H), 2.02(m, 2H), 2.35(s, 3H), 2.50(m, 4H), 3.04(pentet, 1H), 3.53(m, 4H), 4.95(s, 1H), 6.33(s, 1H), 6.60(d, 1H), 6.87(t, 1H), 6.97(t, 1H), 7.03(d, 1H); MS(APCI)m/z(rel intensity)367 (100). |

Example 387

10-((S)-3-[2-(3-Chloro-phenyl)-ethyl]-piperazin-1-yl)-2-methyl-4H-3-thia-4,9-diaza-benzo[f]azulene

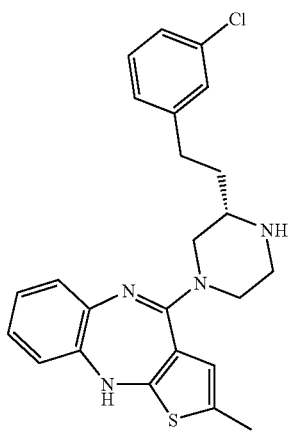

Combine 2-methyl-4H-3-thia-4,9-diaza-benzo[f]azulen-10-ylamine hydrochloride (829.8 mg, 3.12 mmol), (S)-2-[2-(3-chloro-phenyl)-ethyl]-piperazine (1.40 g, 6.24 mmol), N,N-diisopropylethylamine (403.6 mg, 3.12 mmol), DMSO (1.0 ml), and toluene (4.0 ml). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give 673.9 mg (50%) of the title compound as a brown foam: mp 68–74°, dec; mass spectrum (ES+): m/e=437.31.

Example 388

10-((S)-3-[2-(4-Chloro-phenyl)-ethyl]-piperazin-1-yl)-2-methyl-4H-3-thia-4,9-diaza-benzo[f]azulene

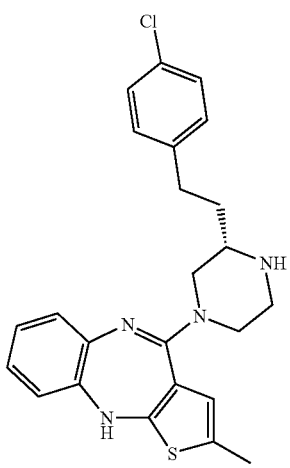

Combine 2-methyl-4H-3-thia-4,9-diaza-benzo[f]azulen-10-ylamine hydrochloride (642.0 mg, 2.42 mmol), (S)-2-[2-(4-chloro-phenyl)-ethyl]-piperazine (1.09 g, 4.83 mmol), N,N-diisopropylethylamine (312.2 mg, 2.42 mmol), DMSO (1.0 ml), and toluene (4.0 ml). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give 501.6 mg (47%) of the title compound as a brown foam: mp 91°, dec; mass spectrum (ion spray): m/z=437.3.

Example 389

10-((S)-3-[2-(2-Chloro-phenyl)-ethyl]-piperazin-1-yl)-2-methyl-4H-3-thia-4,9-diaza-benzo[f]azulene

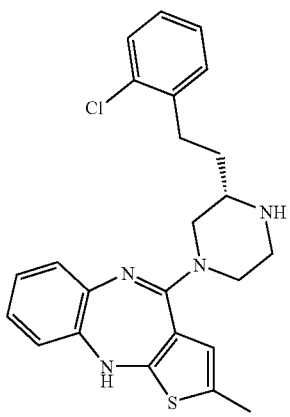

Combine 2-methyl-4H-3-thia-4,9-diaza-benzo[f]azulen-10-ylamine hydrochloride (607.1 mg, 2.28 mmol), (S)-2-[2-(2-chloro-phenyl)-ethyl]-piperazine (1.03 g, 4.57 mmol), N,N-diisopropylethylamine (295.3 mg, 2.28 mmol), DMSO (1.0 ml), and toluene (4.0 ml). Stir and heat the mixture at 105° C. After 64 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give 482.4 mg (48%) of the title compound as a brown foam: mp 72°, dec; mass spectrum (ion spray): m/z=437.3.

Example 390

10-((S)-3-[2-(4-Chloro-phenyl)-ethyl]-4-methyl-piperazin-1-yl)-2-methyl-4H-3-thia-4,9-diaza-benzo[f]azulene

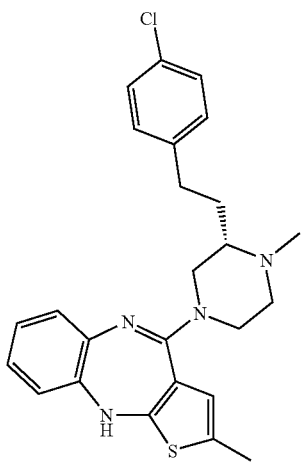

Combine 10-((S)-3-[2-(4-chloro-phenyl)-ethyl]-piperazin-1-yl)-2-methyl-4H-3-thia-4,9-diaza-benzo[f]azulene (430.9 mg, 0.99 mmol), formaldehyde (88.0 μL, 1.08 mmol, 37% in water), and 1,2-dichloroethane (30.0 ml). Stir the mixture at ambient temperature for 5 minutes and then add sodium triacetoxyborohydride (313.5 mg, 1.48 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give 365.2 mg (82%) of the title compound as a brown foam: mp 79°, dec; mass spectrum (ion spray): m/z=451.2 (M+1).

Example 391

10-((S)-3-[2-(3-Chloro-phenyl)-ethyl]-4-methyl-piperazin-1-yl)-2-methyl-4H-3-thia-4,9-diaza-benzo[f]azulene

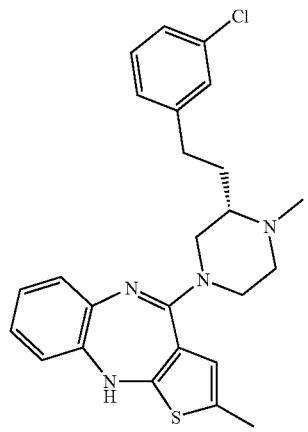

Combine 10-((S)-3-[2-(3-chloro-phenyl)-ethyl]-piperazin-1-yl)-2-methyl-4H-3-thia-4,9-diaza-benzo[f]azulene (608.3 mg, 1.53 mmol), formaldehyde (124.3 μL, 1.53 mmol, 37% in water), and 1,2-dichloroethane (30.0 ml). Stir the mixture at ambient temperature for 5 minutes and then add sodium triacetoxyborohydride (442.5 mg, 2.09 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give 502.3 mg (80%) of the title compound as a brown foam: mp 69°, dec; mass spectrum (ion spray): m/z=451.2 (M+1).

Example 392

10-((S)-3-[2-(2-Chloro-phenyl)-ethyl]-4-methyl-piperazin-1-yl)-2-methyl-4H-3-thia-4,9-diaza-benzo[f]azulene

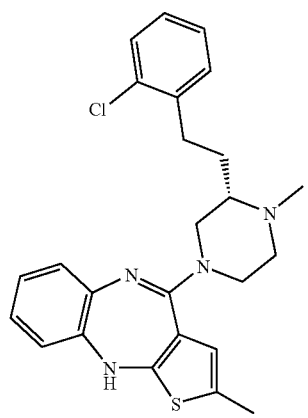

Combine 10-((S)-3-[2-(2-chloro-phenyl)-ethyl]-piperazin-1-yl)-2-methyl-4H-3-thia-4,9-diaza-benzo[f]azulene (398.3 mg, 0.91 mmol), formaldehyde (81.4 μL, 1.00 mmol, 37% in water), and 1,2-dichloroethane (30.0 ml). Stir the mixture at ambient temperature for 5 minutes and then add sodium triacetoxyborohydride (289.7 mg, 1.37 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give 341.6 mg (83%) of the title compound as a brown foam: mp 72°, dec; mass spectrum (ion spray): m/z=451.1 (M+1).

Example 393

10-((S)-3-[2-(4-Trifluoromethyl-phenyl)-ethyl]-piperazin-1-yl)-2-methyl-4H-3-thia-4,9-diaza-benzo[f]azulene

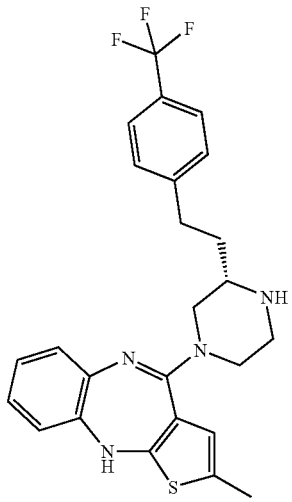

Combine 2-methyl-4H-3-thia-4,9-diaza-benzo[f]azulen-10-ylamine hydrochloride (514.5 mg, 1.94 mmol), (S)-2-[2-(4-trifluoromethyl-phenyl)-ethyl]-piperazine (1.00 g, 3.87 mmol), N,N-diisopropylethylamine (250.2 mg, 1.94 mmol), DMSO (1.0 ml), and toluene (4.0 ml). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give 380.3 mg (42%) of the title compound as a brown foam: mp 78°, dec; mass spectrum (ion spray): m/z=471.1.

Example 394

10-((S)-3-[2-(2-Trifluoromethyl-phenyl)-ethyl]-piperazin-1-yl)-2-methyl-4H-3-thia-4,9-diaza-benzo[f]azulene

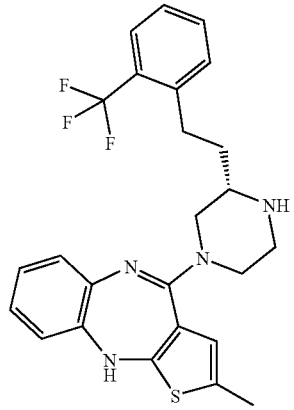

Combine 2-methyl-4H-3-thia-4,9-diaza-benzo[f]azulen-10-ylamine hydrochloride (514.5 mg, 1.94 mmol), (S)-2-[2-(2-trifluoromethyl-phenyl)-ethyl]-piperazine (1.00 g, 3.87 mmol), N,N-diisopropylethylamine (250.2 mg, 1.94 mmol), DMSO (1.0 ml), and toluene (4.0 ml). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give 497.4 mg (55%) of the title compound as a brown foam: mp 73°, dec; mass spectrum (ion spray): m/z=471.1.

Example 395

10-((S)-3-[2-(3-Trifluoromethyl-phenyl)-ethyl]-piperazin-1-yl)-2-methyl-4H-3-thia-4,9-diaza-benzo[f]azulene

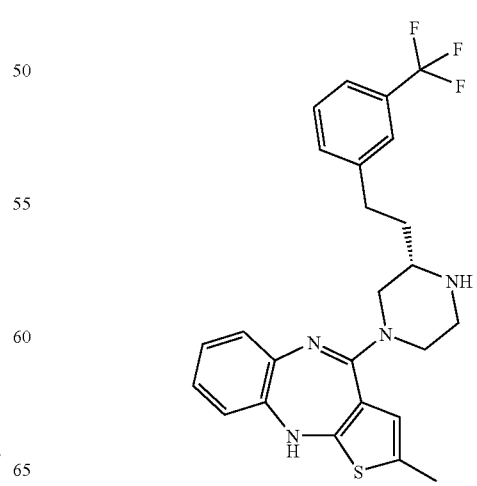

Combine 2-methyl-4H-3-thia-4,9-diaza-benzo[f]azulen-10-ylamine hydrochloride (514.5 mg, 1.94 mmol), (S)-2-[2-(3-trifluoromethyl-phenyl)-ethyl]-piperazine (1.00 g, 3.87 mmol), N,N-diisopropylethylamine (250.2 mg, 1.94 mmol), DMSO (1.0 ml), and toluene (4.0 ml). Stir and heat the mixture at 105° C. After 64 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give 370.6 mg (41%) of the title compound as a brown foam: mp 69°, dec; mass spectrum (ion spray): m/z=471.1.

Example 396

10-((S)-3-[2-(4-Trifluoromethyl-phenyl)-ethyl]-4-methyl-piperazin-1-yl)-2-methyl-4H-3-thia-4,9-diaza-benzo[f]azulene

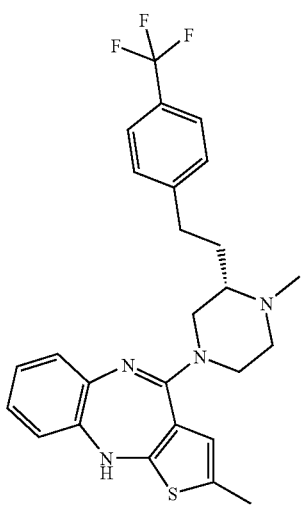

Combine 10-((S)-3-[2-(4-trifluromethyl-phenyl)-ethyl]-piperazin-1-yl)-2-methyl-4H-3-thia-4,9-diaza-benzo[f]azulene (325.3 mg, 0.69 mmol), formaldehyde (61.7 μL, 0.76 mmol, 37% in water), and 1,2-dichloroethane (30.0 ml). Stir the mixture at ambient temperature for 5 minutes and then add sodium triacetoxyborohydride (219.8 mg, 1.04 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give 298.1 mg (89%) of the title compound as a tan foam: mp 72°, dec; mass spectrum (ion spray): m/z=485.2 (M+1).

Example 397

10-((S)-3-[2-(2-Trifluoromethyl-phenyl)-ethyl]-4-methyl-piperazin-1-yl)-2-methyl-4H-3-thia-4,9-diaza-benzo[f]azulene

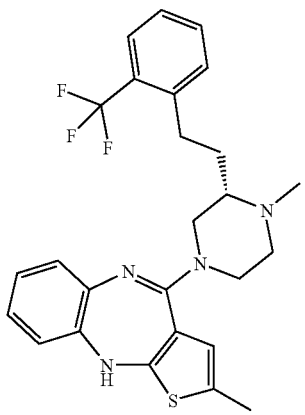

Combine 10-((S)-3-[2-(2-trifluromethyl-phenyl)-ethyl]-piperazin-1-yl)-2-methyl-4H-3-thia-4,9-diaza-benzo[f]azulene (365.7 mg, 0.78 mmol), formaldehyde (69.4 μL, 0.85 mmol, 37% in water), and 1,2-dichloroethane (30.0 ml). Stir the mixture at ambient temperature for 5 minutes and then add sodium triacetoxyborohydride (247.0 mg, 1.17 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give 304.3 mg (81%) of the title compound as a tan foam: mp 68°, dec; mass spectrum (ion spray): m/z=485.2 (M+1).

Example 398

10-C(S)-3-[2-(3-Trifluoromethyl-phenyl)-ethyl]-4-methyl-piperazin-1-yl)-2-methyl-4H-3-thia-4,9-diaza-benzo[f]azulene

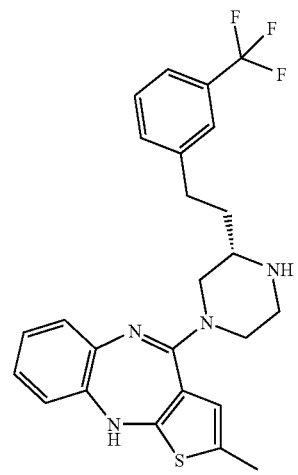

Combine 10-((S)-3-[2-(3-trifluromethyl-phenyl)-ethyl]-piperazin-1-yl)-2-methyl-4H-3-thia-4,9-diaza-benzo[f]azulene (287.3 mg, 0.61 mmol), formaldehyde (54.5 μL, 0.67 mmol, 37% in water), and 1,2-dichloroethane (30.0 ml). Stir the mixture at ambient temperature for 5 minutes and then add sodium triacetoxyborohydride (194.1 mg, 0.92 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (95:5) to give 228.0 mg (77%) of the title compound as a tan foam: mp 62°, dec; mass spectrum (ion spray): m/z=485.3 (N+1).

Example 399

10-((S)-3-[2-(2,4-Difluoro-phenyl)-ethyl]-piperazin-1-yl)-2-methyl-4H-3-thia-4,9-diaza-benzo[f]azulene

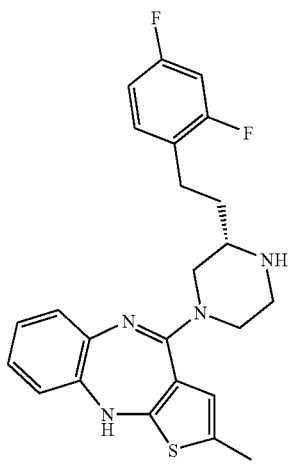

Combine 2-methyl-4H-3-thia-4,9-diaza-benzo[f]azulen-10-ylamine hydrochloride (351.6 mg, 1.32 mmol), (S)-2-[2-(2,4-difluoro-phenyl)-ethyl]-piperazine (600.0 mg, 2.65 mmol), N,N-diisopropylethylamine (171.0 mg, 1.32 mmol), DMSO (0.6 ml), and toluene (2.4 ml). Stir and heat the mixture at 105° C. After 48 hours, cool the mixture to ambient temperature and then dilute it with ethyl acetate and water. Remove the organic layer and wash it with 1N NaOH and brine. Dry (sodium sulfate) and concentrate the organic layer to residue. Purify the residue on silica gel using dichloromethane/methanol (95:5) to give 91.8 mg (16%) of the title compound as a brown foam: mp 69°, dec; mass spectrum (ion spray): m/z=439.0.

Example 400

10-((S)-3-[2-(2,4-Difluoro-phenyl)-ethyl]-4-methyl-piperazin-1-yl)-2-methyl-4H-3-thia-4,9-diaza-benzo[f]azulene

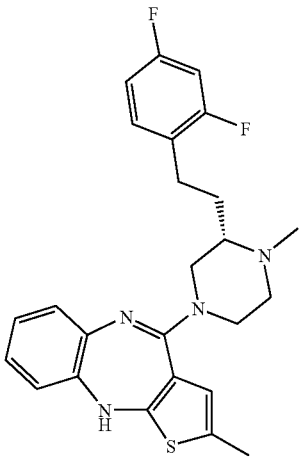

Combine 10-((S)-3-[2-(2,4-difluoro-phenyl)-ethyl]-piperazin-1-yl)-2-methyl-4H-3-thia-4,9-diaza-benzo[f]azulene (57.3 mg, 0.61 mmol), formaldehyde (11.7 μL, 0.14 mmol, 37% in water), and 1,2-dichloroethane (5.0 ml). Stir the mixture at ambient temperature for 5 minutes and then add sodium triacetoxyborohydride (41.5 mg, 0.20 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue to give 54.4 mg (92%) of the title compound: mass spectrum (ion spray): m/z=452.9 (M+1).

Example 401

6-Fluoro-10-{3-[2-(3-fluoro-phenyl)-ethyl]-piperazin-1-yl}-2-methyl-4H-3-thia-4,9-diaza-benzo[f]azulene

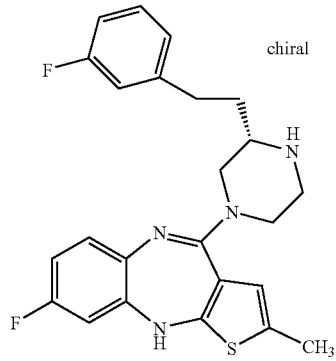

Suspend 2-methyl-4,9-dihydro-3-thia-6-fluoro-4,9-diaza-benzo[f]azulene-10-thione (370 mg, 1.4 mmol) in dichloromethane (30 ml), stir under nitrogen and cool in an ice/water bath. Add methyl trifluoromethanesulfonate (400 μl), and stir the reaction mixture overnight. Concentrate the reaction mixture under reduced pressure, take up in pyridine (10 ml) and add (S-2[2'-(3-fluorophenyl)-ethyl]-piperazine) (300 mg, 1.4 mmol). Stir the reaction mixture under nitrogen and heat at 90° C. overnight. Concentrate the reaction mixture under reduced pressure and purify by flash column chromatography on silica gel (eluent dichloromethane/ methanol) to give the desired as a light green oil 575 mg: mass Spectrum (FIA) 439 (M+1); NMR (¹H, 300 MHz, CDCl₃): 7.2 (m, 1H), 7.0 (m, 1H), 6.93 (m, 1H), 6.85 (m, 2H), 6.68 (m, 1H), 6.49 (m, 1H), 6.22 (s, 1H), 5.95 broad, 1H), 4.12 (m, 1H), 4.0 (m, 1H), 3.28 (m, 2H), 3.05 (m, 3H), 2.69 (m, 2H), 2.29 (s, 3H), 1.88 (m, 2H).

Example: 402

6-Fluoro-10-{3-[2-(4-methoxy-phenyl)-ethyl]-piperazin-1-yl}-2-methyl-4H-3-thia-4,9-diaza-benzo[f]azulene

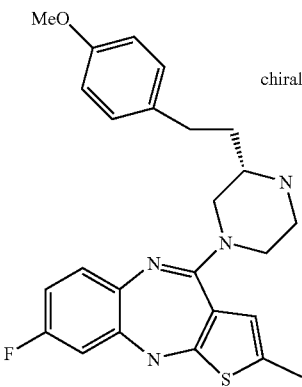

Similarly prepared using Example 401, using 2-methyl-4,9-dihydro-3-thia-6-fluoro-4,9-diazabenzo[f]azulene-10-thione and (5–2[2'-(4-methoxyphenyl)-ethyl]-piperazine): mass Spectrum (FIA) 451 (M+1); NMR (¹H, 300 MHz, CDCl₃): 7.10 (d, 2H), 6.94 (m, 1H), 6.82 (d, 2H), 6.68 (m, 1H), 6.38 (m, 1H), 6.28 (s, 1H), 5.07 broad, 1H), 4.02 (m, 1H), 3.87 (m, 1H), 3.78 (s, 3H), 3.12 (m, 1H), 2.8–2.9 (m, 2H), 2.7 (m, 1H), 2.55 (m, 1H), 2.29 (s, 3H), 1.9 (m, 2H), 1.7 (m, 2H).

Example 403

7-Fluoro-10-{3-[2-(3-fluoro-phenyl)-ethyl]-piperazin-1-yl}-2-methyl-4H-3-thia-4,9-diaza-benzo[f]azulene

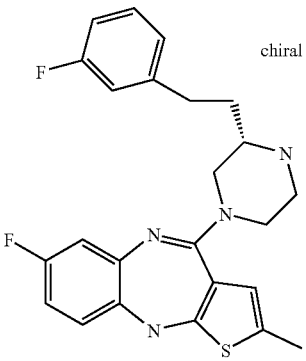

Similarly prepared using Example 401, using 2-methyl-4,9-dihydro-3-thia-7-fluoro-4,9-diazabenzo[f]azulene-10-thione and (S-2[2'-(3-fluorophenyl)-ethyl]-piperazine): mass Spectrum (FIA) 439 (M+1); NMR (¹H, 300 MHz, CDCl₃): 7.22 (m, 1H), 6.95 (m, 1H), 6.88 (m, 2H), 6.72 (m, 1H), 6.5–6.7 (m, 2H), 6.24 (s, 1H), 5.05 (broad, 1H), 4.22 (m, 1H), 4.03 (m, 1H), 3.30 (m, 2H), 3.10 (m, 3H), 2.69 (m, 2H), 2.32 (s, 3H), 1.93 (m, 2H).

Example 404

7-Fluoro-10-{3-[2-(4-methoxy-phenyl)-ethyl]-piperazin-1-yl}-2-methyl-4H-3-thia-4,9-diaza-benzo[f]azulene

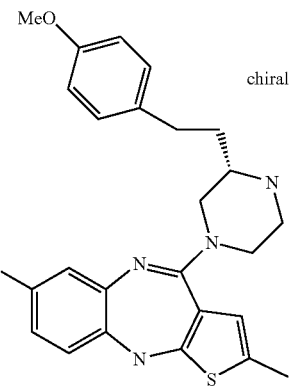

Similarly prepared using Example 401, using 2-methyl-4,9-dihydro-3-thia-7-fluoro-4,9-diazabenzo[f]azulene-10-thione and (S-2[2'-(4-methoxyphenyl)-ethyl]-piperazine): mass Spectrum (FIA) 451 (M+1); NMR (¹H, 300 MHz, CDCl₃): 7.05 (d, 2H), 6.79 (d, 2H), 6.70 (m, 1H), 6.52–6.68 (m, 2H), 6.22 (s, 1H), 5.13 (broad, 1H), 4.22 (m, 1H), 4.02 (m, 1H), 3.74 (s, 3H), 3.3–3.4 (m, 2H), 3.03–3.27 (m, 3H), 2.63 (m, 2H), 2.33 (s, 3H), 1.9–2.1 (m, 2H).

Example 405

6-Fluoro-10-{3-[2-(3-fluoro-phenyl)-ethyl]-4-methyl-piperazin-1-yl}-2-methyl-4H-3-thia-4,9-diaza-benzo[f]azulene hydrochloride

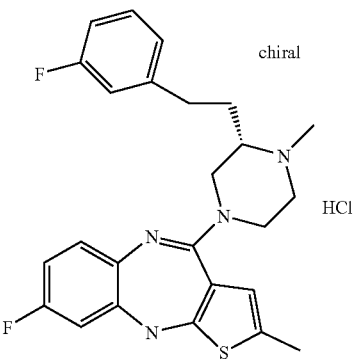

Dissolve 6-fluoro-10-{3-[2-(3-fluoro-phenyl)-ethyl]-piperazin-1-yl}-2-methyl-4H-3-thia-4,9-diaza-benzo[f]azulene (695 mg, 1.58 mmol) in 1,2-dichloroethane (30 ml) and stir at room temperature. Add 37% Aqueous formaldehyde solution (1 ml) followed by sodium triacetoxyborohydride (0.35 g, 1.65 mmol). Stir the reaction mixture at room temperature overnight. Add saturated aqueous sodium and collect the organic phase, dry and concentrate to 1.2 g dark oil. Dissolve in methanol (20 ml), add 2N hydrochloric acid (5 ml) and stir the mixture at room temperature for 2 hours. Concentrate the reaction mixture and partitions between dichloromethane and 2N sodium hydroxide solution. Collect the organic phase, dry and concentrate to a dark oil. Purify the material by flash column chromatography on florisil (eluent dichloromethane/methanol) to give 0.3 g yellow oil. Dissolve this material in ethanol (20 ml), add 2N hydrochloric acid (2 ml) and concentrate the mixture and dry under high vacuum to give the desired title compound as an orange solid 312 mg: mass Spectrum (FIA) 389 (M+1); mp: 191–193° C.

Example: 406

6-Fluoro-10-{3-[2-(4-methoxy-phenyl-ethyl]-4-methyl-piperazin-1-yl}-2-methyl-4H-3-thia-4,9-diaza-benzo[f]azulene hydrochloride

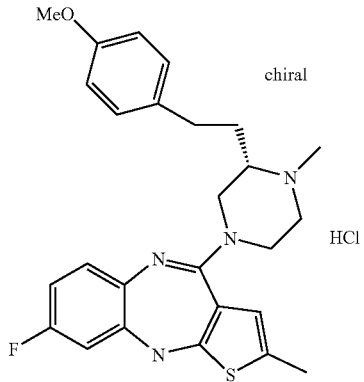

Similarly prepared by using Example 405, using 6-fluoro-10-{3-[2-(4-methoxy-phenyl)-ethyl]-piperazin-1-yl}-2-methyl-4H-3-thia-4,9-diaza-benzo[f]azulene. Mass Spectrum (FIA) 465 (M+1); mp: 191–193° C.

Example 407

7-Fluoro-10-{3-[2-(3-fluoro-phenyl)-ethyl]-4-methyl-piperazin-1-yl}-2-methyl-4H-3-thia-4,9-diaza-benzo[f]azulene hydrochloride

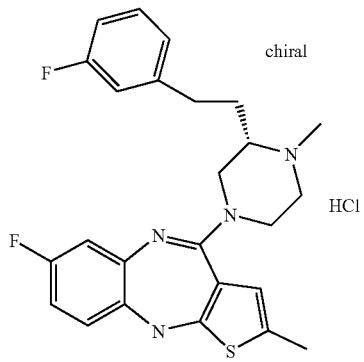

Similarly prepared by using Example 405, using 7-fluoro-10-{3-[2-(3-fluoro-phenyl)-ethyl]-piperazin-1-yl}-2-methyl-4H-3-thia-4,9-diaza-benzo[f]azulene. Mass Spectrum (FIA) 389 (M+1); mp: 178–180° C.

Example 408

7-Fluoro-10-{3-[2-(4-methoxy-phenyl)-ethyl]-4-methyl-piperazin-1-yl}-2-methyl-4H-3-thia-4,9diaza-benzo[f]azulene

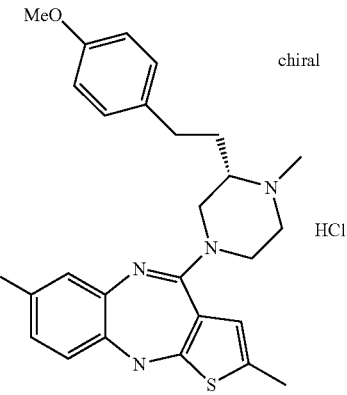

Similarly prepared by using Example 405, using 7-fluoro-10-{3-[2-(4-methoxy-phenyl)-ethyl]-piperazin-1-yl}-2-methyl-4H-3-thia-4,9-diaza-benzo[f]azulene. Mass Spectrum (FIA) 465 (M+1); mp: 180–182° C.

Example 410

2-Ethyl-7-fluoro-4,9-dihydro-3-thia-4,9-diaza-benzo[f]azulene-10-thione

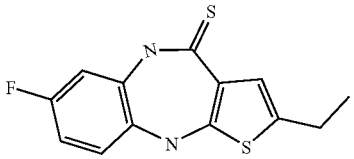

By using a method similar to Example 373, using 2-ethyl-7-fluoro-4,9-dihydro-3-thia-4,9-diaza-benzo[f]azulen-10-one gives the title compound: Mass spectrum M=278.

Example 411

2-Ethyl-7-fluoro-10-{3-[2-(3-fluoro-phenyl)-ethyl]-piperazin-1-yl}-4H-3-thia-4,9-diaza-benzo[f]azulene

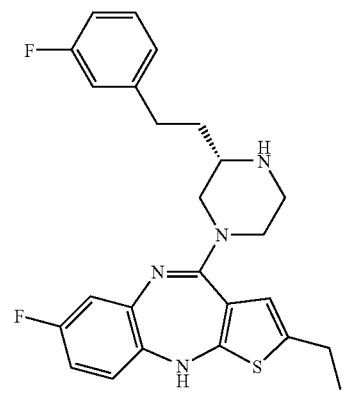

Similarly prepared using Example 401, using 2-ethyl-7-fluoro-4,9-dihydro-3-thia-4,9-diaza-benzo[f]azulene-10-thione to give the title compound: Mass spectrum M+H=453 for free base.

Example 412

2-Ethyl-7-fluoro-10-{3-[2-(3-fluoro-phenyl)-ethyl]-4-methyl-piperazin-1-yl}-4H-3-thia-4,9-diaza-benzo[f]azulene hydrochloride

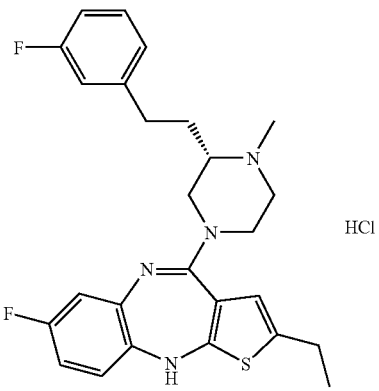

Similarly prepared using Example 405, using 2-ethyl-7-fluoro-10-{3-[2-(3-fluoro-phenyl)-ethyl]-piperazin-1-yl}-4H-3-thia-4,9-diaza-benzo[f]azulene. Mass spectrum M+H=467 for free base. $^1$H NMR (d6-DMSO); 11.73 (bs, 1H), 9.15 (bs, 1H), 7.35 (m, 1H), 7.05 (m, 6H), 6.66 (bs, 1H), 3.66 (m, 8H), 2.87 (m, 3H), 2.68 (m, 3H), 2.33 (m, 1H), 1.91 (m, 1H), 1.18 (m, 3H).

Example 413

2-Ethyl-7-fluoro-10-{3-[2-(4-methoxy-phenyl)-ethyl]-piperazin-1-yl}-4H-3-thia-4,9-diaza-benzo[f]azulene

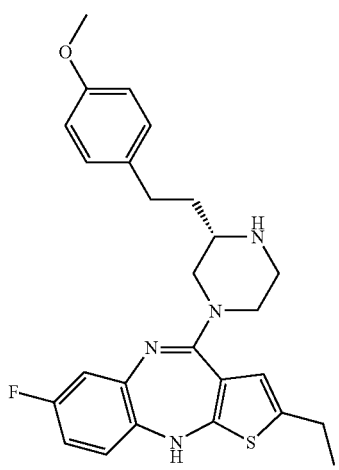

Similarly prepared using Example 401, using 2-ethyl-7-fluoro-4,9-dihydro-3-thia-4,9-diaza-benzo[f]azulene-10-thione to give the title compound: Mass spectrum M+H=465 for free base.

Example 414

2-Ethyl-7-fluoro-10-{3-[2-(4-methoxy-phenyl)-ethyl]-4-methyl-piperazin-1-yl}-4H-3-thia-4,9-diaza-benzo[f]azulene

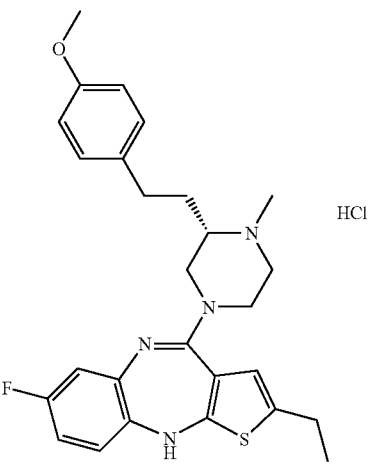

Similarly prepared using Example 405, using 2-ethyl-7-fluoro-10-{3-[2-(4-methoxy-phenyl)-ethyl]-piperazin-1-yl}-4H-3-thia-4,9-diaza-benzo[f]azulene: Mass Spectrum; M+H=479 for free base, $^1$H NMR (d6-DMSO); 11.62 (bs, 1H), 9.19 (bs, 1H), 7.11 (bs, 3H), 6.99 (bs, 1H), 6.86 (m, 4H), 6.69 (bs, 1H), 3.73 (s, 3H), 3.63 (bs, 1H), 3.41 (bs, 2H), 3.38 (q, 2H, J=7.2 Hz), 3.17 (s, 1H), 2.85 (m, 5H), 2.71 (m, 4H), 2.27 (bs), 1.91 (bs), 1.19 (t, 3H J 7.3 Hz).

Example 415

(S)-1,4-Dibenzyl-2-(2-naphthalen-1-yl-ethyl)-piperazine dihydrochloride

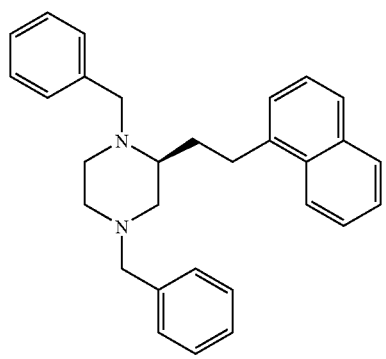

Combine 9-borabicyclo[3.3.1]nonane (119 mL, 59.5 mmol, 0.5 M in THF) and (S)-1,4-dibenzyl-2-vinyl-piperazine (4.35 g, 14,9 mmol) and stir at ambient temperature. After 18 h, add triphenylphosphine (1.25 g, 4.76 mmol), tetrakis(triphenylphosphine)palladium(0) (688 mg, 0.60 mmol), THF (5 mL) and 1-iodonaphthalene (3.26 mL, 22.3 mmol). Add 3M NaOH (12.2 mL, 36.6 mmol) slowly, gas evolution occurs. Heat at reflux. After 24 h, cool to ambient temperature and concentrate under reduced pressure. Add 2N NaOH (200 mL), and stir 1 h. Extract with diethyl ether.

Extract the diethyl ether solution with 1N $H_2SO_4$ and discard the diethyl ether. A white residue forms.

Add 5N NaOH to the 1N $H_2SO_4$ extracts until pH is 12–14. Extract with diethyl ether. Wash the diethyl ether extracts with brine, dry over sodium sulfate, filter and concentrate under reduced pressure to give 900 mg of crude product.

Dissolve the white residue in methanol and methylene chloride, dry over sodium sulfate, filter and concentrate under reduced pressure to give a tan foam. Slurry the foam in 5N HCl (50 mL), add methanol (50 mL) to give a homogeneous solution. Filter the white precipitate that forms to give 4.46 g (61%) of (S)-1,4-di-benzyl-2-(2-naphthalen-1-yl-ethyl)-piperazine dihydrochloride: mp 211–215° C. dec; mass spectrum (ion spray): m/z=421 (M+1). Analysis calculated for $C_{30}H_{34}Cl_2N_2$: C, 73.01; H, 6.94; N, 5.68; Cl, 14.37. Found: C, 72.98; H, 7.27; N, 5.59; Cl, 14.06.

Example 418, Example 419, Example 420

(S)-1-Benzyl-3-(2-naphthalen-1-yl-ethyl)-piperazine (S)-2-(2-Naphthalen-1-yl-ethyl)-piperazine (S)-1-benzyl-2-(2-nalphthalen-1-yl-ethyl)-piperazine

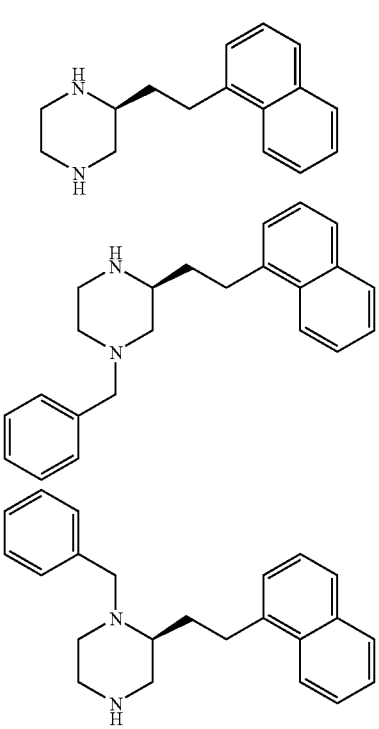

Dissolve (S)-1,4-dibenzyl-2-(2-naphthalen-1-yl-ethyl)-piperazine (3.33 g, 7.92 mmol) in ethanol (100 mL). Add ammonium formate (2.99 g, 47.5 mmol) and palladium (666 mg, 5 wt. % on carbon) and heat to reflux. After 6 h 30 min, filter the palladium on carbon and concentrate the filtrate. Purify by silica gel chromatography using 2N ammonia in methanol-methylene chloride (2.5%–10%) and 7N ammonia in methanol-methylene chloride (20%) as the eluent to give 716 mg (38%) of (S)-2-(2-naphthalen-1-yl-ethyl)-piperazine, 1.1 g of (S)-1-benzyl-3-(2-naphthalen-1-yl-ethyl)-piperazine, and 290 mg of (S)-1-benzyl-2-(2-naphthalen-1-yl-ethyl)-piperazine.

(S)-2-(2-Naphthalen-1-yl-ethyl)-piperazine: mass spectrum (ion spray): m/z=241 (M+1). $^1$H NMR (DMSO-$d_6$, $D_2O$): δ 8.07 (d, 1H), 7.91 (d, 1H), 7.76 (d, 1H), 7.58–7.46 (m, 2H), 7.41 (dd, 1H), 7.36 (br d, 1H), 3.19–2.94 (m, 2H), 2.89–2.46 (m, 6H), 2.25 (dd, 1H), 1.60 (dd, 2H).

(S)-1-Benzyl-2-(2-naphthalen-1-yl-ethyl)-piperazine: mass spectrum (ion spray): m/z=331 (M+1). $^1$H NMR (DMSO-$d_6$, $D_2O$): δ 8.03 (d, 1H), 7.91 (d, 1H), 7.76 (d, 1H), 7.57–7.47 (m, 2H), 7.44–7.18 (m, 7H), 3.90 (d, 1H), 3.23 (d, 1H), 3.17–2.90 (m, 3H), 2.78–2.39 (m, 5H), 2.14–2.04 (m, 1H), 1.99–1.89 (m, 2H).

(S)-1-Benzyl-3-(2-naphthalen-1-yl-ethyl)-piperazine: mass spectrum (ion spray): m/z=331 (M+1). $^1$H NMR (DMSO-$d_6$): δ 8.06 (d, 1H), 7.90 (d, 1H), 7.74 (d, 1H), 7.56–7.45 (m, 2H), 7.40 (dd, 1H), 7.35–7.19 (m, 6H1), 3.42 (dd, 2H), 3.20–3.08 (m, 1H), 3.05–2.91 (m, 1H), 2.87–2.79 (m, 1H), 2.77–2.55 (m, 4H), 1.98–1.87 (m, 1H), 1.74–1.56 (m, 3H).

Example 421

(S)-2-(2-Naphthalen-1-yl-ethyl)-piperazine

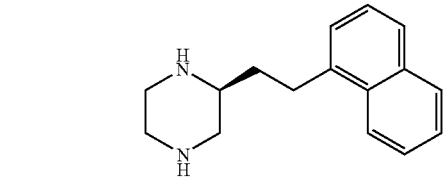

Dissolve (S)-1-benzyl-3-(2-naphthalen-1-yl-ethyl)-piperazine (1.07 g, 3.03 mmol) in ethanol (10 mL). Add ammonium formate (1.2 g, 19.0 mmol) and palladium hydroxide (200 mg, 20 wt. % on carbon) and heat to reflux. After 7 h, filter the palladium hydroxide and concentrate the filtrate. Combine with Example 422 and purify.

Example 422

(S)-2-(2-Naphthalen-1-yl-ethyl)-piperazine

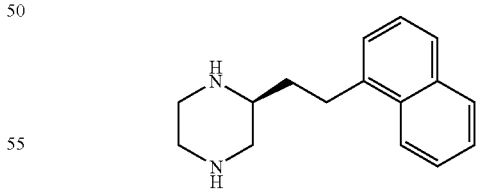

Dissolve (S)-1-benzyl-2-(2-naphthalen-1-yl-ethyl)-piperazine (280 mg, 0.85 mmol) in ethanol (5 mL). Add ammonium formate (320 mg, 5.1 mmol) and palladium hydroxide (60 mg, 20 wt. % on carbon) and heat to reflux. After 5.5 h, filter the palladium hydroxide and concentrate the filtrate. Combine with Example 421 and purify by silica gel chromatography using 2N ammonia in methanol-methylene chloride (5%) and 7N ammonia in methanol-methylene chloride (20%) as the eluent to give 750 mg (81%) of the title compound: mass spectrum (ion spray): m/z=241 (M+1). $^1$H NMR (DMSO-d$_6$): 8.08 (d, 1H), 7.91 (d, 1H), 7.76 (d, 1H), 7.59–7.32 (m, 4H), 3.53 (br s, 2H), 3.22–3.09 (m, 1H), 3.08–2.98 (m, 1H), 2.98–2.73 (m, 3H), 2.71–2.53 (m, 3H), 2.31 (dd, 1H), 1.71–1.57 (m, 2H).

Example 423

(S)-2-Methyl-10-[3-(2-naphthalen-1-yl-ethyl)-piperazin-1-yl]-4H-3-thia-4,9-diaza-benzo[f]azulene

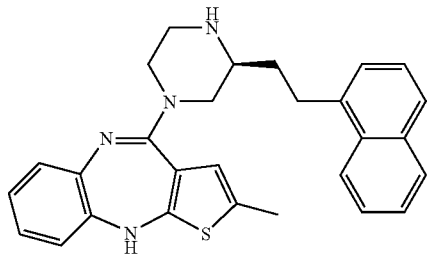

Combine (S)-2-(2-naphthalen-1-yl-ethyl)-piperazine (686 mg, 2.85 mmol), 2-methyl-4H-3-thia-4,9-diaza-benzo[f]azulen-10-ylamine (654 mg, 2.85 mmol), toluene (5.7 mL), DMSO (1.4 mL) and glacial acetic acid (0.5 mL). Add N-ethyldiisopropylamine (2.0 mL). Heat at 105° C. After 48 h, cool to ambient temperature and dilute with ethyl acetate and water. Extract with ethyl acetate. Wash the extracts with water and brine, dry over sodium sulfate, filter and concentrate the filtrate. Purify by silica gel chromatography using 2N ammonia in methanol-methylene chloride (0.5%–5%) as the eluent to give 183 mg. Purify again by radial silica gel chromatography using a 2 mm plate and 2N ammonia in methanol-methylene chloride (1%–2%) as the eluent to give 60 mg (5%) of the title compound: mass spectrum (ion spray): m/z=453 (M+1), 451 (M−1). Analysis calculated for C$_{28}$H$_{28}$N$_4$S.0.2H$_2$O: C, 73.71; H, 6.27; N, 12.28. Found: C, 73.37; H, 6.19; N, 12.00.

Example 424

(S)-2-Methyl-10-[3-(2-naphthalen-1-yl-ethyl)-piperazin-1-yl]-4H-3-thia-4,9-diaza-benzo[f]azulene

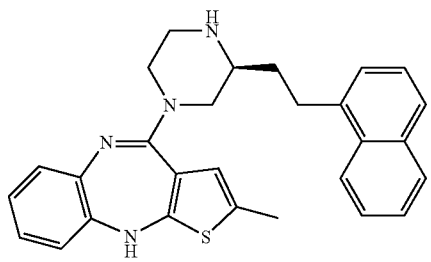

Combine (S)-2-(2-naphthalen-1-yl-ethyl)-piperazine (720 mg, 3.0 mmol), 2-methyl-4H-3-thia-4,9-diaza-benzo[f]azulen-10-ylamine (686 mg, 3.0 mmol), toluene (6 mL), DMSO (1.5 mL) and glacial acetic acid (1 drop). Heat at 105° C. After 48 h, cool to ambient temperature and dilute with ethyl acetate and water. Extract with ethyl acetate. Wash the extracts with water and brine, dry over sodium sulfate, filter and concentrate the filtrate. Purify by silica gel chromatography using 2N ammonia in methanol-methylene chloride (2.5%–3%) as the eluent to give 290 mg (21%) of the title compound: mass spectrum (ion spray): m/z=453 (M+1), 451 (M−1).

Example 425

(S)-2-Methyl-10-[4-methyl-3-(2-naphthalen-1-yl-ethyl)-piperazin-1-yl]-4H-3-thia-4,9-diaza-benzo[f]azulene

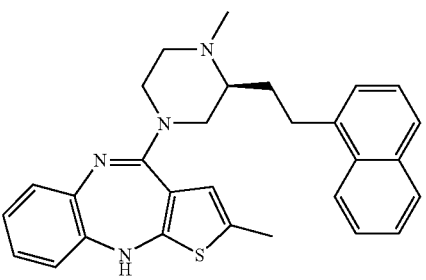

Add formaldehyde (56 μL, 0.70 mmol, 37% in water) to a solution of (S)-2-methyl-10-[3-(2-naphthalen-1-yl-ethyl)-piperazin-1-yl]-4H-3-thia-4,9-diaza-benzo[f]azulene (290 mg, 0.64 mmol) in methylene chloride (20 mL). Stir 15 min at ambient temperature. Add sodium triacetoxyborohydride (204 mg, 0.96 mmol) and stir 30 min at ambient temperature. Dilute with saturated sodium bicarbonate solution and extract with methylene chloride. Dry the extracts with sodium sulfate, filter and concentrate the filtrate. Purify by radial silica gel chromatography using a 2 mm plate and 2N ammonia in methanol-methylene chloride (1%–2%) as the eluent to give 290 mg (97%) of the title compound: mass spectrum (ion spray): m/z=467 (M+1), 465 (M−1). HR-MS calculated for C$_{29}$H$_{31}$N$_4$S: 467.2269. Found 467.2278. HPLC: Symmetry C$_{18}$ column (3.5 μm, 4.6×50 mm). Gradient 5% to 90% solvent B in 7 min. Solvent A was 0.1% (v/v) TFA in water and solvent B was acetonitrile. Retention time 5.7 min; 100% pure.

Example 426

(S)-1,4-Dibenzyl-2-(2-naphthalen-2-yl-ethyl)-piperazine dihydrochloride

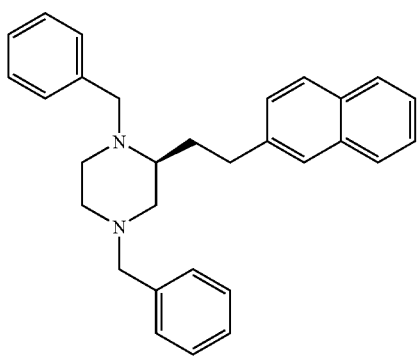

Combine 9-borabicyclo[3.3.1]nonane (163.6 mL, 81.8 mmol, 0.5 M in THF) and (S)-1,4-dibenzyl-2-vinyl-piperazine (5.98 g, 20.4 mmol) and stir at ambient temperature. After 24 h, add triphenylphosphine (1.72 g, 6.54 mmol), tetrakis(triphenylphosphine)palladium(0) (945 mg, 0.82 mmol) and 2-bromonaphthalene (6.35 g, 30.7 mmol). Add 3M NaOH (16.8 mL, 50.4 mmol) slowly, gas evolution occurs. Heat at reflux. After 24 h, cool to ambient temperature and concentrate under reduced pressure. Add 2.5N NaOH (200 mL), and stir 30 min. Extract with diethyl ether. Concentrate the diethyl ether extracts and dissolve the residue in 5N HCl (200 mL). Stir 30 min at ambient temperature. Extract with diethyl ether. Filter the precipitate that forms during the extraction. Slurry the precipitate in methanol, make basic with 5N NaOH, extract with diethyl ether, dry over sodium sulfate, filter and concentrate. Crystallize the residue from ethanol to give 5.9 g (69%) of the title compound: mp 85–8° C.; mass spectrum (ion spray): m/z=421 (M+1).

Example 427

(S)-2-(2-Naphthalen-2-yl-ethyl)-piperazine

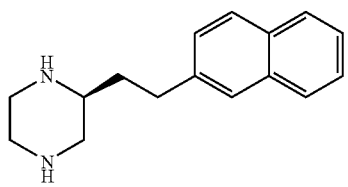

Dissolve (S)-1,4-dibenzyl-2-(2-naphthalen-2-yl-ethyl)-piperazine (6.53 g, 15.5 mmol) in ethanol (80 mL). Add ammonium formate (5.9 g, 93.6 mmol) and palladium hydroxide (1.5 g, 20 wt. % on carbon) and heat to reflux. After 8.5 h, cool and stir at ambient temperature 18 h. Filter the palladium hydroxide and concentrate the filtrate. Purify by silica gel chromatography using 7N ammonia in methanol-methylene chloride (2.5%–10%) as the eluent to give 2.86 g (77%) of the title compound: mp 151–4° C.; mass spectrum (ion spray): m/z=241 (M+1).

Example 428

(S)-2-Methyl-10-[3-(2-naphthalen-2-yl-ethyl)-piperazin-1-yl]-4H-3-thia-4,9-diaza-benzo[f]azulene

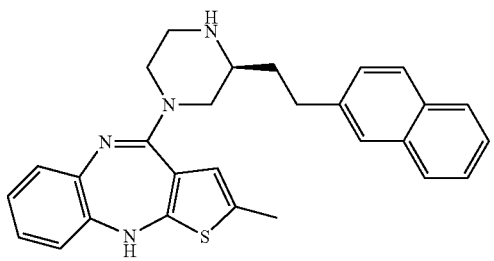

Combine (S)-2-(2-naphthalen-2-yl-ethyl)-piperazine (854 mg, 3.72 mmol), 2-methyl-4H-3-thia-4,9-diaza-benzo[f]azulen-10-ylamine (895 mg, 3.72 mmol) and 1-methyl-2-pyrrolidinone (8 mL). Heat at reflux. After 5 h, cool to ambient temperature and dilute with ethyl acetate and water. Extract with ethyl acetate. Wash the extracts with water and brine, dry over sodium sulfate, filter and concentrate the filtrate. Purify by silica gel chromatography using 2N ammonia in methanol-methylene chloride (2.5%) as the eluent to give 576 mg (34%) of the title compound: mass spectrum (ion spray): m/z=453 (M+1), 451 (M−1). HR-MS calculated for $C_{28}H_{29}N_4S$: 453.2113. Found 453.2116. HPLC: Symmetry $C_{18}$ column (3.5 µm, 4.6×50 mm). Gradient 5% to 90% solvent B in 7 min. Solvent A was 0.1% (v/v) TFA in water and solvent B was acetonitrile. Retention time 5.7 min; 100% pure.

Example 429

(S)-2-Methyl-10-[4-methyl-3-(2-naphthalen-2-yl-ethyl-)piperazin-1-yl]-4H-3-thia-4,9-diaza-benzo[f]azulene

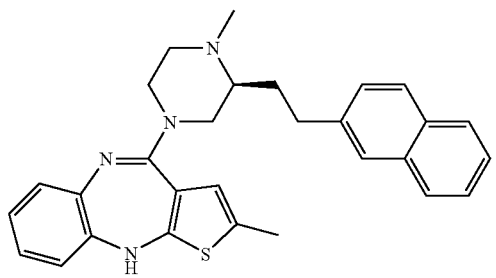

Add formaldehyde (101 µL, 1.28 mmol, 37% in water) to a solution of (S)-2-methyl-10-[3-(2-naphthalen-2-yl-ethyl)-piperazin-1-yl]-4H-3-thia-4,9-diaza-benzo[f]azulene (525 mg, 1.16 mmol) in methylene chloride (20 mL). Stir 15 min at ambient temperature. Add sodium triacetoxyborohydride (369 mg, 1.7 mmol) and stir 1 h at ambient temperature. Dilute with saturated sodium bicarbonate solution and extract with methylene chloride. Dry the extracts with sodium sulfate, filter and concentrate the filtrate. Purify by silica gel chromatography using 2N ammonia in methanol-methylene chloride (2.5%) as the eluent to give 550 mg (100%) of the title compound: mass spectrum (ion spray): m/z=467 (M+1), 465 (M−1). HPLC: Symmetry $C_{18}$ column (3.5 µm, 4.6×50 mm). Gradient 5% to 90% solvent B in 7 min. Solvent A was 0.1% (v/v) TFA in water and solvent B was acetonitrile. Retention time 5.7 min; 100% pure.

Example 430

(S)-2-Methyl-10-[4-methyl-3-(2-naphthalen-2-yl-ethyl)-piperazin-1-yl]-4H-3-thia-4,9-diaza-benzo[f]azulene dihydrochloride

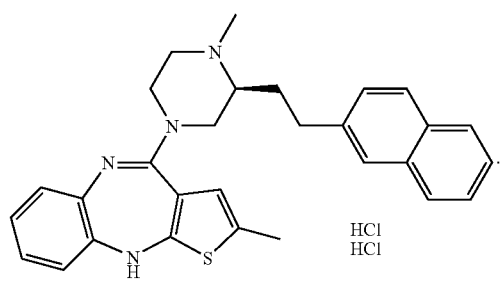

Crystallize the dihydrochloride salt from ethyl acetate and ethanol to give the title compound: mp 209° C. dec. Mass spectrum (ion spray): m/z=467 (M+1), 465 (M−1). Analysis calculated for $C_{29}H_{32}Cl_2N_4S$: C, 64.56; H, 5.98; N, 10.38. Found: C, 64.18; H, 5.74; N, 10.28. HR-MS calculated for $C_{29}H_{31}N_4S$: 467.2269. Found 467.2243. HPLC: Symmetry $C_{18}$ column (3.5 µm, 4.6×50 mm). Gradient 5% to 90% solvent B in 7 min. Solvent A was 0.1% (v/v) TFA in water and solvent B was acetonitrile. Retention time 5.7 min; 100% pure.

Example 431

(S)-1,4-Dibenzyl-2-(2-furan-3-yl-ethyl-piperazine

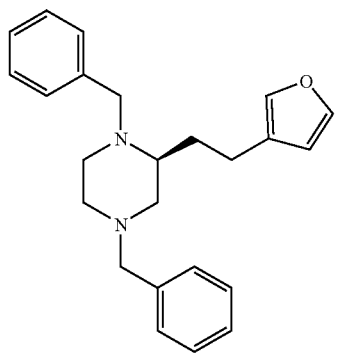

Combine 9-borabicyclo[3.3.1]nonane (165.8 mL, 82.9 mmol, 0.5 M in THF) and (S)-1,4-dibenzyl-2-vinyl-piperazine (6.06 g, 20.7 mmol) and stir at ambient temperature. After 24 h, add triphenylphosphine (1.74 g, 6.6 mmol), tetrakis(triphenylphosphine) palladium(0) (958 mg, 0.83 mmol) and 3-bromofuran (2.8 mL, 31.1 mmol). Add 3M NaOH (17.0 mL, 51.0 mmol) slowly, gas evolution occurs. Heat at reflux. After 24 h, add tetrakis(triphenylphosphine) palladium(0) (958 mg, 0.83 mmol). After 48 h, cool to ambient temperature and concentrate under reduced pressure. Add 2.5N NaOH (200 mL), and stir 30 min. Extract with diethyl ether. Filter the precipitate and discard. Extract the diethyl ether extracts with 1N sulfuric acid. Make basic with 5N sodium hydroxide and extract with diethyl ether, dry over sodium sulfate, filter and concentrate. Purify by silica gel chromatography using ethyl acetate/hexanes (10%) as the eluent to give 2.4 g of a mixture of the title compound and (S)-1,4-dibenzyl-2-ethyl-piperazine: mass spectrum (ion spray): m/z=361 (M+1, (S)-1,4-dibenzyl-2-(2-furan-3-yl-ethyl)-piperazine), m/z=295 (M+1, (S)-1,4dibenzyl-2-ethyl-piperazine).

Example 432

(S)-2-(2-Furan-3-yl-ethyl)-piperazine

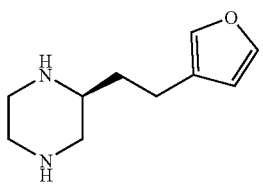

Dissolve a mixture of (S)-1,4-dibenzyl-2-(2-furan-3-yl-ethyl)-piperazine and (S)-1,4-dibenzyl-2-ethyl-piperazine (2.29 g, 6.35 mmol) in 1,2-dichloroethane (10 mL). Cool on an ice bath and add 1-chloroethyl chloroformate (2.06 ml, 19.1 mmol) dropwise. Remove ice bath and heat to 83° C. for 5.5 h. Concentrate the reaction, dissolve the residue in methanol (50 mL) and heat to reflux for 2 h. Cool to ambient temperature and stir 18 h. Filter and concentrate to a solid. Purify by silica gel chromatography using 7N ammonia in methanol-methylene chloride (2.5%–10%) as the eluent to give 330 mg (29%) of the title compound: mp 112–4° C. Mass spectrum (ion spray): m/z=181 (M+1).

Example 433

(S)-2-(2-Furan-3-yl-ethyl)-piperazine

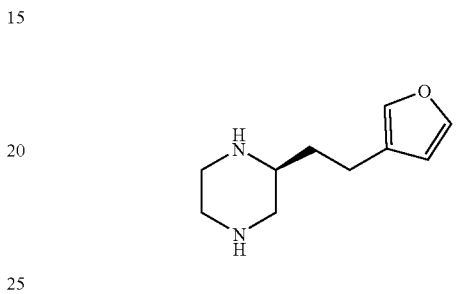

Dissolve (S)-1,4-dibenzyl-2-(2-furan-3-yl-ethyl)-piperazine (810 mg, 2.25 mmol) in ethanol (5 mL). Add ammonium formate (850 mg, 13.5 mmol) and palladium (100 mg, 5 wt. % on carbon) and heat to reflux. After 3.5 h, filter the palladium and concentrate the filtrate. Purify by silica gel chromatography using 7N ammonia in methanol-methylene chloride (5%) as the eluent to give 175 mg (43%) of the title compound: mass spectrum (ion spray): m/z=181 (M+1). Analysis calculated for $C_{10}H_{16}N_2O$: C, 66.63; H, 8.95; N, 11.54. Found: C, 66.53; H, 8.92; N, 11.14.

Example 434

(S)-10-[3-(2-Furan-3-yl-ethyl)-piperazin-1-yl]-2-methyl-4H-3-thia-4,9-diaza-benzo[f]azulene

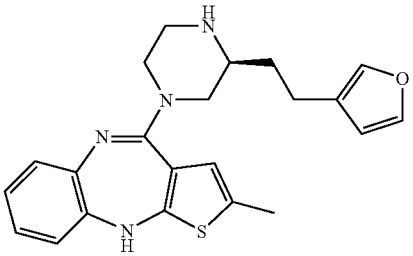

Combine (S)-2-(2-furan-3-yl-ethyl)-piperazine (550 mg, 3.05 mmol), 2-methyl-4H-3-thia-4,9-diaza-benzo[f]azulen-10-ylamine (700 mg, 3.05 mmol), toluene (6 mL) and DMSO (1.5 mL). Heat at 100° C. After 48 h, cool to ambient temperature and dilute with ethyl acetate. Filter the solids and dilute the filtrate with water. Extract with ethyl acetate. Wash the extracts with water and brine, dry over sodium sulfate, filter and concentrate the filtrate. Purify by silica gel chromatography using 2N ammonia in methanol-methylene chloride (2.5%) as the eluent to give 282 mg (24%) of the title compound: mass spectrum (ion spray): m/z=393 (M+1), 391 (M−1). HR-MS calculated for $C_{22}H_{25}N_4OS$: 393.1749. Found 393.1742. HPLC: Symmetry $C_{18}$ column (3.5 µm, 4.6×50 mm). Gradient 5% to 90% solvent B in 7 min. Solvent A was 0.1% (v/v) TFA in water and solvent B was acetonitrile. Retention time 5.4 min; 100% pure.

Example 435

(S)-10-[3-(2-Furan-3-yl-ethyl)-4-methyl-piperazin-1-yl]-2-methyl-4H-3-thia-4,9-diaza-benzo[f]azulene

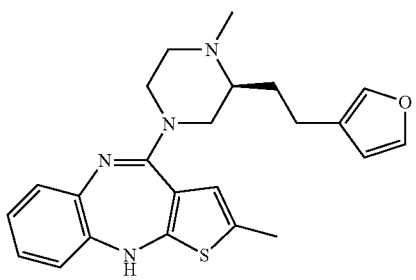

Add formaldehyde (49 µL, 0.61 mmol, 37% in water) to a solution of (S)-10-[3-(2-furan-3-yl-ethyl)-piperazin-1-yl]-2-methyl-4H-3-thia-4,9-diaza-benzo[f]azulene (219 mg, 0.56 mmol) in methylene chloride (20 mL). Stir 15 min at ambient temperature. Add sodium triacetoxyborohydride (177 mg, 0.56 mmol) and stir 1 h at ambient temperature. Dilute with saturated sodium bicarbonate solution and extract with methylene chloride. Dry the extracts with sodium sulfate, filter and concentrate the filtrate. Purify by radial silica gel chromatography using a 2 mm plate and 2N ammonia in methanol-methylene chloride (1%–2.5%) as the eluent to give 179 mg (79%) of the title compound: mass spectrum (ion spray): m/z=407 (M+1), 405 (M−1). HPLC: Symmetry $C_{18}$ column (3.5 µm, 4.6×50 mm). Gradient 5% to 90% solvent B in 7 min. Solvent A was 0.1% (v/v) TFA in water and solvent B was acetonitrile. Retention time 5.4 min; 100% pure;

Example 436

(S)-10-[3-(2-Furan-3-yl-ethyl)-4-methyl-piperazin-1-yl]-2-methyl-4H-3-thia-4,9-diaza-benzo[f]azulene dihydrochloride

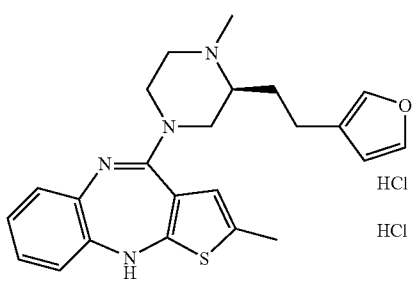

Crystallize the dihydrochloride salt from ethyl acetate and ethanol to give the title compound: mp 198° C. dec. Mass spectrum (ion spray): m/z=407 (M+1), 405 (M−1). Analysis calculated for $C_{23}H_{28}Cl_2N_4OS \cdot 0.3H_2O$: C, 56.97; H, 5.95; N, 11.56. Found: C, 56.73; H, 5.69; N, 11.48. HR-MS calculated for $C_{23}H_{27}N_4OS$: 407.1906. Found 407.1892. HPLC: Symmetry Cis column (3.5 µm, 4.6×50 mm). Gradient 5% to 90% solvent B in 7 min. Solvent A was 0.1% (v/v) TFA in water and solvent B was acetonitrile. Retention time 5.3 min; 100% pure.

Example 437

(S)-1,4-Dibenzyl-2-(2-thiophen-3-yl-ethyl)-piperazine

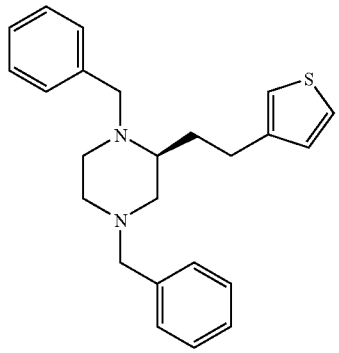

Combine 9-borabicyclo[3.3.1]nonane (54.7 mL, 27.4 mmol, 0.5 M in THF) and (S)-1,4-dibenzyl-2-vinyl-piperazine (2.0 g, 6.84 mmol) and stir at ambient temperature. After 24 h, add triphenylphosphine (574 mg, 2.2 mmol), tetrakis(triphenylphosphine) palladium(0) (316 mg, 0.27 mmol) and 3-iodothiophene (1.93 g, 9.2 mmol). Add 3M NaOH (5.6 mL, 16.8 mmol) slowly, gas evolution occurs. Heat at reflux. After 48 h, cool to ambient temperature, add 5N HCl (12 mL), and stir 1 h. Extract with ethyl acetate and wash the extracts with 1N NaOH, water, brine, dry over sodium sulfate, filter and concentrate. Purify by silica gel chromatography using ethyl acetate/hexanes (10%) as the eluent to give 2.38 g of the title compound as an adduct of 9-BBN: mass spectrum (ion spray): m/z=377 (M+1).

Example 438

(S)-2-(2-Thiophen-3-yl-ethyl)-piperazine

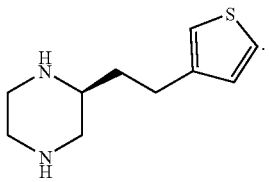

Dissolve (S)-1,4-dibenzyl-2-(2-thiophen-3-yl-ethyl)-piperazine (1.17 g, 3.1 mmol) and (S)-1,4-dibenzyl-2-(2-thiophen-2-yl-ethyl)-piperazine (230 mg, 0.61 mmol) in 1,2-dichloroethane (10 mL). Add 1-chloroethyl chloroformate (2.0 ml, 18.5 mmol) and heat to 80° C. for 18 h. Concentrate the reaction, dissolve the residue in methanol and heat to reflux for 2 h. Concentrate to an oil. Purify by silica gel chromatography using 2N ammonia in methanol-methylene chloride (10%) then 7N ammonia in methanol-methylene chloride (10%) as the eluent to give 400 mg (55%) of a 6:1 mixture of the title compound to (S)-2-(2-thiophen-2-yl-ethyl)-piperazine: mass spectrum (ion spray): m/z=197 (M+1).

Example 439

(S)-2-Methyl-10-[3-(2-thiophen-3-yl-ethyl)-piperazin-1-yl]-4H-3-thia-4,9-diaza-benzo[f]azulene

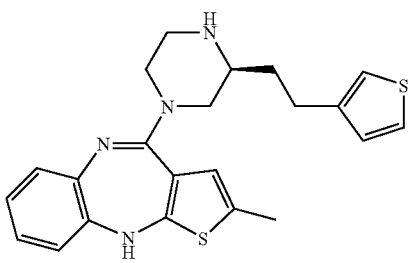

Add methyl trifluoromethanesulfonate (241 μL, 2.13 mmol) to a 0° C. slurry of 2-methyl-4,9-dihydro-3-thia-4,9-diaza-benzo[f]azulene-10-thione (437 mg, 1.77 mmol) in dichloromethane (5 mL). Stir 2 h at 0° C. then warm to ambient temperature and stir 16 h. Concentrate the reaction to an orange powder. Add a 6:1 mixture of (S)-2-(2-thiophen-3-yl-ethyl)-piperazine and (S)-2-(2-thiophen-2-yl-ethyl)-piperazine (346 mg, 1.76 mmol) and pyridine (5 mL). Heat to reflux for 7.5 h and stir at ambient temperature for 18 h. Concentrate the reaction, dissolve the residue in methanol-dichloromethane, apply to a SCX column. Wash the column with methanol-dichloromethane to remove impurities then elute the product with 2N ammonia in methanol-methanol (10%). Concentrate and purify by silica gel chromatography using 2N ammonia in methanol-methylene chloride (1%–4%) as the eluent to give 333 mg of a brown foam. Purify by radial silica gel chromatography using a 4 mm plate and 1% isopropylamine in tetrahydrofuran-hexanes (10%–20%) as the eluent to give 218 mg (30%) of the title compound: mass spectrum (ion spray): m/z=409 (M+1), 407 (M −1). HR-MS calculated for $C_{22}H_{25}N_4S_2$: 409.1521. Found 409.1540. $^1$H NMR (DMSO-$d_6$): δ 7.56 (s, 1H), 7.43 (dd, 1H), 7.13 (s, 1H), 6.99 (d, 1H), 6.87–6.74 (m, 3H), 6.67 (d, 1H), 6.31 (s, 1H), 3.88 (br d, 1H), 3.76 (br d, 1H), 2.88 (br d, 1H), 2.80–2.53 (m, 5H), 2.45–2.38 (m, 1H), 2.27 (s, 3H), 1.61 (dd, 2H).

Example 440

(S)-2-Methyl-10-[4-methyl-3-(2-thiophen-3-yl-ethyl)-piperazin-1-yl]-4H-3-thia-4,9-diaza-benzo[f]azulene dihydrochloride

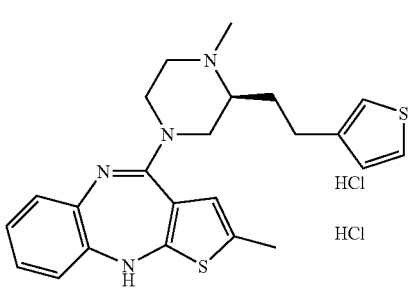

Add formaldehyde (45 μL, 0.56 mmol, 37% in water) to a solution of (S)-2-methyl-10-[3-(2-thiophen-3-yl-ethyl)-piperazin-1-yl]-4H-3-thia-4,9-diaza-benzo[f]azulene (210 mg, 0.51 mmol) in methylene chloride (6 mL). Stir 15 min at ambient temperature. Add sodium triacetoxyborohydride (163 mg, 0.77 mmol) and stir 2h at ambient temperature. Dilute with saturated sodium bicarbonate solution and extract with methylene chloride. Dry the extracts with sodium sulfate, filter and concentrate the filtrate. Purify by radial silica gel chromatography using a 2 mm plate and 2N ammonia in methanol-methylene chloride (2%) as the eluent to give 127 mg (59%) of the free base of the title compound. Crystallize the dihydrochloride salt from ethyl acetate and ethanol to give the title compound: mass spectrum (ion spray): m/z=423 (M+1), 421 (M−1). Analysis calculated for $C_{23}H_{28}Cl_2N_4S_2.0.2HCl.0.3H_2O$: C, 54.35; H, 5.71; N, 11.01; Cl, 15.35. Found: C, 54.10; H, 5.34; N, 10.99; Cl, 15.00. HR-MS calculated for $C_{23}H_{27}N_4S_2$ 423.1677. Found 423.1656.

By the method of Example 59, the following compounds were prepared and isolated as the free base:

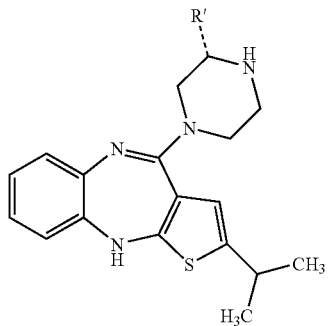

| No. | R' | Data |
|---|---|---|
| 441 | CH$_2$Ph | $^1$H NMR(CDCl$_3$)δ1.19(d, 6H), 2.58–3.04(m, 8H), 3.98(m, 1H), 4.09(m, 1H), 4.97(s, 1H), 6.24(s, 1H), 6.60(d, 1H), 6.87(t, 1H), 6.97(t, 1H), 7.02(d, 1H), 7.18–7.36(m, 5H); MS (APCI)m/z(rel intensity)417(100). Product is yellow powder. |
| 442 | CH$_2$CH$_2$Ph | $^1$H NMR(CDCl$_3$)δ1.23(d, 6H), 1.65–1.82(m, 3H), 2.58–2.97(m, 7H), 3.05(m, 1H), 3.99(m, 1H), 4.11(m, 1H), 4.98(s, 1H), 6.31(s, 1H), 6.60(d, 1H), 6.87(t, 1H), 6.97(t, 1H), 7.04(d, 1H), 7.20–7.32(m, 5H); MS(APCI)m/z(rel intensity)431(100). 10 mg of product. |
| 443 | CH$_2$(2-OCH$_3$)Ph | mp 85–97° C.; $^1$H NMR(CDCl$_3$)δ1.18(d, 3H), 1.20(d, 3H), 2.76–2.61(m, 2H), 2.92–2.79(m, 3H), 3.11–2.95(m, 3H), 3.82(s, 3H), 4.05–3.96(m, 2H), 4.98(s, 1H), 6.24(s, 1H), 6.60(d, 1H), 6.91–6.84(m, 3H), 6.96(ddd, 1H), 7.02(d, 1H), 7.17(d, 1H), 7.21(ddd, 1H); MS(APCI)m/z(rel intensity)447.3(100). 22% yield. |

By the method of Example 90, the following compounds were prepared and isolated as the free base and the (S) isomer:

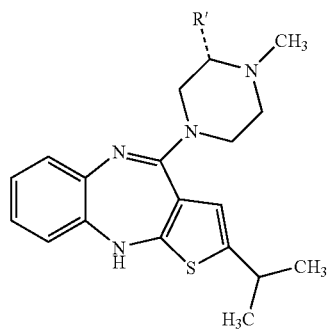

| No. | R' | Data |
|---|---|---|
| 444 | CH₂CH₂Ph | ¹H NMR(CDCl₃)δ1.24(d, 6H), 1.75(septet, 1H), 1.93–2.03(m, 2H), 2.21(m, 1H), 2.35 (s, 1H), 2.38(m, 1H), 2.58(m, 1H), 2.74(m, 1H), 2.88(m, 1H), 2.96(m, 1H), 3.15(ddd, 1H), 3.93(m, 1H), 4.06(m, 1H), 4.98(s, 1H), 6.34(s, 1H), 6.61(d, 1H), 6.88(t, 1H), 6.98(t, 1H), 7.05(d, 1H), 7.17–7.32(m, 5H); MS (APCI)m/z(rel intensity)445(100). 220 mg of product. |
| 444a | CH₂Ph | ¹H NMR(CDCl₃)δ1.11(d, 3H), 1.12(d, 3H), 2.40–2.49(m, 3H), 2.50(s, 3H), 2.77(septet, 1H), 2.85(m, 1H), 2.90(ddd, 1H), 3.16(m, 1H), 3.22(m, 1H), 3.63(m, 1H), 3.93(m, 1H), 4.92(s, 1H), 6.07(s, 1H), 6.57(d, 1H), 6.85(t, 1H), 6.92–6.97(m, 2H), 7.14–7.27 (m, 5H); MS(APCI)m/z(rel intensity)431 (100). 252 mg of product. |
| 444b | CH₂(2-OCH₃—Ph) | mp 79–89° C.: ¹H NMR(CDCl₃)δ1.10(d, 3H), 1.12(d, 3H), 2.50–2.40(m, 3H), 2.52(s, 3H), 2.77(m, 1H), 2.96–2.86(m, 2H), 3.21(d, 1H), 3.24(bt, 1H), 3.61(d, 1H), 3.78(s, 3H), 3.92(bd, 1H), 4.92(s, 1H), 6.07(s, 1H), 6.57(d, 1H), 6.87–6.79(m, 3H), 6.95–6.92(m, 2H), 7.07(d, 1H), 7.17(ddd, 1H); MS(APCI)m/z(rel intensity)461.3(100). 93% yield. |

Example 445

(S)-2-tert-Butyl-10-(3-phenethyl-piperazin-1-yl)-4H-3-thia-4,9-diaza-benzo[f]azulene

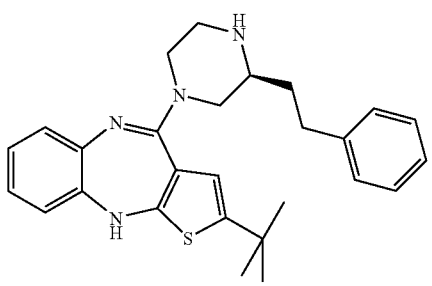

By using a method similar to the method of Example 460, using 2-tert-butyl4H-3-thia-4,9-diaza-benzo[f]azulen-10-ylamine (0.934 g, 3.44 mmol) and (S)-2-phenethyl-piperazine (0.655 g, 3.44 mmol) gives 0.561 g of the title compound as a yellow solid: mp 93–96° C.; mass spectrum (ion spray): m/z=445 (M+1); Analysis for C₂₇H₃₂N₄S(0.5 H₂O): calcd: C, 71.49; H, 7.33; N, 12.35; found: C, 71.27; H, 6.88; N, 12.29.

Example 446

(S)-2-tert-Butyl-10-(4-methyl-3-phenethyl-piperazin-1-yl)-4H-3-thia-4,9-diaza-benzo[f]azulene dihydrochloride

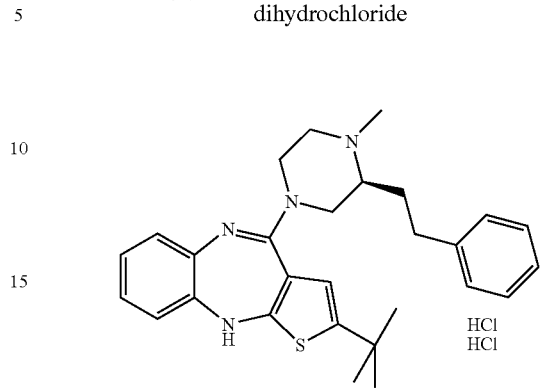

In a manner such as that described in Example 461, using (S)-2-tert-butyl-10-(3-phenethyl-piperazin-1-yl)-4H-3-thia-4,9-diaza-benzo[f]azulene (0.429 g, 0.96 mmol) gives 0.229 g of the title compound as a yellow solid: mp 230° C.; mass spectrum (ion spray): m/z=459 (M+1); Analysis for C₂₈H₃₆Cl₂N₄S(1.5 H₂O): calcd: C, 60.20; H, 7.04; N, 10.03; found: C, 60.57; H, 7.26; N, 10.22.

Example 447

5-Amino-2-methyl-thiazole-4-carboxylic acid ethyl ester

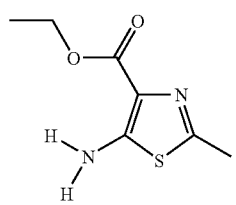

Add acetoamidoacetate (1000 g, 5.88 mol) to a 22 L 3-necked RB flask equipped with reflux condenser, thermometer, mechanical stirrer then add toluene (12 L). Add to this suspension at RT Lawesson's reagent (1187 g, 2.93 mol). Stir the resulting yellow slurry at 70° C. for 16 h, cool to RT. Pour the top yellow solution away from the gummy material on the bottom of the flask into a separation funnel. Add 1N HCl solution (2.5 L) and TBEA (2.5 L) and stir the mixture. After 15 min., combine the bi-phase solution was into the toluene solution in the funnel. Gummy material maybe left in the flask. Repeat the above procedure again. Separate the aqueous and wash the combine organic solution with 1N HCl (2×2.5 L). Separate the organic layer and combine the aqueous and basify with 2N KOH solution. Add ethyl acetate (3×4 L) and extract the product. Combine the organic layer, dry over anhydrous sodium sulfate, and evaporate to give 552 g as a pale yellow solid. Dissolve the remaining gummy in methanol (1 L) and evaporate to dryness. Add MTBE (2.5 L) and 1N HCl (4 L) and stir the mixture. After 15 min., separate the organic layer and basify the aqueous with 2N KOH solution Extract the product with ethyl acetate (2×2 L). Combine the organic layers and dry over anhydrous sodium sulfate and evaporate to give 165 g as a pale yellow solid. (Total: 717 g, 65%). Mass spectrum (m/e): 187 (M+1); $^1$HNMR(300 MHz, DMSO, ppm): 1.21 (t, 3H), 2.38 (s, 3H), 4.21 (q, 2H), 7.21 (bs, 2H). $^{13}$CNMR (75MHz, DMSO, ppm):, 15.1, 19.2, 59.8, 119.3, 145.6, 161.7, 164.1. Formula: $C_7H_{10}N_2O_2S$.

Example 448

2-Methyl-5-(2-nitro-phenylamino)-thiazole-4-carboxylic acid ethyl ester

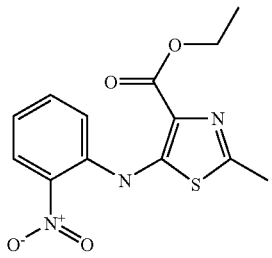

Add a solution of ethyl 5-amino-2-methylthiazole-4-carboxylate (120 g; 645 mmol) and 2-fluoronitrobenzene (68 mL; 645 mmol) in dimethylsulphoxide (1 L) to a 2 L 3-necked RB flask equipped with reflux condenser, thermometer, mechanical stirrer. Add lithium hydroxide monohydrate (54 g; 1290 mmol) to the solution and heat at 50° C. for 3 hours under nitrogen. Cool the purple solution and pour onto ice/water, allow to stir for one hour, filter and wash with water, dry at 50° C. under reduced pressure to give 190 g (96%) as an orange solid: mass spectrum (m/e): 308 (M+1); $^1$HNMR(300 MHz, DMSO, ppm): 1.25 (tr, 3H), 2.56 (s, 3H), 4.25 (q, 2H), 7.20 (m, 1H), 7.78 (m, 2H), 8.20 (d, 1H), 11.42 (s, 1H, NH). $^{13}$CNMR(75 MHz, DMSO, ppm): 24.4, 29.2, 71.2, 127.8, 132.5, 132.8, 137.8, 146.5, 147.0, 147.5, 160.2, 161.5, 173.7. Formula: $C_{13}H_{13}N_3O_4S$.

Example 449

2-Methyl-5-(2-nitrophenylamino)-thiazole-4-carboxylic acid amide

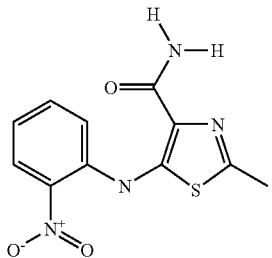

Combine ethyl 2-methyl-5-(2-nitroanilino)thiazole-4-carboxylate (80 g, 260 mmol) and formamide (52 mL, 1.3 mol) in DMF (200 mL) and heat to 105° C. which time the yellow slurry became a dark solution. Add to this reaction mixture at 105° C. dropwise 25% sodium methoxide in methanol (40 mL, 182.4 mmol) during 45 min period and heat to 115° C. and continue stir for 60 h. Cool the reaction to RT, pour into a cold saturated NaHCO$_3$ solution. Stir the resulting slurry for 1 h, filter and wash the solid with DMF/H$_2$O (2:1). Dry in a vacuum oven, to obtain a dark brown solid (62 g, 86%). Another batch starting 100 g of ethyl 2-methyl-5-(2-nitroanilino)thiazole-4-carboxylate to give 82 g (90%) of crude product: mass spectrum (m/e): 279 (M+1); $^1$HNMR(300 MHz, DMSO, ppm): 2.5 (s, 3H), 7.05 (m, 1H), 7.51 (d, 1H), 7.65 (m, 2H), 8.10 (d, 1H), 12.18 (s, 1H). $^{13}$CNMR(75 MHz, DMSO, ppm): 19.4, 116.8, 121.7, 127.3, 129.9, 136.3, 137.0, 137.8, 145.6, 151.2, 166.1. Formula: $C_{11}H_{10}N_4O_3S$.

Example 450

2-Methyl-5-(2-nitro-phenylamino)-thiazole-4-carbonitrile

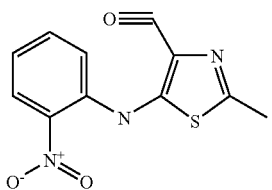

Combine 2-methyl-5-(2-nitroanilino)thiazole-4-carboxylic acid amide (60 g, 215 mmol) and toluene and add POCl$_3$ (40 mL, 430 mmol) and reflux the reaction mixture. After 2.5 h cool to 0° C. Add saturated NaHCO$_3$ solution to quench the extra POCl3 (Caution!!) until the aqueous was around pH 8. Add ethyl acetate (2×2 L) to extract the product. Combined organic layer and wash with brine (2×1 L), dry over MgSO$_4$, and evaporate to give a reddish solid which triturated with 25% ethyl acetate in hexane to give a reddish solid (36 g). Evaporate the filtrate to half volume to give second batch of compound (3.2 g). Total yield (39.2 g, 70%): mass spectrum (m/e): 261 (M+1); $^1$HNMR(300 MHz, DMSO, ppm): 2.70 (s, 1H), 7.02 (t, 1H), 7.22 (d, 1H), 7.58 (t, 1H), 8.25 (d, 1H), 9.78 (s, 1H). ). $^{13}$CNMR(75MHz, DMSO, ppm): 20.4, 113.1, 116.2, 118.7, 121.2 127.0, 134.9, 136.6, 140.0, 148.6, 161.5. Formula: $C_{11}H_8N_4O_2S$ Example 451

2-Methyl-4H-3-thia-1,4,9-triaza-benzo[f]azulen-10-ylamine hydrochloride

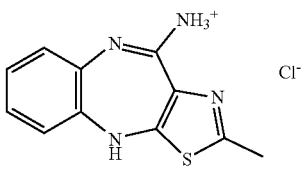

Combine a suspension of 2-methyl-5-(2-nitroanilino)thiazole-4-nitrile (36 g,; 138.5 mmol) in isopropanol (400 ml) in a 2.0 liter 3-necked RB flask equipped with a reflux condenser, thermometer, magnetic stirrer bar and heat with stirring to 65° C. (orange solution obtained). Add tin (II) chloride hydrate (78.7 g; 415.4 mmol) in hydrochloric acid (400 ml; 5M) and heat the resulting solution at reflux. After 2.5 h., cool the reaction to 15° C., filter the suspension, wash with isopropanol/water (2:1) and dry at 50° C. under reduced pressure to leave a yellow solid (36.7 g). Evaporate the filtrate to around 200 mL to form a yellow slurry. Filter the slurry again and dry at 50° C. under reduced pressure to leave a yellow solid (10 g). Combine the solid and suspend in 1 N HCl (700 mL) and heat to reflux for 20 min, cool to 15° C. Filter the resulting yellow slurry and dry at 50° C. under reduced pressure to leave a yellow solid (32.4 g, 88%): mass spectrum (m/e): 231 (M+1); $^1$HNMR(300 MHz, DMSO, ppm): 2.5 (s, 3H), 6.78 (dd, 1H), 6.85 (dd, 1H), 6.98 (t, 1H), 7.02 (t, 1H), 8.80 (s, 1H), 9.10 (s, 1H), 9.98 (s, 1H), 10.78 (s, 1H). $^{13}$CNMR(75 MHz, DMSO, ppm): 19.6, 120.1, 120.8, 123.6, 125.8, 127.8, 129.2, 137.6, 154.4, 159.3, 160.4. Formula $C_{11}H_{11}N_4S$.

Example 452

Cyano-isobutyrylamino-acetic acid ethyl ester

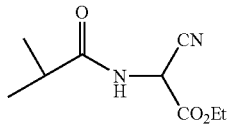

Dilute aqueous saturated sodium bicarbonate (560 mL) with deionized water (700 mL). and stir the solution while adding ethyl cyanoglyoxylate-2-oxime (70.0 g, 493 mmol) in portions (note: some off-gassing and a gentle endotherm were observed). Add sodium dithionite (238 g, 1.37 mol, 2.8 eq.) in portions and stir at rt. After 2.5–3 hours, during this time the reaction was monitored by TLC (EtOAc, I$_2$ stain), saturate the solution with sodium chloride (400 g), and extract the product CH$_2$Cl$_2$ (1×500 mL, 3×250 mL), making sure solid NaCl was visible (more added if necessary) during the extractions. Combine the organic layers, dry over (MgSO$_4$), filter, and concentrate the filtrate to dryness in vacuo on a rotovapor at low bath temperature (30–35° C.) to afford 19.6 g (31%) crude amino-cyano-acetic acid ethyl ester which was used immediately in the next reaction.

Cool a solution of amino-cyano-acetic acid ethyl ester (19.0 g, 148 mmol) in CH$_2$C$_{12}$ (300 mL) to 0–5° C. under N$_2$. Add pyridine (12.0 mL, 148 mmol) followed by isobutyric anhydride (24.6 mL, 148 mmol). Allow the reaction solution to warm to rt overnight until complete by TLC (EtOAc). Wash the solution with aqueous 1N HCl, water, aq. sat'd NaHCO$_3$, then brine (150 mL each). Dry the organic layer over MgSO$_4$, filter, and concentrate the filtrate to dryness in vacuo on a rotovapor to a solid. Triturate the solid with Et$_2$O (500 mL), filter and dry (50° C. vacuum oven) to afford 22.0 g (75%) of the title compound: $^1$H NMR (300 MHz, DMSO-d$_6$) δ 9.05 (d, 1H, J=7.32 Hz), 5.67 (d, 1H, J=7.32 Hz), 4.25–4.13 (m, 2H), 2.46 (dq, 1H, J=6.95 Hz), 1.21 (t, 3H, J=6.95 Hz), 1.03 (d, 6H, J=6.95 Hz). $^{13}$C NMR (75 MHz, DMSO-d$_6$) δ 176.51, 164.13, 115.60, 62.33, 44.07, 33.29, 18.93, 18.86, 13.74. IR (CHCl$_3$) 3425, 3028, 2975, 2933, 2905, 2874, 1757, 1687,1492, 1370, 1284, 1189 cm$^{-1}$. HRMS (FAB+) M/z calculated for C$_9$H$_{15}$N$_2$O$_3$ (M+H) 199.1083 found 199.1075.

Example 453

Cyano-isobutyrylamino-acetic acid ethyl ester

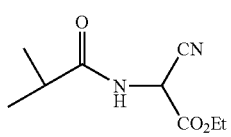

Combine ethyl cyanoglyoxylate-2-oxime (20.0 g, 141 mmol) and 5% Pt/C (2.0 g, 10% wt. load) in acetic acid (120 mL) and EtOAc (60 mL) and hydrogenate under 40 psi H$_2$ overnight until the reaction is complete by TLC (5:1/heptane:EtOAc, I$_2$ stain). Carefully filtered the spent catalyst using partial vacuum through glass fiber paper, and rinse with HOAc/EtOAc without allowing the cake to dry out. Concentrate the filtrate in vacuo on a rotovapor to an oil, leaving 25.5 g (96%) of crude amino-cyano-acetic acid ethyl ester as the HOAc salt. Partition a portion (13.0 g) of the HOAc salt between EtOAc (70 mL) and-water (35 mL). Stir the biphasic solution and add dropwise aqueous 5N NaOH (1 6.5 mL) to adjust the pH to 8.0–8.2. Separate the layers, and extract the aqueous layer with more EtOAc (3×25 mL). Combine the organic layer, dry (MgSO$_4$), filter, and concentrate the filtrate to dryness in vacuo on a rotovapor at low bath temperature (30–35° C.) to afford 5.68 g (65%) crude amino-cyano-acetic acid ethyl ester which was used immediately in the next reaction.

Cool a solution of crude amino-cyano-acetic acid ethyl ester (5.68 g, 44.3 mmol) in CH$_2$Cl$_2$ (60 mL) to 0–5° C. under N$_2$. Add pyridine (3.60 mL, 44.5 mmol), followed by isobutyric anhydride (7.40 mL, 44.6 mmol). Allow the reaction solution to warm to rt overnight (18 h) until complete by TLC (3:1/EtOAc:heptane, 12 stain, co-spot needed to distinguish between SM and impurity). Wash the solution with aqueous 1N HCl, water, aq. sat'd NaHCO$_3$, then brine (50 mL each). Dry the organic layer (MgSO$_4$), filter, and concentrate the filtrate to dryness in vacuo on a rotovapor to a solid. Triturate the solid with Et$_2$O (150 mL), filter and dry (50° C. vacuum oven) to afford 4.33 g (49%) of the title compound.

Example 455

5-Amino-2-isopropyl-thiazole-4-carboxylic acid ethyl ester

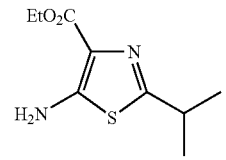

Stir cyano-isobutyrylamino-acetic acid ethyl ester (139 g, 701 mmol) mechanically stir as a slurry in toluene (1.4 L) at rt under N$_2$. Add lawesson's reagent (170 g, 420 mmol, 0.6 eq.) in portions and heat the thick slurry to 70° C. and stir for 12 hours until complete by TLC (2:1/heptane:THF). Cool the mixture and concentrate to dryness in vacuo on a rotovapor to obtain 353 g of thick yellow oil that was partially purified by silica gel plug (1 Kg silica gel 60, 1.5 vol. warm 2:1/THF:heptane as diluent, 2:1/heptane:THF as eluent). Combine the product containing filtrates and concentrate to dryness in vacuo on a rotovapor to obtain 194 g of crude solid. Dissolve the solid in EtOAc (400 mL) at 50–60° C. with stirring, then allow to cool gradually to rt. Precipitate the product and was cool to 0–5° C. with stirring for 30 minutes, isolate by suction filtration, rinse with cold EtOAc (2×50 mL), then dry in a vacuum oven at 50° C. to afford a first crop of 76.3 g (51%) of the title compound. Obtain a second crop of 17.6 g (12%)=from the filtrate after concentration in vacuo and silica gel chromatography (1 Kg silica gel 60, 2:1/heptane:THF). $^1$H NMR (300 MHz, DMSO-d$_6$) δ 7.23 (bs, 2H), 4.21 (q, 2H, J=6.95 Hz), 3.02 (dq, 1H, J=6.95 Hz), 1.27 (t, 3H, J=6.95 Hz), 1.22 (d, 6H, J=6.95 Hz). $^{13}$C NMR (75 MHz, DMSO-d$_6$) δ 163.72, 160.08, 156.20, 118.08, 58.99, 32.27, 22.35 (2), 14.46. IR (CHCl$_3$) 3483, 3347, 2975, 2933, 2868, 1668, 1582, 1530, 1494, 1464, 1409, 1382 cm$^{-1}$. HRMS (ES) M/z calculated for C$_9$H$_{14}$N$_2$O$_2$S 215.0854, found 215.0842.

Example 456

2-Isopropyl-5-(2-nitro-phenylamino)-thiazole-4-carboxylic acid ethyl ester

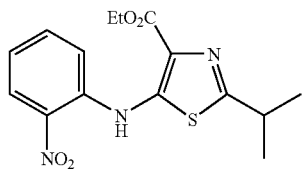

Combine a solution of 5-amino-2-isopropyl-thiazole-4-carboxylic acid ethyl ester (8.71 g, 40.6 mmol) and 2-fluoronitrobenzene (4.28 mL, 40.6 mmol) in DMSO (105 mL) and stir at rt under N$_2$ as LiOH (1.95 g, 81.4 mmol, 2.0 eq.) or LiOH monohydrate (2 eq) is added in one portion. The reaction turns dark. Heat the reaction mixture to 55° C. for 3 h until complete by HPLC (Zorbax SB C18 25 cm, 60:40/ACN:0.1% TFA in water, 233 nm, 1.0 mL/min). Cool to rt overnight, Cool the reaction to 0–5° C. with stirring as deionized water (315 mL) is added at such a rate to maintain the temperature below 20° C. Precipitate the product and the reaction color changes from brown to rust-orange color. Stir the slurry for 3–4 h at rt, filter by vacuum and rinse with minimal 3:1/H$_2$O: DMSO, dry in a vacuum oven at 60° C. to afford 12.4 g (91%) of the title compound as an orange solid: $^1$H NMR (300 MHz, DMSO-d$_6$) δ 11.52 (bs, 1H), 8.23 (d, 1H, J=8.05 Hz), 7.80 (m, 2H), 7.21 (m, 1H), 4.36 (q, 2H, J=7.32 Hz, 6.95 Hz), 3.23 (dq, 1H, J=6.95 Hz), 1.34 (m, 9H). $^{13}$C NMR (75 MHz, DMSO-d$_6$) δ 163.22, 161.85, 149.08, 136.99, 136.37, 136.10, 126.53, 126.48, 121.94, 117.05, 60.45, 32.47, 22.34(2), 14.24. IR (CHCl$_3$) 2976, 2932, 2867, 1709, 1677, 1611, 1580, 1550, 1512, 1415, 1340 cm$^{-1}$. HRMS (ES) M/z calculated for C$_{15}$H$_{17}$N$_3$O$_4$S 336.1018, found 336.1009.

Example 457

2 Isopropyl-5-(2-nitro-phenylamino)-thiazole-4-carboxylic acid amide

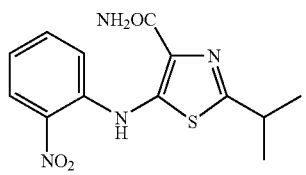

Stir 2-isopropyl-5-(2-nitro-phenylamino)-thiazole-4-carboxylic acid ethyl ester (68.6 g, 204 mmol) at rt under N$_2$ as a slurry in DMF (205 mL). Add formamide (32.4 mL, 816 mmol, 4.0 eq.) in one portion, and heat the thick red slurry to 100° C.; a dark red/purple solution is formed. Add dropwise over 20–30 min, 25% NaOMe in MeOH (32.6 mL, 143 mmol, 0.7 eq.) Increase the temperature 120° C. and stir the dark solution was stirred at 120° C. overnight until complete (<2% Me ester+SM) by HPLC (Zorbax SB C18 25 cm, 60:40/ACN:0.1% TFA in water, 233 nm, 1.0 mL/min). After cooling the reaction to rt, add aqueous 5% NH$_4$Cl (410 mL) at such a rate as to maintain the temperature below 35° C. with no external cooling. Precipitate the product, cool the slurry to 0–5° C., filter by vacuum filtration and dry in a vacuum oven at 60° C. to afford 52.7 g (84% yield) crude title compound as a purple solid that was used without further purification. An aqueous workup may result in bad emulsions/slow separations. $^1$H NMR (300 MHz, DMSO-d$_6$) δ 12.22 (bs, 1H), 8.21 (d, 1H, J=7.69 Hz), 7.78 (m, 2H), 7.59 (bs, 1H), 7.53 (bs, 1H), 7.15 (m, 1H), 3.23 (dq, 1H, J=6.95 Hz), 1.35 (d, 6H, J=6.95 Hz). $^{13}$C NMR (75 MHz, DMSO-d$_6$) δ 165.53, 161.44, 144.58, 137.12, 136.31, 135.72, 128.90, 126.58, 121.08, 116.28, 32.32, 22.35(2). IR (CHCl$_3$) 3520, 3400, 3004, 2967, 2925, 2866, 1658, 1611, 1578, 1513, 1427, 1342 cm$^{-1}$. HRMS(ES) M/z calculated for C$_{13}$H$_{14}$N$_4$O$_3$S$_1$ 329.0684, found 329.0667.

Example 458

2-Isopropyl-5-(2-nitro-phenylamino)-thiazole-4-carbonitrile

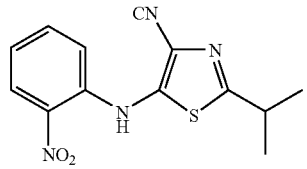

Combine 2-isopropyl-5-(2-nitro-phenylamino)-thiazole-4-carboxylic acid amide (47.5 g, 155 mmol) and 2-dichloroethane (475 mL) and stir at rt under N$_2$ as a dark solution. Pour POCl$_3$ (14.5 mL, 155 mmol) into the solution, and heat the reaction to reflux (80–83° C.) for 2–3 h until complete by HPLC (Zorbax SB C18 25 cm, 60:40/ACN:0.1% TFA in water, 233 nm, 1.0 L/min). Coolthe reaction to rt, cool further to 0–5° C. Adjust the pH to 8–9 by adding aqueous 2N NaOH (275 mL) at such a rate to maintain the temperature below 20° C. Separate the layers, extract the aqueous layer with CH$_2$Cl$_2$ (2×100 mL). Combine the organic layer, wash with brine (2×100 mL), dry (MgSO$_4$), filter, and concentrate the filtrate in vacuo to a dark oil/solid residue (40 g). Purify the crude product by silica gel chromatography (1200 g silica gel 60, CH$_2$Cl$_2$) to afford 29.4 g (66%) of the title compound as a red solid: $^1$H NMR (300 MHz, DMSO-d$_6$) δ 9.78 (bs, 1h), 8.15 (dd, 1H, J=6.95 Hz, 1.46 Hz), 7.67 (dt, 1H, J=7.32 Hz, 1.46 Hz), 7.26 (dd, 1H, J=7.32 Hz, 1.10 Hz), 7.15 (dt, 1H, J=6.95 Hz, 1.10 Hz), 3.26 (dq, 1H, J=6.95 Hz), 1.33 (d, 6H, J=6.95 Hz). $^{13}$C NMR (75 MHz, DMSO-d$_6$) δ 171.85, 150.83, 139.10, 136.22, 136.00, 126.05, 121.41, 118.64, 116.09, 113.73, 33.01, 22.07(2). IR (CHCl$_3$) 3311, 3021, 2970, 2928, 2868, 2223, 1613, 1583, 1518, 1492, 1448, 1403, 1341 cm$^{-1}$. HRMS (ES) M/z calculated for C$_{13}$H$_{12}$N$_4$O$_2$S 289.0759, found 289.0744.

Example 459

2-Isopropyl-4H-3-thia-1,4,9-triaza-benzo[f]azulen-10-ylamine hydrochloride

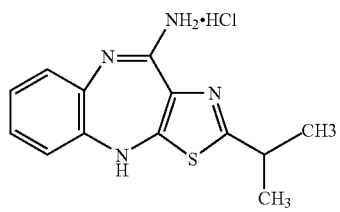

Combine 2-isopropyl-5-(2-nitro-phenylamino)-thiazole-4-carbonitrile (35.1 g, 122 mmol) and IPA (525 mL) stir under $N_2$ and heat to 60° C. to dissolve. Add a solution of $SnCl_2$ (70.0 g, 369 mmol, 3.0 eq.) in aqueous 5M HCl (525 mL) dropwise over 30 min. Heat the reaction mixture at reflux (80–85° C.) for 1 h until complete by HPLC (Zorbax SB C18 25 cm, 60:40/ACN:0.1% TFA in water, 233 nm, 1.0 mL/min). Cooling the reaction to 50° C. Remove most of the solvent in vacuo. Treat the aqueous solid residue (188 g) with IPA (500 mL) and heat to 60–70° C. for a few minutes to form a homogenous slurry. Cool the slurry to rt, then 0–5° C. for 1–2 h. Isolate the product by vacuum filtration and dry in a vacuum oven at 60° C. to afford 45.9 g (128%) of crude product that was heavily contaminated with residual tin. Suspent the crude product in aqueous 1N HCl (2.25 L) and heat to reflux (95° C.) for 1 h, during which time most of the solids dissolve. Cool to rt, isolate the product by vacuum filtration, rinse with aqueous 1N HCl, and dry in a vacuum oven at 70° C. to afford 34.5 g (97%) of the title compound as a yellow/orange solid. Analytical analysis: Sn (9.0%), $H_2O$ (1.2%). $^1H$ NMR (300 MHz, DMSO-$d_6$) δ 10.96 (bs, 1H), 10.15 (bs, 1H), 8.94 (bs, 2H), 7.10–6.95 (m, 2H), 6.93–6.82 (m, 2H), 3.10 (dq, 1H, J=6.95 Hz), 1.28 (s, 3H), 1.26 (s, 3H). $^{13}C$ NMR (75 MHz, DMSO-$d_6$) δ 164.42, 159.24, 158.94, 137.01, 128.58, 127.11, 125.09, 122.87, 120.14, 119.23, 32.41, 21.98(2). IR(KBr) 3301, 3249, 2964, 1653, 1614, 1553, 1509 $cm^{-1}$. HRMS (ES) M/z calculated for $C_{13}H_{15}N_4S$ 259.1017 ($M^+$–Cl), found 259.1010.

Example 460

(S)-2-Methyl-10-(3-phenethyl-piperazin-1-yl)-4H-3-thia-1,4,9-triaza-benzo[f]azulene dihydrochloride hemihydrate

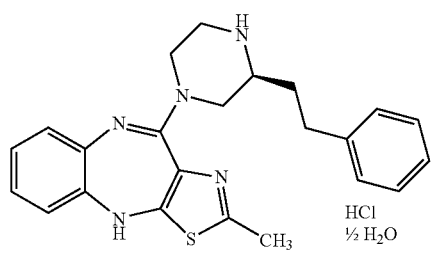

Combine 2-methyl-4H-3-thia-1,4,9-triaza-benzo[f]azulen-10-ylamine(0.712 g, 3.09 mmol)(preparation described in Eur. Pat. Appl. EP 354781(1990) and (S)-2-phenethyl-piperazine (0.588 g, 3.09 mmol) in NMP (6.0 mL) and heat at 200° C. for 3 hours. Cool to ambient temperature and dilute with water (75 mL). Extract with ethyl acetate to give 1.11 g. of the crude product. Silica gel chromatography, eluting with methylene chloride: 2N $NH_3$/methanol (100:5), gives 0.756 g of the title compound as the free base. The dihydrochloride salt precipitates in ethyl acetate as a tan solid: mp 230° C.; mass spectrum (ion spray): m/z=404 (M+1); Analysis for $C_{23}H_{27}Cl_2N_5S(0.5\ H_2O)$: calcd: C, 56.90; H, 5.81; N, 14.43; found: C, 56.61; H, 5.63; N, 14.21.

Example 461

(S)-2-Methyl-10-(4-methyl-3-phenethyl-piperazin-1-yl)-4H-3-thia-1,4,9-triaza-benzo[f]azulene dihydrochloride hemihydrate

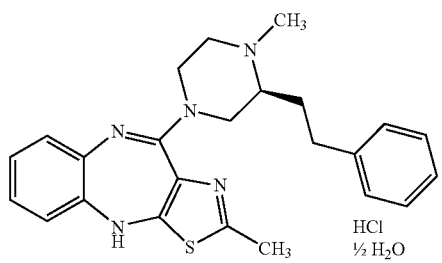

Combine (S)-2-methyl-10-(3-phenethyl-piperazin-1-yl)-4H-3-thia-1,4,9-triaza-benzo[f]azulene (0.5 g, 1.24 mmol) and 37% Formaldehyde solution (0.1 mL, 1.36 mmol)in 1,2-dichloroethane (25 mL). Stir for 10 minutes and add sodium triacetoxy borohydride (0.394, 1.86 mmol). Stir an additional 30 minutes and then pour solution onto saturated Sodium bicarbonate solution. Extract with methylene chloride to give 0.52 g of the crude product. Silica gel chromatography, eluting with methylene chloride: 2N $NH_3$/methanol (100:3), gives 0.296 g of the title compound as the free base. The dihydrochloride salt precipitates in ethyl acetate as a yellow solid: mp 220° C.; mass spectrum (ion spray): m/z=418 (M+1); Analysis for $C_{24}H_{29}Cl_2N_5S(0.5\ H_2O)$: calcd: C, 57.71; H, 6.05; N, 14.02; found: C, 57.81; H, 6.08; N, 13.81.

Example 462

(S)-10-(3-Benzyl-piperazin-1-yl-2-methyl-4H-3-thia-1,4,9-triaza-benzo[f]azulene

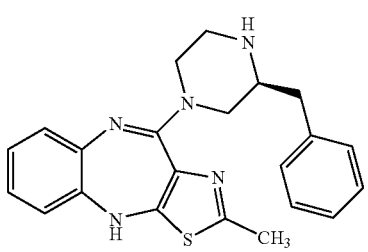

By a similar method to Example 460, using 2-methyl-4H-3-thia-1,4,9-triaza-benzo[f]azulen-10-ylamine(0.703 g, 3.0 mmol) and (S)-2-benzyl-piperazine (0.538 g, 3.0 mmol)

give 0.410 g of the title compound as a yellow solid: mp 250–252° C.; mass spectrum (ion spray): m/z=390 (M+1); Analysis for $C_{22}H_{23}N_5S(0.6\ H_2O)$: calcd: C, 66.01; H, 6.09; N, 17.49; found: C, 65.94; H, 5.66; N, 17.8 1.

Example 463

(S)-10-[3-(2-Methoxy-benzyl)-piperazin-1-yl]-2-methyl-4H-3-thia-1,4,9-triaza-benzo[f]azulene

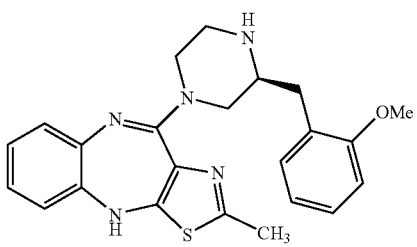

By a similar method to the method of Example 460, using 2-methyl-4H-3-thia-1,4,9-triaza-benzo[f]azulen-10-ylamine (0.687 g, 2.98 mmol) and (S)-2-(2-methoxy-benzyl)-piperazine (0.615 g, 2.98 mmol) gives 0.437 g of the title compound as a yellow solid: mass spectrum (ion spray): m/z=420 (M+1); Analysis for $C_{23}H_{25}N_5OS(0.5\ H_2O)$: calcd: C, 64.46; H, 6.12; N, 16.34; found: C, 64.20; H, 5.77; N, 16.14.

Example 464

(S)-10-{3-[2-(4-Methoxy-phenyl)-ethyl]-piperazin-1-yl}-2-methyl-4H-3-thia-1,4,9-triaza-benzo[f]azulene

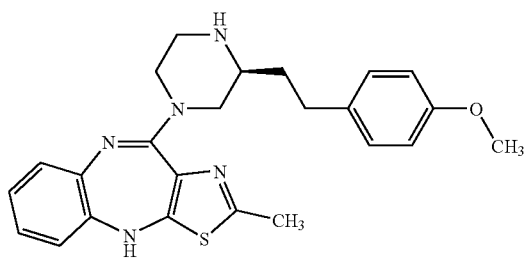

Combine (S)-2-[2-(4-methoxy-phenyl)-ethyl]-piperazine (180 mg, 0.82 mmol), 2-methyl-4H-3-thia-1,4,9-triaza-benzo[f]azulen-10-ylamine (188 mg, 0.82 mmol), 1-methyl-2-pyrrolidinone (5 mL). Heat at 195° C. After 3.75 h, cool to ambient temperature and stir 18 h. Combine with another 2.30 mmol reaction executed under same conditions. Dilute with ethyl acetate and water. Extract with ethyl acetate. Wash the extracts with water and brine, dry over sodium sulfate, filter and concentrate the filtrate. Purify by silica gel chromatography using 2N ammonia in methanol-methylene chloride (2.5%–4%) as the eluent to give 388 mg (29%) of the title compound: mass spectrum (ion spray): m/z=434 (M+1), 432 (M−1). HR-MS calculated for $C_{24}H_{28}N_5OS$: 434.2015. Found 434.201 HPLC: Symmetry $C_{18}$ column (3.5 μm, 4.6×50 mm). Gradient 5% to 90% solvent B in 7 min. Solvent A was 0.1% (v/v) TFA in water and solvent B was acetonitrile. Retention time 5.4 min; 100% pure.

Example 465

(S)-10-{3-[2-(4-Methoxy-phenyl)-ethyl]-4-methyl-piperazin-1-yl}-2-methyl-4H-3-thia-1,4,9-triaza-benzo[f]azulene dihydrochloride

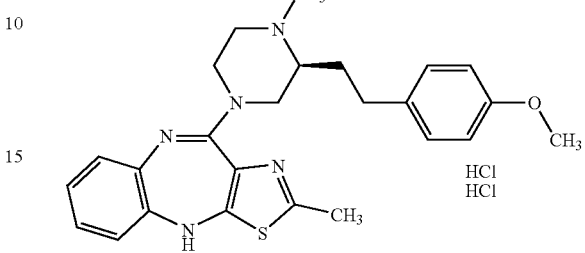

Add formaldehyde (86 μL, 1.09 mmol, 37% in water) to a solution of (S)-10-{3-[2-(4-methoxy-phenyl)-ethyl]-piperazin-1-yl}-2-methyl-4H-3-thia-1,4,9-triaza-benzo[f]azulene (430 mg, 0.99 mmol) in methylene chloride (20 mL). Stir 15 min at ambient temperature. Add sodium triacetoxyborohydride (315 mg, 1.49 mmol) and stir 1 h at ambient temperature. Dilute with saturated sodium bicarbonate solution and extract with methylene chloride. Dry the extracts with sodium sulfate, filter and concentrate the filtrate. Purify by silica gel chromatography using 2N ammonia in methanol-methylene chloride (1%–3%) as the eluent to give 400 mg (90%) of the free base of the title compound. Crystallize the dihydrochloride salt from ethyl acetate and ethanol to give the title compound: mass spectrum (ion spray): m/z=448 (M+1), 446 (M−1). Analysis calculated for $C_{25}H_{31}Cl_2N_5OS.0.3H_2O$: C, 57.09; H, 6.06; N, 13.32. Found: C, 56.98; H, 6.17; N, 12.93. HR-MS calculated for $C_{25}H_{30}N_5OS$: 448.2171. Found 448.2177. HPLC: Symmetry $C_{18}$ column (3.5 μm, 4.6×50 mm). Gradient 5% to 90% solvent B in 7 min. Solvent A was 0.1% (v/v) TFA in water and solvent B was acetonitrile. Retention time 5.4 min; 100% pure.

Example 466

(S)-10-{3-[2-(4-Fluoro-phenyl)-ethyl]-piperazin-1-yl}-2-methyl-4H-3-thia-1,4,9-triaza-benzo[f]azulene

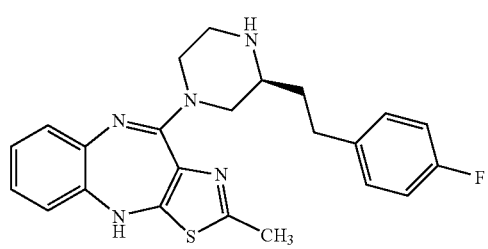

By a similar method to the method of Example 460, using 2-methyl4H-3-thia-1,4,9-triaza-benzo[f]azulen-10-ylamine (1.21 g, 5.25 mmol) and (S)-2-[2-(4-fluoro-phenyl)-ethyl]-piperazine (1.09 g, 5.25 mmol) to give 0.848 g of the title compound as a tan solid: mass spectrum (ion spray): m/z=422 (M+1); Analysis for $C_{23}H_{24}FN_5S(0.3\ H_2O)$: calcd: C, 64.70; H, 5.81; N, 16.40; found: C, 64.97; H, 5.86; N, 16.15.

Example 467

(S)-10-{3-[2-(3-Fluoro-phenyl)-ethyl]-piperazin-1-yl}-2-methyl-4H-3-thia-1,4,9-triaza-benzo[f]azulene

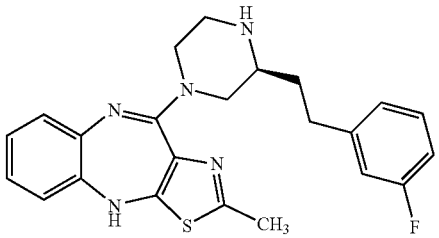

By using a similar method to the method of Example 460, using 2-methyl-4H-3-thia-1,4,9-triaza-benzo[f]azulen-10-ylamine(1.25 g, 5.42 mmol) and (S)-2-[2-(3-fluoro-phenyl)-ethyl]-piperazine (1.13 g, 5.42 mmol) gives 1.06 g of the title compound as a tan solid: mass spectrum (ion spray): m/z=422 (M+1); Analysis for $C_{23}H_{24}FN_5S(0.2\ H_2O)$: calcd: C, 64.98; H, 5.78; N, 16.47; found: C, 65.18; H, 5.91; N, 16.17.

Example 468

(S)-2-Isopropyl-10-(3-phenethyl-piperazin-1-yl)4H-3-thia-1,4,9-triaza-benzo[f]azulene

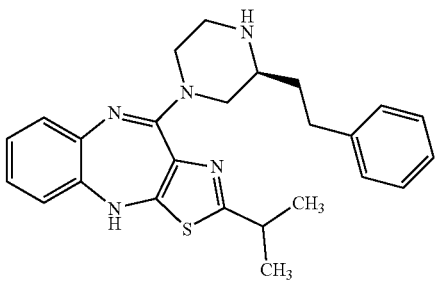

By using a similar method of Example 460, using 2-isopropyl-4H-3-thia-1,4,9-triaza-benzo[f]azulen-10-ylamine (1.47 g, 5.69 mmol) and (S)-2-phenethyl-piperazine (1.08 g, 5.69 mmol) to give 1.04 g of the title compound as a yellow solid: mass spectrum (ion spray): m/z=432 (M+1); Analysis for $C_{25}H_{29}N_5S$: calcd: C, 69.57; H, 6.77; N, 16.22; found: C, 69.40; H, 6.90; N, 15.98.

Example 469

(S)-2-Isopropyl-10-{3-[2-(4-methoxy-phenyl)-ethyl]-piperazin-1-yl}-4H-3-thia-1,4,9-triaza-benzo[f]azulene

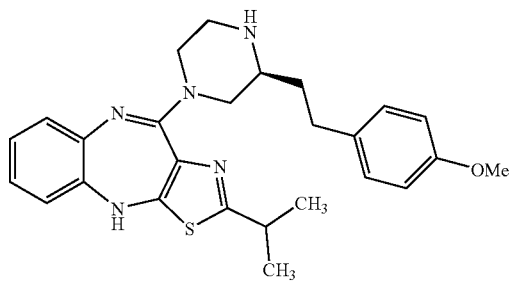

By using a similar method of the method of Example 460, using 2-isopropyl-4H-3-thia-1,4,9-triaza-benzo[f]azulen-10-ylamine(1.48 g, 5.7 mmol) and (S)-2-[2-(4-methoxy-phenyl)-ethyl]-piperazine (1.26 g, 5.7 mmol) to give 1.01 g of the title compound as a yellow solid: mass spectrum (ion spray): m/z=462 (M+1); Analysis for $C_{26}H_{31}N_5OS(0.3\ H_2O)$: calcd: C, 66.87; H, 6.82; N, 15.00; found: C, 66.58; H, 6.35; N, 14.96.

Example 470

(S)-10-(3-Benzyl-piperazin-1-yl)-2-isopropyl-4H-3-thia-1,4,9-triaza-benzo[f]azulene

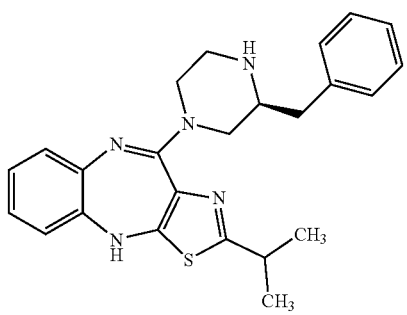

By using a similar method of the method of Example 460, using 2-isopropyl-4H-3-thia-1,4,9-triaza-benzo[f]azulen-10-ylamine(1.44 g, 5.5 mmol) and (S)-2-benzyl-piperazine (0.983 g, 5.5 mmol) to give 0.580 g of the title compound as a yellow solid: mass spectrum (ion spray): m/z=418 (M+1); Analysis for $C_{24}H_{27}N_5S(0.2\ H_2O)$: calcd: C, 68.44; H, 6.56; N, 16.63; found: C, 68.63; H, 6.43; N, 16.74.

Example 471

(S)-10-{3-[2-(3-Fluoro-phenyl)-ethyl]-piperazin-1-yl}-2-isopropyl-4H-3-thia-1,4,9-triaza-benzo[f]azulene

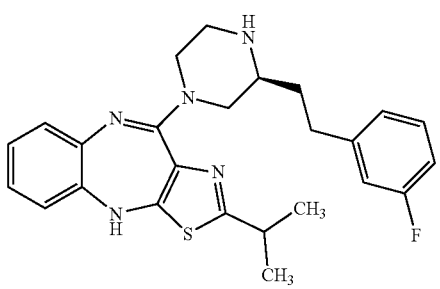

By using a method similar to the method of Example 460, using 2-isopropyl-4H-3-thia-1,4,9-triaza-benzo[f]azulen-10-ylamine (0.566 g, 2.19 mmol) and (S)-2-[2-(3-fluoro-phenyl)-ethyl]-piperazine (0.457 g, 2.19 mmol) to give 0.539 g of the title compound as a solid: mass spectrum (ion spray): m/z=450 (M+1); Analysis for $C_{25}H_{28}FN_5S(0.2\ H_2O)$: calcd: C, 66.26; H, 6.32; N, 15.45; found: C, 65.96; H, 6.11; N, 15.31.

Example 472

(S)-10-{3-[2-(4-Fluoro-phenyl)-ethyl]-piperazin-1-yl}-2-isopropyl-4H-3-thia-1,4,9-triaza-benzo[f]azulene

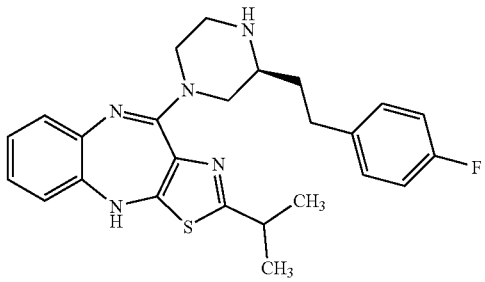

Stir 2-isopropyl-4,9-dihydro-3-thia-1,4,9-triaza-benzo[f]azulene-10-thione (0.551 g, 2.0 mmol) in dichloromethane (10.0 mL) and chilled in an ice bath while adding methyl trifluoromethane sulfonate (0.27 mL, 2.4 mmol). Allow this solution to stir at ambient temperature for 16 hours. Evaporate the solvent to a gray solid. Dissolve this solid and (S)-2-[2-(4-fluoro-phenyl)-ethyl]-piperazine (0.417 g, 2.0 mmol) in pyridine (8.0 mL) and heat at 115° C. for 23 hours. After evaporation of the pyridine, silica gel chromatography, eluting with methylene chloride: 2N NH$_3$/methanol (100:5), gives 0.354 g of the title compound as a yellow solid: mass spectrum (ion spray): m/z=450 (M+1); Analysis for $C_{25}H_{28}FN_5S$(0.2 H$_2$O): calcd: C, 66.26; H, 6.32; N, 15.45; found: C, 66.01; H, 6.15; N, 15.25.

Example 473

(S)-10-(3-Benzyl-4-methyl-piperazin-1-yl)-2-methyl-4H-3-thia-1,4,9-triaza-benzo[f]azulene dihydrochloride

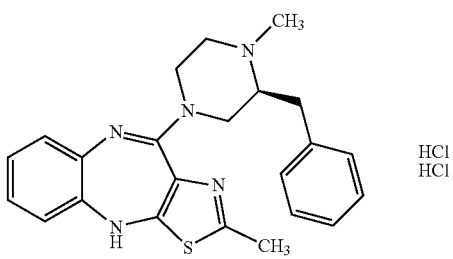

In a manner such as that described in Example 461, (S)-10-(3-benzyl-piperazin-1-yl)-2-methyl-4H-3-thia-1,4,9-triaza-benzo[f]azulene (0.355 g, 0.91 mmol) gives 0.407 g of the title compound as a yellow solid: mp 240° C.; mass spectrum (ion spray): m/z=404 (M+1); Analysis for $C_{23}H_{27}Cl_2N_5S$(0.5 H$_2$O): calcd: C, 56.90; H, 5.81; N, 14.43; found: C, 56.74; H, 5.85; N, 14.23.

Example 474

(S)-10-[3-(2-Methoxy-benzyl)-4-methyl-piperazin-1-yl]-2-methyl-4H-3-thia-1,4,9-triaza-benzo[f]azulene dihydrochloride

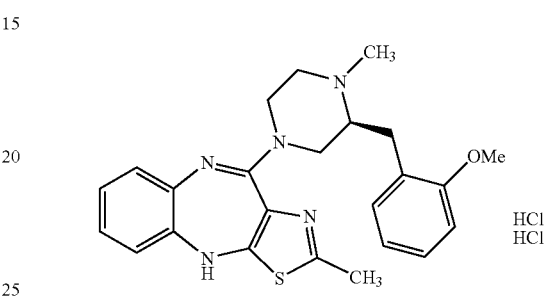

In a manner such as that described in Example 461, using (S)-10-[3-(2-methoxy-benzyl)-piperazin-1-yl]-2-methyl-4H-3-thia-1,4,9-triaza-benzo[f]azulene (0.388 g, 0.92 mmol) gives 0.452 g of the title compound as an orange solid: mp 185° C.; mass spectrum (ion spray): m/z=434 (M+1); Analysis for $C_{24}H_{29}Cl_2N_5OS$(2.1 H$_2$O): calcd: C, 52.96; H, 6.15; N, 12.87; found: C, 52.84; H, 5.75; N, 12.49.

Example 475

(S)-2-Isopropyl-10-(4-methyl-3-phenethyl-piperazin-1-yl)-4H-3-thia-1,4,9-triaza-benzo[f]azulene dihydrochloride

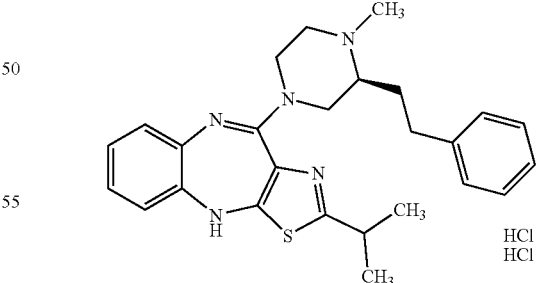
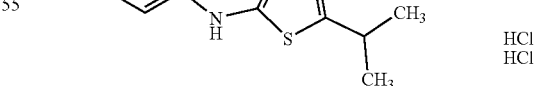

In a manner such as that described in Example 461, using (S)-2-isopropyl-10-(3-phenethyl-piperazin-1-yl)-4H-3-thia-1,4,9-triaza-benzo[f]azulene (0.950 g, 2.2 mmol) gives 0.686 g of the title compound as an orange solid: mp 210° C.; mass spectrum (ion spray): m/z=446 (M+1); Analysis for $C_{26}H_{33}Cl_2N_5S$(1.2 H$_2$O): calcd: C, 57.81; H, 6.61; N, 12.97; found: C, 58.07; H, 6.55; N, 12.56.

Example 476

(S)-2-Isopropyl-10-{3-[2-(4-methoxy-phenyl)-ethyl]-4-methyl-piperazin-1-yl}-4H-3-thia-1,4,9-triaza-benzo[f]azulene dihydrochloride

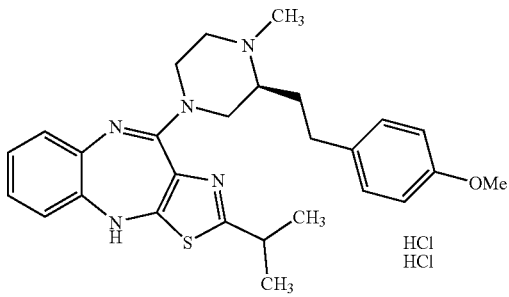

In a manner such as that described in Example 461, using (S)-2-isopropyl-10-{3-[2-(4-methoxy-phenyl)-ethyl]-piperazin-1-yl}-4H-3-thia-1,4,9-triaza-benzo[f]azulene (0.932 g, 2.0 mmol) gives 0.770 g of the title compound as a yellow solid: mp 190° C.; mass spectrum (ion spray): m/z=476 (M+1); Analysis for $C_{27}H_{35}Cl_2N_5OS(0.2\ H_2O)$: calcd: C, 58.73; H, 6.46; N, 12.68; found: C, 58.44; H, 6.01; N, 12.58.

Example 477

(S)-10-(3-Benzyl-4-methyl-piperazin-1-yl)-2-isopropyl-4H-3-thia-1,4,9-triaza-benzo[f]azulene dihydrochloride

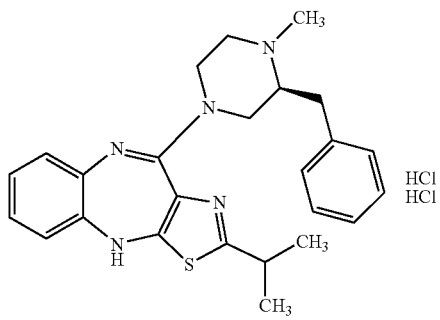

In a manner such as that described in Example 461, using (S)-10-(3-benzyl-piperazin-1-yl)-2-isopropyl-4H-3-thia-1,4,9-triaza-benzo[f]azulene (0.517 g, 1.23 mmol) gives 0.491 g of the title compound as a yellow solid: mp 235° C.; mass spectrum (ion spray): m/z=432 (M+1); Analysis for $C_{25}H_{31}Cl_2N_5S(1.0\ H_2O)$: calcd: C, 57.46; H, 6.37; N, 13.40; found: C, 57.18; H, 5.80; N, 13.39.

Example 478

(S)-10-{3-[2-(4-Fluoro-phenyl)-ethyl]-4-methyl-piperazin-1-yl}-2-methyl-4H-3-thia-1,4,9-triaza-benzo[f]azulene dihydrochloride

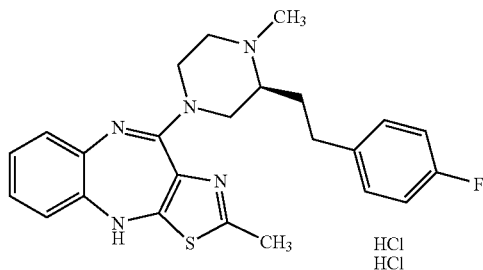

In a manner such as that described in Example 461, using (S)-10-{3-[2-(4-fluoro-phenyl)-ethyl]-piperazin-1-yl}-2-methyl-4H-3-thia-1,4,9-triaza-benzo[f]azulene (0.776 g, 1.84 mmol) gives 0.694 g of the title compound as a yellow solid: mp 230° C.; mass spectrum (ion spray): m/z=436 (M+1); Analysis for $C_{24}H_{28}Cl_2FN_5S(0.7\ H_2O)$: calcd. C, 55.32; H, 5.69; N, 13.44; found: C, 55.20; H, 5.63; N, 13.36.

Example 479

(S)-10-{3-[2-(3-Fluoro-phenyl)-ethyl]-4-methyl-piperazin-1-yl}-2-methyl-4H-3-thia-1,4,9-triaza-benzo[f]azulene dihydrochloride

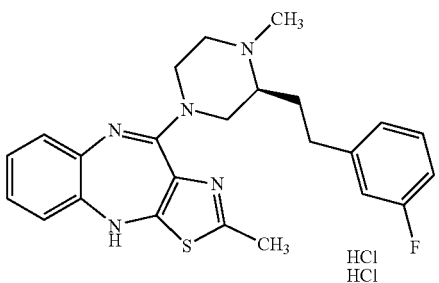

In a manner such as that described in Example 461, using (S)-10-{3-[2-(3-fluoro-phenyl)-ethyl]-piperazin-1-yl}-2-methyl4H-3-thia-1,4,9-triaza-benzo[f]azulene (0.951 g, 2.25 mmol) gives 0.841 g of the title compound as a yellow solid: mp 230° C.; mass spectrum (ion spray): m/z=436 (M+1); Analysis for $C_{24}H_{28}Cl_2FN_5S(0.5\ H_2O)$: calcd C, 55.70; H, 5.65; N, 13.53; found: C, 55.94; H, 5.65; N, 13.37.

Example 480

(S)-10-{3-[2-(3-Fluoro-phenyl)-ethyl]-4-methyl-piperazin-1-yl}-2-isopropyl-4H-3-thia-1,4,9-triaza-benzo[f]azulene dihydrochloride

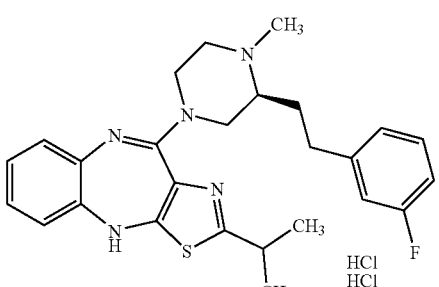

In a manner such as that described in Example 461, using (S)-10-{3-[2-(3-fluoro-phenyl)-ethyl]-piperazin-1-yl}-2-isopropyl-4H-3-thia-1,4,9-triaza-benzo[f]azulene (0.4301 g, 0.95 mmol) gives 0.440 g of the title compound as an orange solid: mp 180° C.; mass spectrum (ion spray): m/z=464 (M+1).

Example 481

(S)-10-{3-[2-(4-Fluoro-phenyl)-ethyl]-4-methyl-piperazin-1-yl}-2-isopropyl-4H-3-thia-1,4,9-triaza-benzo[f]azulene dihydrochloride

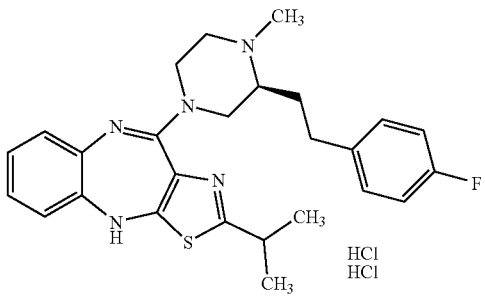

In a manner such as that described in Example 461, using (S)-10-{3-[2-(4-fluoro-phenyl)-ethyl]-piperazin-1-yl}-2-isopropyl-4H-3-thia-1,4,9-triaza-benzo[f]azulene (0.316 g, 0.7 mmol) gives 0.338 g of the title compound as an orange solid: mp 228° C.; mass spectrum (ion spray): m/z=464 (M+1); Analysis for $C_{26}H_{32}Cl_2FN_5S(0.6\ H_2O)$: calcd: C, 57.05; H, 6.11; N, 12.80; found: C, 56.72; H, 5.73; N, 12.54.

Example 482

Pentanoic acid (2,4-dioxo-2,3,4,5-tetrahydro-1H-benzo[b][1,4]diazepin-3-yl)-amide

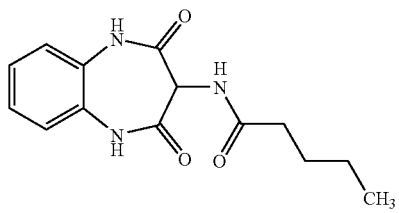

Add valeryl chloride (3.92 mL, 33.0 mmol) dropwise to a solution of 3-Amino-1,5-dihydro-benzo[b][1,4]diazepine-2,4-dione (5.74 g, 30.0 mmol) and triethylamine (4.60 mL, 33.0 mmol) in anhydrous dimethylformamide (123 mL) and stir. After 6 hours, concentrate under reduced pressure to a residue and reconstitute the residue in a solution of isopropanol:chloroform (1:3, 500 mL). Stir overnight to give a solid and isolate the solid by suction filtration, washing the solid with dichloromethane. Vacuum dry the solid at ambient temperature 2 hours to afford the title compound. Wash the filtrate with a saturated aqueous solution of sodium bicarbonate (2×200 mL), and filter the extraction mixture to remove salt formed in the wash. Separate the organic phase and wash it with saturated aqueous sodium chloride (150 mL). Back extract the bicarbonate aqueous phase with dichloromethane. Combine all organics, and dry (sodium sulfate), filter, and concentrate under reduced pressure to a residue. Triturate the residue in diethyl ether, filter the resulting solid, and wash it with diethyl ether; repeat 2×. Dry the solid at ambient temperature under vacuum to give the title compound: mass spectrum (APCI, m/e): 276 (M+1); $^1$H NMR (300 MHz, DMSO-$d_6$): 10.68 (s, 2H), 8.23 (d, 1H, J=7.5 Hz), 7.20 (m, 4H), 4.71 (d, 1H, J=7.5 Hz), 2.25 (t, 2H, J=7.5 Hz), 1.43 (m, 2H), 1.25 (m, 2H), 0.83 (t, 3H, J=7.5 Hz).

Example 483

2-Butyl-4,9-dihydro-3-thia-1,4,9-triaza-benzo[f]azulene-10-thione

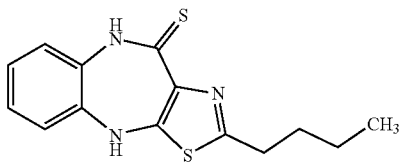

Combine pentanoic acid (2,4-dioxo-2,3,4,5-tetrahydro-1H-benzo[b][1,4]diazepin-3-yl)-amide (4.13 g, 15.0 mmol) and Lawesson's reagent (9.10 g, 22.5 mmol) in anhydrous dichloroethane (250 mL), heat to 85° C., and stir. After 16 hours, cool to ambient temperature, collect the reaction solid by suction filtration, and dry the solid at ambient temperature under vacuum to give the title compound: mass spectrum (APCI, m/e): 290 (M+1); $^1$H NMR (300 MHz, DMSO-$d_6$) 10.95 (s, 1H), 9.01 (s, 1H), 6.93 (m, 3H), 6.71 (d, 1H, J=7.5 Hz), 2.68 (t, 2H, J=7.5 Hz), 1.53 (m, 2H), 1.30 (m, 2H), 0.85 (t, 3H, J=7.5 Hz).

Example 484

(S)-2-Butyl-10-(3-phenethyl-piperazin-1-yl)-4H-3-thia-1,4,9-triaza-benzo[f]azulene

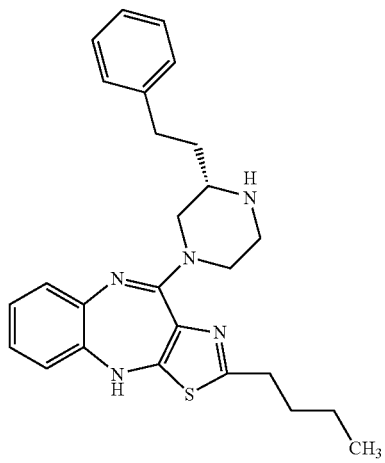

Add methyl trifluoromethanesulfonate (0.850 mL, 7.51 mmol) to a 0° C. solution of 2-Butyl-4,9-dihydro-3-thia-1,4,9-triaza-benzo[f]azulene-10-thione (1.45 g, 5.01 mmol) in anhydrous dichloromethane. Rinse solids into reaction with dichloromethane and stir allowing reaction to slowly reach ambient temperature. After an overnight period, concentrate under reduced pressure to afford crude methylated intermediate. Take 1.06 g of this intermediates (2.0 mmol), and combine the intermediate and 2-(S)-Phenethyl-piperazine (0.38 g, 2.0 mmol), with anhydrous pyridine, heat to 100° C. and stir. After an overnight period, cool to ambient temperature and concentrate under reduced pressure to an oil (2.16 g), followed by two chromatographic purifications, eluting with a gradient of a 8% solution of 2M ammonia in methanol, in dichloromethane (0–100% in dichloromethane), gives the title compound (0.078 g). Mass spectrum (APCI+, m/e): 446 (M+1); $^1$H NMR (300 MHz, DMSO-d$_6$), δ (ppm): 7.79 (s, 1H), 7.31–7.10 (m, 5H), 6.90–6.74 (m, 3H), 6.71–6.64 (m, 1H), 4.14–3.92 (br. m, 1H), 3.44–3.22 (m, 1H), 2.93–2.52 (m, 10H), 1.65–1.49 (m, 4H), 1.36–1.20 (m, 2H, J=7.1 Hz), 0.82 (t, 3H, J=7.1 Hz).

Example 485

(S)-2-Butyl-10-(3-phenethyl-piperazin-1-yl)-4H-3-thia-1,4,9-triaza-benzo[f]azulene dihydrochloride

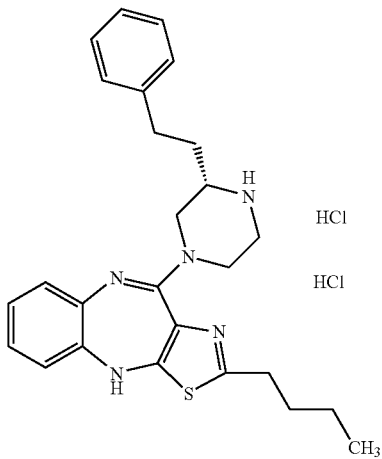

Add a solution of acetyl chloride (0.0601 mL, 0.842 mmol) in absolute ethanol at ambient temperature to (S)-2-Butyl-10-(3-phenethyl-piperazin-1-yl)-4H-3-thia-1,4,9-triaza-benzo[f]azulene (0.075 g, 0.17 mmol) in absolute ethanol, with added drops of methanol to solubilize the freebase, stir and concentrate under reduced pressure to give the title compound (0.078 g): Mass spectrum (ES+, m/e): 446 (M+1−2HCl); exact mass spectrum (ES+, m/e, C$_{26}$H$_{31}$N$_5$S.2HCl): calc. 446.2378 (M+1−2HCl), found 446.2397.

Example 486

(S)-2-Butyl-10-(4-methyl-3-phenethyl-piperazin-1-yl)-4H-3-thia-1,4,9-triaza-benzo[f]azulene

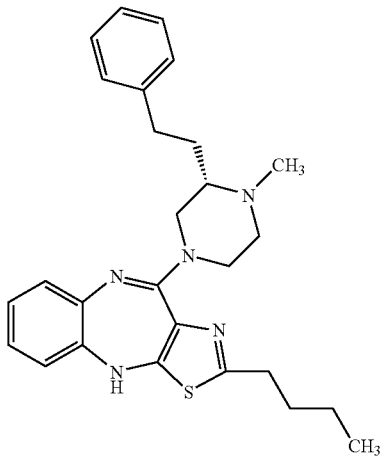

Add sodium triacetoxyborohydride and aqueous formaldehyde (37%w/w, to a solution of (S)-2-Butyl-10-(3-phenethyl-piperazin-1-yl)-4H-3-thia-1,4,9-triaza-benzo[f]azulene (0.50 g, 1.1 mmol) in dichloroethane (12 mL) and stir. After 5 hours, dilute with a saturated aqueous solution of sodium bicarbonate, and separate the layers. Extract the aqueous layer with dichloromethane (3×), combine organics, and dry (sodium sulfate), filter, and concentrate under reduced pressure to an oil (0.24 g). Purify the oil by flash chromatography, eluting with a gradient of a 5% solution of 2M ammonia in methanol, in dichloromethane (0–100% over 30 minutes), and then with a 5% solution of 2M ammonia in methanol, in dichloromethane to give the title compound (0.19 g): Mass spectrum (APCI+, m/e): 460 (M+1); $^1$H NMR (300 MHz, CDCl$_3$), δ (ppm): 7.39–7.11 (m, 5H), 7.11–6.95 (m, 2H), 6.94–6.81 (m, 1H), 6.69–6.57 (m, 1H), 5.01 (s, 1H), 4.40–3.93 (br. m, 1H), 3.34–3.16 (m, 1H), 3.08–2.92 (m, 1H), 2.93–2.40 (m, 7H), 2.40–2.23 (m, 4H), 2.06–1.51 (m, 4H), 1.38 (d, 2H, J=7.1 Hz), 0.90 (t, 3H, J=7.1 Hz).

Example 487

(S)-2-Butyl-10-(4-methyl-3-phenethyl-piperazin-1-yl)-4H-3-thia-1,4,9-triaza-benzo[f]azulene dihydrochloride

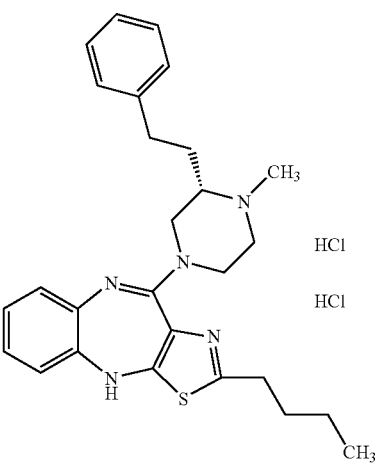

Add a solution of acetyl chloride (0.15 mL, 2.1 mmol) in absolute ethanol at ambient temperature to (S)-2-Butyl-10-(4-methyl-3-phenethyl-piperazin-1-yl)-4H-3-thia-1,4,9-triaza-benzo[f]azulene (0.19 g, 0.41 mmol) in absolute ethanol, with added drops of methanol to solubilize the freebase, and concentrate under reduced pressure gives the title compound (0.18 g). Mass spectrum (APCI+, m/e): 460 (M+1−2HCl); exact mass spectrum (ES+, m/e, C$_{27}$H$_{33}$N$_5$S.2HCl): calc. 460.2535 (M+1−2HCl), found 460.2556.

Example 488

Cyclopentanecarboxylic acid (2,4-Dioxo-2,3,4,5-tetrahydro-1H-benzo[b][1,4]diazapin-3-yl)-amide

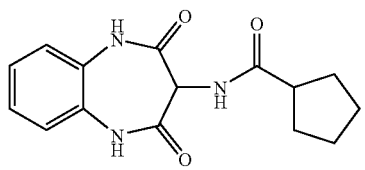

Combine 3-amino-1H-1,5-benzodiazepine-2,4-(3H, 5H)-dione (7.0 g, 36.6 mmol) and triethyl amine (4.07 g, 40.3 mmol) in 120 mL DMF and add dropwise cyclopentanecarbonyl chloride (5.34 g, 40.3 mmol) at RT. After stirring overnight, remove DMF under reduced pressure, suspend the residue in a mixed solvent (CHCl$_3$/i-PrOH=3/1, 400 mL). Collect an off-white solid via suction filtration to give the title compound. Wash the filtrate with NaHCO$_3$ (sat.2× 100 mL) and dry with Na$_2$SO$_4$. Concentrate the the solvent to give second crop of title compound, total 9.13 g, yield 87%; $^1$H NMR (300 MHz, DMSO-d$_6$): 10.70 (s, 2H), 8.11 (d, 1H, J=7.8 Hz), 7.24–7.15 (m, 4H), 4.73 (d, 1H, J=7.5 Hz), 2.96–2.87 (m, 1H), 1.74–1.45 (m, 8H).

Example 489

2-cyclopentyl-4,9-dihydro-3-thia-1,4,9-triaza-benzo[f]azulene-10-thione

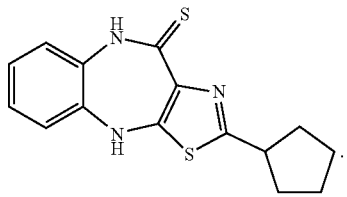

Combine cyclopentanecarboxylic acid (2,4-Dioxo-2,3,4,5-tetrahydro-1H-benzo[b][1,4]diazapin-3-yl)-amide (1.90 g, 6.6 mmol) and Lawesson's reagent (4.01 g, 9.9 mmol) in 120 mL 1,2-dichloroethane and heat to reflux under N$_2$. Cool the reaction to RT, after 4 hour, collect 1.56 g orange solid via suction filtration, yield 78%. $^1$H NMR (400 MHz, DMSO-d$_6$): 10.96 (s, 1H), 9.05 (s, 1H), 7.00–6.89 (m, 3H), 6.78–6.76 (m, 1H), 3.21–3.10 (m, 1H), 2.00–1.90 (m, 2H), 1.7–1.55 (m, 6H).

Example 490

2-Cyclopentyl-10-(4-methyl-piperazin-1-yl)-4H-3-thia-1,4,9-triaza-benzo[f]azulene

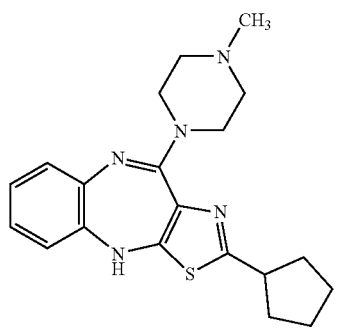

Combine N-methyl piperazine (0.264 g, 2.64 mmol) and 2-cyclopentyl-4,9-dihydro-3-thia-1,4,9-triaza-benzo{f}azulene-10-thione (0.205 g, 0.66 mmol) in 7 ml of pyridine, and heat to reflux over night. Cool to room temperature, remove pyridine, the residue purify on silica gel using 2N ammonia in methanol/ dichloromethane (1:10) as the eluent to give 165 mg foam, which recrystallize in methanol to give 110 mg of title compound: Mass spectrum (electrospray) (m/e): C$_{20}$H$_{25}$N$_5$S, Cacl. Mass (M): 367.18, Found: 368.18 (M+1); $^1$H NMR (400 MHz, CDCl$_3$) δ ppm: 6.97–6.90 (m, 2H), 6.81 (dt, 1H, J=7.3 Hz, J=1.0 Hz), 6.55 (dd, 1H, J=7.8 Hz, J=1.5 Hz), 4.96 (br, 1H), 3.2–3.17 (m, 1H), 2.49–2.47 (m, 4H), 2.28 (s, 3H), 2.03–1.97 (m, 2H), 1.71–1.55 (m, 10H).

Example 491

(S)-2-Cyclopentyl-10-(3-phenethyl-piperazin-1-yl)-4H-3-thia-1,4,9-triaza-benzo[f]azulene

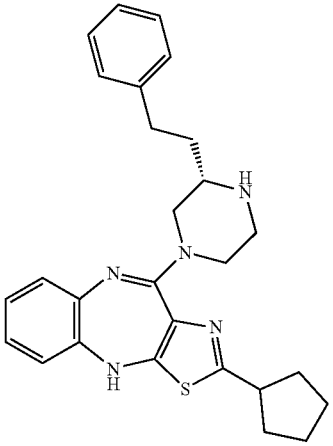

Combine (S)-2-phenethyl-piperazine (0.537 g, 3.0 mmol) and 2-cyclopentyl-4,9-dihydro-3-thia-1,4,9-triaza-benzo{f}azulene-10-thione (0.451 g, 1.5 mmol) in 10 ml of pyridine, and heat to 85° C. for 20 hour. Cool to room temperature, remove pyridine, the residue purify on silica gel using 2N ammonia in methanol/dichloromethane (1:10) as the eluent to give 265 mg of title compound as yellow solid. Mass spectrum (electrospray) (m/e): C$_{27}$H$_{31}$N$_5$S, Cacl. Mass: 457.2; Found: 458.3 (M+1); $^1$H NMR (400 MHz, CDCl$_3$) δ ppm: 7.31–7.27 (m, 2H), 7.24–7.16 (m, 3H), 7.05–6.97 (m, 2H), 6.86 (dt, 1H, J=7.8 Hz, J=1.9 Hz), 6.62 (dd, 1H, J=7.8 Hz, J=1.0 Hz), 5.00 (br, 1H), 4.25 (br, 1H), 3.25 (t, 1H, J=7.8 Hz), 3.02–2.88 (m, 4H), 2.73–2.63 (m, 3H), 2.07–2.03 (m, 2H), 1.77–1.61 (m, 10H).

Example 492

(S)-2-Cyclopentyl-10-(3-phenethyl-4-methyl-piperazin-1-yl)-4H-3-thia-1,4,9-triaza-benzo[f]azulene dihydrochloride

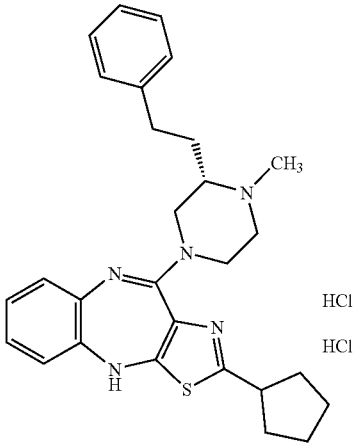

Combine 2-cyclopentyl-10-(3-phenethyl-piperazin-1-yl)-4H-3-thia-1,4,9-triaza-benzo[f]azulene (220 mg, 0.48 mmol), formaldehyde (37%, w/w, aq) (47 mg, 0.58 mmol) and sodium triacetoxyborohydride (152.6 mg, 0.72 mmol) in 12 mL 1,2-dichloroethane and stir at RT for 4 hours. Quench the reaction by adding water, then extract with CH$_2$Cl$_2$, dry the combined organic solvents over Na$_2$SO$_4$. The crude material purify by flash chromatography on silica gel, gradient 100% CH$_2$Cl$_2$ to 100% mixed solvent of (15% 2N ammonia in methanol of dichloromethane) over 55 min, give 225 mg yellow foam, 2-Cyclopentyl-10-(3-phenethyl-4-methyl-piperazin-1-yl)-4H-3-thia-1,4,9-triaza-benzo[f]azulene. The dihydrochloric salt is form by adding 3 eq of acetyl chloride (111.4 mg, 1.42 mmol) to the free base (223 mg, 0.437 mmol) in ethanol (5 mL). After removing the solvent, the residue dissolve in 15 ml mix solvent of $CH_3CN/H_2O=50/50$, lyophilize overnight, afford 235 mg of orange solid. Mass spectrum (electrospray) (m/e): $C_{28}H_{33}N_5S$, Cacl. Mass: 471.2; Found: 472.2 (M+1).

Example 493

(S)-2-Cyclopentyl-10-(3-benzyl-piperazin-1-yl)-4H-3-thia-1,4,9-triaza-benzo[f]azulene

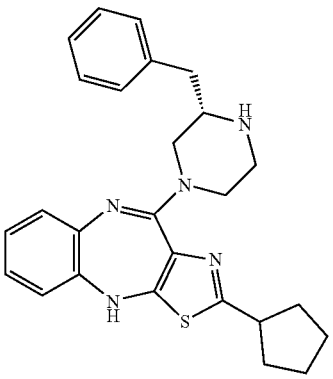

Using a method similar to the method of Example 491, using (S)-2-benzyl-piperazine (1.23 g, 7.0 mmol), 2-cyclopentyl-4,9-dihydro-3-thia-1,4,9-triaza-benzo{f}azulene-10-thione (0.602 g, 2.0 mmol) in 8 ml of pyridine Obtain 240 mg light brown foam of title compound. Mass spectrum (electrospray) (m/e): $C_{26}H_{29}N_5S$, Cacl. Mass: 443.36; Found: 444.1 (M+1); $^1H$ NMR (400 MHz, $CDCl_3$) δ ppm: 7.32–7.21 (m, 5H), 7.03–6.97 (m, 2H), 6.86 (dt, 1H, J=7.8 Hz, J=1.9 Hz), 6.61 (d, 1H, J=7.8 Hz), 5.00 (br, 1H), 3.21–2.90 (m, 4H), 2.78–2.72 (m, 1H), 2.62–2.56 (m, 1H), 2.03–1.95 (m, 2H), 1.77–1.62 (m, 10H).

Example 494

(S)-2-Cyclopentyl-10-(3-benzyl-4-methyl-piperazin-1-yl)-4H-3-thia-1,4,9-triaza-benzo[f]azulene, dihydrochloride

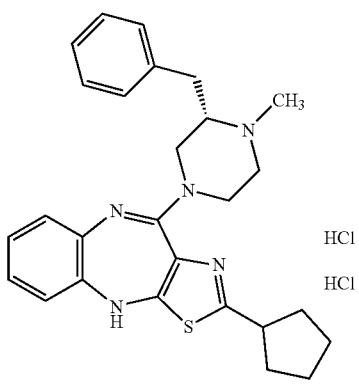

Using a method similar to the method of Example 492, using (S)-2-cyclopentyl-10-(3-benzyl-piperazin-1-yl)-4H-3-thia-1,4,9-triaza-benzo[f]azulene (185 g, 0.418 mmol), formaldehyde (37%, w/w, aq) (42.3 mg, 0.52 mmol) and sodium triacetoxyborohydride (132 mg, 0.63 mmol) in 5 mL 1,2-dichloroethane and stir at RT for 5 hours After purification, give 157 mg of free base as yellow solid: mass spectrum (electrospray) (m/e): $C_{27}H_{31}N_5S$, Calc. Mass: 457.23; Found: 458.1 (M+1); The dihydrochloric salt is form by adding 3 eq of acetyl chloride (77.3 mg, 0.98 mmol) to the free base (150 mg, 0.33 mmol) in ethanol (5 mL). After removing the solvent, the residue dissolve in 10 ml mix solvent of $CH_3CN/H_2O=50/50$, lyophilize overnight, afford 176 mg of orange solid.

Example 495

(S)-2-Cyclopentyl-10-{3-[2-(3-methoxy-phenyl)-ethyl]-piperazin-1-yl}-4H-3-thia-1,4,9-triaza-benzo[f]azulene

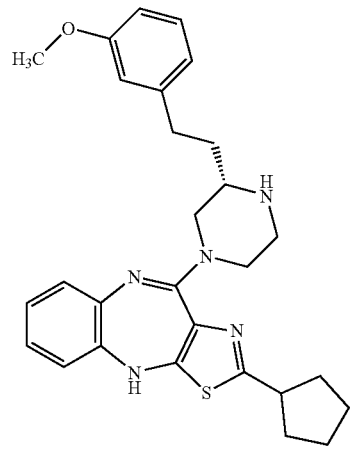

By using a method similar to the method of Example 491, using (S)-2-(3-methoxy-phenyl)-piperazine (1.10 g, 5.0 mmol) and 2-cyclopentyl-4,9-dihydro-3-thia-1,4,9-triaza-benzo{f}azulene-10-thione (0.540 g, 1.79 mmol) in 6 ml of pyridine, and heat to 85° C. for 5 hour. After purification, give 310 mg of title compound as brown solid. Mass spectrum (electrospray) (m/e): $C_{28}H_{33}N_5OS$, Cacl. Mass: 487.24; Found: 488.1 (M+1); $^1H$ NMR (400 MHz, $CDCl_3$) δ ppm: 7.21–7.17 (m, 1H), 7.05–6.97 (m, 2H), 6.86 (dt, 1H, J=7.3 Hz, J=1.9 Hz), 6.79–6.72 (m, 3H), 6.61 (dd, 1H, J=7.8 Hz, J=1.5 Hz), 5.00 (br, 1H), 4.25 (br, 1H), 3.78 (s, 3H), 3.02–2.89 (m, 4H), 2.69–2.63 (m, 3H), 2.07–2.04 (m, 2H1), 1.77–1.48 (m, 10M).

Example 496

(S)-2-Cyclopentyl-10-{3-[2-(3-methoxy-phenyl)-ethyl]-4-methyl-piperazin-1-yl}-4H-3-thia-1,4,9-triaza-benzo[f]azulene, dihydrochloride

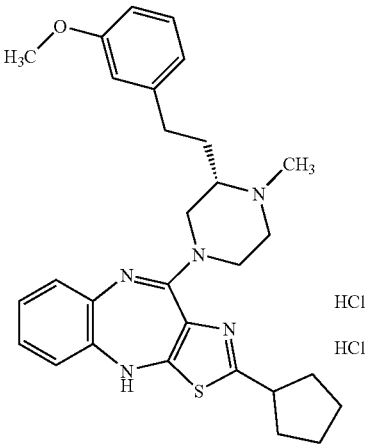

By using the method similar to the Example 492, using (S)-2-cyclopentyl-10-{3-[2-(3-methoxy-phenyl)-ethyl]-piperazin-1-yl}-4H-3-thia-1,4,9-triaza-benzo[f]azulene, (270 mg, 0.55 mmol), formaldehyde (37%, w/w, aq) (0.56 g, 0.69 mmol) and sodium triacetoxyborohydride (174.8 mg, 0.825 mmol) in 8 mL 1,2-dichloroethane and stir at RT. After purification, give 230 mg of free base as brown oil. Mass spectrum (electrospray) (m/e): $C_{29}H_{35}N_5OS$, Cacl. Mass: 501.26; Found: 502.1 (M+1); $^1$H NMR (400 MHz, $CDCl_3$) δ ppm: 7.21–7.17 (m, 1H), 7.06–6.96 (m, 2H), 6.87 (dt, 1H, J=7.8 Hz, J=1.5 Hz), 6.79–6.72 (m, 3H), 6.62 (dd, 1H, J=7.8 Hz, J=1.5 Hz), 5.05 (br, 1H), 3.78 (s, 3H), 3.27–3.21 (m, 1H), 3.02–2.72 (m, 3H), 2.60–2.42 (m, 2H), 2.38–2.28 (m, 4H), 2.12–1.83 (m, 3H), 1.76–1.60 (m, 10H). The dihydrochloric salt is form by adding 3 eq of acetyl chloride (105.8 mg, 1.37 mmol) to the free base (225 mg, 0.45 mmol) in ethanol (5 mL). After removing the solvent, the residue dissolve in 10 ml mix solvent of $CH_3CN/H_2O=50/50$, lyophilize overnight, afford 252 mg of orange solid.

Example 497

(S)-2-Cyclopentyl-10-{3-[2-(4-methoxy-phenyl)-ethyl]-piperazin-1-yl}-4H-3-thia-1,4,9-triaza-benzo[f]azulene

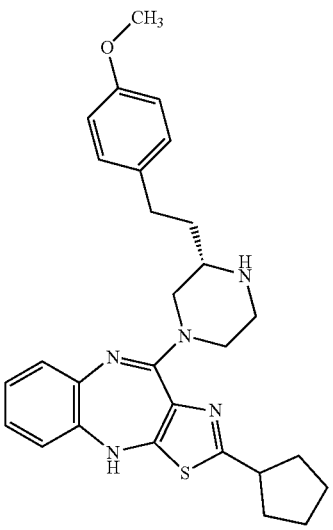

Slowly add (S)-2-(4-methoxy-phenyl)-piperazine (440 mg, 2.0 mmol) in 5.0 mL of pyridine to 2-cyclopentyl-4,9-dihydro-3-thia-1,4,9-triaza-benzo {f}azulene-10-thione (602 mg, 2.0 mmol) in 5 ml of pyridine over 2.5 h at 85° C., then stir for 5 h at 85° C. Cool to RT, remove the solvent, the residue purified on silica gel, using gradient (dichloromethane to 15% of 2N ammonia in methanol/dichloromethane), give 450 mg of title compound. Mass spectrum (electrospray) (m/e): $C_{28}H_{33}N_5OS$, Cacl. Mass: 487.24; Found: 488.1 (M+1); $^1$H NMR (400 MHz, $CDCl_3$) δ ppm: 7.11–6.97 (m, 4H), 76.89–6.81 (m, 3H), 6.63 (m, 1H), 5.02 (br, 1H), 4.25 (br, 1), 3.78 (s, 3H), 3.26–3.23 (m, 1H), 2.99–2.88 (m, 41), 2.68–2.62 (m, 3H), 2.10–2.03 (m, 2H), 1.76–1.16 (m, 10H).

Example 498

(S)-2-Cyclopentyl-10-{3-[2-(4-methoxy-phenyl)-ethyl]-4-methyl-piperazin-1-yl}-4H-3-thia-1,4,9-triaza-benzo[f]azulene, dihydrochloride

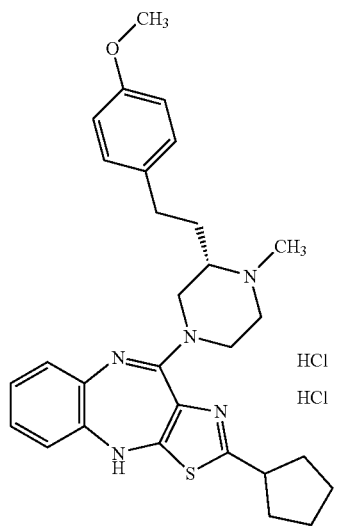

By using a method similar to the method of Example 492, using (S)-2-Cyclopentyl-10-{3-[2-(4-methoxy-phenyl)-ethyl]-piperazin-1-yl}-4H-3-thia-1,4,9-triaza-benzo[f]azulene, (220 mg, 0.45 mmol), formaldehyde (37%, w/w, aq) (45.8 mg, 0.56 mmol) and sodium triacetoxyborohydride (143 mg, 0.675 mmol) in 5 mL 1,2-dichloroethane and stir at RT. After purification, give 200 mg of free base as brown oil. $^1$H NMR (400 MHz, $CDCl_3$) δ ppm: 7.11–6.97 (m, 4H), 6.89–6.80 (m, 3H), 6.61 (dd, 1H, J=7.8 Hz, J=1.0 Hz), 5.02 (br, 1H), 3.78 (s, 3H), 3.27–3.21 (m, 1H), 3.02–2.60 (m, 2H), 2.56–2.42 (m, 2H), 2.34–2.28 (m, 5H), 2.12–2.06 (m, 2H), 1.95–1.83 (m, 1H), 1.77–1.61 (m, 10H). The dihydrochloric salt is form by adding 3 eq of acetyl chloride (94.2 mg, 1.20 mmol) to the free base (200 mg, 0.40 mmol) in ethanol (5 mL). After removing the solvent, the residue dissolve in 10 ml mix solvent of $CH_3CN/H_2O=50/50$, lyophilize overnight, afford 223 mg of title compound as orange solid.

Example 499

N-(2,4-Dioxo-2,3,4,5-tetrahydro-1H-benzo[b][1,4]diazapin-3-yl)-propionamide

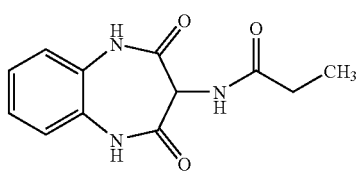

Combine 3-amino-1H-1,5-benzodiazepine-2,4-(3H, 5H)-dione (5.7 g, 30.0 mmol) and triethyl amine(3.33 g, 33.0 mmol) in 120 mL DMF and add propionyl chloride (3.05 g, 33.0 mmol) dropwise at RT. After stirring overnight, remove DMF under reduced pressure, suspend the residue in a mixed solvent ($CHCl_3$/i-PrOH=3/1, 400 mL). Collect an off-white solid via suction filtration to give the title compound. Wash the filtrate with NaHCO$_3$ (sat.2×100 mL) and dry with Na$_2$SO$_4$. Concentrate the organic solvent down to a residue, treat with ether, collect the solid as title compound: mass spectrum (APCI) (m/e): 248.1 (M+1). $^1$H NMR (400 MHz, DMSO-d$_6$): 10.70 (s, 2H), 8.19 (d, 1H, J=7.2 Hz), 7.23–7.15 (m, 4H), 4.73 (d, 1H, J=8.0 Hz), 2.27 (q, 2H, J=8.0 Hz), 0.94 (t, 3H, J=8.0 Hz).

Example 500

2-Ethyl-4,9-dihydro-3-thia-1,4,9-triaza-benzo[f]azulene-10-thione

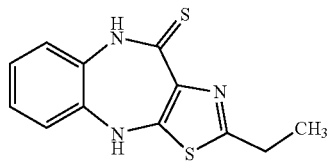

Combine N-(2,4-dioxo-2,3,4,5-tetrahydro-1H-benzo[b][1,4]diazapin-3-yl)-propionamide (3.7 g, 15.0 mmol) and Lawesson's reagent (9.09 g, 22.5 mmol) in 225 mL 1,2-dichloroethane, heat to reflux under N$_2$. After refluxing overnight, cool the reaction to RT, collect the orange solid via suction filtration, and dry under vacuum to obtain 3.3 g crude material. Take crude material (1.0 g), mix with Lawesson's reagent (0.75 g) in 1,2-dichloroethane (30 mL), heat to reflux overnight, cool to RT, collect the orange-red solid via suction filtration to obtain the title compound. Treat the remaining of the intermediate similarly (2.3 g) to obtain additional title compound: mass spectrum (electrospray) (m/e): 261.8 (M+1), 260.0 (M−1); $^1$H NMR (300 MHz, DMSO-d$_6$): 10.97 (s, 1H), 9.17 (s, 1H), 7.00–6.91 (m, 3H), 6.79–6.70 (m, 1H), 2.73 (q, 2H, J=7.5 Hz), 1.16 (t, 3H, J=7.5 Hz),

Example 501

(S)-2-Ethyl-10-{3-[2-(4-methoxy-phenyl)-ethyl]-piperazin-1-yl}-4H-3-thia-1,4,9-triaza-benzo[f]azulene

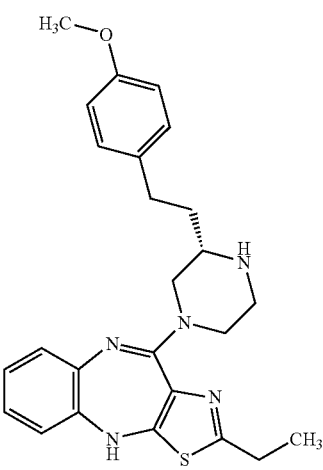

Add methyl trifluoromethanesulfonate (4.2 g, 26.0 mmol) overnight, to a suspension of 2-ethyl-4,9-dihydro-3-thia-1,4,9-triaza-benzo{f}azulene-10-thione (3.4 g, 13.0 mmol) in 35 mL CH$_2$Cl$_2$, LC-MS showed still had 50% of starting material, added another 0.1 mL of methyl trifluoromethanesulfonate, and heated to 35° C. for 1 h. Concentrate the reaction mixture under reduced pressure to give a red-brown solid. Dissolve the solid in 32.5 mL of pyridine to make 0.4 M of solution. Take 5 mL of the solution (2.0 mmol), mix with (S)-2-(4-methoxy-phenyl)-piperazine (440 mg, 2.0 mmol) and heat to 100° C. for 2.5 hours. Cool the reaction to RT, concentrate down to a residue, which purify by flash chromatography on silica gel, gradient 100% CH$_2$Cl$_2$ to 100% mixed solvent of (CH$_2$Cl$_2$: 2N NH$_3$/MeOH=20:1) over 55 min. give 250 mg of the title compound. Mass spectrum (APCI) (m/e): C$_{25}$H$_{29}$N$_5$OS, Cacl. Mass: 447.21, Found: 448.2 (M+1); $^1$H NMR (300 MHz, CDCl$_3$) δ ppm: 7.12–6.80 (m, 7H), 6.68–6.65 (m, 1H), 5.30 (br, 1H), 4.25 (m, 2H), 3.77 (s, 3H), 3.21–2.88 (m, 4H), 2.85–2.79 (m, 3H), 2.67–2.62 (m, 2H), 1.77–1.75 (m, 2H), 1.29 (t, 3H, J=7.3 Hz).

Example 502

(S)-2-Ethyl-10-{3-[2-(4-fluoro-phenyl)-ethyl]-piperazin-1-yl}-4H-3-thia-1,4,9-benzo[f]azulene

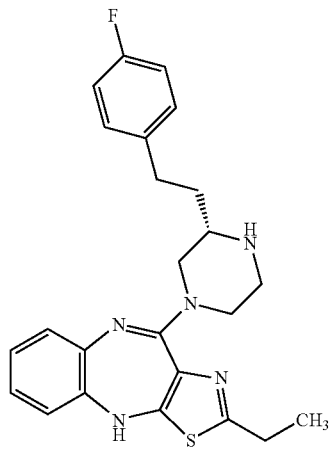

By using a method similar to the method of Example 501, using a suspension of 2-ethyl-4,9-dihydro-3-thia-1,4,9-triaza-benzo{f}azulene-10-thione (3.4 g, 13.0 mmol) in 35 mL CH$_2$Cl$_2$, add methyl trifluoromethanesulfonate (4.2 g, 26.0 mmol) overnight, LC-MS showed still had 50% of starting material, added another 0.1 mL of methyl trifluoromethanesulfonate, and heated to 35° C. for 1 h. Concentrate the reaction mixture under reduced pressure, give a red-brown solid. Dissolve the solid in 32.5 mL of pyridine to make 0.4 M of solution. Take 6.25 mL of the solution (2.5 mmol), mix with (S)-2-(4-fluoro-phenyl)-piperazine (520 mg, 2.5 mmol) and heat to 100° C. for 3 hours. Cool the reaction to RT, concentrate down to a residue, which purify by flash chromatography on silica gel, gradient 100% CH$_2$Cl$_2$ to 100% mixed solvent of (CH$_2$Cl$_2$:2N NH$_3$/MeOH=20:1) over 55 min. give 360 mg of the title compound as orange-brown foam. Mass spectrum (APCI) (m/e): C$_{24}$H$_{26}$FN$_5$S, Cacl. Mass: 435.15, Found: 436.2 (M+1); $^1$H NMR (300 MHz, CDCl$_3$) δ ppm: 7.17–6.86 (m, 7H), 6.66–6.63 (m, 1H), 5.30 (br, 1H), 4.25–4.15 (m, 2H), 3.10–2.66 (m, 10H), 1.76–1.71 (m, 2H), 1.28 (t, 3H, J=7.7 Hz).

Example 503

(S)-2-Ethyl-10-{3-[2-(3-fluoro-phenyl)-ethyl]-piperazin-1-yl}-4H-3-thia-1,4,9-triaza-benzo[f]azulene

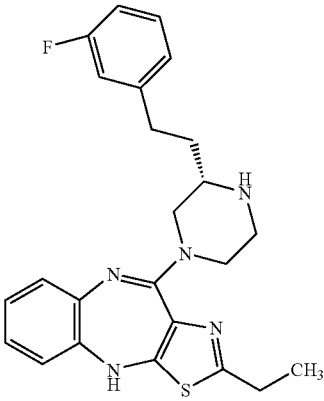

By using a method similar to the method of Example 501, using a suspension of 2-ethyl-4,9-dihydro-3-thia-1,4,9-triaza-benzo{f}azulene-10-thione (3.4 g, 13.0 mmol) in 35 mL $CH_2Cl_2$, add methyl trifluoromethanesulfonate (4.2 g, 26.0 mmol) overnight, LC-MS showed still had 50% of starting material, added another 0.1 mL of methyl trifluoromethanesulfonate, and heated to 35° C. for 1 h. Concentrate the reaction mixture under reduced pressure, give a red-brown solid. Dissolve the solid in 32.5 mL of pyridine to make 0.4 M of solution. Take 6.25 mL of the solution (2.5 mmol), mix with (S)-2-(3-fluoro-phenyl)-piperazine (520 mg, 2.5 mmol) and heat to 100° C. for 3 hours. Cool the reaction to RT, concentrate down to a residue, which purify by flash chromatography on silica gel, gradient 100% CH2C12 to 100% mixed solvent of ($CH_2Cl_2$: 2N $NH_3$/MeOH=20:1) over 55 min. give 412 mg of the title compound Mass spectrum (APCI) (m/e): $C_{24}H_{26}FN_5S$, Cacl. Mass: 435.15, Found: 436.2 (M+1); $^1$H NMR (300 MHz, $CDCl_3$) δ ppm: 7.24–6.85 (m, 7H), 6.66–6.65 (m, 1H), 5.30 (br, 1H), 4.25–4.15 (m, 2H), 3.20–2.68 (m, 10H), 1.90–1.75 (m, 2H), 1.29 (t, 3H, J=7.3 Hz).

Example 504

(S)-2-Ethyl-10-{3-[2-(3-methoxy-phenyl)-ethyl]-piperazin-1-yl}-4H-3-thia-1,4,9-triaza-benzo[f]azulene

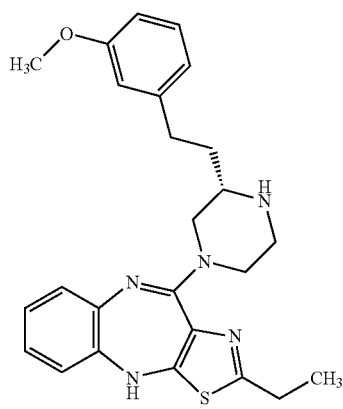

By using a method similar to the Example 501, using a suspension of 2-ethyl-4,9-dihydro-3-thia-1,4,9-triaza-benzo{f}azulene-10-thione (3.4 g, 13.0 mmol) in 35 mL $CH_2Cl_2$, add methyl trifluoromethanesulfonate (4.2 g, 26.0 mmol) overnight, LC-MS showed still had 50% of starting material, added another 0.1 mL of methyl trifluoromethanesulfonate, and heated to 35° C. for 1 h. Concentrate the reaction mixture under reduced pressure, give a red-brown solid. Dissolve the solid in 32.5 mL of pyridine to make 0.4 M of solution. Take 6.25 mL of the solution (2.5 mmol), mix with (S)-2-(3-methoxy-phenyl)-piperazine (550 mg, 2.5 mmol) and heat to 100° C. for 3 hours. Cool the reaction to RT, concentrate down to a residue, which purify by flash chromatography on silica gel, gradient 100% $CH_2Cl_2$ to 100% mixed solvent of ($CH_2Cl_2$: 2N $NH_3$/MeOH=20:1) over 55 min. give 306 mg of the title compound. Mass spectrum (APCI) (m/e): $C_{25}H_{29}N_5OS$, Cacl. Mass: 447.21, Found: 448.2 (M+1); $^1$H NMR (300 MHz, $CDCl_3$) δ ppm: 7.21–7.16 (m, 1H), 7.08–6.96 (m, 2H), 6.91–6.86 (m, 1H), 6.80–6.71 (m, 3H), 6.65–6.64 (m, 1H), 5.40 (br, 1H), 4.35–4.25 (m, 2H), 3.78 (s, 3H), 3.16–2.69 (m, 10H), 1.79–1.76 (m, 2H), 1.29 (t, 3H, J=7.7 Hz).

Example 506

(S)-2-Ethyl-10-{3-[2-(4-methoxy-phenyl)-ethyl]-4-methyl-piperazin-1-yl}-4H-3-thia-1,4,9-triaza-benzo[f]azulene, dihydrochloride

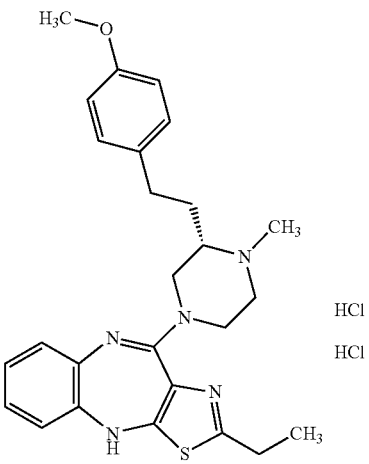

By using a similar method to Example 492, using (S)-2-ethyl-10-{3-[2-(4-methoxy-phenyl)-ethyl]-piperazin-1-yl}-4H-3-thia-1,4,9-triaza-benzo[f]azulene, (190 mg, 0.42 mmol), formaldehyde (37%, w/w, aq) (42.7 mg, 0.53 mmol) and sodium triacetoxyborohydride (134.9 mg, 0.64 mmol) in 5 mL 1,2-dichloroethane and stir at RT. After purification, give 145 mg of free base as brown oil: mass spectrum (APCI) (m/e): $C_{26}H_{31}N_5OS$, Cacl. Mass: 461.22, Found: 462.2(M+1); The dihydrochloric salt is form by adding 5 eq of acetyl chloride (115 mg, 1.46 mmol) to the free base (135 mg, 0.292 mmol) in ethanol (5 mL). After removing the solvent, the residue dissolve in 10 ml mix solvent of $CH_3CN/H_2O$=50/50, lyophilize overnight, afford 142 mg of title compound as orange solid.

Example 507

(S)-2-Ethyl-10-{3-[2-(4-fluoro-phenyl)-ethyl]-4-methyl-piperazin-1-yl}-4H-3-thia-1,4,9-triaza-benzo[f]azulene dihydrochloride

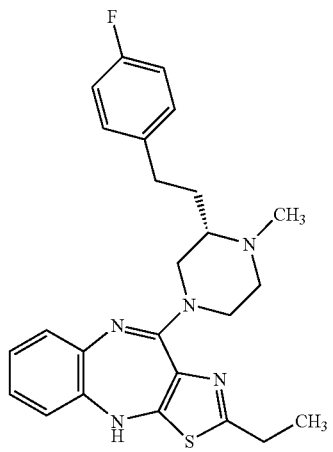

By using a method similar to Example 492, using (S)-2-ethyl-10-{3-[2-(4-fluoro-phenyl)-ethyl]-piperazin-1-yl}-4H-3-thia-1,4,9-triaza-benzo[f]azulene, (292 mg, 0.67 mmol), formaldehyde (37%, w/w, aq) (68 mg, 0.84 mmol) and sodium triacetoxyborohydride (213 mg, 1.01 mmol) in 6 mL 1,2-dichloroethane and stir at RT. After purification, give 272 mg of free base as yellow solid. Mass spectrum (APCI) (m/e): $C_{25}H_{28}FN_5S$, Cacl. Mass: 449.15, Found: 450.2; The dihydrochloric salt is form by adding 5 eq of acetyl chloride (115 mg, 1.46 mmol) to the free base (135 mg, 0.292 mmol) in ethanol (5 mL). After removing the solvent, the residue dissolve in 10 ml mix solvent of $CH_3CN/H_2O=50/50$, lyophilize overnight, afford 300 mg of title compound as yellow solid.

Example 508

(S)-2-Ethyl-10-{3-[2-(3-fluoro-phenyl)-ethyl]-4-methyl-piperazin-1-yl}-4H-3-thia-1,4,9-triaza-benzo[f]azulene dihydrochloride

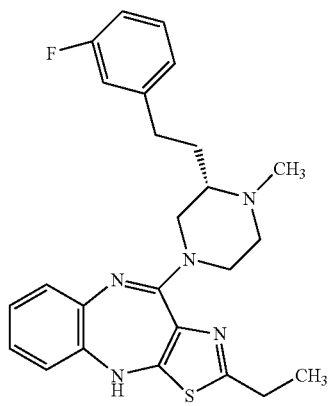

By using a method similar to Example 492, using (S)-2-ethyl-10-{3-[2-(3-fluoro-phenyl)-ethyl]-piperazin-1-yl}-4H-3-thia-1,4,9-triaza-benzo[f]azulene, (236 mg, 0.54 mmol), formaldehyde (37%, w/w, aq) (55 mg, 0.68 mmol) and sodium triacetoxyborohydride (172 mg, 0.81 mmol) in 6 mL 1,2-dichloroethane and stir at RT. After purification, give 140 mg of free base: mass spectrum (APCI) (m/e): $C_{25}H_{28}FN_5S$, Cacl. Mass: 449.20, Found: 450.2 (M+1); $^1$H NMR (300 MHz, CDCl$_3$) δ ppm: 7.24–7.19 (m, 1H), 7.07–6.84 (m, 6H), 6.64–6.61 (m, 1H), 5.29 (br, 1H), 4.35–4.25 (m, 2H), 3.27–3.23 (m, 1H), 3.04–2.71 (m, 5H), 2.62–2.42 (m, 2H), 2.33–2.29 (m, 4H), 2.00–1.74 (m, 2H), 1.29 (t, 3H, J=7.7 Hz). The dihydrochloric salt is form by adding 5 eq of acetyl chloride (122 mg, 1.56 mmol) to the free base (140 mg, 0.31 mmol) in ethanol (5 mL). After removing the solvent, the residue dissolve in 10 ml mix solvent of $CH_3CN/H_2O=50/50$, lyophilize overnight, afford 139 mg of title compound as orange solid.

Example 509

(S)-2-Ethyl-10-{3-[2-(3-methoxy-2-phenyl)-ethyl]-4-methyl-piperazin-1-yl}-4H-3-thia-1,4,9-triaza-benzo[f]azulene dihydrochloride

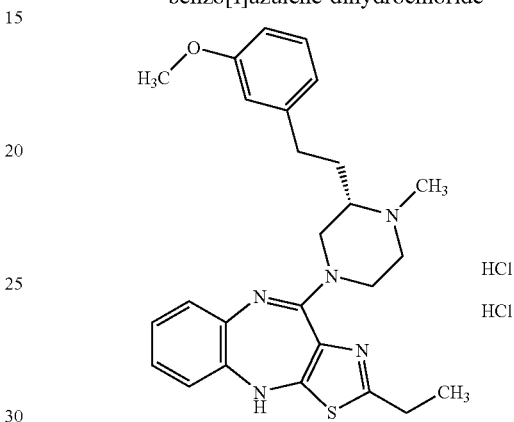

By using a method similar to the method of Example 492, using (S)-2-ethyl-10-{3-[2-(3-methoxy-phenyl)-ethyl]-piperazin-1-yl}-4H-3-thia-1,4,9-triaza-benzo[f]azulene, (252 mg, 0.56 mmol), formaldehyde (37%, w/w, aq) (57 mg, 0.70 mmol) and sodium triacetoxyborohydride (179.2 mg, 0.85 mmol) in 5 mL 1,2-dichloroethane and stir at RT. After purification, give 215 mg of free base. Mass spectrum (APCI) (m/e): $C_{26}H_{31}N_5OS$, Cacl. Mass: 461.22, Found: 462.2(M+1); The dihydrochloric salt is form by adding 5 eq of acetyl chloride (168.8 mg, 2.15 mmol) to the free base (200 mg, 0.43 mmol) in ethanol (5 mL). After removing the solvent, the residue dissolve in 10 ml mix solvent of $CH_3CN/H_2O=50/50$, lyophilize overnight, afford 225 mg of title compound.

Example 510

N-(2,4-Dioxo-2,3,4,5-tetrahydro-1H-benzo[b][1,4]diazepin-3-yl)-2,2,2-trifluoro-acetamide

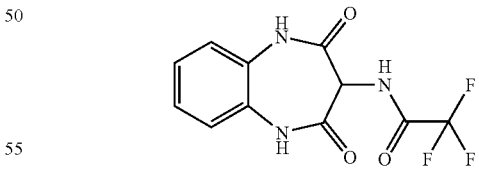

Add 1-(3-dimethylaminopropyl)-3-ethylcarbodiimide hydrochloride (7.67 g, 40.0 mmol), and 4-(dimethylamino) pyridine (0.244 g, 2.00 mmol) to a solution of 3-amino-1,5-dihydro-benzo[b][1,4]diazepine-2,4-dione (7.65 g, 40.0 mmol) in anhydrous N,N-dimethylformamide (50 mL). Rinse solids into reaction with anhydrous N,N-dimethylformamide (50 mL), and cool reaction to 0° C. in an ice/water bath. Add via syringe trifluoroacetic acid (3.08 mL, 40.0 mmol). After 10 minutes, remove cooling, and after 5.5 hours at ambient temperature, add an additional 0.2 equivalents of 1-(3-dimethylaminopropyl)-3-ethylcarbodiimide hydrochloride (1.53 g) and trifluoroacetic acid (0.62 mL) and stir at ambient temperature. After an overnight period, concentrate under reduced pressure to give a residue. Reconstitute the residue in isopropanol: chloroform (1:3, 20 mL) and set 5 minutes. Collect solid formed by suction filtration, wash with isopropanol: chloroform (3:1), and dry at ambient temperature under vacuum to give the title compound. Filter the filtrate, which contained precipitated solid and dry this solid at ambient temperature under vacuum to give a second crop of the title compound: mass spectrum (ES neg., m/e): 286.0 (M−1); $^1$H NMR (300 MHz, DMSO-d$_6$): 10.93 (s, 2H), 9.42 (d, 1H, J=6.9 Hz), 7.29–7.15 (m, 4H), 4.91 (d, 1H, J=7.2 Hz).

Example 511

2-Trifluoromethyl-4,9-dihydro-3-thia-1,4,9-triaza-benzo[f]azulene-10-thione

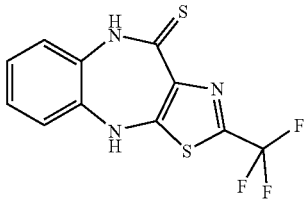

Combine N-(2,4-dioxo-2,3,4,5-tetrahydro-1H-benzo[b][1,4]diazepin-3-yl)-2,2,2-trifluoro-acetamide (3.02 g, 10.5 mmol) with Lawesson's Reagent, [2,4-bis(4-methoxyphenyl)-1,3-dithia-2,4-diphosphetane-2,4-disulfide], (6.38 g, 15.8 mmol) in anhydrous toluene (60 mL), heat to reflux, and stir. After 16 hours, cool and stir for a few hours. Collect the reaction solid by suction filtration, wash with a small amount of toluene, and dry at 40° C. for a few hours to give crude product (3.6 g). Adsorb material on Silica gel 60 and purify by flash chromatography, eluting with a solution of 35% ethyl acetate in hexane. Combine and concentrate the product-containing fractions under reduced pressure, and dry the product at 54° C. under vacuum for 4.5 hours to give the title compound: mass spectrum (APCI, m/e): 302 (M+1); $^1$H NMR (300 MHz, DMSO-d$_6$): 11.39 (s, 1H), 9.57 (s, 1H), 7.03 (m, 3H), 6.77 (m, 1H).

Example 512

(S)-10-{3-[2-(3-Fluoro-phenyl)-ethyl]-piperazin-1-yl}-2-trifluoromethyl-4H-3-thia-1,4,9-triaza-benzo[f]azulene

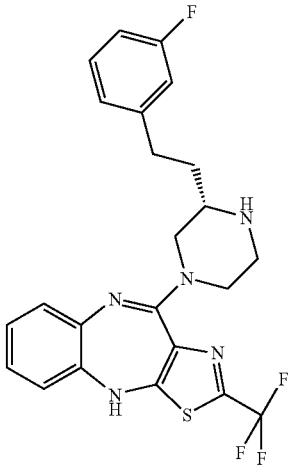

Following a method similar as described in Example 484, using 2-trifluoromethyl-4,9-dihydro-3-thia-1,4,9-triaza-benzo[f]azulene-10-thione (4.025 g, 13.36 mmol) and methyl trifluoromethanesulfonate (2.27 mL, 20.0 mmol), to formed the methylated intermediate. Take 1.38 g of this intermediate (3.0 mmol), combine and then (S)-2-[2-(3-fluoro-phenyl)-ethyl]-piperazine (0.62 g, 3.0 mmol), followed by two chromatographic purifications, the first with a pre-packed silica gel column, eluting with a gradient of a 3.5% solution of 2M ammonia in methanol, in dichloromethane (0–100% in dichloromethane); and the second with a pre-packed cation exchange column, loading with methanol, and then eluting the product with increasing concentrations of 2M ammonia in methanol, in dichloromethane gives the title compound (0.754 g): mass spectrum (APCI+, m/e): 476 (M+1); $^1$H NMR (300 MHz, DMSO-d$_6$), δ (ppm): 8.45 (s, 1H), 7.33–7.23 (m, 1H), 7.05–6.80 (m, 6H), 6.74–6.68 (m, 1H), 4.06–3.80 (br. m, 2H), 2.94–2.76 (m, 2H), 2.74–2.52 (m, 5H), 2.35 (br. s, 1H), 1.67–1.49 (m, 2H).

Example 513

(S)-10-{3-[2-(3-Fluoro-phenyl)-ethyl]-1-piperazin-1-yl}-2-trifluoromethyl-4H-3-thia-1,4,9-triaza-benzo[f]azulene dihydrochloride

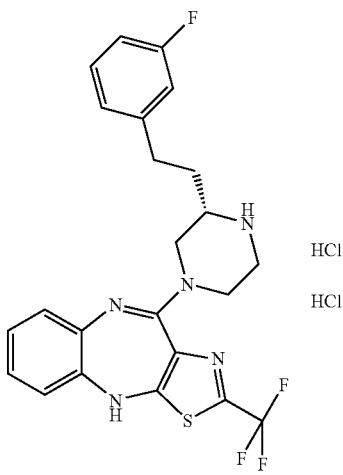

Add a solution of acetyl chloride (0.566 mL, 7.93 mmol) in absolute ethanol to a solution of (S)-10-{3-[2-(3-fluoro-phenyl)-ethyl]-piperazin-1-yl}-2-trifluoromethyl-4H-3-thia-1,4,9-triaza-benzo[f]azulene (0.754 g, 1.59 mmol) in absolute ethanol and stir at ambient temperature. Isolate the precipitated solid by suction filtration, washing with diethyl ether to give the title compound (0.660 g): mass spectrum (APCI+, m/e): 476 (M+1−2HCl); exact mass spectrum (ES+, m/e, C$_{23}$H$_{21}$F$_4$N$_5$S.2HCl): calc. 476.1532 (M+1−2HCl), found 476.1530.

Example 514

(S)-10-{3-[2-(4-Fluoro-phenyl)-ethyl]-piperazin-1-yl}-2-trifluoromethyl-4H-3-thia-1,4,9-triaza-benzo[f]azulene

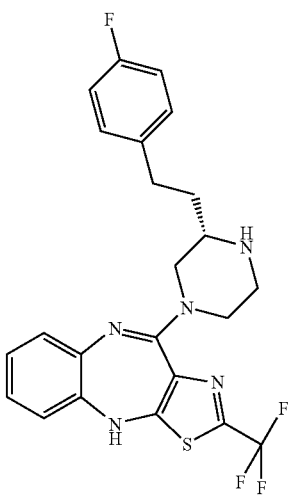

Using a method similar to in Example 484, using 2-trifluoromethyl-4,9-dihydro-3-thia-1,4,9-triaza-benzo[f]azulene-10-thione (4.025 g, 13.36 mmol) and methyl trifluoromethanesulfonate (2.27 mL, 20.0 mmol), to form the methylated intermediate. Take 1.38 g of this intermediate (3.0 mmol), combine with (S)-2-[$^2$-(4-fluoro-phenyl)-ethyl]-piperazine (0.62, 3.0 mmol), followed by chromatographic purification, eluting with a gradient of a 3.5% solution of 2M ammonia in ethanol, in dichloromethane (0–100% in dichloromethane) gives the title compound (1.11 g): mass spectrum (APCI+, m/e): 476 (M+1); $^1$H NMR (300 MHz, DMSO-$d_6$), δ (ppm): 8.67–8.36 (m, 2H), 7.27–7.16 (m, 2H), 7.13–7.03 (m, 2H), 7.01–6.86 (m, 3H), 6.75–6.68 (m, 1H), 4.24–3.96 (br. m, 2H), 3.39–2.91 (m, 5H), 2.75–2.51 (m, 2H), 1.88–1.73 (m, 2H).

Example 515

(S)-10-{3-[2-(4-Fluoro-phenyl)-ethyl]-piperazin-1-yl}-2-trifluoromethyl-4H-3-thia-1,4,9-triaza-benzo[f]azulene dihydrochloride

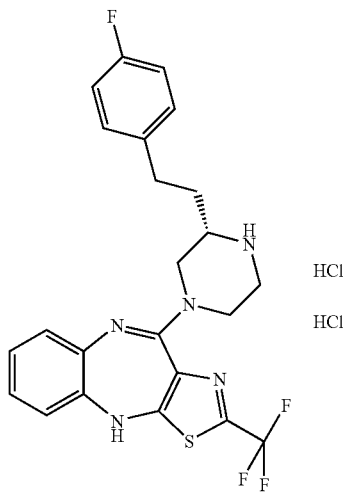

Using a method similar to Example 513, using (S)-10-{3-[2-(4-fluoro-phenyl)-ethyl]-piperazin-1-yl}-2-trifluoromethyl-4H-3-thia-1,4,9-triaza-benzo[f]azulene (0.27 g, 0.57 mmol) and a solution of acetyl chloride (0.203 mL, 2.84 mmol) in absolute ethanol at ambient temperature gives the title compound (0.276 g): Exact mass spectrum (ES+, m/e, $C_{23}H_{21}F_4N_5S.2HCl$): calc. 476.1532 (M+1−2HCl), found 476.1532.

Example 516

(S)-10-{3-[2-(3-Methoxy-phenyl)-ethyl]-piperazin-1-yl}-2-trifluoromethyl-4H-3-thia-1,4,9-triaza-benzo[f]azulene

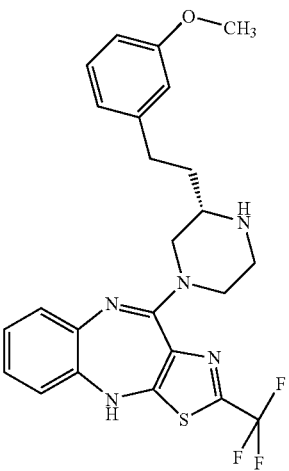

Using a method similar to Example 484, using 2-trifluoromethyl-4,9-dihydro-3-thia-1,4,9-triaza-benzo[f]azulene-10-thione (4.025 g, 13.36 mmol) and methyl trifluoromethanesulfonate (2.27 mL, 20.0 mmol), to form the methylated intermediate. Take 1.38 g of this intermediate (3.0 mmol), combine with (S)2-[2-(3-Methoxy-phenyl)-ethyl]-piperazine (0.65 g, 3.0 mmol), followed by chromatographic purification, eluting with a gradient of a 3.5% solution of 2M ammonia in methanol, in dichloromethane (0–100% in dichloromethane) gives the title compound (0.99 g): mass spectrum (APCI+, m/e): 488 (M+1); $^1$H NMR (300 MHz, DMSO-$d_6$), δ (ppm): 8.73–8.49 (m, 2H), 7.21–7.15 (m, 1H), 6.99–6.88 (m, 3H), 6.79–6.69 (m, 4H), 4.25–3.98 (br. m, 2H), 3.70 (s, 3H), 3.38–3.17 (m, 3H), 3.14–2.97 (m, 2H), 2.74–2.52 (m, 2H), 1.90–1.80 (m, 2H).

Example 517

(S)-10-{3-[2-(3-Methoxy-phenyl)-ethyl]-piperazin-1-yl}-2-trifluoromethyl-4H-3-thia-1,4,9-triaza-benzo[f]azulene dihydrochloride

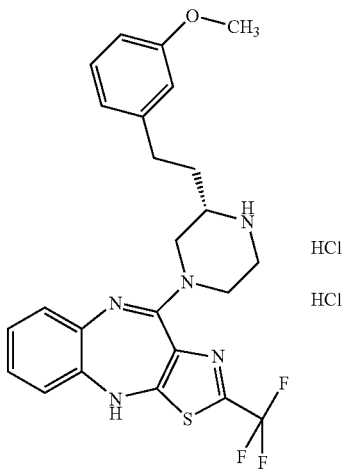

Using a similar method to the method of Example 513, using (S)-10-{3-[2-(3-methoxy-phenyl)-ethyl]-piperazin-1-yl}-2-trifluoromethyl-4H-3-thia-1,4,9-triaza-benzo[f]azulene (0.29 g, 0.59 mmol) and a solution of acetyl chloride (0.212 mL, 2.97 mmol) in absolute ethanol at ambient temperature gives the title compound (0.297 g): Exact mass spectrum (ES+, m/e, $C_{24}H_{24}F_3N_5OS2HCl$): calc. 488.1732 (M+1−2HCl), found 488.1724.

Example 518

(S)-10-{3-[2-(4-Methoxy-phenyl)-ethyl]-piperazin-1-yl}-2-trifluoromethyl-4H-3-thia-1,4,9-triaza-benzo[f]azulene

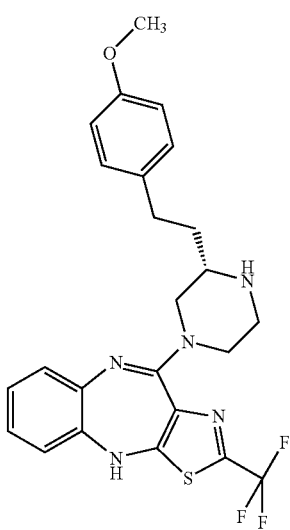

Using a method similar to Example 484, using 2-trifluoromethyl-4,9-dihydro-3-thia-1,4,9-triaza-benzo[f]azulene-10-thione (4.025 g, 13.36 mmol) and methyl trifluoromethanesulfonate (2.27 mL, 20.0 mmol), to form the methylated intermediate. Take 1.38 g of this intermediate (3.0 mmol), combine with (S)-2-[2-(4-methoxy-phenyl)-ethyl]-piperazine (0.40 g, 1.8 mmol), followed by chromatographic purification, eluting with a gradient of a 3.5% solution of 2M ammonia in methanol, in dichloromethane (0–100% in dichloromethane) gives the title compound (0.625 g): mass spectrum (APCI+, m/e): 488 (M+1); $^1$H NMR (300 MHz, DMSO-$d_6$), δ (ppm): 8.58 (s, 1H), 7.13–7.03 (m, 2H), 6.99–6.86 (m, 3H), 6.85–6.78 (m, 2H), 6.75–6.69 (m, 1H), 4.22–3.97 (br. m, 2H), 3.70 (s, 3H), 3.44–2.87 (m, 6H), 2.68–2.46 (m, 2H), 1.84–1.71 (m, 2H).

Example 519

(S)-10-{3-[2-(4-Methoxy-phenyl)-ethyl]-piperazin-1-yl}-2-trifluoromethyl-4H-3-thia-1,4,9-triaza-benzo[f]azulene dihydrochloride

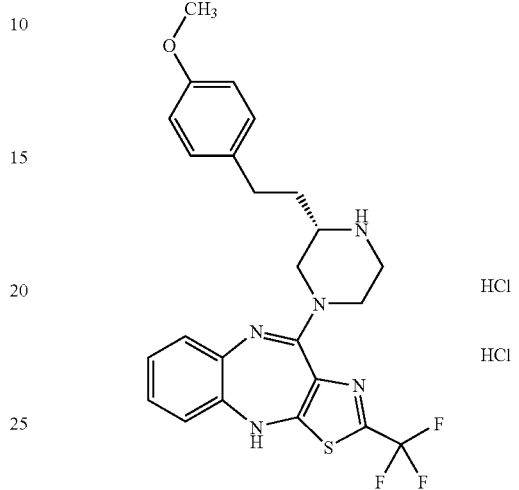

Using a method similar to Example 513, using (S)-10-{3-[2-(4-methoxy-phenyl)-ethyl]-piperazin-1-yl}-2-trifluoromethyl-4H-3-thia-1,4,9-triaza-benzo[f]azulene (0.252 g, 0.517 mmol) and a solution of acetyl chloride (0.184 mL, 2.58 mmol) in absolute ethanol at ambient temperature gives the title compound (0.258 g): Exact mass spectrum (ES+, m/e, $C_{24}H_{24}F_3N_5OS.2HCl$): calc. 488.1732 (M+1−2HCl), found 488.1732.

Example 520

(S)-10-{3-[2-(3-Methoxy-phenyl)-ethyl]-4-methyl-piperazin-1-yl}-2-trifluoromethyl-4H-3-thia-1,4,9-triaza-benzo[f]azulene

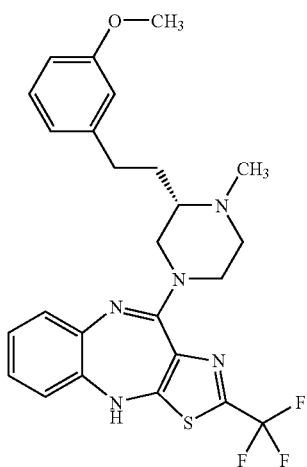

Add sodium triacetoxyborohydride (0.23 g, 1.1 mmol) and aqueous formaldehyde (37% w/w, 0.083 mL, 1.1 mmol) to a solution of (S)-10-{3-[2-(3-methoxy-phenyl)-ethyl]-piperazin-1 yl}-2-trifluoromethyl-4H-3-thia-1,4,9-triaza-benzo[f]azulene (0.36 g, 0.74 mmol) in methanol: dichloroethane (1:1) and stir. After 1.5 hours, concentrate the reaction under reduced pressure to remove methanol, and then dilute with a saturated aqueous solution of sodium bicarbonate and dichloromethane, and separate the layers. Extract the aqueous layer with dichloromethane (2×), combine organics, and dry (sodium sulfate), filter, and concentrate under reduced pressure to a residue. Purify the residue by flash chromatography, eluting with a gradient of a solution of ethyl acetate: hexane (1:1) with 1% 2M ammonia in methanol added (40–100% in hexane over 30 minutes, then 100% for 10 minutes) to give the title compound (0.223 g, 60%): mass spectrum (APCI+, m/e): 502 (M+1); $^1$H NMR (300 MHz, DMSO-$d_6$), δ (ppm): 8.48 (s, 1H), 7.19–7.10 (m, 1H), 6.97–6.81 (m, 3H), 6.76–6.67 (m, 4H), 3.96–3.76 (br. m, 2H), 3.68 (s, 3H), 3.15–3.02 (m, 1H), 2.93–2.81 (m, 1H), 2.80–2.69 (m, 1H), 2.65–2.34 (m, 2H), 2.27–2.04 (m, 5H), 1.91–1.75 (m, 1H), 1.66–1.48 (m, 1H).

Example 521

(S)-10-{3-[2-(3-Methoxy-phenyl)-ethyl]-4-methyl-piperazin-1-yl}-2-trifluoromethyl-4H-3-thia-1,4,9-triaza-benzo[f]azulene dihydrochloride

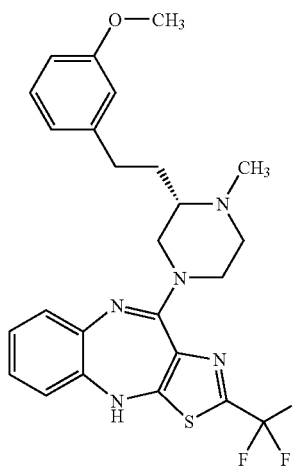

Using a method similar to Example 513, using (S)-10-{3-[2-(3-methoxy-phenyl)-ethyl]-4-methyl-piperazin-1-yl}-2-trifluoromethyl-4H-3-thia-1,4,9-triaza-benzo[f]azulene (0.223 g, 0.445 mmol) and a solution of acetyl chloride (0.157 mL, 2.22 mmol) in absolute ethanol at ambient temperature gives the title compound. Exact mass spectrum (ES+, m/e, $C_{25}H_{26}F_3N_5OS$·2HCl): calc. 502.1888 (M+1−2HCl), found 502.1885.

Example 522

(S)-10-{3-[2-(3-Fluoro-phenyl)-ethyl]-4-methyl-piperazin-1-yl}-2-trifluoromethyl-4H-3-thia-1,4,9-triaza-benzo[f]azulene

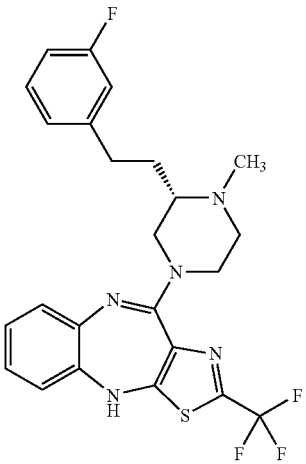

Following the method similar to Example 520, using (S)-10-{3-[2-(3-fluoro-phenyl)-ethyl]-piperazin-1-yl}-2-trifluoromethyl-4H-3-thia-1,4,9-triaza-benzo[f]azulene (0.37 g, 0.78 mmol), sodium triacetoxyborohydride (0.25 g, 1.2 mmol), and aqueous formaldehyde (0.0875 mL, 1.17 mmol) in methanol: dichloroethane gives the title compound (0.213 g): mass spectrum (APCI+, m/e): 490 (M+1); $^1$H NMR (300 MHz, DMSO-$d_6$), δ (ppm): 8.47 (s, 1H), 7.32–7.22 (m, 1H), 7.06–6.81 (m, 6H), 6.75–6.67 (m, 1H), 4.00–3.75 (m, 2H), 3.17–3.03 (m, 1H), 2.93–2.81 (m, 1H), 2.80–2.70 (m, 1H), 2.69–2.40 (m, 2H), 2.29–2.04 (m, 5H), 1.91–1.76 (m, 1H), 1.68–1.51 (m, 1H).

Example 523

(S)-10-{3-[2-(3-Fluoro-phenyl)-ethyl]-4-methyl-piperazin-1-yl}-2-trifluoromethyl-4H-3-thia-1,4,9-triaza-benzo[f]azulene dihydrochloride

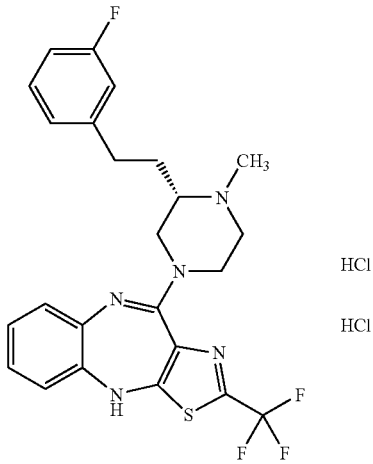

Using a method similar to Example 520, using (S)-10-{3-[2-(3-fluoro-phenyl)-ethyl]-4-methyl-piperazin-1-yl}-2-trifluoromethyl-4H-3-thia-1,4,9-triaza-benzo[f]azulene (0.213 g, 0.435 mmol) and a solution of acetyl chloride (0.155 mL, 2.18 mmol) in absolute ethanol at ambient temperature gives the title compound: mass spectrum (APCI+, m/e): 490 (M+1−2HCl); exact mass spectrum (ES+, m/e, $C_{24}H_{23}F_4N_5S$·2HCl calc. 490.1689 (M+1−2HCl), found 490.1686.

Example 524

(S)-10-{3-[2-(4-Methoxy-phenyl)-ethyl]-4-methyl-piperazin-1-yl}-2-trifluoromethyl-4H-3-thia-1,4,9-triaza-benzo[f]azulene

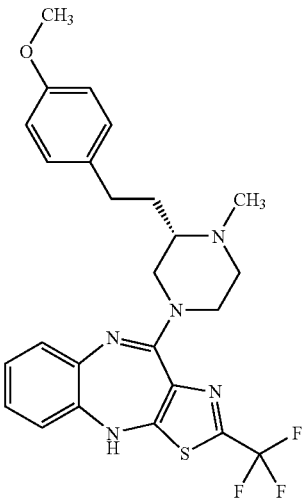

Following a method similar to the method of Example 520, using (S)-10-{3-[2-(4-methoxy-phenyl)-ethyl]-piperazin-1-yl}-2-trifluoromethyl-4H-3-thia-1,4,9-triaza-benzo[f]azulene (0.36 g, 0.74 mmol), sodium triacetoxyborohydride (0.23 g, 1.1 mmol), and aqueous formaldehyde (0.083 mL, 1.1 mmol) in methanol: dichloroethane gives the title compound (0.255 g): mass spectrum (APCI+, m/e): 502 (M+1); $^1$H NMR (300 MHz, DMSO-$d_6$), δ (ppm): 8.48 (s, 1H), 7.11–7.00 (m, 2H), 6.97–6.82 (m, 3H), 6.82–6.75 (m, 2H), 6.75–6.68 (m, 1H), 3.96–3.78 (m, 2H), 3.69 (s, 3H), 3.15–3.02 (m, 1H), 2.91–2.67 (m, 2H), 2.61–2.28 (m, 2H), 2.25–2.00 (m,. 5H),.1.88–1.72 (m, 1H), 1.61–1.44 (m, 1H).

Example 525

(S)-10-{3-[2-(4-Methoxy-phenyl)-ethyl]-4-methyl-piperazin-1-yl}-2-trifluoromethyl-4H-3-thia-1,4,9-triaza-benzo[f]azulene dihydrochloride

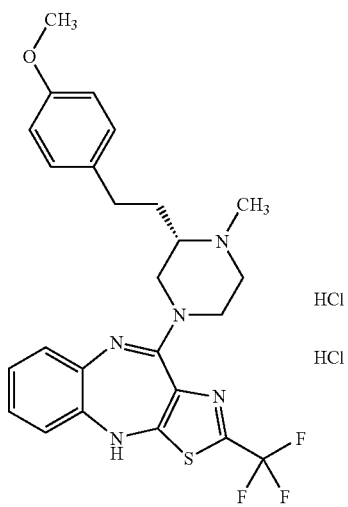

Using a method similar to the method of 513, using (S)-10-{3-[2-(4-methoxy-phenyl)-ethyl]-4-methyl-piperazin-1-yl}-2-trifluoromethyl-4H-3-thia-1,4,9-triaza-benzo[f]azulene (0.255 g, 0.508 mmol) and a solution of acetyl chloride (181 mL, 2.54 mmol) in absolute ethanol at ambient temperature gives the title compound (0.269 g): mass spectrum (APCI+, m/e): 502 (M+1−2HCl); exact mass spectrum (ES+, m/e, $C_{25}H_{26}F_3N_5OS$.2HCl): calc. 502.1888 (M+1−2HCl), found 502.1881.

Example 526

(S)-10-{3-[2-(4-Fluoro-phenyl)-ethyl]-4-methyl-piperazin-1-yl}-2-trifluoromethyl-4H-3-1,4,9-triaza-benzo[f]azulene

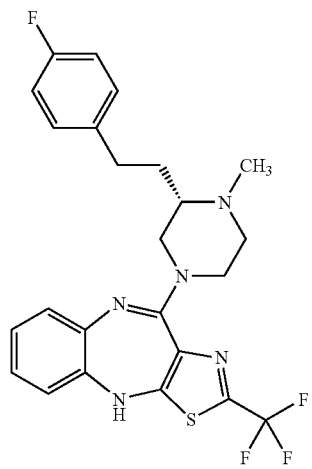

Using a method similar to Example 486, using (S)-10-{3-[2-(4-fluoro-phenyl)-ethyl]-piperazin-1-yl}-2-trifluoromethyl-4H-3-thia-1,4,9-triaza-benzo[f]azulene (0.36 g, 0.76 mmol) gives partial conversion to the title compound after overnight stirring at ambient temperature. Add another 1.3 equivalents of aqueous formaldehyde (0.074 mL, 0.98 mmol), methanol, and deionized water. After 2.5 hours, concentrate the reaction under reduced pressure to remove methanol and water. Dilute the reaction with a saturated aqueous solution of sodium bicarbonate, and dichloromethane, and separate the layers. Extract the aqueous layer with dichloromethane (2×), combine the organics, and dry (sodium sulfate), filter, and concentrate them under reduced pressure to a residue. Purify the residue by flash chromatography, eluting with a gradient of a solution of ethyl acetate: hexane (1:1) with 1% 2M ammonia in methanol added (40–100% in hexane over 30 minutes, then 100% for 10 minutes) to give the title compound (0.392 g). Mass spectrum (APCI+, m/e): 490 (M+1); $^1$H NMR (300 MHz, DMSO-$d_6$), δ (ppm): 8.49 (s, 1H), 7.24–7.13 (m, 2H), 7.11–7.00 (m, 2H), 6.97–6.81 (m, 3H), 6.75–6.68 (m, 1H), 3.96–3.75 (m, 2H), 3.16–3.03 (m, 1H), 2.92–2.80 (m, 1H), 2.79–2.69 (m, 1H), 2.66–2.37 (m, 2H), 2.28–2.01 (m, 5H), 1.89–1.73 (m, 1H), 1.65–1.47 (m, 1H).

Example 527

(S)-10-{3-[2-(4-Fluoro-phenyl)-ethyl]-4-methyl-piperazin-1-yl}-2-trifluoromethyl-4H-3-thia-1,4,9-triaza-benzo[f]azulene dihydrochloride

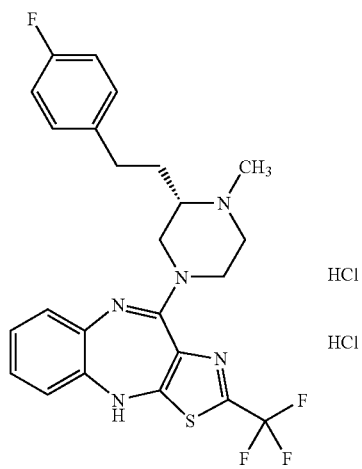

Using the method similar to Example 513, using (S)-10-{3-[2-(4-fluoro-phenyl)-ethyl]-4-methyl-piperazin-1-yl}-2-trifluoromethyl-4H-3-thia-1,4,9-triaza-benzo[f]azulene (0.392 g, 0.801 mmol) and a solution of acetyl chloride (0.286 mL, 4.01 mmol) in absolute ethanol at ambient temperature gives the title compound (0.269 g): mass spectrum (APCI+, m/e): 490 (M+1−2HCl); exact mass spectrum (ES+, m/e, $C_{24}H_{23}F_4N_5S·2HCl$): calc. 490.1689 (M+1−2HCl), found 490.1690.

Example 528

3-Bromo-2-nitro-benzo[b]thiophene

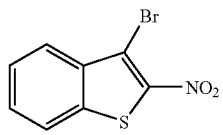

Add dropwise fuming nitric acid(90%, 8.6 mL, 183 mmol) to a mixture of 3-bromo benzo[b]thiophene (39g, 183 mmol) in TFA(100 mL) and dichloromethane (400mL) at 0° C. The reaction turn greenish, then yellow precipitates. To this reaction mixture, add dichloromethane (200 mL) and the reaction stir at 0° C. for 30 min. Then pour the reaction into ice-water (2 L). Extract with dichloromethane (3×500mL) and the organic layer dry over MgSO4. Evaporation give a yellow solid. The resulting yellow solid triturate with diethyl ether to give a yellow solid. (Total: 34.8 g, 73%). Mass spectrum (m/e): 259 (M+1); $^1$HNMR(300 MHz, DMSO-$d_6$) δ ppm: 7.70 (tt, 2H), 8.04 (d, 1H), 8.17 (d, 1H). $^3$CNMR(75 MHz, DMSO-$d_6$) δ ppm: 112.5, 124.8, 126.9, 127.9, 131.3, 137.0, 137.2, 166.1.

Example 529

2-Nitro-Benzo[b]thiophene-3-carbonitrile

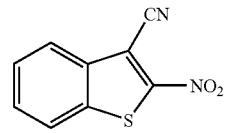

Combine 3-bromo-2-nitro-benzo[b]thiophene (33.0 g, 127.4 mmol), copper cyanide (17.1 g, 191.1 mmol) in DMF(150 mL), heat to 120 ° C. for three hours. The reaction cool to RT, pour on ice, then filter. The filter cake wash with dichloromethane. The organic layer separate and dry over MgSO$_4$, evaporation to give a DMF solution. Add water (400 mL) and the yellow solid precipitate out. After filtration, obtain a brownish solid (23.5 g, 90%). Mass spectrum (m/e): 205 (M+1); $^1$HNMR (300 MHz, DMSO-d6) δ: 7.78 (m, 2H), 8.04 (d, 1H), 8.29 (d, 1H). $^{13}$CNMR(75 MHz, DMSO-d6)δppm: 105.9, 112.1, 125.0, 125.2, 128.8, 131.2, 135.9, 137.8, 158.0.

Example 530

2-Amino-benzo[b]thiophene-3-carbonitrile

Combine in a 500 mL schlenk flask, 2-nitro-benzo[b]thiophene-3-carbonitrile (5.8 g, 28.4 mmol) and Pd/C (3.0 g, 10% w/w, 2.84 mmol) in 1,2-dichloroethane (120 ml), the reaction mixture is charged with a balloon of hydrogen. After overnight stirring, release the hydrogen, remove the catalyst by filtration, and wash the catalyst by 1,2-dichloroethane several times. Concentrate down to a residue, which purified by flash chromatography on silica gel, gradient (100% hexane to 100% of Hexane:CH$_2$Cl$_2$:EtOAc=50:50:2.5), afford brownish solid 3.6 g of title compound (yield 73%). Mass spectrum: ES(+)(m/e): 175 (M+1); $^1$H NMR (300MHz, DMSO-d6, ppm): δ 7.81 (br, 2H), 7.65–7.62 (m, 1H), 7.28–7.24 (m, 2H), 7.11–7.01 (m, 1 H).

Example 531

2-(5-Fluoro-2-nitro-phenylamino)-benzo[b]thiophene-3-carbonitrile

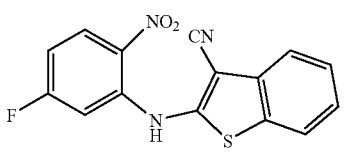

Combine 2-amino-benzo[b]thiophene-3-carbonitrile (2.25 g, 12.5 mmol), 2,4-difluoro-nitrobenzene (1.99 g, 12.5 mmol and Lithium hydroxide (0.58 g, 25 mmol) ) in 30 mL of DMSO and heat to 50 ° C., after 4 hours, cool the reaction to the RT, and pour on ice, stir for 30 min, extract with CH$_2$Cl$_2$, the combined solvent wash with water and brine, dry over Na$_2$SO$_4$. Concentrate down to a residue treat with MeOH, the orange precipitate collect by suction filtration give title compound, 2.15 g. Concentrate the filtrate and purify by flash chromatography to give 0.22 g orange solid. Total 2.35 g, yield 61%. Mass spectrum: ES(+) (m/e): 314 ((M+1): $^1$H NMR (300 MHz, DMSO-d6) δ: 10.35 (br, 1H), 8.31–8.25 (m, 1H), 8.00–7.96 (m, 1H), 7.68–7.65 (m, 1H), 7.53–7.37 (m, 3H), 7.13–7.07 9 m, 1H); $^{13}$CNMR (75 MHz, DMSO-d6) δ ppm: 165.5 (d, J=254.5 Hz), 156.2, 139.8 (d, J=12.5 Hz), 135.9, 134.8, 132.2, 129.3 (d, J=11.7 Hz), 126.3, 125.2, 123.0, 120.4, 113.5, 110.4 (d, J=24.0 Hz), 107.6 (d, J=27.4 Hz), 92.9.

Example 532

9-Fluoro-11H-12-thia-6,11-diaza-dibenzo[a,f]azulen-5-ylamine, hydrochloride

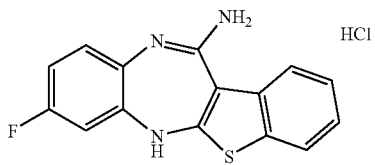

Combine 2-(5-fluoro-2-nitro-phenylamino)-benzo[b]thiophene-3-carbonitrile (2.15 g, 6.87 mmol) and Tin(II) chloride, dihydrate (4.65 g, 20.6 mmol) in a mixed solvent of EtOH (25 mL) and 5.0 N HCl (25 mL), heat the suspension to reflux for 3 hours, cool to RT. The title compound 1.73 g (yield 78%) is obtained as a yellow solid by suction filtration. Mass spectrum: ACPI (m/e): 284 ((M+1-HCl); $^1$H NMR (300 MHz, DMSO-d6) δ 11.46 (br, 1H), 10.02 (br, 1H), 9.02 (br, 2H), 7.90–7.87 (m, 1H), 7.71–7.68 (m, 1H), 7.46–7.40 (m, 1H), 7.33–7.28 (m, 1H), 7.12–6.94 (m, 2H), 6.85–6.81 (m, 1H).

Example 533

(S)-9-Fluoro-5-[3-phenethyl-piperazine-1-yl]-11H-12-thia-6,11-diaza-dibenzo[a,f]azulene

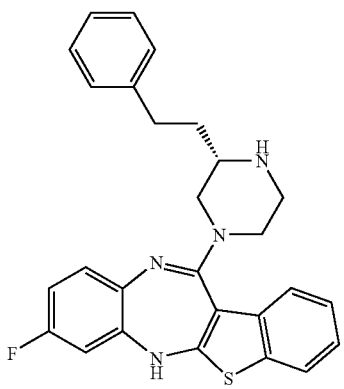

Combine 9-fluoro-11H-12-thia-6,11-diaza-dibenzo[a,f]azulen-5-ylamine hydrogen chloride (287 mg, 0.9 mmol), (S)-2-phenethyl-piperazine (340 mg, 1.80 mmol) and diisopropylethyl amine (116 mg, 0.9 mmol) in DMSO (0.5 mL) and toluene (2.0 mL), stir and microwave (300 W, 125 ° C.) for 8 h, then heat to 115 ° C. for 22 h. Cool the reaction to RT, dilute with CH$_2$Cl$_2$, wash with H$_2$O and brine. Dry the organic layer with by Na$_2$SO$_4$. The crude material purify by chromatography on silica gel, gradient (100% CH$_2$Cl$_2$ to 100% CH$_2$Cl$_2$:2N NH$_3$/MeOH=25:1), give 137 mg of title compound.

Example 534

(S)-9-Fluoro-5-[3-phenethyl-4-methyl-piperazine-1-yl]-11H-12-thia-6,11-diaza-dibenzo[a,f]azulene, dihydrochloride

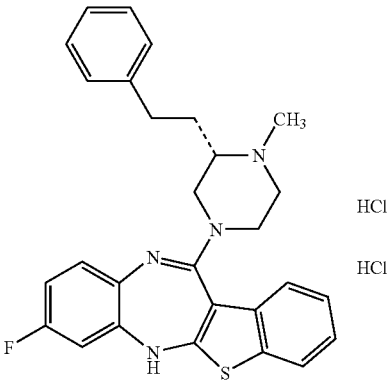

By using a method similar to the method of Example 492, using (S)-9-fluoro-5-[3-phenethyl-piperazine-1-yl]-11H-12-thia-6,11-diaza-dibenzo[a,f]azulene, (92 mg, 0.2 mmol), formaldehyde (37%, w/w, aq) (20 mg, 0.25 mmol) and sodium triacetoxyborohydride (64 mg, 0.30 mmol) in 3 mL 1,2-dichloroethane and stir at RT. After purification, give 82 mg of free base. Mass spectrum: ACPI (m/e): 471.10 ((M+1-HCl) The dihydrochloric salt is form by adding 5 eq of acetyl chloride (68.4 mg, 0.89 mmol) to the free base (82 mg, 0.17 mmol) in ethanol (5 mL). After removing the solvent, the residue dissolve in 10 ml mix solvent of CH$_3$CN/H$_2$O=50/50, lyophilize overnight, afford 81 mg of title compound as yellow solid.

Example 535

(S)-9-Fluoro-5-{3-[2-(4-methoxy-phenyl)-ethyl]-piperazin-1-yl}-11H-12-thia-6,11-diaza-dibenzo[a,f]azulene

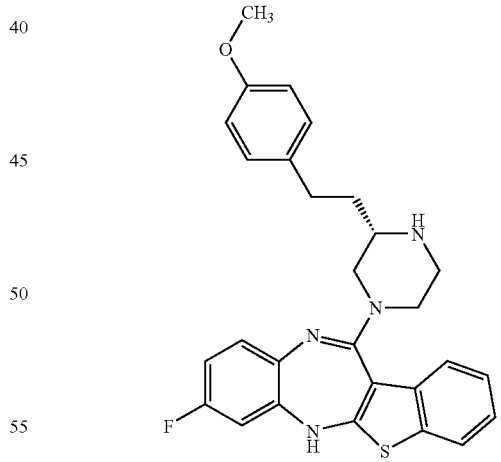

Add 9-fluoro-11H-12-thia-6,11-diaza-dibenzo[a,f]azulen-5-ylamine hydrochloride (0.66 g, 2.1 mmol) to a solution of (S)-2-[2-(4-methoxy-phenyl)-ethyl]-piperazine (0.91 g, 4.1 mmol) in dimethyl sulfoxide: toluene (1:8, 9 mL). Add diisopropylethylamine (0.36 mL, 2.1 mmol), heat to 110° C., and stir. After 51 hours, cool to ambient temperature, and dilute with ethyl acetate and 0.1 N NaOH. Separate the aqueous layer and extract it with ethyl acetate (2×). Wash all organics with a saturated solution of sodium chloride, and then dry (sodium sulfate), filter, and concentrate them under reduced pressure to an oil (1.27 g). Purify the oil by flash chromatography, eluting with a gradient of a 3% solution of 2M ammonia in methanol, in dichloromethane (0–100% in dichloromethane). Reconstitute the material in ethyl acetate and wash it with a saturated solution of sodium chloride (2×) to remove residual dimethylsulfoxide. Back extract the combined aqueous layers with ethyl acetate. Dry (sodium sulfate) the organic phases, filter, and concentrate them under reduced pressure to give the title compound (0.389 g): mass spectrum (APCI+, m/e): 487 (M+1).

Example 536

(S)-9-Fluoro-5-{3-[2-(4-methoxy-phenyl)-ethyl]-piperazin-1-yl}-11H-12-thia-6,11-diaza-benzo[a,f]azulene dihydrochloride

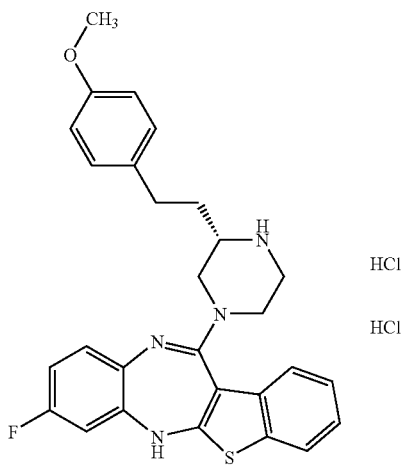

Using a method similar to the method Example 513, using (S)-9-fluoro-5-{3-[2-(4-methoxy-phenyl)-ethyl]-piperazin-1-yl}-11H-12-thia-6,11-diaza-dibenzo[a,f]azulene (0.070 g, 0.14 mmol) and a solution of acetyl chloride (0.052 mL, 0.72 mmol) in absolute ethanol at ambient temperature gives the title compound (0.76 g): mass spectrum (APCI+, m/e): 487 (M+1–2HCl); exact mass spectrum (ES+, m/e, $C_{28}H_{27}FN_4OS \cdot 2HCl$): calc. 487.1968 (M+1–2HCl), found 487.1972.

Example 537

(S)-9-Fluoro-5-{3-[2-(3-methoxy-phenyl)-ethyl]-piperazin-1-yl}-11H-12-thia-6,11-diaza-benzo[a,f]azulene

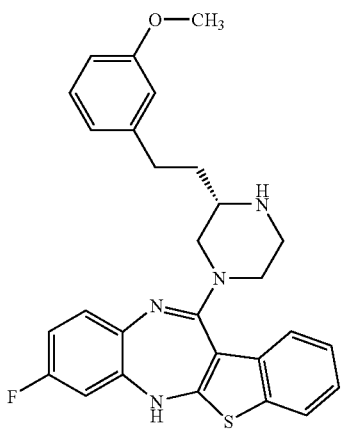

Using a method similar to the method of Example 535, using 9-fluoro-11H-12-thia-6, 11-diaza-dibenzo[a,f]azulen-5-ylamine hydrochloride (0.62 g, 1.9 mmol) and (S)-2-[2-(3-methoxy-phenyl)-ethyl]-piperazine (0.85 g, 3.9 mmol), and purifying by flash chromatography, eluting with a solution of 2% 2M ammonia in methanol, in dichloromethane (33–66% in dichloromethane over 7 minutes, 66–100% over 28 minutes, 100% for 23 minutes) gives the title compound (0.251 g): mass spectrum (APCI+, m/e): 487 (M+1).

Example 538

(S)-9-Fluoro-5-{3-[2-(3-methoxy-phenyl)-ethyl]-piperazin-1-yl}-11H-12-thia-6,11-diaza-benzo[a,f]azulene dihydrochloride

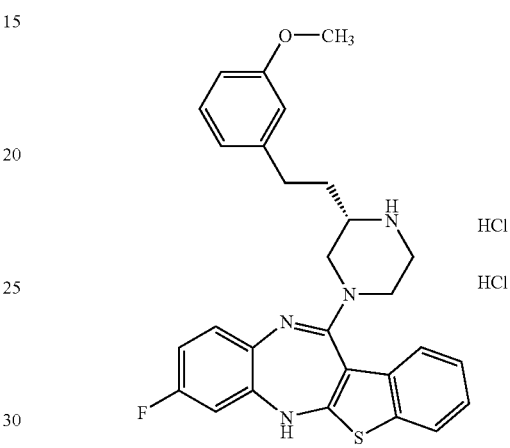

Using a method similar to the method of 513, using (S)-9-fluoro-5-{3-[2-(3-methoxy-phenyl)-ethyl]-piperazin-1-yl}-11H-12-thia-6,11-diaza-dibenzo[a,f]azulene (0.070 g, 0.14 mmol) and a solution of acetyl chloride (0.0514 mL, 0.720 mmol) in absolute ethanol at ambient temperature gives the title compound (0.081 g). Exact mass spectrum (ES+, m/e, $C_{28}H_{27}FN_4OS \cdot 2HCl$): calc. 487.1968 (M+1–2HCl), found 487.1973.

Example 539

(S)-9-Fluoro-5-{3-[2-(3-fluoro-phenyl)-ethyl]-piperazin-1-yl}-11H-12-thia-6,11-diaza-benzo[a,f]azulene

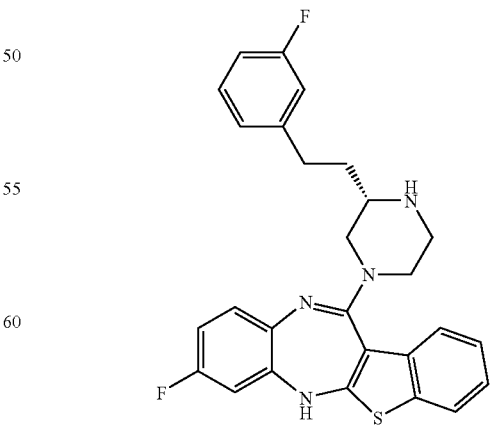

Using a method similar to the method of Example 535, using 9-fluoro-11H-12-thia-6,11-diaza-dibenzo[a,f]azulen- 5-ylamine hydrochloride (0.66 g, 2.1 mmol) and (S)-2-[2-(3-fluoro-phenyl)-ethyl]-piperazine (0.86 g, 4.1 mmol), stirring at 110° C. for 24 hours, and purifying by flash chromatography, eluting with a solution of 3% 2M ammonia in methanol, in dichloromethane (33–66% in dichloromethane over 15 minutes, 66–100% over 30 minutes, 100% for 13 minutes) gives the title compound (0.307 g). Mass spectrum (APCI+, m/e): 475 (M+1).

Example 540

(S)-9-Fluoro-5-{3-[2-(3-fluoro-phenyl)-ethyl]-piperazin-1-yl}-11H-12-thia-6,11-diaza-benzo[a,f]azulene dihydrochloride

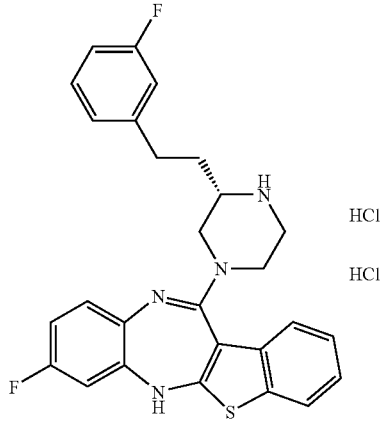

Using a method similar to the method 513, using (S)-9-Fluoro-5-{3-[2-(3-fluoro-phenyl)-ethyl]-piperazin-1-yl}-11H-12-thia-6,11-diaza-dibenzo[a,f]azulene (0.055 g, 0.12 mmol) and a solution of acetyl chloride (0.041 mL, 0.58 mmol) in absolute ethanol at ambient temperature gives the title compound (0.062 g). Mass spectrum (APCI+, m/e): 475 (M+1–2HCl); exact mass spectrum (ES+, m/e, $C_{27}H_{24}F_2N_4.S2HCl$): calc. 475.1768 (M+1–2HCl), found 475.1781.

Example 541

(S)-9-Fluoro-5-{3-[2-(4-fluoro-phenyl)-ethyl]-piperazin-1-yl}-11H-12-thia-6,11-diaza-benzo[a,f]azulene

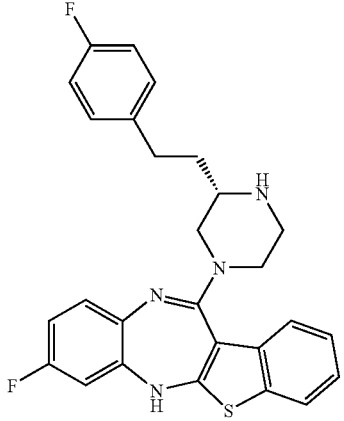

Using a method similar to the method of Example 535, using 9-fluoro-11H-12-thia-6,11-diaza-dibenzo[a,f]azulen-5-ylamine hydrochloride (0.66 g, 2.1 mmol) and (S)-2-[2-(4-fluoro-phenyl)-ethyl]-piperazine (0.86 g, 4.1 mmol), and stirring at 110 ° C. for 47.5 hours gives the title compound (0.426 g). Mass spectrum (APCI+, m/e): 475 (M+1).

Example 542

(S)-9-Fluoro-5-{3-[2-(4-fluoro-phenyl)-ethyl]-piperazin-1-yl}-11H-12-thia-6,11-diaza-benzo[a,f]azulene dihydrochloride

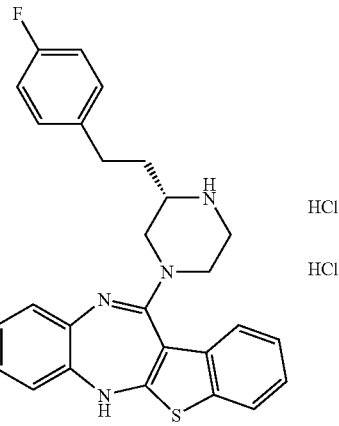

Using a method similar to the method 513, using (S)-9-fluoro-5-{3-[2-(4-fluoro-phenyl)-ethyl]-piperazin-1-yl}-11H-12-thia-6,11-diaza-dibenzo[a,f]azulene (0.062 g, 0.13 mmol) and a solution of acetyl chloride (0.047 mL, 0.66 mmol) in absolute ethanol at ambient temperature gives the title compound (0.072 g). Mass spectrum (APCI+, m/e): 475 (M+1–2HCl); exact mass spectrum (ES+, m/e, $C_{27}H_{24}F_2N_4S.2HCl$): calc. 475.1768 (M+1–2HCl), found 475.1787.

Example 543

(S)-9-Fluoro-5-{3-[2-(4-methoxy-phenyl)-ethyl]-4-methyl-piperazin-1-yl}-11H-12-thia-6,11-diaza-dibenzo[a,f]azulene

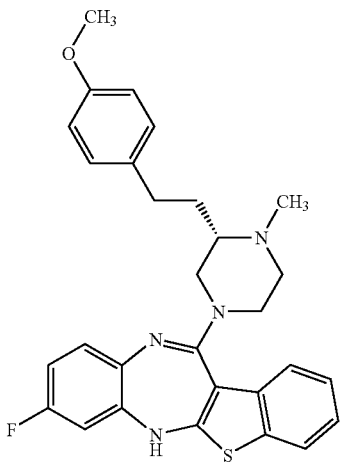

Add sodium triacetoxyborohydride (0. 183 g, 0.863 mmol) and aqueous formaldehyde (37% w/w, 0.065 mL, 0.86 mmol) to a solution of(S)-9-fluoro-5-{3-[2-(4-methoxy-phenyl)-ethyl]-piperazin-1-yl}-11H-12-thia-6,11-diaza-dibenzo[a,f]azulene (0.28 g, 0.58 mmol) in dichloroethane and stir. After 2 hours, dilute with a saturated aqueous solution of sodium bicarbonate and dichloromethane, and separate the layers. Extract the aqueous layer with dichloromethane. (2×), combine organics, and wash them with a saturated solution of sodium chloride. Dry (sodium sulfate) the organics, filter, and concentrate them under reduced pressure to a residue (0.38 g). Purify the residue by flash chromatography, eluting with a gradient of a solution of ethyl acetate: hexane (3:2) with 1% 2M ammonia in methanol added (in hexane) to give the title compound: (0.214 g, 74%). Mass spectrum (APCI+, m/e): 501 (M+1).

Example 544

(S)-9-Fluoro-5-{3-[2-(4-methoxy-phenyl)-ethyl]-4-methyl-piperazin-1-yl}-11H-12-thia-6,11-diaza-dibenzo[a,f]azulene dihydrochloride

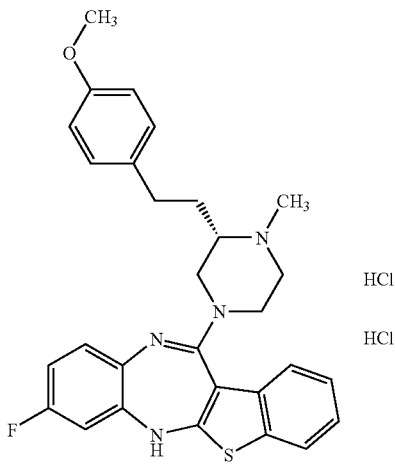

Add a solution of acetyl chloride (0.144 mL, 2.02 mmol) in absolute ethanol to a solution of (S)-9-fluoro-5-{3-[2-(4-methoxy-phenyl)-ethyl]-4-methyl-piperazin-1-yl}-11H-12-thia-6,11-diaza-dibenzo[a,f]azulene (0.174 g, 0.348 mmol) in absolute ethanol and stir briefly at ambient temperature. Concentrate solution under reduced pressure to give an orange solid. Reconstitute the solid in acetonitrile: water (1:1), freeze-dry the solution in a dry-ice/acetone bath, and lyophilize overnight to give the title compound (0.208 g) as a yellow solid: mass spectrum (APCI+, m/e): 501 (M+1−2HCl); exact mass spectrum (ES+, m/e, $C_{29}H_{29}FN_4OS \cdot 2HCl$): calc. 501.2124 (M+1−2HCl), found 501.2130.

Example 545

(S)-9-Fluoro-5-{3-[2-(3-methoxy-phenyl)-ethyl]-4-methyl-piperazin-1-yl}-11H-12-thia-6,11-diaza-dibenzo[a,f]azulene

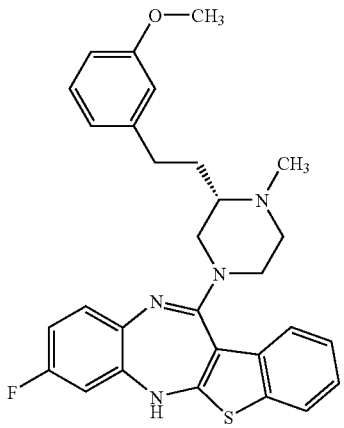

Using a method similar to the method of Example 543, using (S)-9-fluoro-5-{3-[2-(3-methoxy-phenyl)-ethyl]-piperazin-1-yl}-11H-12-thia-6,11-diaza-dibenzo[a,f]azulene (0.164 g, 0.337 mmol), sodium triacetoxyborohydride (0.107 g, 0.505 mmol), and aqueous formaldehyde (0.038 mL, 0.50 mmol) in dichloroethane gives the title compound (0.136 g): mass spectrum (APCI+, m/e): 501 (M+1).

Example 546

(S)-9-Fluoro-5-{3-[2-(3-methoxy-phenyl)-ethyl]-4-methyl-piperazin-1-yl}-11H-11-thia-6,11-diaza-dibenzo[a,f]azulene dihydrochloride

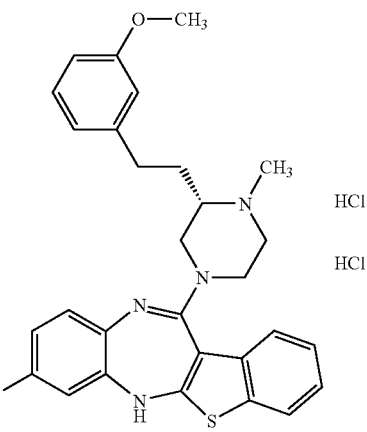

Using a method similar to the method of Example 544, using (S)-9-fluoro-5-{3-[2-(3-methoxy-phenyl)-ethyl]-4-methyl-piperazin-1-yl}-11H-12-thia-6,11-diaza-dibenzo[a,f]azulene (0.110 g, 0.220 mmol) and a solution of acetyl chloride (0.0784 mL, 1.10 mmol) in absolute ethanol at ambient temperature gives the title compound (0.123 g). Mass spectrum (APCI+, m/e): 501 (M+1−2HCl); exact mass spectrum (ES+, m/e, $C_{29}H_{29}FN_4OS \cdot 2HCl$): calc. 501.2124 (M+1−2HCl), found 501.2136.

Example 547

(S)-9-Fluoro-5-{3-[2-(3-fluoro-phenyl)-ethyl]-4-methyl-piperazin-1-yl}-11H-12-thia-6,11-diaza-dibenzo[a,f]azulene

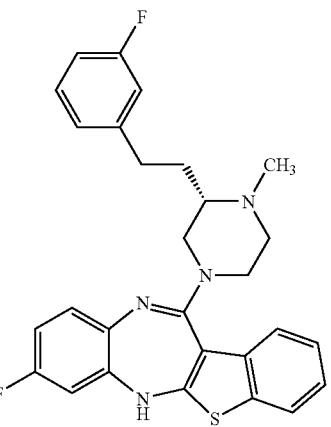

Using a method similar to Example 543, using (S)-9-fluoro-5-{3-[2-(3-fluoro-phenyl)-ethyl]-piperazin-1-yl}-1H-12-thia-6,11-diaza-dibenzo[a,f]azulene (0.218 g, 0.459 mmol), sodium triacetoxyborohydride (0.146 g, 0.689 mmol), and aqueous formaldehyde (0.052 mL, 0.69 mmol) in dichloroethane gives the title compound (0.185 g). Mass spectrum (APCI+, m/e): 489 (M+1).

Example 548

(S)-9-Fluoro-5-{3-[2-(3-fluoro-phenyl)-ethyl]-4-methyl-piperazin-1-yl}-11H-12-thia-6,11-diaza-dibenzo[a,f]azulene dihydrochloride

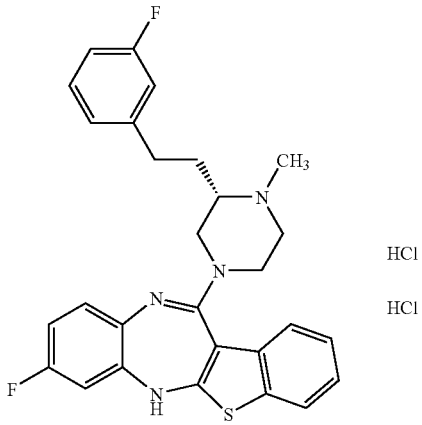

Using a method similar to the method of Example 544, using (S)-9-fluoro-5-{3-[2-(3-fluoro-phenyl)-ethyl]-4-methyl-piperazin-1-yl}-11H-12-thia-6,11-diaza-dibenzo[a,f]azulene (0.144 g, 0.294 mmol) and a solution of acetyl chloride (0.105 mL, 1.47 mmol) in absolute ethanol at ambient temperature gives the title compound (0.179 g). Mass spectrum (APCI+, m/e): 489 (M+1–2HCl); exact mass spectrum (ES+, m/e, $C_{28}H_{26}F_2N_4S$.2HCl): calc. 489.1924 (M+1–2HCl), found 489.1918.

Example 549

(S)-9-Fluoro-5-{3-[2-(4-fluoro-phenyl)-ethyl]-4-methyl-piperazin-1-yl}-11H-12-thia-6,11-diaza-dibenzo[a,f]azulene

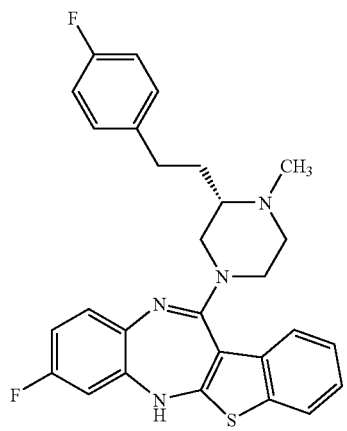

Using a method similar to the method of Example 543, using (S)-9-fluoro-5-{3-[2-(4-fluoro-phenyl)-ethyl]-piperazin-1-yl}-11H-12-thia-6,11-diaza-dibenzo[a,f]azulene (0.339 g, 0.714 mmol), sodium triacetoxyborohydride (0.227 g, 1.07 mmol), and aqueous formaldehyde (0.080 mL, 1.1 mmol) in dichloroethane, and employing a second chromatographic purification, eluting with a gradient of a solution of ethyl acetate: hexane (1:1) with 2% 2M ammonia in methanol (in hexane) added, gives the title compound (0.238 g). Mass spectrum (APCI+, m/e): 489 (M+1).

Example 550

(S)-9-Fluoro-5-{3-[2-(4-fluoro-phenyl)-ethyl]-4-methyl-piperazin-1-yl}-11H-12-thia-6,11-diaza-dibenzo[a,f]azulene dihydrochloride

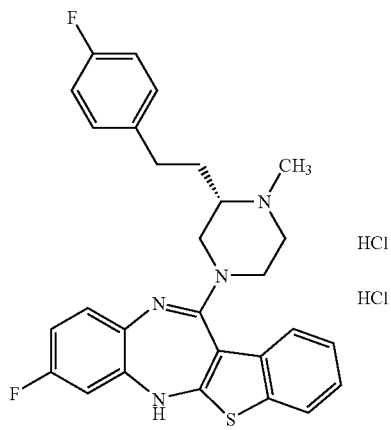

Using a method similar to the method of Example 544, using (S)-9-fluoro-5-{3-[2-(4-fluoro-phenyl)-ethyl]-4-methyl-piperazin-1-yl}-11H-12-thia-6,11-diaza-dibenzo[a,f]azulene (0.206 g, 0.422 mmol) and a solution of acetyl chloride (0.151 mL, 2.12 mmol) in absolute ethanol at ambient temperature gives the title compound (0.228 g): mass spectrum (APCI+, m/e): 489 (M+1–2HCl); exact mass spectrum (ES+, m/e, $C_{28}H_{26}F_2N_4S$.2HCl): calc. 489.1924 (M+1–2HCl), found 489.1918.

Example 551

2-(2-nitro-phenylamino)-benzo[b]thiophene-3-carbonitrile

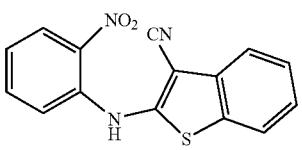

By using a method similar to the method of Example 490, combine 2-amino-benzo[b]thiophene-3-carbonitrile (3.56 g, 20.5 mmol), 2-fluoro-nitrobenzene (2.88 g, 20.5 mmol) and Lithium hydroxide (0.96 g, 41.0 mmol) ) in 50 mL of DMSO and heat to 50 ° C., after over night heating to give 5.0 g, yield 83%. Mass spectrum: ES(+) (m/e): 296.0 ((M+1); $^1$H NMR (400 MHz, DMSO-d6) ppm: 10.27 (s, 1H), 8.13 (dd, 1H, J=1.7 Hz, J=8.3 Hz), 7.91–7.89 (m, 1H), 7.76–7.72 (m, 1H), 7.64–7.57 (m, 2 H), 7.48–7.44 (m, 1H), 7.36–7.32 (m, 2H).

Example 552

11H-12-thia-6,11-diaza-dibenzo[a,f]azulen-5-ylamine hydrochloride

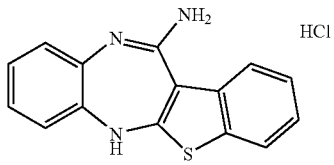

By using a method similar to the method of Example 532, combine 2-(2-nitro-phenylamino)-benzo[b]thiophene-3-carbonitrile (5.0 g, 17.0 mmol) and Tin(II) chloride (9.65 g, 51.0 mmol) in a mixed solvent of EtOH (50 mL) and 5.0 N HCl (50 mL), heat the suspension to reflux for 3 hours, cool to RT. The title compound 4.65 g (yield 91%) is obtained as a yellow solid by suction filtration. Mass spectrum: ACPI (m/e): 266.0 ((M+1-HCl); $^1$H NMR (300 MHz, DMSO-d6) ppm: 11.7 (br, 1H), 10.00 (br, 1H), 9.10 (br, 2H), 7.90–7.85 (m, 1H), 7.72–7.65 (m, 1H), 7.48–7.38 (m, 1H), 7.35–7.28 (m, 1H), 7.22–6.98 (m, 4H).

Example 553

2-(2-Nitro-phenylamino)-benzonitrile

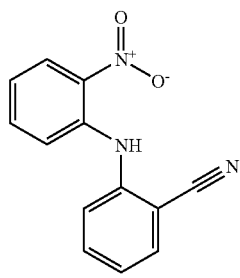

Combine 1-fluoro-2-nitro-benzene (5.00 g, 35.44 mmol), 2-amino-benzonitrile (4.19 g, 35.44 mmol), lithium hydroxide monohydrate (2.97 g, 70.87 mmol) and DMSO (50.0 ml). Stir the mixture at 55 °C. for 19 hours then cool to ambient temperature. Pour the mixture onto ice chips and stir for 1 hour. Remove the resulting precipitate by vacuum filtration. Dry the precipitate under vacuum to give 6.14 g (72%) of an orange solid: mp 134–138°.

Example 554

5H-Dibenzo[b,e][1.4]diazepin-11-ylamine hydrochloride

Combine 2-(2-Nitro-phenylamino)-benzonitrile (6.14 g, 25.66 mmol), tin(II) chloride dihydrate (17.37 g, 76.99 mmol), 5N HCl (105 ml), and ethanol (65.0 ml). Stir the mixture at reflux for 24 hours then cool it to ambient temperature and chill it in the refrigerator for 2 hours. Remove the ethanol under vacuum and chill in the refrigerator again. Filter off the resulting precipitate by vacuum filtration and dry it in a vacuum oven to give 6.31 g (100%) of a yellow solid: mass spectrum (ion spray): m/z=210.0 (M+1).

Example 555

2-Amino-5-isopropyl-benzonitrile

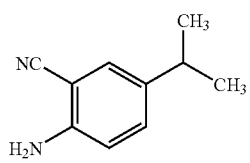

Combine 2-bromo-4-isopropyl aniline (7.5 g, 35 mmol) and copper (I) cyanide (3.76 g, 42 mmol) in NMP (30.0 mL) and heat at 200° C. for 2 hours. Cool to ambient temperature and dilute with water (300 mL). Extract with ethyl acetate to give 4.58 g of the crude product. Silica gel chromatography, eluting with methylene chloride, gives 3.20 g of the title compound as a red oil: mass spectrum (ion spray): m/z=161 (M+1); $^1$H NMR (300 MHz, DMSO-d$_6$): δ 7.21 (m, 2H), 6.73 (d, 1H), 5.79 (s, 2H), 2.73 (quintet, 1H), 1.12 (d, 6H).

Example 556

5-Isopropyl-2-(2-nitro-phenylamino)-benzonitrile

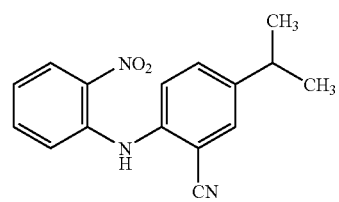

Combine 2-amino-5-isopropyl-benzonitrile (3.19 g, 20 mmol), 1-fluoro-2-nitro benzene (2.1 mL, 20 mmol) and lithium hydroxide (1.68 g, 40 mmol) in DMSO (40.0 mL) and heat at 55° C. for 19 hours. Cool to ambient temperature and dilute with water (200 mL). The title compound precipitates as 4.56 g of an orange solid: mp 91–96° C.; mass spectrum (ion spray) m/z=280 (M+1).

Example 557

2-Isopropyl-5H-dibenzo[b,e][1,4]diazepin-11-ylamine hydrochloride

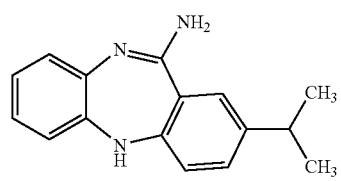

Combine 5-isopropyl-2-(2-nitro-phenylamino)-benzonitrile (4.54 g, 16.1 mmol) and tin (II) chloride (10.92 g, 48.4 mmol) in 65.0 mL of 5N HCl solution and 65.0 mL of ethanol. Heat this mixture at 86° C. for 18 hours. Chilling the mixture precipitates the title compound as 4.22 g of a yellow solid: mp>250° C.; mass spectrum (ion spray): m/z=252 (M+1).

Example 558

2-Amino-5-isopropyl-benzonitrile

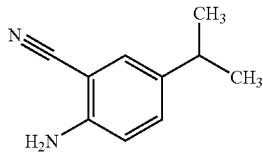

Heat a mixture of copper (I) cyanide (2.5 g, 28.02 mmol), and 2-bromo4-isopropyl-phenylamine (5.0 g, 23.35 mmol) in 1-methyl-2-pyrrolidinone (20 ml) to 195° C. for four hours. Dilute the reaction mixture with 100 ml of ethyl acetate and wash the dark solution twice with 28% aqueous ammonium hydroxide, twice with saturated aqueous sodium chloride (brine) and twice with water. Collect the organic layer, dry over sodium sulfate and remove the solvent under reduced pressure. Purify the residue via flash chromatography eluting with a step gradient starting with hexanes and going to 80% hexanes with 20% ethyl acetate to obtain 3.31 g (20.66 mmol, 88% yield) of the title compound as an orange oil: Mass Spectrum (m/e): 161(M+1).

Example 559

2-(4-Fluoro-2-nitro-phenylamino)-5-isopropyl-benzonitrile

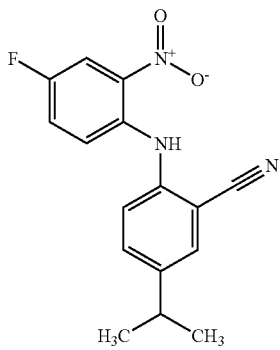

Heat a solution of 2-amino-5-isopropyl-benzonitrile (1.482 g, 9.25 mmol) with 1,4-difluoro-2-nitro-benzene (1.47 g, 9.25 mmol) and lithium hydroxide monohydrate (0.78 g, 18.50 mmol) in DMSO (20 ml) to 70° C. for 38 hours. Cool the reaction to ambient temperature and then pour into approximately 200 ml of ice water and stir for one hour. The title compound precipitates and collection by filtration to obtain 2.236 g (7.47 mmol, 81% yield) of the title compound as an orange amorphous solid: Mass Spectrum (m/e): 300(M+1).

Example 560

8-Fluoro-2-isopropyl-5H-dibenzo[b,e][1,4]diazepin-11-ylamine hydrochloride

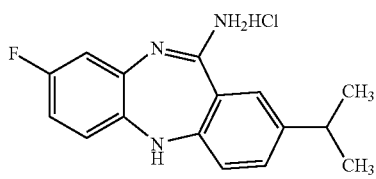

By using a method similar to the method of Example 532, using 2-(4-fluoro-2-nitro-phenylamino)-5-isopropyl-benzonitrile (0.559 g, (1.87 mmol), tin (II) chloride(1.06 g, 5.60 mmol) to obtain (0.422 g, 1.38 mmol, 74% yield) of the title compound as a yellow amorphous solid: Mass Spectrum (m/e): 270(M+1).

Example 561

2-(4-Fluoro-2-nitro-phenylamino)-5-methyl-benzonitrile

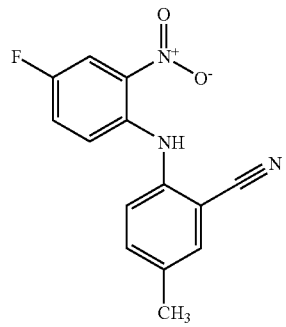

Combine 4-fluoro-2-nitro-phenylamine (2.9 g, 18.50 mmol), 2-fluoro-5-methyl-benzonitrile (2.5 g, 18.50 mmol) and lithium hydroxide monohydrate (2.4 g, 57.20 mmol) in methyl sulfoxide (DMSO, 40 ml). Heat the resulting mixture to 55° C. for 40 hours. Cool the reaction mixture to ambient temperature, then pour into approximately 250 ml of ice water and stir for one hour. Filter the resulting mixture and collect the precipitate. Chromatograph the solid using flash chromatography and elute with mobile phase: 90% hexanes, 5% ethyl acetate, and 5% dichloromethane. Obtained 2.267 g of the title compound (8.36 mmol, 45% yield) as an orange amorphous solid.

Mass Spectrum (m/e): 272(M+1).

Example 562

8-Fluoro-2-methyl-5H-dibenzo[b,e][1,4]diazepin-11-ylamine hydrochloride

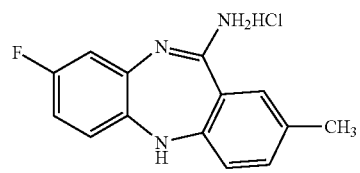

Heat a solution of 2-([4]-fluoro-2-nitro-phenylamino)-5-methyl-benzonitrile (1.747 g, 6.44 mmol) in ethanol (35 ml) to 60° C. and add a solution of tin (II) chloride (6.06 g, 31.96 mmol) in 5.0 N hydrochloric acid (35 ml). Reflux the resulting mixture to reflux for 40 hours. Cool the reaction to room temperature and place in a freezer for 16 hours. The product precipitates from the solution and is collected by filtration to obtain 1.3 g of the title compound (4.68 mmol, 73% yield) as a yellow-green amorphous solid: Mass Spectrum (m/e): 241 (M+1).

Example 563

4-methyl-2-(2-nitro-phenylamino)-benzonitrile

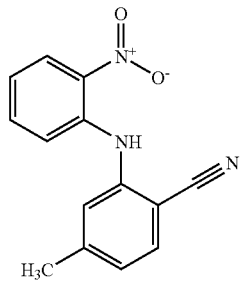

Combine 1-fluoro-2-nitro-benzene (5.34 g, 37.83 mmol), 2-amino-4-methyl-benzonitrile (5.00 g, 37.83 mmol), lithium hydroxide monohydrate (3.17 g, 75.66 mmol) and DMSO (70.0 ml). Stir the mixture at 55° C. for 16 hours then cool it to ambient temperature. Pour the mixture onto ice chips and stir for 1 hour. Remove the resulting yellow precipitate by vacuum filtration. Dry the precipitate under vacuum then recrystallize it in ethanol to give 5.15 g (54%) of fine, amber colored needles: mp 162–164°; mass spectrum (ion spray): m/z=254.0 (M+1).

Example 564

5-methyl-2-(2-nitro-phenylamino)-benzonitrile

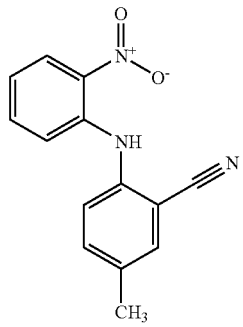

Combine 1-fluoro-2-nitro-benzene (4.34 g, 30.79 mmol), 2-amino-5-methyl-benzonitrile (4.07 g, 30.79 mmol), lithium hydroxide monohydrate (2.58 g, 61.58 mmol) and DMSO (50.0 ml). Stir the mixture at 55° C. for 22 hours then cool it to ambient temperature. Pour the mixture onto ice chips and stir for 1 hour. Remove the resulting precipitate by vacuum filtration. Dry the precipitate under vacuum then purify it on silica gel using dichloromethane/hexanes (75:25) to give 4.45 g (57%) of an orange solid: mp 135–139°; mass spectrum (ion spray): m/z=254.0 (M+1).

Example 565

2-Amino-5-methyl-benzonitrile

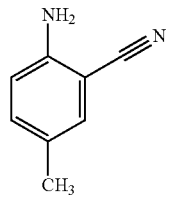

Combine 2-bromo-4-methyl-phenylamine (8.00 g, 43.0 mmol), CuCN (4.62 g, 51.6 mmol), and NMP (30.0 ml). Stir the mixture at reflux for 75 minutes then cool it to ambient temperature. Pour the mixture onto ice chips and stir for 1 hour. Remove the resulting precipitate by vacuum filtration. Dissolve the precipitate in NH$_4$OH and extract it with dichloromethane. Combine, wash (brine), dry (sodium sulfate), and reduce the extracts to residue. Purify the residue on silica gel using dichloromethane/hexanes (75:25) to give 3.39 g (60%) of an orange solid: mass spectrum (ion spray): m/z=133.1 (M+1).

Example 566

2-Methyl-5H-dibenzo[b,e][1,4]diazepin-11-ylamine hydrochloride

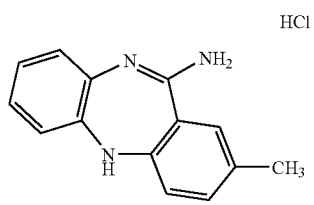

Combine 5-methyl-2-(2-nitro-phenylamino)-benzonitrile (4.03 g, 15.91 mmol), tin(II) chloride dihydrate (10.77 g, 47.74 mmol), 5N HCl (65 ml), and ethanol (40.0 ml). Stir the mixture at reflux for 7 hours then cool it to ambient temperature and chill it in the refrigerator overnight. Remove the resulting precipitate by vacuum filtration. Place the precipitate in ethanol (100.0 ml) and 5N HCl (20.0 ml) and heat at reflux for 19 hours. Cool the reaction mixture to ambient temperature then chill it in the refrigerator. Filter off the resulting precipitate by vacuum filtration and dry it in a vacuum oven to give 2.59 g (63%) of an orange solid: mass spectrum (ion spray): m/z=224.0 (M+1).

Example 567

3-Methyl-5H-dibenzo[b,e][1,4]diazepin-11-ylamine hydrochloride

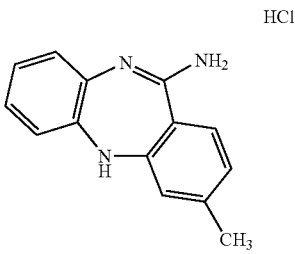

Combine 4-methyl-2-(2-nitro-phenylamino)-benzonitrile (2.46 g, 9.71 mmol), tin(II) chloride dihydrate (6.57 g, 29.71 mmol), 5N. HCl (40 ml), and ethanol (40.0 ml). Stir the mixture at reflux for 8 hours then cool it to ambient temperature. Allow the mixture to stand at ambient temperature overnight then chill it for 3 hours in the refrigerator. Remove the resulting precipitate by vacuum filtration and dry it under vacuum to give 1.24 g (49%) of the desired compound as a yellow solid: mass spectrum (ion spray): m/z=224.0 (M+1).

Example 568

(S)-8-Fluoro-11-{3-[2-(4-fluoro-phenyl)-ethyl]-piperazin-1-yl}-2-methyl-5H-dibenzo[b,e][1,4]diazepine succinate

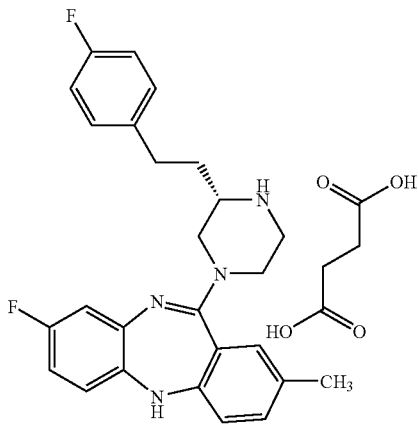

Heat a solution of 8-fluoro-2-methyl-5H-dibenzo[b,e][1,4]diazepin-11-ylamine hydrochloride (0.391 g, 1.62 mmol) and (S)-2-[2-(4-fluoro-phenyl)-ethyl]-piperazine (0.68 g, 3.24 mmol) in 1-methyl-2-pyrrolidinone (8mL) to 195° C. for 14 hours. Cool reaction mixture to ambient temperature. Dilute with 100 ml of ethyl acetate and wash twice with brine, twice with water, and once again with brine. Collect the organic layer and dry over sodium sulfate. Remove solvent under reduced pressure. Purification via flash chromatography, eluting with a step gradient starting with 100% of a stock mixture of 75% ethyl acetate with 25% dichloromethane and going to 90% of the stock mixture with 10% 2M ammonia in methanol, gives the free base of the title compound (0.108 g, 0.25 mmol, 15% yield) as a yellow amorphous solid. Convert the product to the succinate salt by dissolving the product in methanol and adding one equivalent of succinic acid, swirl or sonicate the mixture until no solid succinic acid remains, then removing the solvent under reduced pressure gives the title compound: Mass Spectrum (m/e): 433(M+1).

Example 569

(S)-8-Fluoro-11-{3-[2-(4-fluoro-phenyl)-ethyl]-4-methyl-piperazin-1-yl}-2-methyl-5H-dibenzo[b,e][1,41]diazepine succinate

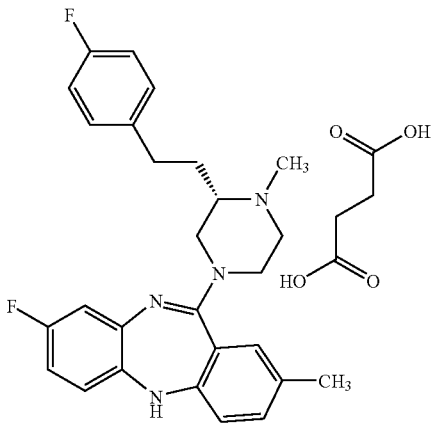

Dissolve (S)-8-fluoro-11-{3-[2-(4-fluoro-phenyl)-ethyl]-piperazin-1-yl}-2-methyl-5H-dibenzo[b,e][1,4]diazepine (0.076 g, 0.18 mmol) in dichloromethane (10 ml). Add sodium triacetoxyborohydride (0.112 g, 0.53 mmol) and formaldehyde (0.011 g, 0.35 mmol, 0.029 g of a 37% aqueous solution) and stir the mixture for one hour at ambient temperature. Dilute the mixture with brine and extract three times with dichloromethane. Combine the organic layers, dry over sodium sulfate and remove the solvent under reduced pressure. Purification via flash chromatography, eluting with a step gradient starting with 100% of a stock mixture of 70% hexanes with 30% dichloromethane and going to 90% of the stock mixture with 10% 2M ammonia in methanol, gives the free base of the title compound (0.028 g, 0.06 mmol, 36% yield) as a yellow foam. Convert to to the succinate salt as described previously: Mass Spectrum (m/e): 446(M+1).

Example 570

(S)-8-Fluoro-11-{3-[2-(4-fluoro-phenyl)-ethyl]-piperazin-1-yl}-2-isopropyl-5H-dibenzo[b,e][1,4]diazepine succinate

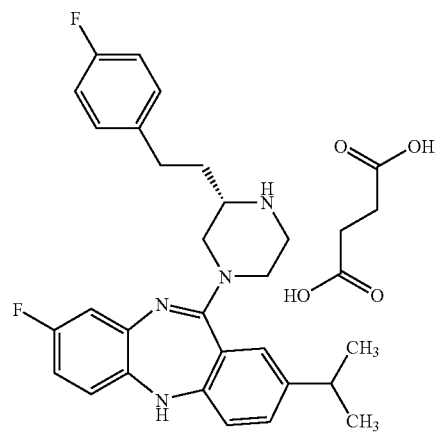

Heat a solution of 8-fluoro-2-isopropyl-5H-dibenzo[b,e][1,4]diazepin-11-ylamine hydrochloride (0.308 g, 1.01 mmol) and (S)-2-[2-(4-fluoro-phenyl)-ethyl]-piperazine (0.629 g, 3.02 mmol) in 1-methyl-2-pyrrolidinone (8 mL) to 195° C. for 14 hours. Cool reaction mixture to ambient temperature. Dilute with 50 ml of ethyl acetate and wash twice with brine, twice with water, and once again with brine. Collect the organic layer and dry over sodium sulfate. Remove solvent under reduced pressure. Purification via flash chromatography, eluting with a step gradient starting with 100% of a stock mixture of 80% ethyl acetate with 20% dichloromethane and going to 95% of the stock mixture with 5% 2M ammonia in methanol, gives the free base of the title compound (0.132 g, 0.29 mmol, 28% yield) as a yellow amorphous solid. Convert to the succinate salt as described previously: Mass Spectrum (m/e): 461(M+1).

Example 571

(S)-8-Fluoro-11-{3-[2-(4-fluoro-phenyl)-ethyl]-4-methyl-piperazin-1-yl}-2-isopropyl-5H-dibenzo[b,e][1,4]diazepine succinate

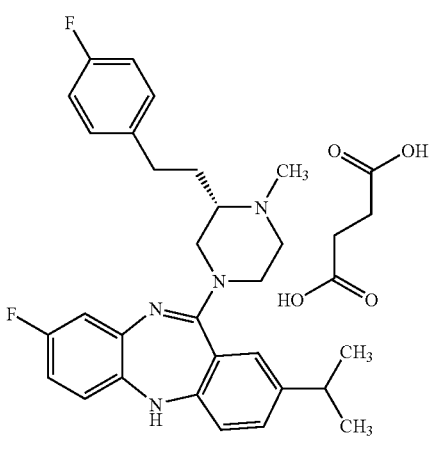

Dissolve (S)-8-fluoro-11-{3-[2-(4-fluoro-phenyl)-ethyl]-piperazin-1-yl}-2-isopropyl-5H-dibenzo[b,e][1,4]diazepine (0.066 g, 0.14 mmol) in dichloromethane (8 ml). Add sodium triacetoxyborohydride (0.091 g, 0.43 mmol) and formaldehyde (0.009 g, 0.29 mmol, 0.023 g of a 37% aqueous solution) and stir the mixture for one hour at ambient temperature. Dilute the mixture with brine and extract three times with dichloromethane. Combine the organic layers, dry over sodium sulfate and remove the solvent under reduced pressure. Purification via flash chromatography, eluting with a step gradient starting with 100% of a stock mixture of 70% hexanes with 30% dichloromethane and going to 90% of the stock mixture with 10% 2M ammonia in methanol, gives the free base of the title compound (0.032 g, 0.07 mmol, 47% yield) as a yellow foam. Convert to the succinate salt as described previously: Mass Spectrum (m/e): 475(M+1).

Example 572

(S)-11-{3-[2-(3-Fluoro-phenyl)-ethyl]-piperazin-1-yl}-2-isopropyl-5H-dibenzo[b,e][1,4]diazepine

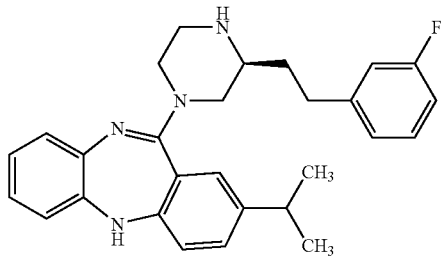

Combine 2-isopropyl-5H-dibenzo[b,e][1,4]diazepin-11-ylamine (0.665 g, 2.31 mmol) and (S)-2-[2-(3-fluoro-phenyl)-ethyl]-piperazine (0.962 g, 4.62 mmol)in toluene (4.0 mL) and DMSO (1.0 mL) and heat at 110° C. for 18 hours. Cool to ambient temperature and dilute with ethyl acetate (75 mL). Wash with 0.1N NaOH solution, water and evaporate to give 0.996 g of the crude product. Silica gel chromatography, eluting with methylene chloride: 2N NH$_3$/methanol (100:4), gives 0.216 g of the title compound as a tan solid: mass spectrum (ion spray): n/z=443 (M+1).

Example 573

(S)-11-{3-[2-(3-Fluoro-phenyl)-ethyl]-4-methyl-piperazin-1-yl}-2-isopropyl-5H-dibenzo[b,e][1,4]diazepine dihydrochloride

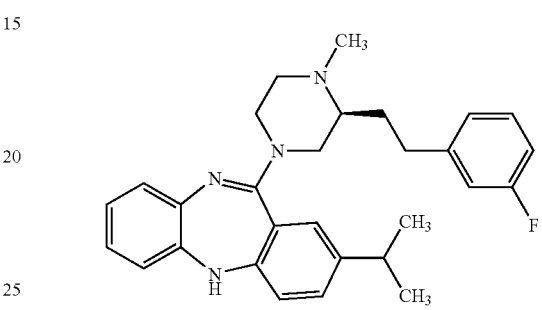

In a manner such as that described in Example 461, using (S)-11-{3-[2-(3-fluoro-phenyl)-ethyl]-piperazin-1-yl}-2-isopropyl-5H-dibenzo[b,e][1,4]diazepine (0.351 g, 0.79 mmol) gives 0.176 g of the title compound as an orange solid: mp 227° C.; mass spectrum (ion spray): m/z=457 (M+1); Analysis for $C_{29}H_{35}Cl_2FN_4(0.2H_2O)$: calcd: C, 65.33; H, 6.69; N, 10.51; found: C, 65.22; H, 6.70; N, 10.39.

Example 574

3-Methyl-11-(4-methyl-piperazin-1-yl)-3-methyl-5H-dibenzo[b,e][1,4]diazepine

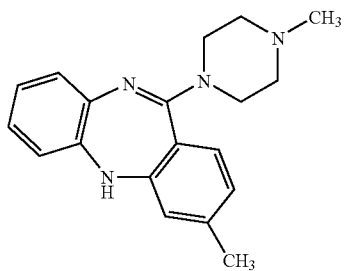

Combine 3-methyl-5H-dibenzo[b,e][1,4]diazepin-11-ylamine hydrochloride (636.4 mg, 2.85 mmol), N-methylpiperazine (444.2 mg, 3.08 mmol), N,N-diisopropylethylamine (856.5 mg, 8.55 mmol), DMSO (2.0 ml), and toluene (4.0 ml). Stir and heat the mixture at 110° C. After 48 hours, add one drop of 5N HCl. After 72 hours, cool the mixture to ambient temperature and then dilute it with ethyl acetate. Wash the organic layer with DI H$_2$O and brine. Dry (sodium sulfate) and concentrate the organic layer to residue. Purify the residue on silica gel using dichloromethane/methanol (90:10) to give 362.9 mg (42%) of a tan foam: mp 84°, dec; mass spectrum (ion spray): m/z=307.1 (M+1).

Example 575

3-Methyl-11-[(S)-3-phenethyl-piperazin-1-yl]-5H-dibenzo[b,e][1,4]diazepine

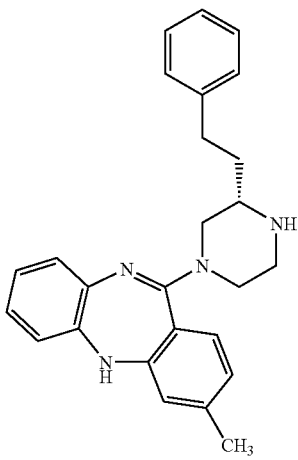

Combine 3-methyl-5H-dibenzo[b,e][1,4]diazepin-11-ylamine hydrochloride (400.0 mg, 1.54 mmol), (S)-2-phenethyl-piperazine (879.1 mg, 4.62 mmol), N,N-diisopropylethylamine (199.0 mg, 1.54 mmol), DMSO (0.7 ml), and toluene (2.8 ml). Stir and heat the mixture at 110° C. After 65 hours, cool the mixture to ambient temperature and then dilute it with ethyl acetate. Wash the organic layer with 0.1 N NaOH and brine. Dry (sodium sulfate) and concentrate the organic layer to residue. Purify the residue on silica gel using dichloromethane/methanol (90:10) to give 518.7 mg (85%) of a tan foam: mp 64°–80°; mass spectrum (ion spray): m/z=397.2 (M+1).

Example 576

3-Methyl-11-[4-methyl-(S)-3-phenethyl-piperazin-1-yl]-5H-dibenzo[b,e][1,4]diazepine

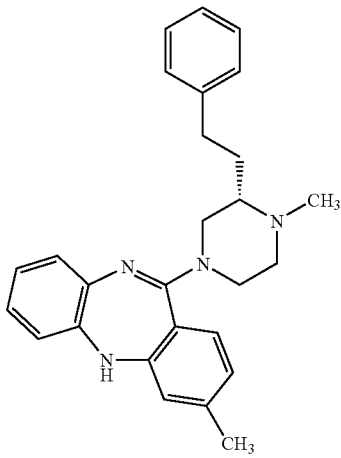

Combine 3-methyl-11-[(S)-3-phenethyl-piperazin-1-yl]-5H-dibenzo[b,e][1,4]diazepine (375.0 mg, 0.95 mmol), formaldehyde (84.4 μL, 1.04 mmol, 37% in water), and 1,2-dichloroethane (30.0 ml). Stir the mixture at ambient temperature for 5 minutes and then add sodium triacetoxyborohydride (300.6 mg, 1.42 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using dichloromethane/methanol (90:10) to give 329.5 mg (85%) of the title compound as a tan foam: mp 65°, dec; mass spectrum (ion spray): m/z=411.3 (M+1).

Example 577

11-{(S)-3-[2-(3-Fluoro-phenyl)-ethyl]-piperazin-1-yl}-3-methyl-5H-dibenzo[b,e][1,4]diazepine

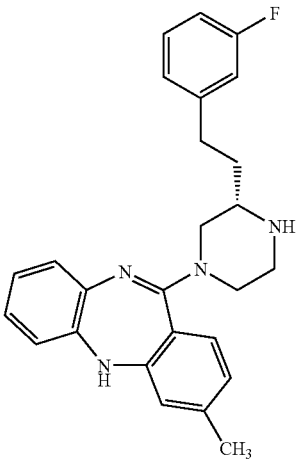

Combine 3-methyl-5H-dibenzo[b,e][1,4]diazepin-1-ylamine hydrochloride (400.0 mg, 1.54 mmol), (S)-2-[2-(3-Fluoro-phenyl)-ethyl]-piperazine (641.5 mg, 3.08 mmol), N,N-diisopropylethylamine (199.0 mg, 1.54 mmol), DMSO (0.7 ml), and toluene (2.8 ml). Stir and heat the mixture at 110° C. After 64 hours, cool the mixture to ambient temperature and then dilute it with ethyl acetate. Wash the organic layer with 0.1 N NaOH and brine. Dry (sodium sulfate) and concentrate the organic layer to residue. Purify the residue on silica gel using dichloromethane/methanol (90:10) to give 423.2 mg (66%) of a tan foam: mp 81°, dec; mass spectrum (ion spray): m/z 415.2 (M+1).

Example 578

11-{(S)-3-[2-(3-Fluoro-phenyl)-ethyl]-4-methyl-piperazin-1-yl}-3-methyl-5H-dibenzo[b,e][1,4]diazepine

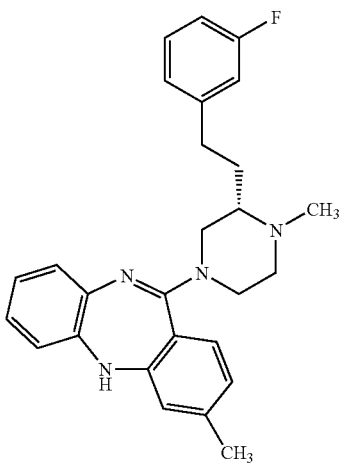

Combine 11-{(S)-3-[2-(3-fluoro-phenyl)-ethyl]-piperazin-1-yl}-3-methyl-5H-dibenzo[b,e][1,4]diazepine (385.5 mg, 0.93 mmol), formaldehyde (83.0 μL, 1.02 mmol, 37% in water), and 1,2-dichloroethane (30.0 ml). Stir the mixture at ambient temperature for 5 minutes and then add sodium triacetoxyborohydride (295.6 mg, 1.39 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using dichloromethane/methanol (90:10) to give 366.2 mg (92%) of the title compound as a yellow foam: mp 63°, dec; mass spectrum (ion spray): m/z=429.3 (M+1).

Example 579

2-Methyl-11-(4-methyl-piperazin-1-yl)-3-methyl-5H-dibenzo[b,e][1,4]diazepine

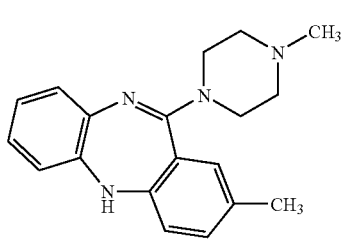

Combine 2-methyl-5H-dibenzo[b,e][1,4]diazepin-11-ylamine hydrochloride (600.0 mg, 2.31 mmol), N-methylpiperazine (1.39 g, 13.86 mmol), N,N-diisopropylethylamine (298.6 mg, 2.31 mmol), DMSO (1.0 ml), and toluene (4.0 ml). Stir and heat the mixture at 110° C. After 48 hours, cool the mixture to ambient temperature and stir it overnight. Dilute the mixture with ethyl acetate and wash the organic layer with 0.1N NaOH and brine. Dry (sodium sulfate) and concentrate the organic layer to residue. Purify the residue on silica gel using dichloromethane/methanol (90:10) to give 550.5 mg (78%) of a tan foam: mp 170°–177°, dec; mass spectrum (ion spray): m/z=307.2 (M+1).

Example 580

2-Methyl-11-[(S)-3-phenethyl-piperazin-1-yl]-5H-dibenzo[b,e][1,4]diazepine

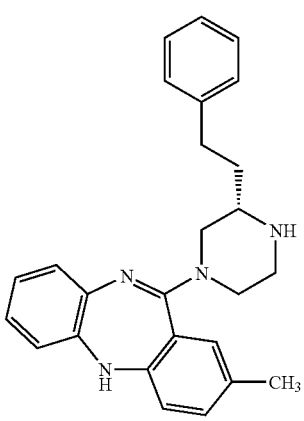

Combine 2-methyl-5H-dibenzo[b,e][1,4]diazepin-11-ylamine hydrochloride (600.0 mg, 2.31 mmol), (S)-2-phenethyl-piperazine (879.1 mg, 4.62 mmol), N,N-diisopropylethylamine (298.6 mg, 2.31 mmol), DMSO (1.0 ml), and toluene (4.0 ml). Stir and heat the mixture at 110° C. After 67 hours, cool the mixture to ambient temperature and then dilute it with ethyl acetate. Wash the organic layer with 0.1 N NaOH and brine. Dry (sodium sulfate) and concentrate the organic layer to residue. Purify the residue on silica gel using dichloromethane/methanol (90:10) to give 646.3 mg (71%) of a tan foam: mp 67°, dec; mass spectrum (ion spray): m/z=397.3 (M+1).

Example 581

2-Methyl-11-[4-methyl-(S)-3-phenethyl-piperazin-1-yl]-5H-dibenzo[b,e][1,4]diazepine

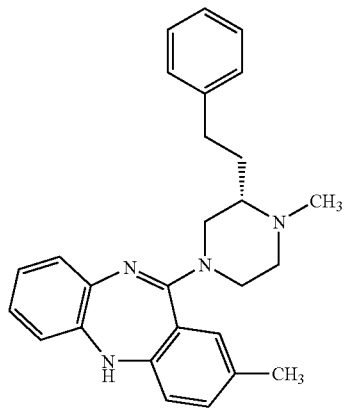

Combine 2-methyl-11-[(S)-3-phenethyl-piperazin-1-yl]-5H-dibenzo[b,e][1,4]diazepine (300.0 mg, 0.76 mmol), formaldehyde (67.5 µL, 0.83 mmol, 37% in water), and 1,2-dichloroethane (25.0 ml). Stir the mixture at ambient temperature for 5 minutes and then add sodium triacetoxyborohydride (240.5 mg, 1.13 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using dichloromethane/methanol (90:10) to give 279.7 mg (90%) of the title compound as a yellow foam: mp 65°, dec; mass spectrum (ion spray): m/z=411.2 (M+1).

Example 582

11-(4-Methyl-piperazin-1-yl)-5H-dibenzo[b,e][1,4]diazepine

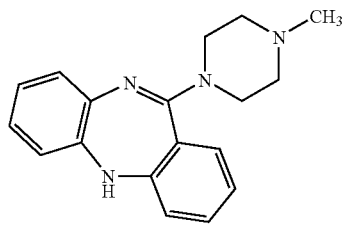

Combine 5H-dibenzo[b,e][1,4]diazepin-11-ylamine hydrochloride (600.0 mg, 2.44 mmol), N-methylpiperazine (1.47 g, 14.65 mmol), N,N-diisopropylethylamine (315.6 mg, 2.44 mmol), DMSO (1.0 ml), and toluene (4.0 ml). Stir and beat the mixture at 110° C. After 21 hours, cool the mixture to ambient temperature and stir it overnight. Dilute the mixture with ethyl acetate and wash the organic layer with 0.1N NaOH and brine. Dry (sodium sulfate) and concentrate the organic layer to residue. Purify the residue on silica gel using dichloromethane/methanol (90:10) to give 319.7 mg (45%) of a tan foam: mp 173° C. –179° C., dec; mass spectrum (ion spray): m/z=293.1 (M+1).

Example 583

2-(4-Chloro-2-nitro-phenylamino)-benzonitrile

Combine anthranilonitrile (2.36 g, 20 mmol), sodium hydride (1.2 g (60% in oil), 30 mmol) and THF (50 mL), stir at ambient temperature for 30 minutes. Add 1-bromo4-chloro-2-nitro-benzene (7.1 g, 30 mmol) and stir at ambient temperature for 3 days. Pour the reaction mixture in ice-cold concentrated hydrochloric acid (200 mL) and filter the resulting solid. Purify by flash chromatography (dichloromethane) and recrystallize from hot ethyl acetate to give (1.62 g, 30%) of the title compound as orange needles: $^1$H NMR (CDCl$_3$) δ 7.17 (d, 1H), 7.26 (t, 1H), 7.40–7.51 (m, 2H), 7.61 (t, 1H), 7.72 (d, 1H), 8.22 (d, 1H), 9.54 (bs, 1H).

Example 584

8-Chloro-5H-dibenzo[b,e][1,4]diazepin-11-ylamine hydrochloride

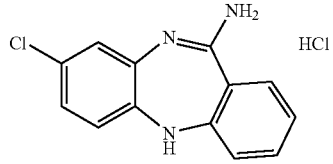

Combine 2-(4-chloro-2-nitro-phenylamino)-benzonitrile (1.2 g, 4.4 mmol) in ethanol (40 mL) with a solution of stannous chloride dihydrate (2.9 g, 13.2 mmol) in 12 N hydrochloric acid (13 mL). Stir and reflux for 2 hours, cool to ambient temperature and concentrate. Add water (200 mL), filter and dry to give (890 mg, 72%) of the title compound as a yellow solid: $^1$H NMR (DMSO-d$_6$) δ 6.84–6.69 (m, 5E), 7.27–7.17 (m, 2H), 8.02 (s, 1H), 8.83 (bs, 1H), 9.36 (bs, 1H); MS (APCI) m/z (rel intensity) 244.3 (100).

Example 585

11-(3-(S)-Benzyl-piperazin-1-yl)-8-chloro-5H-dibenzo[b,e][1,4]diazepine

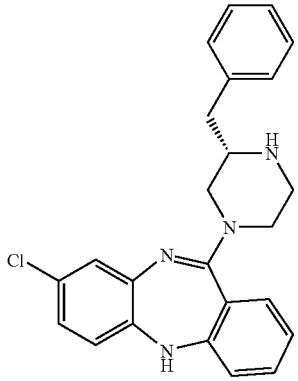

Combine 3-(S)-benzyl-piperazine (800 mg, 4.5 mmol), 8-chloro-5H-dibenzo[b,e][1,4]diazepin-11-ylamine hydrochloride (424 mg, 1.5 mmol), toluene (8 mL), dimethylsulfoxide (2 mL) and reflux for 3 days. Concentrate and pour into water (50 mL), filtrate the resulting solid, redissolve in dichloromethane (200 mL), wash with water and dry over magnesium sulfate. After concentration, purify by flash chromatography (dichloromethane then gradient of methanol 3–10%) to give (316 mg, 53%) of the title compound as a yellow foam: mp 79–92° C.; $^1$H NMR (CDCl$_3$): δ 2.59 (dd, 1H), 2.90–2.66 (m, 3H), 3.09–2.94 (m, 3H), 3.85 (bm, 1H), 4.03 (bm, 1H), 4.88 (s, 1H), 6.61 (dd, 1H), 6.79–6.84 (m, 2H), 6.97 (t, 1H), 7.06 (t, 1H), 7.35–7.19 (m, 7H); MS (APCI) m/z (rel intensity) 403.4 (100).

By a method similar to Example 585, using 8-chloro-5H-dibenzo[b,e][1,4]diazepin-11-ylamine hydrochloride, the following compound was prepared and isolated as the (S) isomer.

| No: | ArAlk | Data |
|---|---|---|
| 586 | CH$_2$CH$_2$Ph | mp 78–92° C.; $^1$H NMR(CDCl$_3$): δ1.76–1.64(m, 2H), 2.74–2.54(m, 4H), 3.07–2.78(m, 4H), 3.84(bm, 1H), 4.00(bm, 1H), 4.88(s, 1H), 6.61(dd, 1H), 6.83–6.80(m, 2H), 7.08–6.99(m, 2H), 7.32–7.15(m, 7H); MS(APCI)m/z(rel intensity) 417.4(100). 49% yield. |

By a similar method to Example 90, the following compounds were prepared and isolated, using 8-Chloro-5H-dibenzo(b,e)(1,4)diazepin-11-ylamine hydrochloride, as the (S) isomer.

| No: | ArAlk | Data |
|---|---|---|
| 587 | CH$_2$CH$_2$Ph | mp 64–78° C.; $^1$H NMR(CDCl$_3$): δ1.80–1.69(m, 1H), 2.00–1.89(m, 1H), 2.28–2.19(m, 1H), 2.35(s, 3H), 2.44–2.34(m, 1H), 2.59–2.48(m, 1H), 2.75–2.64(m, 1H), 2.85(d, 1H), 2.93(t, 1H), 3.22–3.10(m, 1H), 3.80(bm, 1H), 3.93(bm, 1H), 4.87(s, 1H), 6.61(d, 1H), 6.82(dd, 2H), 7.01(dt, 1H), 7.08(d, 1H), 7.21–7.14(m, 3H), 7.33–7.24(m, 4H); MS(APCI)m/z(rel intensity) 431.3(90), 270.4(100). 83% yield. |
| 588 | CH$_2$Ph | mp 69–81° C.; $^1$H NMR(CDCl$_3$): δ2.50–2.39(m, 3H), 2.48(s, 3H), 2.94–2.71(m, 2H), 3.24–3.10(m, 2H), 3.51(bm, 1H), 3.85(bm, 1H), 4.83(s, 1H), 6.57(dd, 1H), 6.81–6.71(m, 3H), 6.97(s, 1H), 7.25–7.02(m, 7H); MS(APCI)m/z(rel intensity)417.3(100). 96% yield. |

Example 589

5-Amino-4-carboxamido-1H-1,2,3-triazole

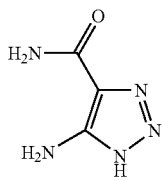

Dissolve 4-toluenesulphonyl chloride (481.3 g; 2.52 mol) in hot ethanol (2900 ml) and allow the resulting clear solution to cool to room temperature. Dissolve sodium azide (198.31 g; 3.05 mol) in water (360 ml) and mix the two solutions with stirring. Allow the mixture to stand for one and a half hours at room temperature, pour onto water (7250 ml) and separate the resulting two phase mixture, wash the clear oil with water, dry over magnesium sulphate and filter to leave the desired 4-toluene sulphonyl azide (weight=470.57 g).

Add to the Chem Reactor sodium methoxide in methanol (25% by weight; 470 ml) and further methanol (470 ml). Add malonamidine hydrochloride (300 g; 2.18 mol) to the solution with stirring. Stir the white slurry formed for half an hour under nitrogen, cool to 0–5° C. using an ice-water bath. Add at this temperature, ethanol (3600 ml) and stir the mixture stir for one hour at 10° C. Filter the mixture to remove sodium chloride and wash the latter with further ethanol (1000 ml). Place the resultant amidine solution back in the Chem Reactor and cool to 5° C. Add the solution of 4-toluenesulphonyl azide (470.57 g) in ethanol (380 ml) add dropwise over 30 minutes. Stir the mixture at room temperature overnight, filter and wash with ethanol to leave a white solid, dry at 60° C. in a vacuum oven to give 5-amino4-carboxamido-1H-1,2,3-triazole=245.6 g (88.6% yield).

Example 590

5-Amino-2-isopropyl-2H-1,2,3-triazole-4-carboxamide

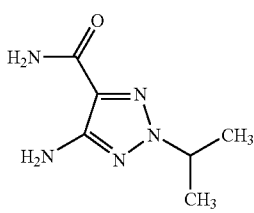

Combine 5-amino-4-carboxamido-1H-1,2,3-triazole (127 g, 1.0 mol) and 2-bromopropane (160 g, 1.3 mol) in toluene (1500 ml) and stir at 70° C. for eighteen hours in the presence of 50% aqueous sodium hydroxide (2.0 ml) and potassium carbonate (276 g; 2.0 mol) with Adogen 464 (25 g) as the phase transfer catalyst. After cooling water add and extract the product using ethyl acetate. Wash the combined organic phases with water, dry over magnesium sulphate and remove the solvent in vacuo to leave a residue that is triturated with diethyl ether. Collect the white solid by filtration and dry under vacuum at room temperature to give 5-amino-2-isopropyl-2H-1,2,3-triazole-4-carboxamide (94.68 g, 56% yield). Alkylation occurs at other positions including the exocyclic $NH_2$ position too varying degrees depending on the alkyl halide used. Normally the 2-substituted product is the major isomer and crystallises readily. Chromatography is sometimes necessary. $^1$HNMR/c: 1.44 ppm (m, 6H), 4.55 ppm (m, 1H), 5.5 ppm (m, 2H), 7.18 ppm (bs, 1H), 7.35 ppm (bs, 1H).

Example 591

5-Amino-2-isopropyl-2H-1,2,3-triazole-4-carbonitrile

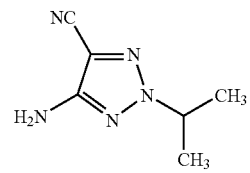

Add phosphorous oxychloride (99 ml, 1.06 mol) slowly to a stirring solution of 5-amino-2-isopropyl-2H-1,2,3, -triazole-4-carboxamide (94.68 g, 0.56 mol) in anhydrous N,N-dimethylformamide (275 ml). Allow the reaction mixture to stir for three hours, add ice and stir the whole reaction until homogeneous, adjust the to pH 5.5 using ammonia. Extract the organics with diethyl ether and combine ethereal phases, wash with water, dry over magnesium sulphate and finally concentrate in vacuo. Dissolve the residue in 2N hydrochloric acid (825 ml) and heat under reflux for 1 hour. Cool the solution in an ice-water bath and filter to give a yellow/white solid. Extract the aqueous phase with dichloromethane (2×500 ml), combine the organic phase, wash with water, dry over magnesium sulphate, filter and evaporate to give an orange solid. Combine solids and dissolve in dichloromethane and pass through a pad of flash silica (500 g) to give a white solid of 5-amino-2-isopropyl-2H-1,2,3-triazole-4-carbonitrile (44.2 g, 52% yield): $^1$HNMR/c: 1.51 ppm (d, 6H), 4.27 ppm (bs, 2H), 4.62 ppm (m, 1H).

Example 592

2-Isopropyl-5-(2-nitroanilino)-2H-1,2,3-triazole-4-carbonitrile

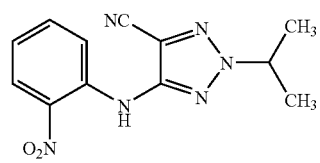

Combine 5-amino-2-isopropyl-2H-1,2,3-triazole-4-carbonitrile (44.2 g, 0.292 mol) and 2-fluoronitrobenzene (41.25 g, 0.292 mol) in dimethylsulphoxide (590 ml) and stir in the presence of lithium hydroxide monohydrate (24.56 g;0.584 mol) for eighteen hours at 55° C. Pour the reaction mixture onto ice-water, stir for one hour, filter and wash the filter pad well with water to leave a yellow crystalline solid to give 2-isopropyl-5-(2-nitroanilino)-2H-1,2,3-triazole4-carbonitrile (73.7 g, 93% yield): $^1$HNMR/c: 1.6 ppm (d, 6H), 4.8 ppm (m, 1H), 7.05 ppm (tr, 1H), 7.64 ppm (tr, 1H), 8.2 ppm (dd, 1H), 8.28 ppm (dd, 1H), 10.25 ppm (s, 1H).

Example 593

2-Isopropyl-2,4-dihydro[1,2,3]triazolo[4,5-b][1,5]benzazepin-10-amine hydrochloride

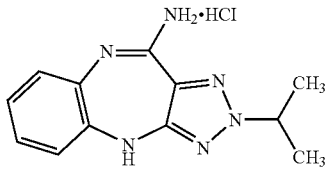

Combine 2-isopropyl-5-(2-nitroanilino)-2H-1,2,3-triazole-4-carbonitrile (51.5 g, 0.1 87 mol) in ethanol (700 ml) and warm to 60° C. Add stannous chloride dihydrate (130 g, 0.561 mol) in 5N hydrochloric acid (700 ml) and add as a single portion and heat the resultant mixture under reflux for four hours. Chill the reaction mixture overnight to give the product as yellow crystals and collect by filtration and wash with ethanol. Dry at 50° C. under reduced pressure to give 2-isopropyl-2,4-dihydro[1,2,3]triazolo[4,5-b][1]benzazepin-10-amine hydrochloride (52.1 g, 100% yield).

Example 594

(S)-2-Isopropyl-10-(3-phenethyl-piperazin-1-yl)-2,4-dihydro-1,2,3,4.9-pentaaza-benzo[f]azulene dihydrochloride hemihydrate Combine 2-isopropyl-2,4-dihydro-1,2,3,4,9-pentaazabenzo[f]azulen-10-ylamine (0.863 g, 3.56 mmol), (S)-2-phenethyl-piperazine (0.678 g, 3.56 mmol) in NMP (6.0 mL) and heat at 200° C. for 3 hours. Cool to ambient temperature and dilute with water (75 mL). Extract with ethyl acetate to give 1.59 g of the crude product. Silica gel chromatography, eluding with methylene chloride:methanol (100:7.5), to give the title compound as the free base. The dihydrochloride salt precipitates in ethyl acetate as a yellow solid: mp 210° C.; mass spectrum (ion spray): m/z=416 (M+1); Analysis for $C_{24}H_{31}Cl_2N_7(0.5\ H_2O)$: calcd: C, 57.95; H, 6.48; N, 19.71; found: C, 58.01; H, 6.22; N, 19.70.

Example 595

(S)-2-Isopropyl-10-(4-methyl-3-phenethyl-piperazin-1-yl)-2,4-dihydro-1,2,3,4,9-pentaaza-benzo[f]azulene dihydrochloride hemihydrate Combine (S)-2-isopropyl-10-(3-phenethyl-piperazin-1-yl)-2,4-dihydro-1,2,3,4,9-pentaaza-benzo[f]azulene (0.59 g, 1.42 mmol)and 37% formaldehyde solution (0.13 mL, 1.56 mmol) in 1,2-dichloroethane (25 mL). Stir for 10 minutes and add sodium triacetoxy borohydride (0.451 g, 2.13 mmol). Stir an additional 30 minutes and then pour solution onto saturated sodium bicarbonate solution. Extract with methylene chloride to give the crude product. Silica gel chromatography, eluding with methylene chloride:methanol (100:2.5), gives the title compound as the free base. The dihydrochloride salt precipitates in ethyl acetate as a yellow solid: m.p. 200° C.; mass spectrum (ion spray): m/z=430 (M+1); Analysis for $C_{25}H_{33}Cl_2N_7(0.5\ H_2O)$: calcd: C, 58.71; H, 6.70; N, 19.17; found: C, 58.77; H, 6.60; N, 19.05.

Example 596

(S)-2-(1,4-Dibenzyl-piperazin-2-yl)-1-phenyl-ethanol

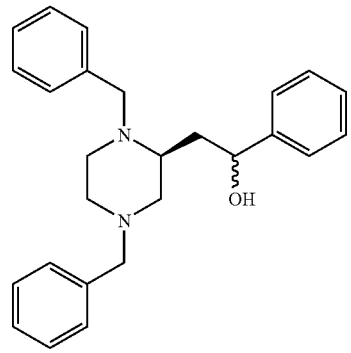

Add phenyllithium (11.3 mL, 20.4 mmol, 1.8 M in cyclohexane-ether) dropwise to a −78° C. solution of (S)-(1,4-dibenzyl-piperazin-2-yl)-acetaldehyde (4.2 g, 13.6 mmol) in THF (60 mL). Stir 30 min at −78° C. and 4 h at ambient temperature. Add ice, brine, and extract with ether. Wash the extracts with brine, dry with sodium sulfate, filter and concentrate the filtrate. Purify by silica gel chromatography using 2N ammonia in methanol-methylene chloride (1%–4%) as the eluent to give 3.98 g (76%) of the title compound: mass spectrum (ion spray): m/z=387 (M+1). HR-MS calculated for $C_{26}H_{31}N_2O$: 387.2436. Found 387.2442.

Example 597

(S)-1-Phenyl-2-piperazin-2-yl-ethanol

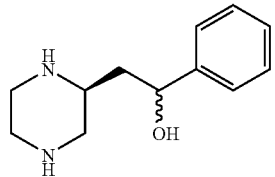

Dissolve (S)-2-(1,4-dibenzyl-piperazin-2-yl)-1-phenylethanol (3.89 g, 10.1 mmol) in ethanol (50 mL). Add ammonium formate (3.8 g, 60.4 mmol), palladium hydroxide (1.6 g, 20 wt. % on carbon) and ethanol (25 mL). Heat to reflux. After 6.5 h, cool and stir at ambient temperature 18 h. Filter the palladium hydroxide and concentrate the filtrate. Purify by silica gel chromatography using 2N ammonia in methanol-methylene chloride (10%) then 7N ammonia in methanol-methylene chloride (10%) as the eluent to give 860 mg (41%) of the title compound: mass spectrum (ion spray): m/z=207 (M+1).

Example 598 and Example 599

(S,R)-2-[4-(2-Methyl-4H-3-thia-4,9-diaza-benzo[f]azulen-10-yl)-piperazin-2-yl]-1-phenyl-ethanol

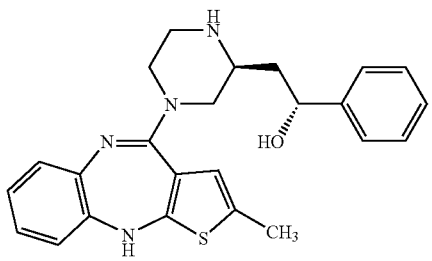

(S,S)-2-[4-(2-Methyl-4H-3-thia-4,9-diaza-benzo[f]azulen-10-yl)-piperazin-2-yl]-1-phenyl-ethanol

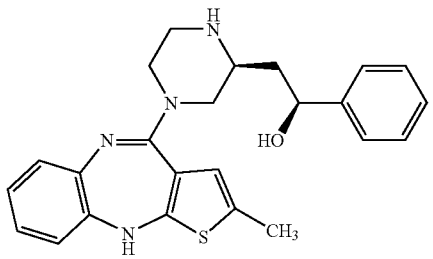

Add methyl trifluoromethanesulfonate (174 μL, 1.53 mmol) to a 0° C. slurry of 2-methyl-4,9-dihydro-3-thia-4,9-diaza-benzo[f]azulene-10-thione (315 mg, 1.28 mmol) in dichloromethane (4 mL). Stir 1 h at 0° C. then warm to ambient temperature and stir 18 h. Concentrate the reaction to an orange powder. Add (S)-1-phenyl-2-piperazin-2-yl-ethanol (264 mg, 1.28 mmol) and pyridine (5 mL). Heat to 110° C. for 5.5 h and stir at ambient temperature for 18 h. Concentrate the reaction, dissolve the residue in methanol-dichloromethane, apply to a SCX column. Wash the column with methanol-dichloromethane to remove impurities then elute the product with 2N ammonia in methanol-dichloromethane (10%). Concentrate and purify by radial silica gel chromatography using a 2 mm plate and 2N ammonia in methanol-methylene chloride (2.5%–3%) as the eluent to give 39 mg of (S,R)-2-[4-(2-methyl-4H-3-thia-4,9-diazabenzo[f]azulen-10-yl)-piperazin-2-yl]-1-phenyl-ethanol and 130 mg of (S,S)-2-[4-(2-methyl-4H-3-thia-4,9-diaza-benzo[f]azulen-10-yl)-piperazin-2-yl]-1-phenyl-ethanol.

(S,R)-2-[4-(2-Methyl-4H-3-thia-4,9-diaza-benzo[f]azulen-10-yl)-piperazin-2-yl]-1-phenyl-ethanol: mass spectrum (ion spray): m/z=419 (M+1). HR-MS calculated for $C_{24}H_{27}N_4OS$: 419.1906. Found 419.1919. $^1H$ NMR (DMSO-d6): δ 7.55 (s, 1H), 7.37–7.26 (m, 4H), 7.25–7.17 (m, 1H), 6.87–6.73 (m, 3H), 6.67 (br d, 1H), 6.30 (s, 1H), 5.52 (br s, 1H), 4.75–4.66 (m, 1H), 3.84 (br d, 1H), 3.72 (br d, 1H), 2.88 (d, 1H), 2.82–2.60 (m, 3H), 2.56–2.45 (m, 1H), 2.41 (br s, 1H), 2.26 (s, 3H), 1.50–1.73 (m, 2H).

(S,S)-2-[4-(2-Methyl-4H-3-thia-4,9-diaza-benzo[f]azulen-10-yl)-piperazin-2-yl]-1-phenyl-ethanol: mass spectrum (ion spray): m/z=419 (M+1). HR-MS calculated for $C_{24}H_{27}N_4OS$: 419.1906. Found 419.1909. $^1H$ NMR (DMSO-d$_6$): δ 7.56 (s, 1H), 7.37–7.15 (m, 5H), 6.87–6.74 (m, 3H), 6.67 (br d, 1H), 6.31 (s, 1H), 5.29 (br s, 1H), 4.74–4.67 (m, 1H), 3.88 (br d, 1H), 3.80 (br d, 1H), 2.86 (d, 1H), 2.80–2.59 (m, 3H), 2.53–2.42 (m, 2H), 2.28 (s, 3H), 1.62–1.53 (m, 2H).

Example 600

(S,S)-2-[1-Methyl-4-(2-methyl-4H-3-thia-4,9-diaza-benzo[f]azulen-10-yl)-piperazin-2-yl]-1-phenyl-ethanol

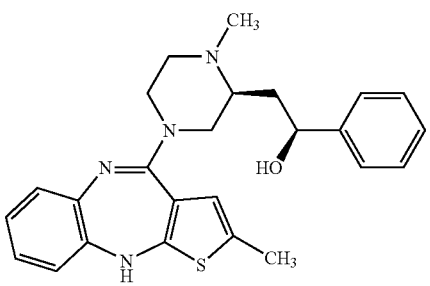

Add formaldehyde (33 μL, 0.42 mmol, 37% in water) to a solution of (S,S)-2-[4-(2-methyl-4H-3-thia-4,9-diaza-benzo[f]azulen-10-yl)-piperazin-2-yl]-1-phenyl-ethanol (160 mg, 0.38 mmol) in methylene chloride (6 mL). Stir 15 min at ambient temperature. Add sodium triacetoxyborohydride (121 mg, 0.57 mmol) and stir 2 h at ambient temperature. Dilute with saturated sodium bicarbonate solution and extract with methylene chloride. Dry the extracts with sodium sulfate, filter and concentrate the filtrate. Purify by radial silica gel chromatography using a 2 mm plate and 2N ammonia in methanol-methylene chloride (1%–5%) as the eluent to give 70 mg (42%) of the title compound: mass spectrum (ion spray): m/z=433 (M+1), 431 (M−1). HR-MS calculated for $C_{25}H_{29}N_4OS$: 433.2062. Found 433.2061. $^1H$ NMR (DMSO-d$_6$): δ 7.60 (s, 1H), 7.36–7.17 (m, 5H), 6.88–6.75 (m, 3H), 6.68 (br d, 1H), 6.35 (s, 1H), 5.34 (br d, 1H), 4.60–4.50 (m, 1H), 3.85 (br d, 1H), 3.70 (br d, 1H), 3.04–2.92 (m, 1H), 2.85–2.66 (m, 2H), 2.29 (s, 3H), 2.17 (s, 3H), 2.20–2.10 (m, 1H) 2.08–1.98 (m, 1H), 1.97–1.85 (m, 1H), 1.66–1.52 (m, 1H).

Example 601 and Example 602

(S,R)-2-[4-(2-Isopropyl-4H-3-thia-1,4,9-triaza-benzo[f]azulen-10-yl)-piperazin-2-yl]-1-phenyl-ethanol

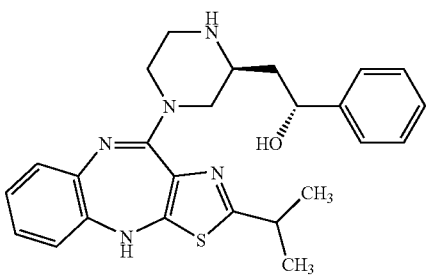

215

(S,S)-2-[4-(2-Isopropyl-4H-3-thia-1,4,9-triaza-benzo[f]azulen-10-yl)-piperazin-2-yl]-1-phenyl-ethanol

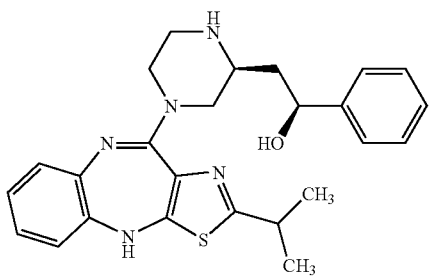

Add methyl trifluoromethanesulfonate (806 μL, 7.13 mmol) to a 0° C. slurry of 2-isopropyl-4,9-dihydro-3-thia-1,4,9-triaza-benzo[f]azulene-10-thione (1.31 g, 4.75 mmol) in dichloromethane (15 mL). Stir 18 h, gradually allowing reaction to warm to ambient temperature. Concentrate the reaction to an orange powder. Add (S)-1-phenyl-2-piperazin-2-yl-ethanol (980 mg, 4.75 mmol) and pyridine (11 mL). Heat to 115° C. for 5 h. Concentrate and purify by silica gel chromatography using 2N ammonia in methanol-methylene chloride (0%–10%) then 7N ammonia in methanol-methylene chloride (20%) as the eluent to give 520 mg. Purify again, in two portions, by radial silica gel chromatography using a 2 mm plate and 2N ammonia in methanol-methylene chloride (2.5%–4.5%) as the eluent to give 28 mg of (S,R)-2-[4-(2-isopropyl-4H-3-thia-1,4,9-triaza-benzo[f]azulen-10-yl)-piperazin-2-yl]-1-phenyl-ethanol and 155 mg of (S,S)-2-[4-(2-isopropyl-4H-3-thia-1,4,9-triaza-benzo[f]azulen-10-yl)-piperazin-2-yl]-1-phenyl-ethanol after combining both radial purifications.

(S,R)-2-[4-(2-Isopropyl-4H-3-thia-1,4,9-triaza-benzo[f]azulen-10-yl)-piperazin-2-yl]-1-phenyl-ethanol: mass spectrum (ion spray): m/z=448 (M+1), 446 (M−1). HR-MS calculated for $C_{25}H_{30}N_5OS$: 448.2171. Found 448.2181. $^1$H NMR (DMSO-$d_6$): δ 7.78 (s, 1H), 7.37–7.16 (m, 5H), 6.89–6.73 (m, 3H), 6.67 (br d, 1H), 5.44 (br s, 1H), 4.74–4.67 (m, 1H), 4.04–3.87 (m, 2H), 3.05 (quintet, 1H), 2.93–2.79 (m, 2H), 2.76–2.54 (m, 3H), 1.73–1.60 (m, 1H), 1.59–1.47 (m, 1H), 1.21 (d, 6H).

(S,S)-2-[4-(2-Isopropyl-4H-3-thia-1,4,9-triaza-benzo[f]azulen-10-yl)-piperazin-2-yl]-1-phenyl-ethanol: mass spectrum (ion spray): m/z=448 (M+1), 446 (M−1). HR-MS calculated for $C_{25}H_{30}N_5OS$: 448.2171. Found 448.2156. $^1$H NMR (DMSO-$d_6$): δ 7.80 (s, 1H), 7.35–7.16 (m, 5H), 6.90–6.74 (m, 3H), 6.68 (br d, 1H), 5.44 (br s, 1H), 4.75–4.63 (m, 1H), 4.19–3.89 (m, 2H), 3.08 (quintet, 1H), 2.90–2.50 (m, 5H), 1.64–1.51 (m, 2H), 1.23 (d, 6H).

216

Example 603

(S,S)-2-[4-(2-Isopropyl-4H-3-thia-1,4,9-triaza-benzo[f]azulen-10-yl)-1-methyl-piperazin-2-yl]-1-phenyl-ethanol

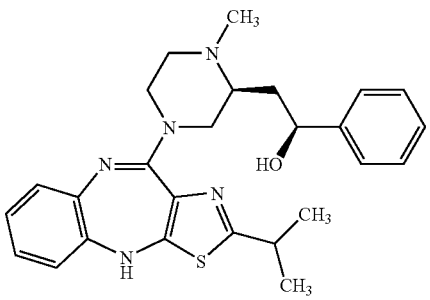

Add formaldehyde (23 μL, 0.29 mmol, 37% in water) to a solution of (S,S)-2-[4-(2-isopropyl-4H-3-thia-1,4,9-triaza-benzo[f]azulen-10-yl)-piperazin-2-yl]-1-phenyl-ethanol (117 mg, 0.26 mmol) in dichloroethane (5 mL). Stir 15 min at ambient temperature. Add sodium triacetoxyborohydride (83 mg, 0.39 mmol) and stir 2 h at ambient temperature. Dilute with saturated sodium bicarbonate solution and extract with methylene chloride. Dry the extracts with sodium sulfate, filter and concentrate the filtrate. Purify by radial silica gel chromatography using a 2 mm plate and 2N ammonia in methanol-methylene chloride (1%–4%) as the eluent to give 68 mg (56%) of the title compound: mass spectrum (ion spray): m/z=462 (M+1), 460 (M−1). HR-MS calculated for $C_{26}H_{32}N_5OS$: 462.2328. Found 462.2322. $^1$H NMR (DMSO-d6): δ 7.82 (s, 1H), 7.35–7.18 (m, 5H), 6.91–6.76 (m, 3H), 6.69 (br d, 1H), 5.29 (s, 1H), 4.58–4.46 (m, 1H), 4.14–3.77 (m, 2H), 3.02–3.17 (m, 2), 2.90 (dd, 1H), 2.74–2.65 (m, 1H), 2.28–2.11 (m, 1H), 2.14 (s, 3H), 2.03–1.84 (m, 2H) 1.70–1.54 (m, 1H), 1.26 (d, 6H).

Example 604

2-(2-Nitro-phenylamino)-5-trifluoromethyl-benzonitrile

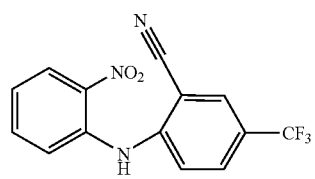

Add cesium carbonate (1.3 g, 4 mmol) to a solution of 2-nitro-aniline (276 mg, 2 mmol) and 2-fluoro-5-trifluoromethyl-benzonitrile (378 mg, 2 mmol) in DMF (10 mL) at room temperature then stir the resulting dark red solution at room temperature for 16 hours and 2 hours at 50° C. Cool down and pour into a mixture of ice and concentrated hydrochloric acid (50 mL, v/v). Extract the aqueous phase with dichloromethane (3×300 mL), wash with water and brine and dry over MgSO$_4$ to yield the titled compound as a yellow solid (480 mg, 80%): mp 160–161° C.; $^1$H NMR (CDCl$_3$) δ 7.14 (ddd, 1H), 7.48 (dd, 1H), 7.58 (dd, 1H), 7.60 (d, 1H), 7.76 (dd, 1H), 7.92 (d, 1H), 8.27 (dd, 1H), 9.63 (bs, 1H). MS (ES/neg) m/z (rel intensity) 306.1 (100).

Example 605

2-Trifluoromethyl-5H-dibenzo[b,e][1,4]diazepin-11-ylamine hydrochloride salt

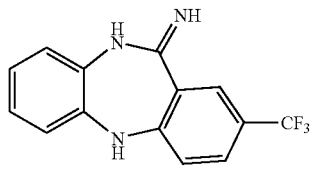

Add a solution of tin(II) chloride (567 mg, 3 mmol) in 12 N hydrochloric acid (1.8 mL) to a solution of 2-(2-nitro-phenylamino)-5-trifluoromethyl-benzonitrile (307 mg, 1 mmol) in ethanol (10 mL). Reflux for 24 hours, then concentrate under vacuum, add water and filter. Wash the resulting solid with water and dichloromethane then dry under vaccum to yield the titled compound as a yellow solid (282 mg, 90%): mp 334–336° C.; $^1$H NMR (DMSO-d$_6$) δ 7.05–7.19 (m, 4H), 7.34 (d, 1H), 7.86 (dd, 1H), 7.87 (s, 1H), 8.79 (s, 1H), 9.26 (s, 1H), 9.75 (s, 1H), 12.40 (s, 1H). MS (ESI/neg) m/z (rel intensity) 276.1 (100).

Example 606

11-(4-Methyl-piperazin-1-yl)-2-trifluoromethyl-5H-dibenzo[b,e][1,4]diazepine

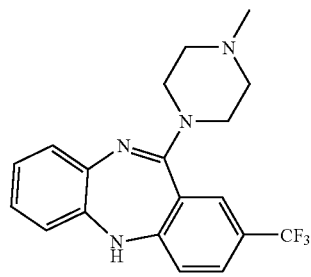

By a method similar to Example 59, 2-trifluoromethyl-5H-dibenzo[b,e][1,4]diazepin-11-ylamine hydrochloride salt (600 mg, 1.9 mmol) and N-methyl piperazine (960 mg, 9.6 mmol) afforded the title compound as a yellow solid (555 mg, 81%): mp 68–72° C.; $^1$H NMR (CDCl$_3$) δ 2.36 (s, 3H), 2.53 (bs, 4H), 3.42 (m, 4H), 5.12 (s, 1H), 6.70 (d, 1H), 6.90 (d, 1H), 6.92 (dt, 1H), 7.01 (dd, 1H), 7.10 (d, 1H), 7.52 (d, 1H), 7.55 (s, 1H); $^{19}$F NMR (CDCl$_3$) δ −328.38; MS (ESI/neg) m/z (rel intensity) 359.2 (100).

Example 607

2-(4-Fluoro-2-nitro-phenylamino)-5-trifluoromethyl-benzonitrile

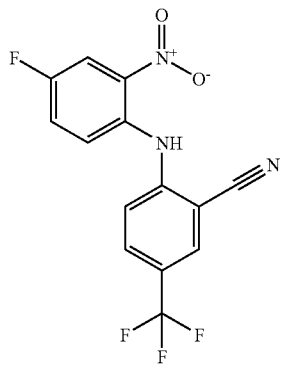

Combine 4-fluoro-2-nitro-phenylamine (5.9 g, 32.03 mmol), 2-fluoro-5-trifluoromethyl-benzonitrile (6.07 g, 32.03 mmol) and lithium hydroxide monohydrate (4.03 g, 96.08 mmol) in methyl sulfoxide (DMSO, 60 ml). Heat the resulting mixture to 70° C. for 16 hours. Cool the reaction mixture to ambient temperature, then pour into approximately 400 ml of ice water and stir for one hour. Filter the resulting mixture and collect the precipitate. Obtained 9.995 g of the title compound (30.73 mmol, 96% yield) as an orange amorphous solid. Product used as is with no further purification: Mass Spectrum (m/e): 326(M+1).

Example 608

8-Fluoro-2-trifluoromethyl-5H-dibenzo[b,e][1,4]diazepin-11-ylamine hydrochloride

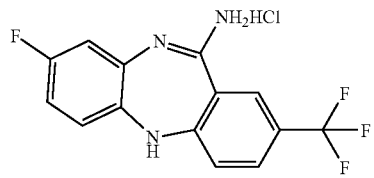

Heat a solution of 2-(4-fluoro-2-nitro-phenylamino)-5-trifluoromethyl-benzonitrile (9.995 g, 30.73 mmol) in ethanol (170 ml) to 60° C. Add to a solution of tin (II) chloride (29.1 g, 153.67 mmol) in 5.0 N hydrochloric acid (170 ml) and heat to reflux. After 18 hours, cool the reaction to room temperature and place in a freezer for 24 hours. The product precipitates from the solution and is collected by filtration. Obtained 2.253 g of the title compound (6.79 mmol, 22% yield) as a yellow amorphous solid: Mass Spectrum (m/e): 296(M+1).

Example 609

8-Fluoro-11-{3-[2-(4-methoxy-phenyl)-ethyl]-piperazin-1-yl}-2-trifluoromethyl-5H-dibenzo[b,e][1,4]diazepine succinate

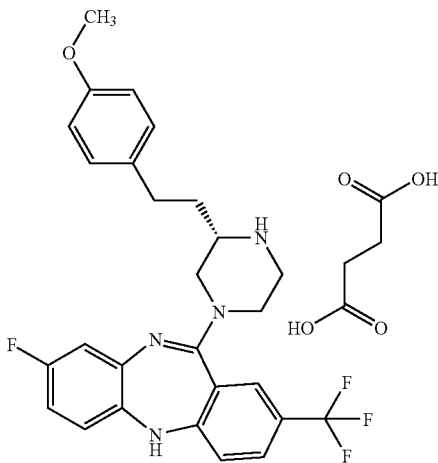

Heat a solution of 8-fluoro-2-trifluoromethyl-5H-dibenzo[b,e][1,4]diazepin-11-ylamine hydrochloride (0.2 g, 0.60 mmol) and diisopropylethylamine (0.086 g, 0.66 mmol) in 1-methyl-2-pyrrolidinone (4mL) to 60° C. for 30 minutes. Add 2-[2-(4-methoxy-phenyl)-ethyl]-piperazine (0.398 g, 1.81 mmol) and heat the reaction mixture to 195° C. for 14 hours. Cool reaction mixture to ambient temperature. Dilute with 50 ml of ethyl acetate and wash twice with saturated aqueous sodium chloride then twice with water. Collect the organic layer and dry over sodium sulfate. Remove solvent under reduced pressure. Purification via flash chromatography, eluting with a linear gradient starting with 100% dichloromethane and going to 85% dichloromethane with 15% 2M ammonia in methanol, gives the free base of the title compound (0.107 g, 0.21 mmol, 36% yield) as a yellow amorphous solid. Convert the product to the succinate salt by dissolving the product in methanol and adding one equivalent of succinic acid, swirl or sonicate the mixture until no solid succinic acid remains, then removing the solvent under reduced pressure gives the title compound: Mass Spectrum (m/e): 499(M+1); Exact Mass Spec: Calc. 499.2121; Found 499.2136.

Example 610

8-Fluoro-11-{3-[2-(4-methoxy-phenyl)-ethyl]-4-methyl-piperazin-1-yl}-2-trifluoromethyl-5H-dibenzo[b,e][1,4]diazepine

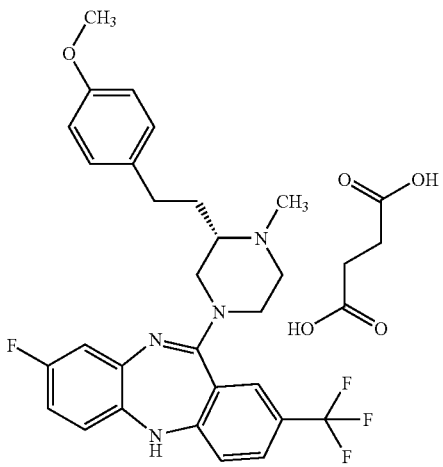

Dissolve the free base obtained from Example 609 (0.078 g, 0.16 mmol) in dichloromethane (8 ml). Add sodium triacetoxyborohydride (0.066 g, 0.31 mmol) and formaldehyde (0.005 g, 0.16 mmol, 0.013 g of a 37% aqueous solution) and stir the mixture for two hours at ambient temperature. Dilute the mixture with saturated aqueous sodium chloride (50 mL) and extract three times with dichloromethane. Combine the organic layers, dryover sodium sulfate and remove the solvent under reduced pressure. Purification via flash chromatography, eluting with a linear gradient starting with 100% of a stock mixture of 80% dichloromethane with 20% hexanes and going to 85% of the stock mixture with 15% 2M ammonia in methanol, gives the free base of the title compound (0.062 g, 0.12 mmol, 77% yield) as a yellow amorphous solid. It is then converted to the succinate salt as described previously: Mass Spectrum (m/e): 513(M+1); Exact Mass Spec: Calc. 513.2278; Found 513.2284.

Example 611

8-Fluoro-11-{3-[2-(4-fluoro-phenyl)-ethyl]-piperazin-1-yl}-2-trifluoromethyl-5H-dibenzo[b,e][1,4]diazepine

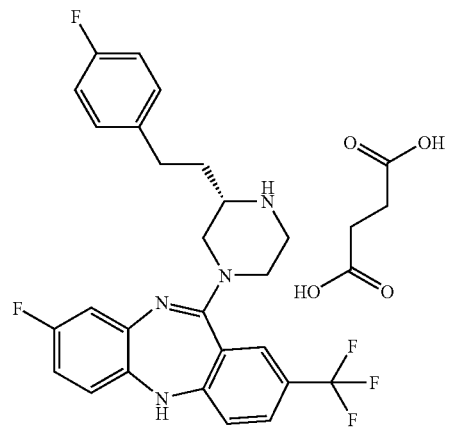

Heat a solution of 8-fluoro-2-trifluoromethyl-5H-dibenzo[b,e][1,4]diazepin-11-ylamine hydrochloride (0.2 g, 0.60 mmol) and diisopropylethylamine (0.086 g, 0.66 mmol) in 1-methyl-2-pyrrolidinone (4 mL) to 60° C. After 30 minutes, add 2-[2-(4-fluoro-phenyl)-ethyl]-piperazine (0.38 g, 1.81 mmol) and heat the reaction mixture to 195° C. for 16 hours. Cool reaction mixture to ambient temperature. Dilute with of ethyl acetate (50 ml) and wash twice with saturated aqueous sodium chloride then twice with water. Collect the organic layer and dry over sodium sulfate. Remove solvent under reduced pressure. Purification via flash chromatography, eluting with a linear gradient starting with 100% dichloromethane and going to 85% of dichloromethane with 15% 2M ammonia in methanol, gives the free base of the title compound (0.083 g, 0.17 mmol, 28% yield) as a yellow amorphous solid: Mass Spectrum (m/e): 487(M+1).

Example 612

8-Fluoro-1-{3-[2-(4-fluoro-phenyl)-ethyl]-4-methyl-piperazin-1-yl}-2-trifluoromethyl-5H-dibenzo[b,e][1,4]diazepine

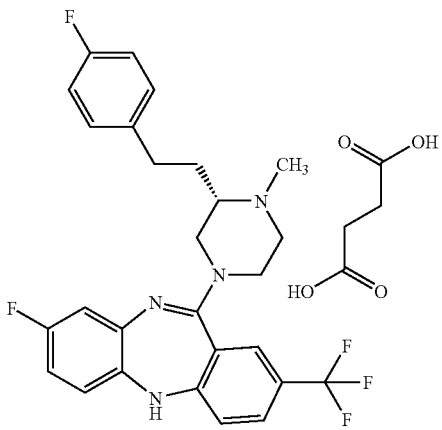

Dissolve the product obtained from Example 611 (0.083 g, 0.17 mmol) in dichloromethane (8 ml). Add sodium triacetoxyborohydride (0.072 g, 0.34 mmol) and formaldehyde (0.005 g, 0.17 mmol, 0.014 g of a 37% aqueous solution) and stir the mixture for two hours at ambient temperature. Dilute the mixture with of saturated aqueous sodium chloride (50 mL) and extract three times with dichloromethane. Combine the organic layers, dry over sodium sulfate and remove the solvent under reduced pressure. Purification via flash chromatography, eluting with a linear gradient starting with 100% of dichloromethane and going to 85% dichloromethane with 15% 2M ammonia in methanol, gives the free base of the title compound (0.032 g, 0.06 mmol, 37% yield) as a yellow amorphous solid. It is then converted to the succinate salt as described previously: Mass Spectrum (m/e): 501(M+1); Exact Mass Spec. Calc 501.2078; Found 501.2093.

Receptor Binding Assays

Serotonin 5-HT$_6$ and Dopamine D$_2$ Binding Assay Protocol

The assay buffers used are 50 mM Tris-HCl pH 7.4, 120 mM NaCl, 5 mM KCl, 5 mM MgCl$_2$, 1 mM EDTA for the Dopamine D$_2$s receptor binding assay. The radioligand used is [$^{125}$I]iodospiperone from New England Nuclear Cat #NEX284-2200 Ci/mmole. The membranes used are from Receptor Biology (now owned by NEN), Cat #RBHD2CM for the D$_2$ receptor.

Compounds are obtained as 10 mM stocks in 100% DMSO. They are diluted to 1 mM in 100% DMSO by adding 180 µL DMSO to 20 µL of stock in 96 well plates using a multidrop. The 1 mM stocks are then diluted to make an 11 point concentration range from 125 µM down to 1.25 µM in half log increments using 10% DMSO as diluent. This is done using a TECAN robot. The final DMSO at this stage is 10–21.25% DMSO The radioligand is diluted in assay buffer to provide 0.1 nM for the D$_2$ assay. Each vial of membranes is diluted up to 92 mL in assay buffer. The final assay volume is 250 µL consisting of 210 µl of diluted membranes, 20 µL of compound or 10% DMSO for total binding, and 20 µL of diluted radioligand. The compounds are transferred from drug dilution plates into coming 96 well assay plates using a 96 well Multimek pipettor. Radioligand and membranes are added to assay plates using multidrop pipettors. Non-specific binding is determined in wells containing a final concentration of 5 µM haloperidol. The final drug concentration range in half logs is from 10 µM down to 0.1 nM. The final DMSO in the assay is 1–1.7%.

After addition of drug, membrane, and ligand, the plates are incubated for 2 hours at room temperature. During this time 96 well Millipore filter plates (MAFBNOB50) are soaked for a least 30 minutes with 200 µL per well of 0.5% polyethyleneimine.

The 0.5% PEI is removed from filterplate wells using a TiterTek MAP aspirator and 200 µL of the incubation mixture is transferred from the incubation plate to the filterplate after mixing. This transfer is done using the 96 tip Mutimek pipettor. After transfer to the filterplate filterplates are extracted and ished twice with 220 µL per well of cold buffer on the MAP aspirator. The peel away bottoms are removed from the filterplates and 60 µL per well of microscint 20 scintillation fluid is added per well using a multidrop. Plates are placed into suitable holders and are left at room temperature for 3 hours and are counted for $^3$H in either a Wallac Microbeta counter or on a Packard Topcount.

[$^{125}$I]DOI SPA Binding to Rhesus 5-HT$_{2A}$ Receptors Protocol

Incubations are performed in a total volume of 200 µl in 96 well assay plates. 50 µL [$^{125}$I]DOI (NEN, 2200 Ci/mmol, final concentration=0.075nM) is added to 50 µL of test compounds dissolved in water (±DMSO and/or glacial acetic acid). 50 µL Wheat Germ Agglutinin (WGA) SPA beads, at 1 mg/well, (Amersham Life Sciences) in assay buffer (67mM Tris-HCl pH 7.4, 13mM MgCl$_2$, 0.67 mM EDTA) are then added. Membrane homogenate from cells expressing rhesus 5-HT$_{2A}$ receptors, approximately 0.9 million cells/well, is added last. The plates are covered with sealing tape (FasCal) and allowed to incubate at room temperature for 2 hours. The plates are then centrifuged at approximately 200× g for 10 minutes at room temperature. The amount of $^{125}$I-DOI bound to the membranes, i.e. proximate to the WGA SPA beads, is then determined using a Wallac Micro-Beta Trilux Scintillation Counter (Wallac, Inc.).

Pharmaceutical Formulations

Capsule

A pulvule formulation is prepared by blending the active with silicone starch, and filling it into hard gelatin capsules.

|  | Per 300 mg capsule |
|---|---|
| Compound of formula (I) | 5.0 mg |
| Silicone | 2.9 mg |
| Starch flowable | 292.1 mg |

Tablet

A tablet formulation is made by granulating the active with appropriate diluent, lubricant, disintegrant and binder and compressing.

|  | Per 300 mg tablet |
|---|---|
| Compound of formula (I) | 10.0 mg |
| Magnesium stearate | 0.9 mg |
| Microcrystalline cellulose | 75.0 mg |
| Povidone | 15.0 mg |
| Starch, directly compressible | 199.1 mg |

Injection

An aqueous injection of active is prepared as a freeze-dried plug, for reconstitution in a suitable, sterile diluent before use (to a total volume of 10 ml).

| | |
|---|---|
| Compound of formula (I) | 20.0 mg |
| Mannitol | 20.0 mg |
| N Hydrochloric acid and/or N sodium hydroxide to adjust pH to 5–5.5. | |

Controlled Release Injection

A controlled release injection for intramuscular injection is formed from a sterile suspension of micronised active in an oleaginous vehicle.

| | |
|---|---|
| Compound of formula (I) | 65.0 mg |
| Aluminium stearate | 0.04 mg |
| Sesame oil | 2 ml |

What is claimed is:

1. A compound of formula (I):

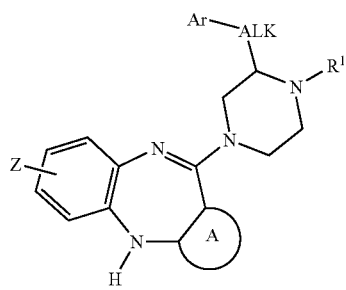

wherein,

A is

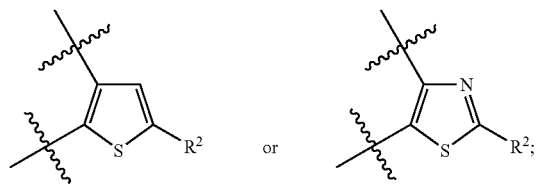

ALK is $(C_{1-4})$ alkylene optionally substituted with OH, methoxy, ethoxy, or F;

Ar is optionally substituted phenyl, naphthyl, monocyclic heteroaromatic, or bicyclic heteroaromatic;

$R^1$ is hydrogen or $(C_{1-4})$ alkyl optionally substituted with OH, $OR^3$, or $OCH_2CH_2OH$;

$R^2$ is H, $(C_{1-6})$ alkyl, halogen, fluorinated $(C_{1-6})$ alkyl, $OR^4$, $SR^4$, $NO_2$, CN, $COR^4$, $CONR^5R^6$, $SO_2NR^5R^6$, $NR^5R^6$, $NR^5COR^4$, $NR^5SO_2R^4$, or optionally substituted phenyl;

$R^3$ is $(C_{1-2})$ alkyl;

$R^4$ is hydrogen, $(C_{1-6})$ alkyl, fluorinated $(C_{1-6})$ alkyl, benzyl, or optionally substituted phenyl, $R^5$ and $R^6$ are independently hydrogen, $(C_{1-6})$ alkyl, or optionally substituted phenyl;

Z is absent or is one or two substituents independently selected from halogen, $(C_{1-6})$ alkyl, fluorinated $(C_{1-6})$ alkyl, $OR^7$, $SR^7$, $NO_2$, CN, $COR^7$, $CONR^8R^9$, $SO_2NR^8R^9$, $NR^8SO_2R^7$, $NR^8R^9$, or optionally substituted phenyl;

$R^7$ is hydrogen, $(C_{1-6})$ alkyl, fluorinated $(C_{1-6})$ alkyl, benzyl, or optionally substituted phenyl, $R^8$ and $R^9$ are independently hydrogen, $(C_{1-6})$ alkyl, or optionally substituted phenyl; or a pharmaceutically acceptable salt thereof.

2. A compound of claim 1 in which

ALK is —CH$_2$— or —CH$_2$CH$_2$—.

3. A compound of claim 2 in which Ar is optionally substituted phenyl, furan, or thiophene.

4. A compound of claim 3 in which $R^1$ is hydrogen, methyl, or —CH$_2$CH$_2$—O—CH$_2$CH$_2$—OH.

5. A compound of claim 4 in which $R^2$ is hydrogen, $(C_{1-6})$ alkyl, fluorinated $(C_{1-6})$ alkyl, or halogen.

6. A compound of claim 5 in which Z is absent or is halogen.

7. A compound of claim 6 in which the stereo configuration is "S" about the carbon of the piperazine group bound to ALK.

8. A compound of claim 6 in which the stereo configuration is "R" about the carbon of the piperazine group bound to ALK.

9. A pharmaceutical composition comprising an effective amount of a compound of claim 1 in association with a pharmaceutically acceptable carrier, diluent or excipient.

* * * * *